(12) United States Patent
Yan et al.

(10) Patent No.: US 11,254,941 B2
(45) Date of Patent: Feb. 22, 2022

(54) RNA NANOSTRUCTURES AND METHODS OF MAKING AND USING RNA NANOSTRUCTURES

(71) Applicant: ARIZONA BOARD OF REGENTS ON BEHALF OF ARIZONA STATE UNIVERSITY, Scottsdale, AZ (US)

(72) Inventors: Hao Yan, Chandler, AZ (US); Yung Chang, Tempe, AZ (US); Xiaowei Liu, Tempe, AZ (US); Fei Zhang, Chandler, AZ (US); Xiaodong Qi, Tempe, AZ (US)

(73) Assignee: ARIZONA BOARD OF REGENTS ON BEHALF OF ARIZONA STATE UNIVERSITY, Scottsale, AZ (US)

( * ) Notice: Subject to any disclaimer, the term of this patent is extended or adjusted under 35 U.S.C. 154(b) by 0 days.

(21) Appl. No.: 16/642,792

(22) PCT Filed: Aug. 30, 2018

(86) PCT No.: PCT/US2018/048973
§ 371 (c)(1),
(2) Date: Feb. 27, 2020

(87) PCT Pub. No.: WO2019/147308
PCT Pub. Date: Aug. 1, 2019

(65) Prior Publication Data
US 2021/0246452 A1 Aug. 12, 2021

Related U.S. Application Data

(60) Provisional application No. 62/637,807, filed on Mar. 2, 2018, provisional application No. 62/630,020, filed on Feb. 13, 2018, provisional application No. 62/625,965, filed on Feb. 2, 2018, provisional application No. 62/596,697, filed on Dec. 8, 2017, provisional application No. 62/594,473, filed on Dec. 4, 2017, provisional application No. 62/594,471, filed on Dec. 4, 2017, provisional application No. 62/552,183, filed on Aug. 30, 2017.

(51) Int. Cl.
*C12N 15/117* (2010.01)
*B82Y 5/00* (2011.01)

(52) U.S. Cl.
CPC ............... *C12N 15/117* (2013.01); *B82Y 5/00* (2013.01); *C12N 2310/51* (2013.01)

(58) Field of Classification Search
None
See application file for complete search history.

(56) References Cited

U.S. PATENT DOCUMENTS

| 4,559,157 | A | 12/1985 | Smith et al. |
|---|---|---|---|
| 4,608,392 | A | 8/1986 | Jacquet et al. |
| 4,820,508 | A | 4/1989 | Wortzman |
| 4,938,949 | A | 7/1990 | Borch |
| 4,992,478 | A | 2/1991 | Geria |
| 6,773,885 | B1 | 8/2004 | Walder |
| 8,440,811 | B2 | 5/2013 | Chang et al. |
| 8,552,167 | B2 | 10/2013 | Chang et al. |
| 8,685,894 | B2 | 4/2014 | Chaput et al. |
| 9,202,867 | B2 | 12/2015 | Yan et al. |
| 9,732,273 | B2 | 8/2017 | Yan et al. |
| 9,944,923 | B2 | 4/2018 | Blattman et al. |
| 10,189,874 | B2 | 1/2019 | Han et al. |
| 10,669,534 | B2 | 6/2020 | Fu et al. |
| 10,774,107 | B2 | 9/2020 | Han et al. |
| 10,987,373 | B2 | 4/2021 | Yan et al. |
| 2003/0219790 | A1 | 11/2003 | Seeman et al. |
| 2006/0035255 | A1 | 2/2006 | Seeman et al. |
| 2010/0216658 | A1 | 8/2010 | Chaput et al. |
| 2011/0275702 | A1 | 11/2011 | Chang et al. |
| 2012/0190732 | A1 | 7/2012 | Chang et al. |
| 2014/0252316 | A1 | 9/2014 | Yan et al. |
| 2016/0053174 | A1 | 2/2016 | Yan et al. |
| 2016/0122752 | A1 | 5/2016 | Blattman et al. |
| 2017/0066796 | A1 | 3/2017 | Han et al. |
| 2018/0016569 | A1 | 1/2018 | Fu et al. |
| 2018/0044372 | A1* | 2/2018 | Han ............... C12Y 207/00 |
| 2018/0044663 | A1 | 2/2018 | Yan |
| 2018/0216102 | A1 | 8/2018 | Blattman et al. |
| 2019/0144491 | A1 | 5/2019 | Han et al. |
| 2019/0156911 | A1* | 5/2019 | Veneziano ............ G16B 15/00 |

(Continued)

FOREIGN PATENT DOCUMENTS

EP 3676380 A2 7/2020
TW 201932100 A 8/2019

(Continued)

OTHER PUBLICATIONS

International Search Report and Written Opinion in International Patent Application No. PCT/US18/48973, dated Dec. 19, 2019, in 19 pages.
Krill A. Afonin et al, "Specific RNA Self-Assembly with Minimal Paranemic Motifs", Journal of the American Chemical Society,vol. 130, No. 1, Dec. 12, 2007 (Dec. 12, 2007), pp. 93-102.
Megumi Tatematsu et al, "Beyond dsRNA: Toll-like receptor 3 signalling in RNA-induced immune responses", Biochemical Journal,vol. 458, No. 2, Feb. 14, 2014 (Feb. 14, 2014), p. 195-201.
Emil F. Khisamutdinov et al, "Enhancing immunomodulation on innate immunity by shape transition among RNA triangle, square and pentagon nanovehicles", Nucleic Acids Research,vol. 42, No. 15, Aug. 4, 2014 (Aug. 4, 2014), p. 9996-10004.

(Continued)

*Primary Examiner* — Tracy Vivlemore
(74) *Attorney, Agent, or Firm* — Duane Morris LLP

(57) ABSTRACT

Certain embodiments provide RNA nanostructure (e.g., comprising one single-stranded RNA (ssRNA) molecule, wherein the RNA nanostructure comprises at least one paranemic cohesion crossover), as well as compositions and methods of use thereof. In certain embodiments, such RNA nanostructures are immuno-modulatory (e.g., immunostimulatory).

10 Claims, 62 Drawing Sheets

Specification includes a Sequence Listing.

(56) References Cited

U.S. PATENT DOCUMENTS

| | | |
|---|---|---|
| 2019/0240248 A1 | 8/2019 | Yan et al. |
| 2020/0101101 A1 | 4/2020 | Yan et al. |
| 2020/0270599 A1 | 8/2020 | Fu et al. |
| 2020/0385734 A1 | 12/2020 | Chang et al. |
| 2020/0390814 A1 | 12/2020 | Yan et al. |
| 2021/0061845 A1 | 3/2021 | Han et al. |

FOREIGN PATENT DOCUMENTS

| | | |
|---|---|---|
| WO | WO2007139849 A2 | 12/2007 |
| WO | WO2011049750 A1 | 4/2011 |
| WO | WO2013052541 A2 | 4/2013 |
| WO | WO2014200933 A1 | 12/2014 |
| WO | WO2015130805 A1 | 9/2015 |
| WO | 2015196146 A2 | 12/2015 |
| WO | WO2018165465 A1 | 9/2018 |
| WO | WO2019109707 A1 | 6/2019 |
| WO | 2019140140 A1 | 7/2019 |
| WO | 2019147309 A2 | 8/2019 |
| WO | WO2019147308 A2 | 8/2019 |
| WO | WO2019152957 A1 | 8/2019 |
| WO | WO2020036654 A2 | 2/2020 |

OTHER PUBLICATIONS

Inna Novikova et al, "Paranemic and Receptor-Loop RNA Motifs: Versatile Interactions for Biosensing Platforms and Nanotechnology Scaffolds", Dec. 2010 (Dec. 2010), Retrieved from the Internet: URL:https://etd.ohiolink.edu/letd.send_file?accession=bgsu1288300501 &disposition=inline XP055601521.

Cody Geary et al, "A single-stranded architecture for cotranscriptional folding of RNA nanostructures", Science, vol. 345, No. 6198, Aug. 14, 2014 (Aug. 14, 2014), p. 799-804.

Tsukasa Seya et al, "Targeting TLR3 with no RIG-I/MDA5 activation is effective in immunotherapy for cancer", Expert Opinion on Therapeutic Targets,vol. 17, No. 5, Feb. 18, 2013 (Feb. 18, 2013), p. 533-544.

Dongran Han et al, "Single-stranded DNA and RNA origami", Science,vol. 358, No. 6369, Dec. 14, 2017 (Dec. 14, 2017), p. eaao2648,.

Acuna et al., Fluorescence enhancement at docking sites of DNA-directed self-assembled nanoantennas. Science 338,506-510 (2012). doi: 10.1126/science.1228638; pmid: 23112329.

Aldaye et al., Assembling materials with DNA as the guide. Science 321, 1795-1799 (2008).

Alexander et al., On types of knotted curves, in The Annals of Mathematics, Second Series (Annals of Mathematics, 1926), pp. 562-586.

Alexander, Topological invariants of knots and links. Trans. Am. Math. Soc. 30, 275-306 (1928). doi: 10.1090/S0002-9947-1928-1501429-1.

Alexopoulou et al., Recognition of double-stranded RNA and activation of NF-kappa B by Toll-like receptor 3. Nature 413, 732-738, doi:Doi 10.1038/35099560 (2001).

Altschul et al., 'Basic Local Alignment Search Tool', J. Mol. Biol., 215, 403-410 (1990).

Ammi Rachid et al.: "Poly(I:C) as cancer vaccine adjuvant: Knocking on the door of medical breakthroughs", Pharmacology and Therapeutics, vol. 146, Oct. 14, 2014 (Oct. 14, 2014), pp. 120-131.

Andersen et al., DNA origami design of dolphin-shaped structures with flexible tails. Acs Nano 2, 1213-1218 (2008).

Andersen et al., Self-assembly of a nanoscale DNA box with a controllable lid. Nature 459, 73-76 (2009). doi: 10.1038/nature07971; pmid: 19424153.

Avakyan et al., Reprogramming the assembly of unmodified DNA with a small molecule. Nat. Chem. 8, 368-376 (2016). doi: 10.1038/nchem.2451; pmid: 27001733.

Ball, "Small Problems" Nanosystems—Molecular Machinery, Manufacturing, and Computation—Drexler, KE. Nature 362, p. 123 (1993).

Beaucage, S. L., and Caruthers, M. H., Tet. Let. 22:1859,1981.

Bell et al., Digitally encoded DNA nanostructures for multiplexed, single-molecule protein sensing with nanopores. Nat. Nanotechnol. 11, 645-651 (2016). doi: 10.1038/nnano.2016.50; pmid: 27043197.

Benson et al., DNA rendering of polyhedral meshes at the nanoscale. Nature 523, 441-444 (2015). doi: 10.1038/nature14586; pmid: 26201596.

Buck D, "DNA Topology" Proceedings of Symposia in Applied Mathematics 2009; 66: 1-33, pp. 47-80.

Butcher et al., The Molecular Interactions That Stabilize RNA Tertiary Structure: RNA Motifs, Patterns, and Networks. Accounts Chem Res 44, 1302-1311 (2011).

Castro-Mesta et al., Bases and foundations of the treatment of peritoneal carcinomatosis: Review article. Medicina Universitaria 18, 98-104 (2016).

Chen et al., Synthesis from DNA of a molecule with the connectivity of a cube. Nature 350, 631-633 (1991). doi: 10.1038/350631a0; pmid: 2017259.

Chou, Ting-Chao, and Paul Talalay. "Quantitative analysis of dose-effect relationships: the combined effects of multiple drugs or enzyme inhibitors." Advances in Enzyme Regulation 22 (1984): 27-55.

Christopher et al., Use of Toll-Like Receptor 3 Agonists Against Respiratory Viral Infections. Anti-Inflamm. & Anti-Allergy Agents in Med. Chem. 10, 327-338 (2011).

Chworos et al., Building programmable jigsaw puzzles with RNA. Science 306, 2068-2072 (2004). doi: 10.1126/science.1104686; pmid: 15604402.

Coccolini et al., Peritoneal carcinomatosis. World J Gastroenterol 19, 6979-6994, doi: 10.3748/wjg.v19.i41.6979 (2013).

Conforti, Rosa, et al. "Opposing effects of toll-like receptor (TLR3) signaling in tumors can be therapeutically uncoupled to optimize the anticancer efficacy of TLR3 ligands." Cancer Research 70.2 (2010): 490-500.

Corpet et al., Nucl. Acids Res., 16, 10881 (1988).

Delebecque et al., Organization of intracellular reactions with rationally designed RNA assemblies. Science 333, 470-474 (2011). doi: 10.1126/science.1206938; pmid: 21700839.

Diebold et al., Innate antiviral responses by means of TLR7-mediated recognition of single-stranded RNA. Science 303, 1529-1531, doi:10.1126/science.1093616 (2004).

Diebold, Sandra S. "Recognition of viral single-stranded RNA by Toll-like receptors." Advanced Drug Delivery Reviews 60.7 (2008): 813-823.

Dietz et al., Folding DNA into twisted and curved nanoscale shapes. Science 325, 725-730 (2009). doi: 10.1126/science.1174251; pmid: 19661424.

Doherty et al., Ribozyme structures and mechanisms. Annu Rev Bioph Biom 30, 457-475 (2001).

Douglas et al., A logic-gated nanorobot for targeted transport of molecular payloads. Science 335, 831-834 (2012). doi: 10.1126/science.1214081; pmid: 22344439.

Douglas et al., DNA-nanotube-induced alignment of membrane proteins for NMR structure determination. Proc. Natl. Acad. Sci. U.S.A. 104, 6644-6648 (2007). doi: 10.1073/pnas.0700930104; pmid: 17404217.

Douglas et al., Rapid prototyping of 3D DNA-origami shapes with caDNAno. Nucleic Acids Res 37, 5001-5006 (2009).

Douglas et al., Self-assembly of DNA into nanoscale three-dimensional shapes. Nature 459, 414-418 (2009). doi: 10.1038/nature08016; pmid: 19458720.

Ducani et al., Enzymatic production of 'monoclonal stoichiometric' single stranded DNA oligonucleotides. Nat. Methods 10, 647-652 (2013). doi: 10.1038/nmeth.2503; pmid: 23727986.

Dunn et al., Guiding the folding pathway of DNA origami. Nature 525, 82-86 (2015). doi: 10.1038/nature14860; pmid: 26287459.

Elbashir et al., Duplexes of 21-nucleotide RNAs mediate RNA interference in cultured mammalian cells. Nature 411, 494-498 (2001).

Froehler et al., Nucl. Acid. Res. 14:5399-5407, 1986.

Fu et al., Multi-enzyme complexes on DNA scaffolds capable of substrate channelling with an artificial swinging arm. Nat. Nanotechnol. 9, 531-536 (2014). doi: 10.1038/nnano.2014.100; pmid: 24859813.

Gaffney et al., Tet. Let. 29:2619-2622,1988.

(56) References Cited

OTHER PUBLICATIONS

Garegg et al., Tet. Let. 27:4051-4054,1986.
Garegg et al., Tet. Let. 27:4055-4058, 1986.
Gatti et al., Direct effect of dsRNA mimetics on cancer cells induces endogenous IFN-b production capable of improving dendritic cell function. Eur. J. Immunol 43, 1849-1861 (2013).
Gerling et al., Dynamic DNA devices and assemblies formed by shape-complementary, non-base pairing 3D components. Science 347, 1446-1452 (2015). doi: 10.1126/science.aaa5372; pmid: 25814577.
Gitlin et al., Essential role of mda-5 in type IIFN responses to polyriboinosinic:polyribocytidylic acid and encephalomyocarditis picornavirus. Proc Natl Acad Sci U S A 103, 8459-8464, doi:10.1073/pnas.0603082103 (2006).
Gopinath et al., Engineering and mapping nanocavity emission via precision placement of DNA origami. Nature 535, 401-405 (2016). doi: 10.1038/nature18287; pmid: 27398616.
Gu et al., Dynamic patterning programmed by DNA tiles captured on a DNA origami substrate. Nat. Nanotechnol. 4, 245-248 (2009). doi: 10.1038/ nnano.2009.5; pmid: 19350035.
Gungor et al., CpG ODN Nanorings Induce IFN alpha from Plasmacytoid Dendritic Cells and Demonstrate Potent Vaccine Adjuvant Activity. Science Translational Medicine 6, doi:ARTN 235ra61 10.1126/scitranslmed.3007909 (2014), 12 pages.
Guzhova, I.V. & Margulis, B. A. 2016. HSP70-based anti-cancer immunotherapy. Human Vaccines & Immunotherapuetics. 12: 2529-2535.
Hahn et al., Addressing the Instability of DNA Nanostructures in Tissue Culture. Acs Nano 8, 8765-8775, doi:10.1021/nn503513p (2014).
Han et al., DNA gridiron nanostructures based on four-arm junctions. Science 339, 1412-1415 (2013). doi: 10.1126/ science.1232252; pmid: 23520107.
Han et al., DNA origami with complex curvatures in three dimensional space. Science 332, 342-346 (2011). doi: 10.1126/ science.1202998; pmid: 21493857.
Han et al., Unidirectional scaffold-strand arrangement in DNA origami. Angew. Chem. Int. Ed. 52, 9031-9034 (2013). doi: 10.1002/anie.201302177; pmid: 23852715.
He et al., Hierarchical self-assembly of DNA into symmetric supramolecular polyhedra. Nature 452, 198-201 (2008). doi: 10.1038/nature06597; pmid: 18337818.
Heil et al., Species-specific recognition of single-stranded RNA via toll-like receptor 7 and 8. Science 303, 1526-1529, doi: 10.1126/science.1093620 (2004).
Hemmi et al., A Toll-like receptor recognizes bacterial DNA. Nature 408, 740-745 (2000).
Higgins et al., CABIOS, 5, 151 (1989).
Hock et al., iRFP is a sensitive marker for cell number and tumor growth in high-throughput systems. Cell Cycle 13, 220-226, doi:10.4161/cc.26985 (2014).
Horiya et al., RNA Lego: Magnesium-dependent formation of specific RNA assemblies through kissing interactions. Chem. Biol. 10, 645-654 (2003). doi: 10.1016/S1074-5521(03)00146-7; pmid: 12890538.
Huang et al., CABIOS, 8, 155 (1992).
Iinuma et al., Polyhedra self-assembled from DNA tripods and characterized with 3D DNA-Paint. Science 344, 65-69 (2014). doi: 10.1126/science.1250944; pmid: 24625926.
Iribarren et al., Trial Watch: Immunostimulation with Toll-like receptor agonists in cancer therapy. Oncoimmunology 5, el088631, doi: 10.1080/2162402X.2015.1088631 (2016).
Itoh et al., The clathrin-mediated endocytic pathway participates in dsRNA-induced IFN-g production. J. Immunol. 181, 5222-5229 (2008).
Jaeger et al., Tecto-RNA: One-dimensional self-assembly through tertiary interactions. Angew. Chem. Int. Ed. 39, 2521-2524 (2000). doi: 10.1002/1521-3773(20000717)39:14<2521::AIDANIE2521>3.0.CO;2-P; pmid: 10941124.

Jaeger et al., The architectonics of programmable RNA and DNA nanostructures. Curr. Opin. Struct. Biol. 16, 531-543 (2006). doi: 10.1016/j.sbi.2006.07.001; pmid: 16843653.
Jasinski, Daniel, et al. "Advancement of the emerging field of RNA nanotechnology." ACS nano 11.2 (2017): 1142-1164.
Jiang et al., DNA Origami as a Carrier for Circumvention of Drug Resistance. Journal of the American Chemical Society 134, 13396-13403, doi:10.1021/ja304263n (2012).
Jin et al., Metallized DNA nanolithography for encoding and transferring spatial information for graphene patterning. Nat. Commun. 4, 1663 (2013). doi: 10.1038/ncomms2690; pmid: 23575667.
Karlin and Altschul, Proc. Natl. Acad. Sci. USA 90, 5873 (1993).
Karlin and Altschul, Proc. Natl. Acad. Sci. USA, 87, 2264 (1990).
Kato et al., Differential roles of MDA5 and RIG-I helicases in the recognition of RNA viruses. Nature 441, 101-105, doi:10.1038/nature04734 (2006).
Kato et al., Length-dependent recognition of doublestranded ribonucleic acids by retinoic acid—inducible gene-I and melanoma diff erentiation—associated gene 5. J. Exp. Med. 205, 1601-1610 (2008).
Kawai et al., Innate immune recognition of viral infection. Nature Immunology 7, 131-137, doi:10.1038/nil303 (2006).
Ke et al., DNA brick crystals with prescribed depths. Nat. Chem. 6, 994-1002 (2014). doi: 10.1038/nchem.2083; pmid: 25343605.
Ke et al., Three-dimensional structures self-assembled from DNA bricks. Science 338, 1177-1183 (2012). doi: 10.1126/science.1227268; pmid: 23197527.
Kilchherr et al., Single-molecule dissection of stacking forces in DNA. Science 353, aaf5508 (2016). doi: 10.1126/science. aaf5508; pmid: 27609897.
Kim et al., Quantitative prediction of 3D solution shape and flexibility of nucleic acid nanostructures. Nucleic Acids Res 40, 2862-2868 (2012).
Kistner et al., Interferon-inducible CXC-chemokines are crucial immune modulators and survival predictors in colorectal cancer. Oncotarget 8, 89998-90012 (2017).
Klinman, Immunotherapeutic uses of CpG oligodeoxynucleotides. Nature Reviews Immunology 4, 248-257, doi:10.1038/nril329 (2004).
Knudsen et al., Routing of individual polymers in designed patterns. Nat. Nanotechnol. 10, 892-898 (2015). doi: 10.1038/nnano.2015.190; pmid: 26322946.
Kranz, Lena M., et al. "Systemic RNA delivery to dendritic cells exploits antiviral defence for cancer immunotherapy." Nature 534. 7607 (2016): 396-401.
Kuzyk et al., DNA-based self-assembly of chiral plasmonic nanostructures with tailored optical response. Nature 483, 311-314 (2012). doi: 10.1038/nature10889; pmid: 22422265.
Lacour et al., Adjuvant Treatment with Polyadenylic-Polyuridylic Acid in Operable Breast-Cancer—Updated Results of a Randomized Trial. British Medical Journal 288, 589-592, doi:DOI 10.1136/bmj.288.6417.589 (1984).
Lee et al., Molecularly self-assembled nucleic acid nanoparticles for targeted in vivo siRNA delivery. Nature Nanotechnology 7, 389-393, doi:10.1038/Nnano.2012.73 (2012).
Lee et al., Rate and molecular spectrum of spontaneous mutations in the bacterium *Escherichia coli* as determined by whole-genome sequencing. Proc. Natl. Acad. Sci. U.S.A. 109, E2774 E2783 (2012). doi: 10.1073/pnas.1210309109; pmid: 22991466.
Lehár, Joseph, et al. "Chemical combination effects predict connectivity in biological systems." Molecular Systems Biology 3.1 (2007): 80.
Leontis et al., Geometric nomenclature and classification of RNA base pairs. Rna 7, 499-512 (2001).
Li et al., A DNA nanorobot functions as a cancer therapeutic in response to a molecular trigger in vivo. Nature Biotechnology 36, 258-+, doi:10.1038/nbt.4071 (2018).
Li et al., A replicable tetrahedral nanostructure self assembled from a single DNA strand. J. Am. Chem. Soc. 131, 13093-13098 (2009). doi: 10.1021/ja903768f; pmid: 19737020.
Limmon et al., Scavenger receptor class-A is a novel cell surface receptor for double-stranded RNA. FASEB J 22, 159-167, doi:10.1096/fj.07-8348com (2008).

(56) References Cited

OTHER PUBLICATIONS

Lin et al., In vivo cloning of artificial DNA nanostructures. Proc. Natl. Acad. Sci. U.S.A. 105, 17626-17631 (2008).doi: 10.1073/pnas.0805416105; pmid: 18927233.
Lin et al., Rolling circle enzymatic replication of a complex multi-crossover DNA nanostructure. J. Am. Chem. Soc. 129, 14475-14481 (2007). doi: 10.1021/ja0760980; pmid: 17963390.
Lin et al., Rolling-circle amplification of a DNA nanojunction. Angew. Chem. Int. Ed. 45, 7537-7539 (2006). doi: 10.1002/anie. 200602113; pmid: 17048296.
Liu, Xiaowei, et al. "Targeted Cell-Cell Interactions by DNA Nanoscaffold-Templated Multivalent Bispecific Aptamers." Small 7.12 (2011): 1673-1682.
Liu et al., A DNA Nanostructure Platform for Directed Assembly of Synthetic Vaccines. Nano Letters 12, 4254-4259, doi:10.1021/nl301877k (2012).
Liu et al., Creating complex molecular topologies by configuring DNA four-way junctions. Nat. Chem. 8, 907-914 (2016). doi: 10.1038/nchem.2564; pmid: 27657865.
Mansfield, Are there knots in proteins? Nat. Struct. Mol. Biol. 1, 213-214 (1994). doi: 10.1038/nsb0494-213; pmid: 7656045.
Martin et al., Design of a molecular support for cryo-EM structure determination. Proc. Natl. Acad. Sci. U.S.A. 113, E7456-E7463 (2016). doi: 10.1073/pnas.1612720113; pmid: 27821763.
Matsumoto et al., Cell type-specific role of Raftlin in the regulation of endosomal TLR signaling. Inflammation and Cell Signaling 3, 1-8 (2016).
Matsumoto et al., Defined TLR3-specific adjuvant that induces NK and CTL activation without significant cytokine production in vivo. Nature Communications 6, doi:ARTN 6280 10.1038/ncomms7280 (2015), 12 pages.
Matsumoto et al., Toll-Like Receptor 3 Signal in Dendritic Cells Benefits Cancer Immunotherapy. Frontiers in Immunology 8, doi:ARTN 1897 10.3389/fimmu.2017.01897 (2017), 7 pages.
Mikula-Pietrasik et al., The peritoneal "soil" for a cancerous "seed": a comprehensive review of the pathogenesis of intraperitoneal cancer metastases. Cell Mol Life Sci 75, 509-525, doi:10.1007/s00018-017-2663-1 (2018).
Myers and Miller, CABIOS, 4, pp. 11-17 (1988).
Needleman and Wunsch, JMB, 48, 443-453 (1970).
Nickels et al., Molecular force spectroscopy with a DNA origami-based nanoscopic force clamp. Science 354, 305-307 (2016). doi: 10.1126/science.aah5974; pmid: 27846560.
Pearson and Lipman, Proc. Natl. Acad. Sci. USA, 85, 2444-2448 (1988).
Pearson et al., Meth. Mol. Biol., 24, 365-389 (1994).
Pinheiro et al., Challenges and opportunities for structural DNA nanotechnology. Nat Nanotechnol 6, 763-772 (2011).
Qi, Xiaodong, et al. "Programming molecular topologies from single-stranded nucleic acids." Nature Communications 9.1 (2018): 1-9.
Radovic-Moreno, Aleksandar F., et al. "Immunomodulatory spherical nucleic acids." Proceedings of the National Academy of Sciences 112.13 (2015): 3892-3897.
Rajendran et al., Programmed two-dimensional self-assembly of multiple DNA origami jigsaw pieces. ACS Nano 5, 665-671 (2011). doi: 10.1021/nnl031627; pmid: 21188996.
Ranjith-Kumar et al., Single-Stranded oligonucleodides can inhibit cytokine production induced by human Toll-like receptor 3. Mol. Cell. Biol. 28, 4507-4519 (2008).
Robinson et al., A Phase I-II trial of multiple-dose polyriboinosic-polyribocytidylic acid in patients with leukemia or solid tumors. J. Natl. Cancer. Inst. 57, 599-602 (1976).
Rodriguez del Villar, R. "The Adjuvant Properties of RNA Origami for Immunotherapy in a CT26 Cancer Model" Masters Thesis, Arizona State University, Aug. 2018, 72 pages.
Rothemund, Folding DNA to create nanoscale shapes and patterns. Nature 440, 297-302 (2006). doi: 10.1038/nature04586; pmid: 16541064.

Rybenkov VV et al. Proc Natl Acad Sci USA. 1993; 90(11): 5307-5311.
Schlee et al., Discriminating self from non-self in nucleic acid sensing. Nat Rev Immunol 16, 566-580, doi:10.1038/nri.2016.78 (2016).
Seeman, De NovoDesign of Sequences for Nucleic Acid Structural Engineering. Journal of Biomolecular Structure and Dynamics 8, 573-581 (1990).
Seeman, Nanomaterials Based on DNA. Annu Rev Biochem 79, 65-87 (2010).
Seeman, The design and engineering of nucleic acid nanoscale assemblies. Curr. Opin. Struct. Biol. 6, 519-526 (1996). doi: 10.1016/S0959-440X(96)80118-7; pmid: 8794156.
Service, DNA Nanotechnology Grows Up. Science 332, 1140-1142 (2011).
Seya et al., Tumor vaccines with dsRNA adjuvant ARNAX induces antigen-specific tumor shrinkage without cytokinemia. Oncoimmunology 5, e1043506, doi: 10.1080/2162402X.2015.1043506 (2016).
Shajani, Z., M. T. Sykes, J. R. Williamson, Assembly of Bacterial Ribosomes. Annual Review of Biochemistry, vol. 80 80, 501-526 (2011).
Shen et al., Paranemic crossover DNA: A generalized Holliday structure with applications in nanotechnology. J. Am. Chem. Soc. 126, 1666-1674 (2004). doi: 10.1021/ja038381e; pmid: 14871096.
Shevtsov M. and Multhoff G. Heat Shock Protein-Peptide and HSP-Based Immunotherapies for the Treatment of Cancer, Apr. 29, 2016;7:171, Frontiers in Immunology.
Shih, et al., A 1.7-kilobase single-stranded DNA that folds into a nanoscale octahedron. Nature 427, 618-621 (2004). doi: 10.1038/nature02307; pmid: 14961116.
Shime et al., Toll-like receptor 3 signaling converts tumor-supporting myeloid cells to tumoricidal effectors. Proc Natl Acad Sci U S A 109, 2066-2071, doi:10.1073/pnas.1113099109 (2012).
Smith et al., Adv. Appl. Math., 2, 482-489 (1981).
Sparvath et al., Computer-aided design of RNA origami structures. Methods Mol. Biol. 1500, 51-80 (2017). doi: 10.1007/978-1-4939-6454-3; pmid: 27813001.
Stangl, Stefan, et al. "Selective In Vivo Imaging of Syngeneic, Spontaneous, and Xenograft Tumors Using a Novel Tumor Cell-Specific Hsp70 Peptide-Based Probe." Cancer Research 74.23 (2014): 6903-6912.
Sun et al., Casting inorganic structures with DNA molds. Science 346, 1258361 (2014). doi: 10.1126/science.1258361; pmid: 25301973.
Takeda et al., A TLR3-Specific Adjuvant Relieves Innate Resistance to PD-L1 Blockade without Cytokine Toxicity in Tumor Vaccine Immunotherapy. Cell Rep 19, 1874-1887, doi:10.1016/j.celrep.2017.05.015 (2017).
Takeda et al., Vaccine immunotherapy with ARNAX induces tumor-specific memory T cells and durable anti-tumor immunity in mouse models. Cancer Sci 109, 2119-2129, doi:10.1111/cas.13649 (2018).
Takusagawa et al., A real knot in protein. J. Am. Chem. Soc. 118, 8945-8946 (1996). doi: 10.1021/ja961147m.
Tatematsu et al., Toll-like receptor 3 recognizes incomplete stem structures in single-stranded viral RNA. Nat Commun 4, 1833, doi:10.1038/ncomms2857 (2013).
Taylor, A deeply knotted protein structure and how it might fold. Nature 406, 916-919 (2000). doi: 10.1038/35022623; pmid: 10972297.
Tikhomirov, et al., Programmable disorder in random DNA tilings. Nat. Nanotechnol. 12, 251-259 (2017). doi: 10.1038/nnano.2016.256; pmid: 27893729.
Van Baal et al., Development of Peritoneal Carcinomatosis in Epithelial Ovarian Cancer: A Review. J Histochem Cytochem 66, 67-83, doi:10.1369/0022155417742897 (2018).
Veneziano et al., Designer nanoscale DNA assemblies programmed from the top down. Science 352, 1534 (2016). doi: 10.1126/science.aaf4388; pmid: 27229143.
Wagner et al., A light sensing knot revealed by the structure of the chromophore binding domain of phytochrome. Nature 438, 325-331 (2005). doi: 10.1038/nature04118; pmid: 16292304.
Wei et al., Complex shapes self-assembled from single-stranded DNA tiles. Nature 485, 623-626, (2012) doi:10.1038/nature11075.

(56) References Cited

OTHER PUBLICATIONS

Wei et al., Mapping the Thermal Behavior of DNA Origami Nanostructures. Journal of the American Chemical Society 135, 6165-6176, doi:10.1021/ja4000728 (2013).

Williams et al., Tiamat: A three-dimensional editing tool for complex DNA structures, in International Workshop on DNA-Based Computers (Springer, 2009), pp. 90-101.

Winfree, et al., Design and self-assembly of two-dimensional DNA crystals. Nature 394,539-544 (1998). doi: 10.1038/28998; pmid: 9707114.

Woo, et al., Programmable molecular recognition based on the geometry of DNA nanostructures. Nat. Chem. 3, 620-627 (2011). doi: 10.1038/nchem.1070; pmid: 21778982.

Zadegen et al., Structural DNA Nanotechnology: From Design to Applications. Int J Mol Sci 13, 7149-7162 (2012).

Zadeh et al., NUPACK: Analysis and Design of Nucleic Acid Systems. J Comput Chem 32, 170-173 (2011).

Zhang et al., Complex wireframe DNA origami nanostructures with multi-arm junction vertices. Nat. Nanotechnol. 10, 779-784 (2015). doi: 10.1038/nnano.2015.162; pmid: 26192207.

Zhang et al., Paranemic cohesion of topologically-closed DNA molecules. J. Am. Chem. Soc. 124, 12940-12941 (2002). doi: 10.1021/ja026973b; pmid: 12405808.

Zhang et al., Structural DNA Nanotechnology: State of the Art and Future Perspective. J Am Chem Soc 136, 11198-11211 (2014).

Zheng et al., From molecular to macroscopic via the rational design of a self-assembled 3D DNA crystal. Nature 461, 74-77 (2009). doi: 10.1038/nature08274; pmid: 19727196.

Zhou et al., TLR3 activation efficiency by high or low molecular mass poly I:C. Innate Immun 19, 184-192, (2012).

Zhu et al., Poly-ICLC promotes the infiltration of effector T cells into intracranial gliomas via induction of CXCL10 in IFN-alpha and IFN-gamma dependent manners. Cancer Immunol Immunother 59, 1401-1409, doi:10.1007/s00262-010-0876-3 (2010).

Zhu, Guizhi, et al. "Intertwining DNA-RNA nanocapsules loaded with tumor neoantigens as synergistic nanovaccines for cancer immunotherapy." Nature Communications 8.1 (2017): 1-13.

\* cited by examiner

Formaldehyde agarose gel

20 X 50nm

FIGURE 9
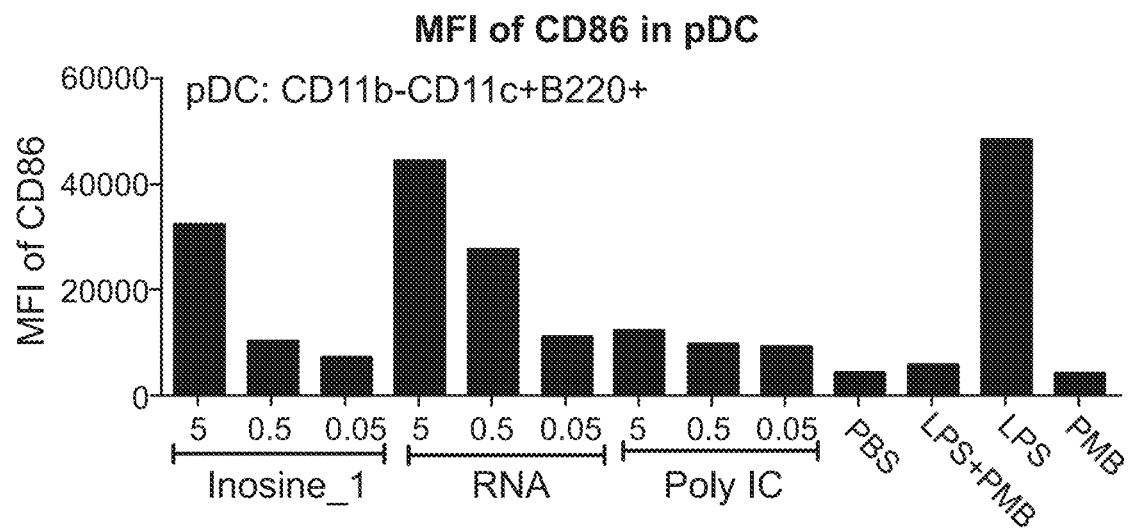
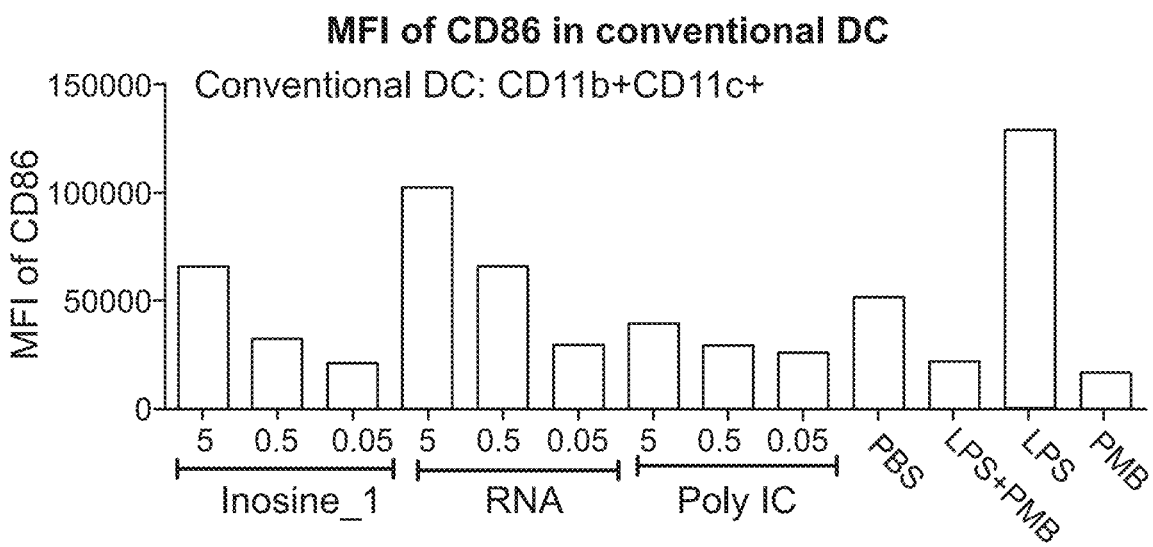

FIGURE 10
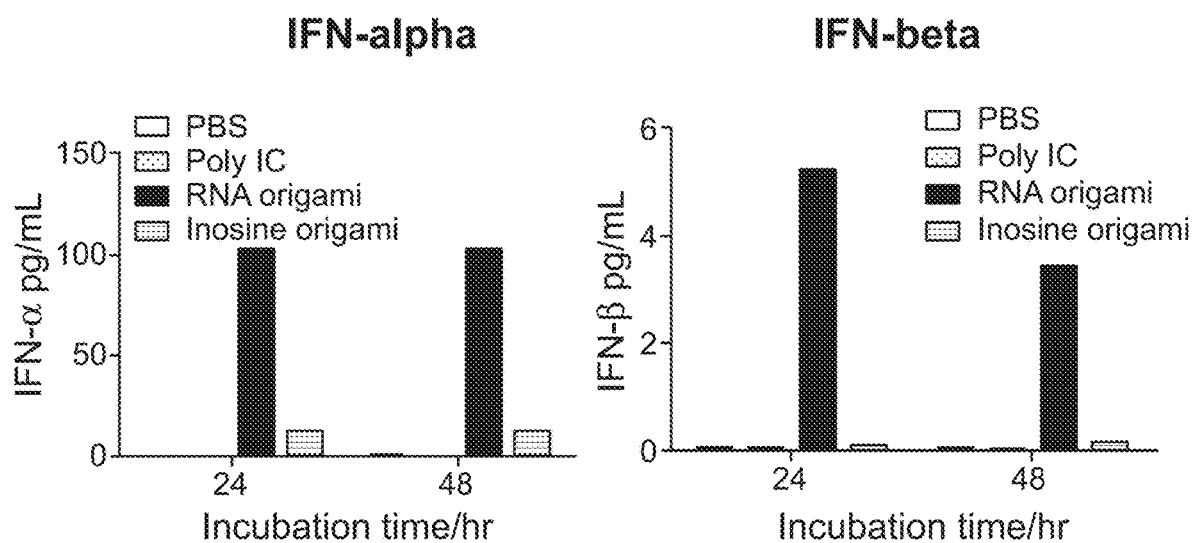
FIGURE 11
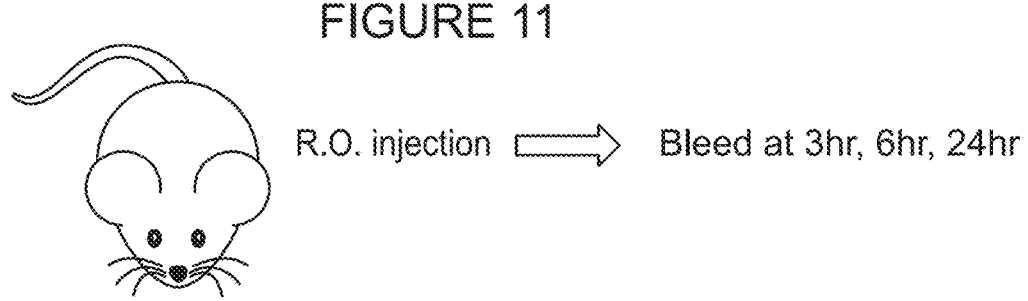
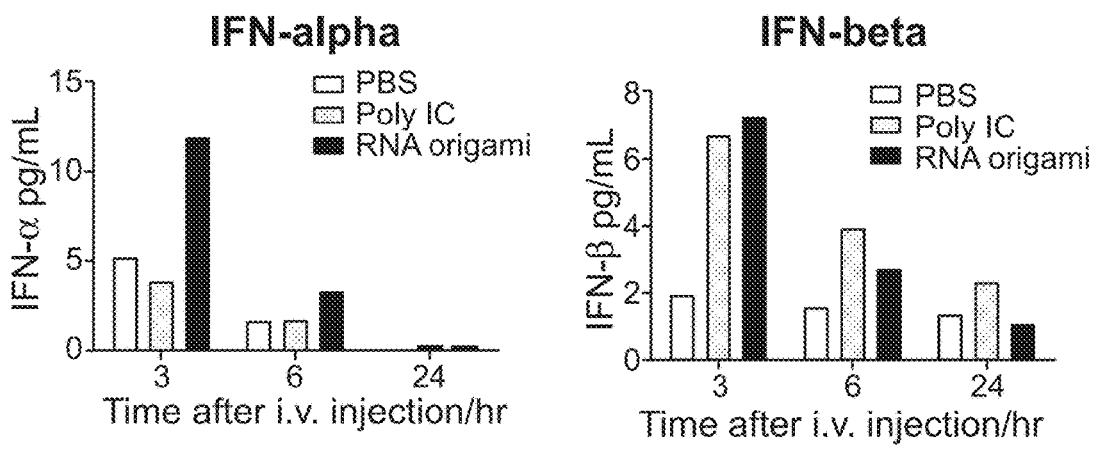

MuLE (Multiple Lentiviral Expression) Destination vector
[Addgene Plasmid #62716]

- Co-expresses iRFP under the control of a PGK promoter

- Tfr-OVA gene along with SV40 promoter replaces ccdb gene in the vector by gateway cloning Increases in tumor-inhibitory cytokines Reduction of immunosuppressive cytokines

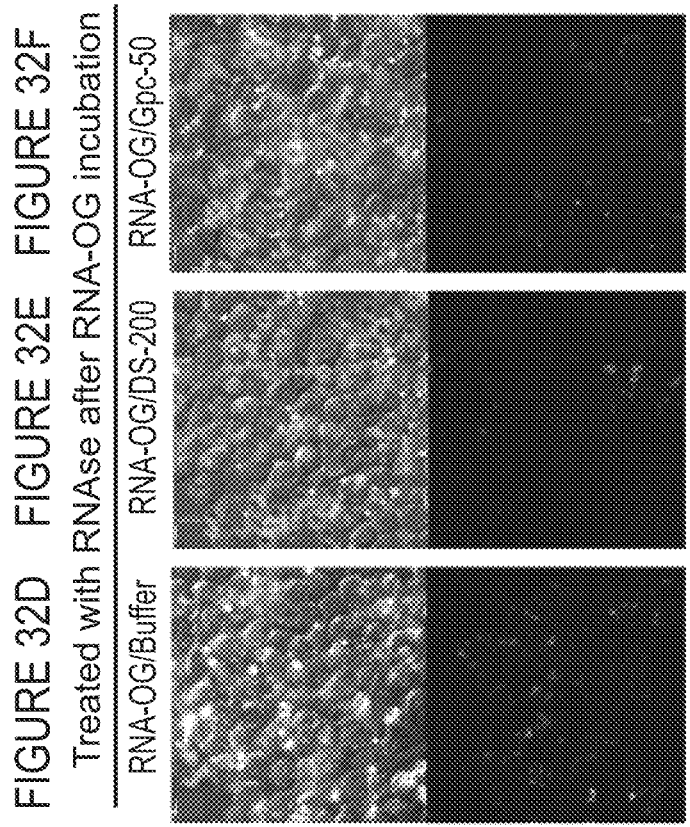
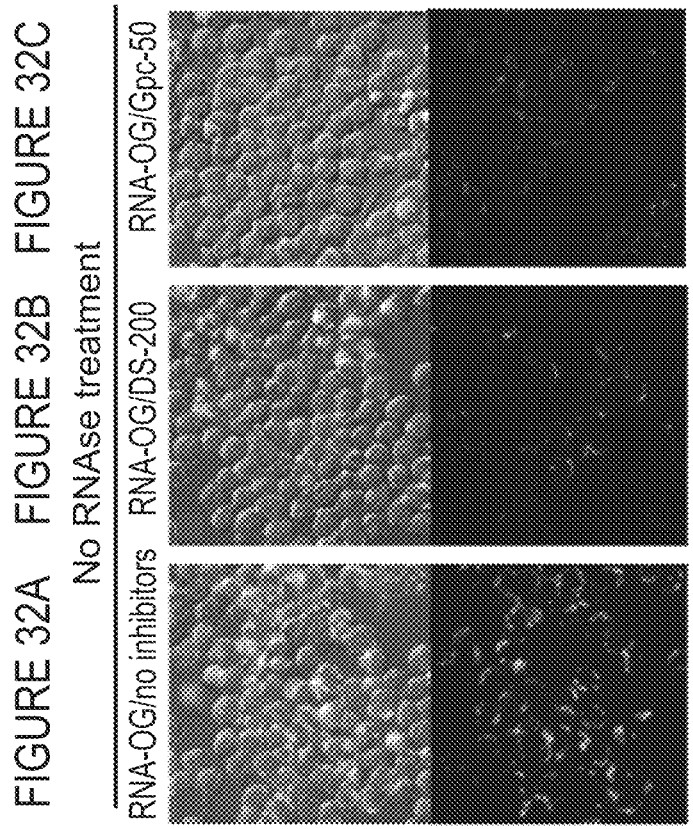
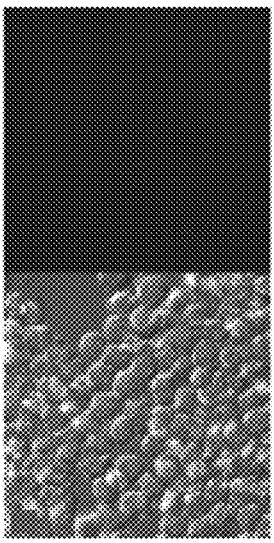
FIGURE 32A  FIGURE 32B  FIGURE 32C  FIGURE 32D  FIGURE 32E  FIGURE 32F  FIGURE 32G

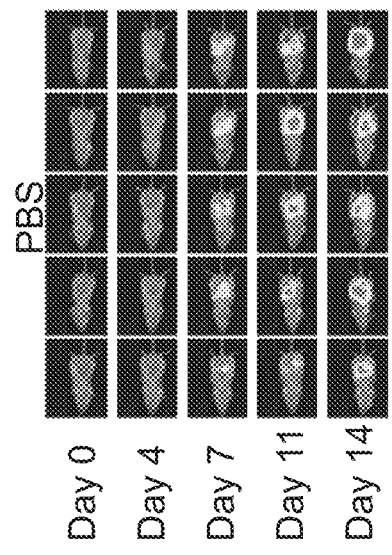
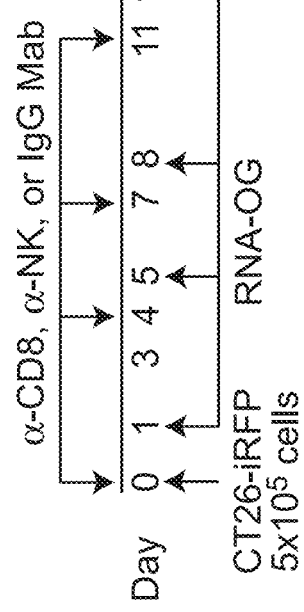
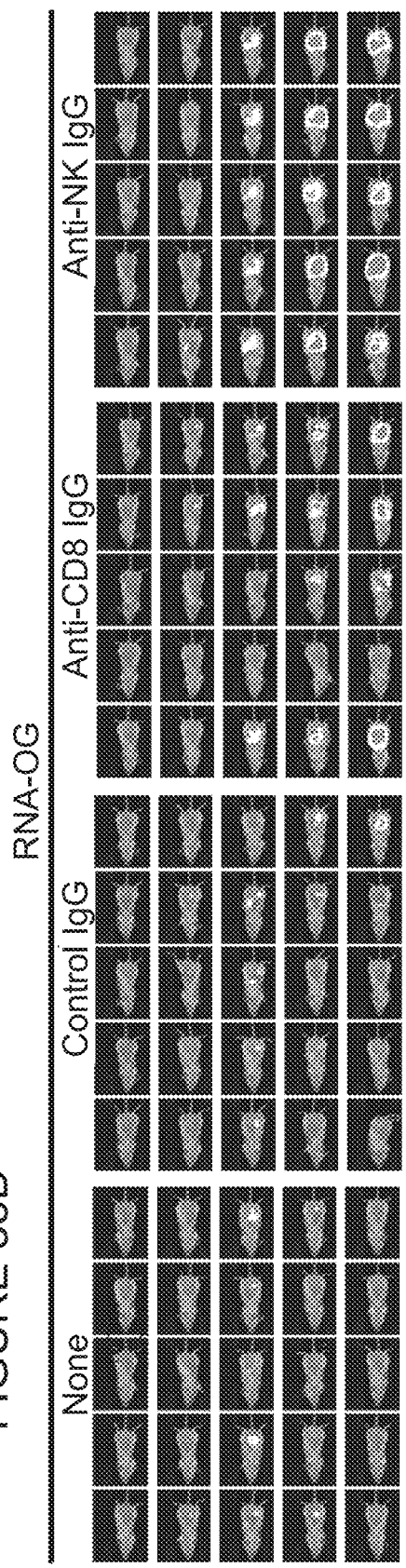

Software can generate sequence base these parameters

We can also manually change the sequence

FIGURE 45
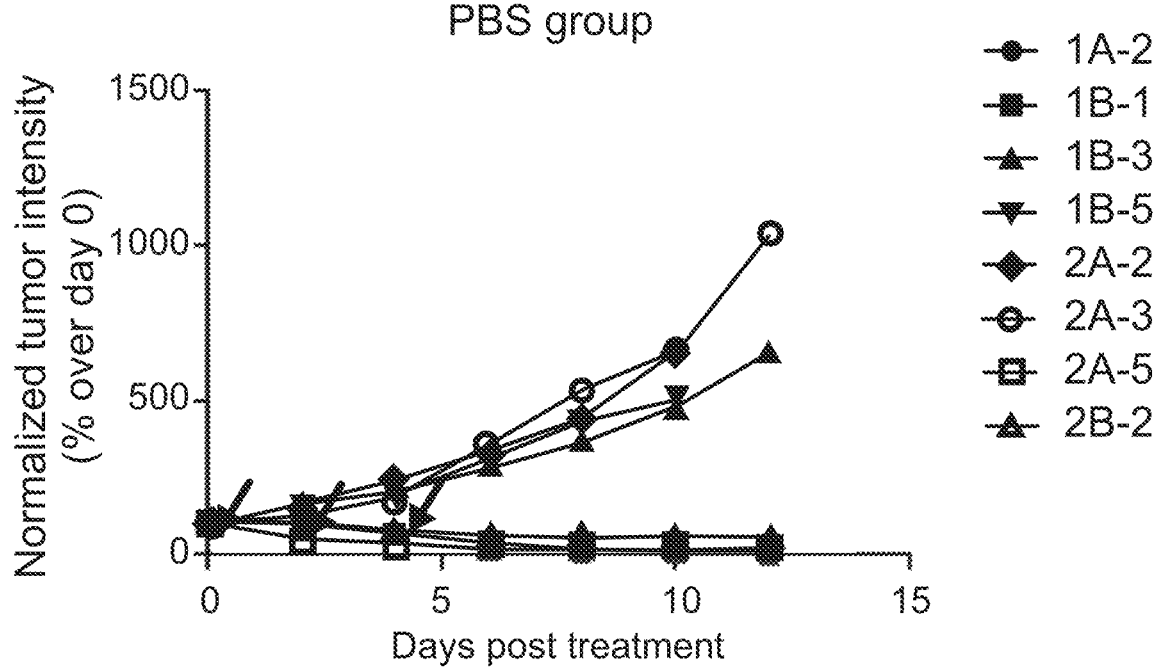
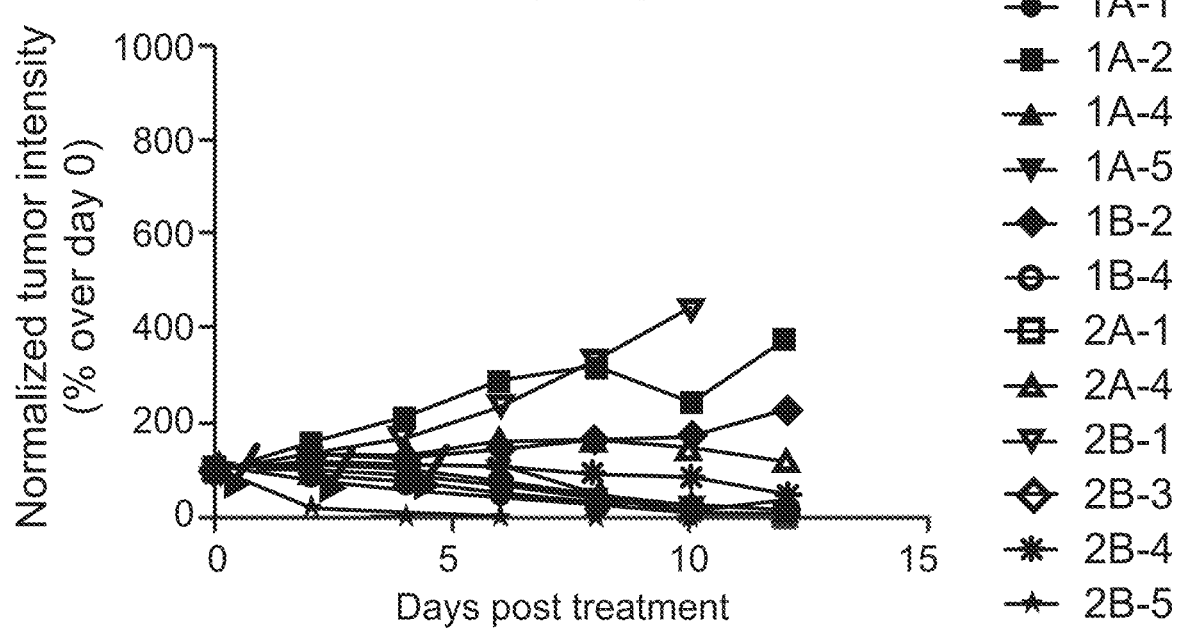

Role of CD8 and NK cells in RNA-OG mediated anti-tumor immunity
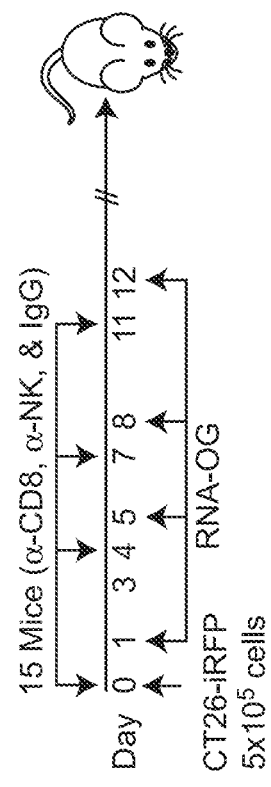
FIGURE 46A
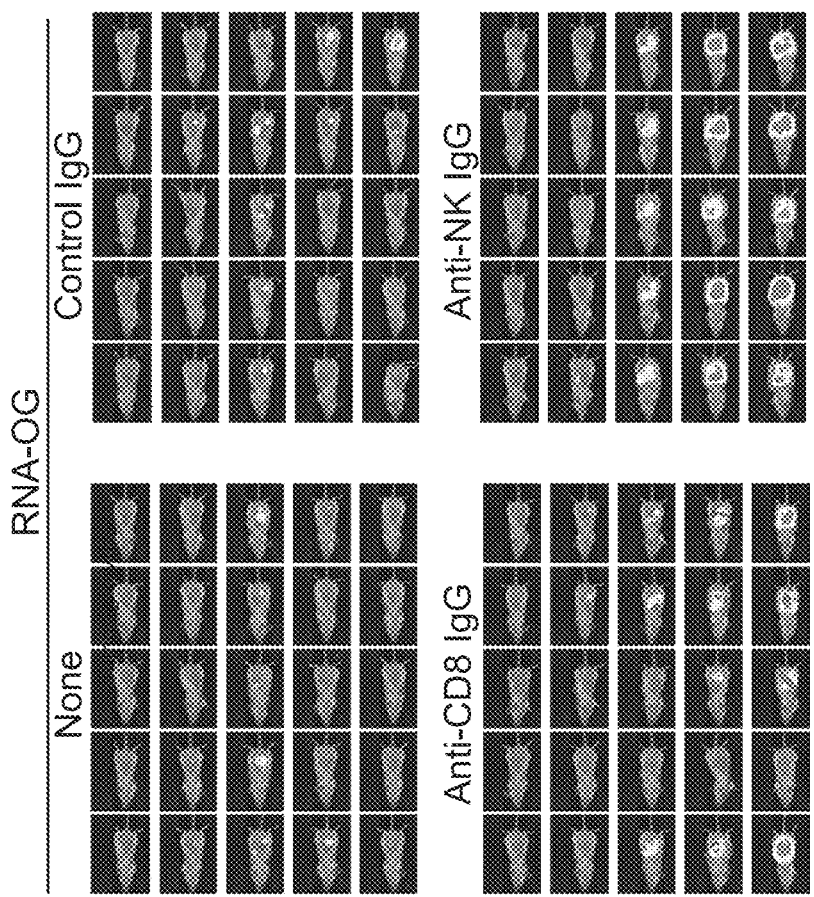
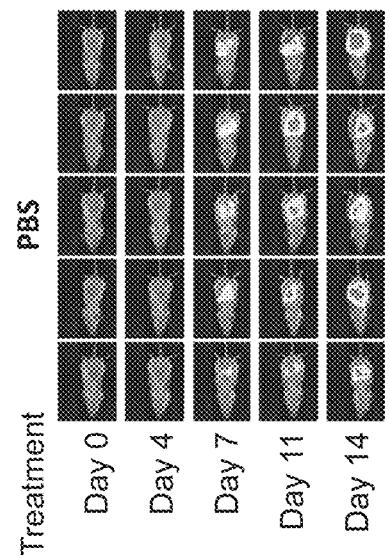
FIGURE 46B

FIGURE 47
Other RNA origamis
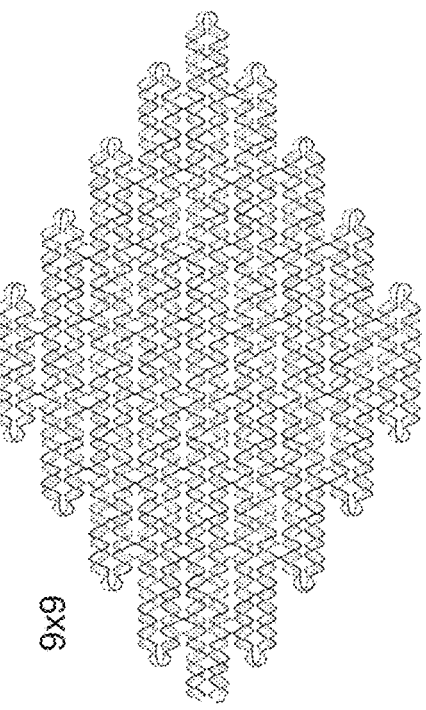
9x9
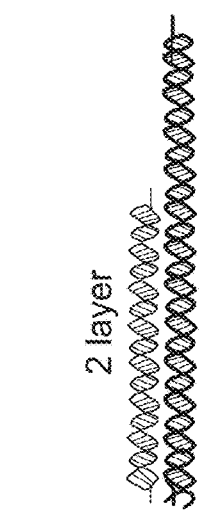
2 layer
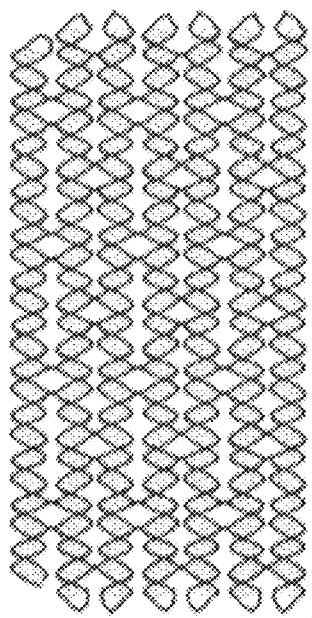
RNA-Rec
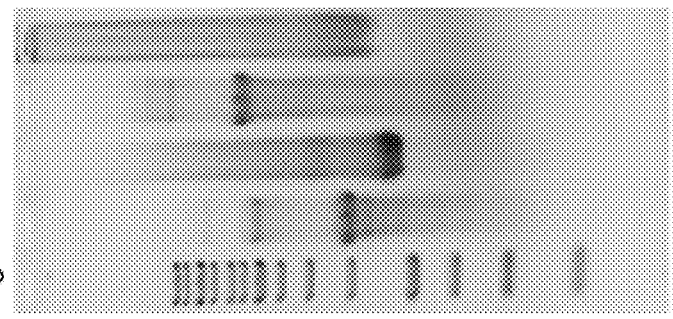

M: 1kb marker
1: RNA origami
2: RNA origami + RNase I  10 min
3: RNA origami + RNase I  30 min
4: Poly IC LMW
5: Poly IC LMW + RNase I  10 min
6: Poly IC LMW + RNase I  30 min
7: Poly IC HMW
8: Poly IC HMW + RNase I  10 min
9: Poly IC HMW + RNase I  30 min 1ug of RNA incubate with 1U of RNase I at room temperature for 10 or 30 min.

FIGURE 63
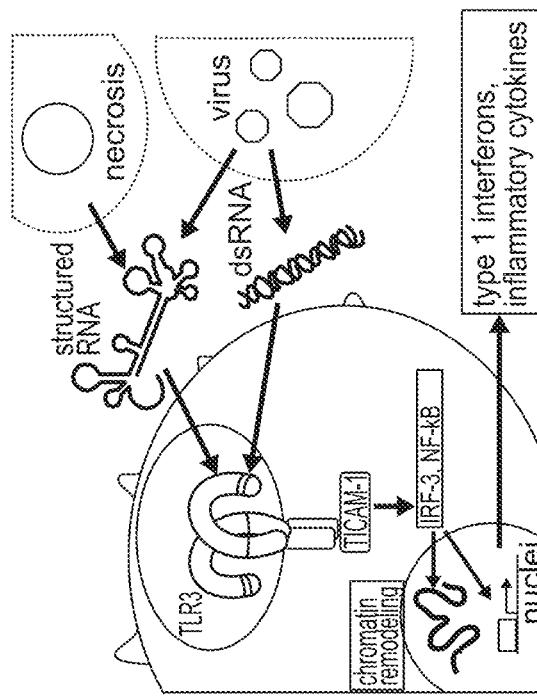
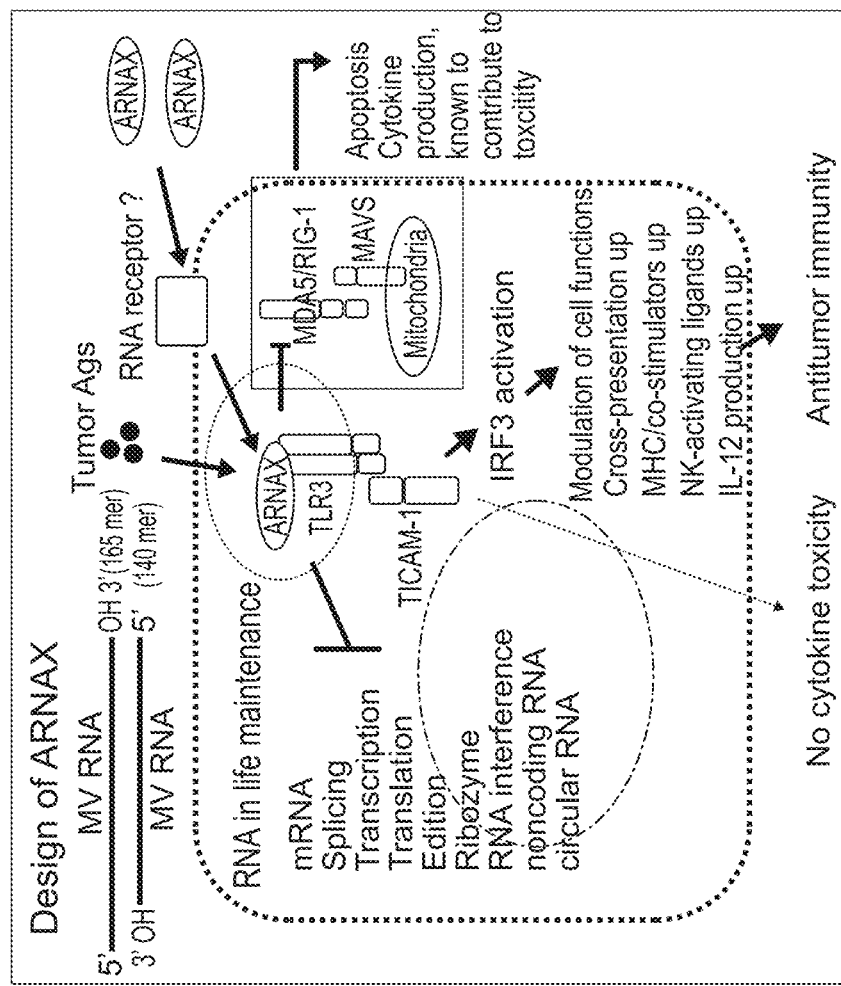

*3hrs post adjuvant injection (i.p.)*

- As compared to polyIC-H, RNA OG induces a high level of chemokines (CXCL10), but very low level of IFNα/β
- RNA OG may be a safer adjuvant, making it possible to be utilized systemically (unlike polyIC that is currently tested only locally in clinical trials, due to its high toxicity in human)

RNA:TTP

SEQUENCE LISTING

<160> NUMBER OF SEQ ID NOS: 22

<210> SEQ ID NO 1
<211> LENGTH: 2002
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| gggagagagc | ucgagcgaac | acuagccacu | ugaucacgcu | gagcgcucgu | acaaugaaac | 60 |
| acaggugugu | cagugcuaug | cacguucgaa | gagcuguauc | agcguucgug | ugaaugaguu | 120 |
| caacggagug | uugacuaagc | cgguugcuac | auuucuguag | cacacauagu | caagauuugc | 180 |
| accagacgau | acucucccuc | aguccuguuu | augcaagucg | ucuaguccu | gacguacuuc | 240 |
| cuaagcucgu | cacguacug | augauuccac | ugaucaagau | gcacguaucu | ucaguuuccu | 300 |
| gaagaucgga | guaggcacua | uaaucgacaa | guaacgcuua | cgauuccauc | acgagugacu | 360 |
| uaccugaacc | auaacugaca | agggaccacg | cagaggucau | acucacagga | cuucaaaucu | 420 |
| ugagucgggu | ucgaucauuu | cugaucgaga | caccagugug | agguaaucgu | acgucacuug | 480 |
| auaggagcuc | uaaguagagu | ugagagccug | uuaacuagac | acgaguaacg | agguuagccu | 540 |
| guacgagaua | ucgggcuaua | gugcggacac | gauugcacca | uuucggugc | aacgaaggug | 600 |
| agcauguaug | gacaggucag | ugugacucaa | gucgauaguc | caaguagguu | aucgacucgc | 660 |
| auagcucaau | gacugucauc | gccagaguau | cuaggugucu | accucacgaa | ucgcgucguu | 720 |
| acauuucugu | aacgcucaua | ccgugcgau | cuaugggaca | cgucgcuuau | ucuuggguca | 780 |
| ugacaguugc | cacaaacaag | gcacgaccuc | acaccugcga | acuucaagcg | uuaggcugac | 840 |
| guuacaugcu | ugcgugcacu | gauucguuuc | cgaaucagag | accuacgaag | ccagaguucg | 900 |
| uucacuauca | uaagugcacu | gaugcauuug | ugccaacauu | gaaggcaucg | agauaaacag | 960 |
| ccgucuuaau | caagugagca | ccugagauca | gcaugauucg | ucuauuucua | gacgaaucaa | 1020 |
| cuuccauuca | ggugccuugc | uacuuaagac | gggauuaacu | cucgaugcaa | cgugcauugg | 1080 |
| cacaacucgu | gaugugcacu | uucacacugg | aacgaacucu | ggcuucguag | gucuguuugu | 1140 |
| cauuucgac | aaacugcacg | cacuguuagu | acgucagcca | cuuaaccgaa | guucgucaua | 1200 |
| aguaggucgu | gcgacuacga | uggcaacuuc | uacuuaccaa | gaauaagcga | cgugucccau | 1260 |
| aauggaaguc | gguaugaggu | augacuuucg | ucauacacgc | gauuccacaa | ugugacaccu | 1320 |
| aacguuugag | gcgaugaccu | gauacaagcu | augcaugguu | caaaccuacu | uggacuaucg | 1380 |
| acuugagaug | auaguaccug | uccaacuaac | agcaccuucg | auaccucguu | uccgagguau | 1440 |
| ucguguccug | ugucaggccc | gauauuaaug | ugguggcuaac | ccuuaggaac | gugucuaguu | 1500 |
| aacaggcucu | caacgucaug | acgagcuccu | aguagcaagc | guacgauaca | uugugacugg | 1560 |
| ugucuacugg | auuucuccag | uaacccgacu | ccgacuacaa | agccugacu | cauucaccuc | 1620 |
| ugcgguguccc | cuugucaguu | gagucgaugg | uaagucaaug | caucaggaau | cguggguuaag | 1680 |
| ucuugucgau | cugacacacu | acuccgcugu | ccuguuucca | ggacagacgu | gcauuagcag | 1740 |
| uuguggaauc | aucaguacag | ugacgagucg | uuacuguacg | ucagcuuguu | ugcgacuugc | 1800 |
| aguuaaucga | cugagggguca | aacgugucug | guguguaguc | ggacuaugug | acguucauuu | 1860 |
| cugaacguac | cggcuuagc | aacacuccgu | ugaugaguau | gacacgaacg | agucauuggc | 1920 |
| ucuucgcuuc | aaugguagcac | ugaacuuaug | auguucaua | cacauuacgc | ucagcgaacu | 1980 | gcuauggcua guguucggau cc 2002

<210> SEQ ID NO 2
<211> LENGTH: 2002
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 2

| gggagagagc tcgagcgaac actagccact tgatcacgct gagcgctcgt acaatgaaac | 60 |
|---|---|
| acaggtgtgt cagtgctatg cacgttcgaa gagctgtatc agcgttcgtg tgaatgagtt | 120 |
| caacggagtg ttgactaagc cggttgctac atttctgtag cacacatagt caagatttgc | 180 |
| accagacgat actctccctc agtcctgttt atgcaagtcg tcgtagtcct gacgtacttc | 240 |
| ctaagctcgt cactgtactg atgattccac tgatcaagat gcacgtatct tcagtttcct | 300 |
| gaagatcgga gtaggcacta taatcgacaa gtaacgctta cgattccatc acgagtgact | 360 |
| tacctgaacc ataactgaca agggaccacg cagaggtcat actcacagga cttcaaatct | 420 |
| tgagtcgggt tcgatcattt ctgatcgaga caccagtgtg aggtaatcgt acgtcacttg | 480 |
| ataggagctc taagtagagt tgagagcctg ttaactagac acgagtaacg aggttagcct | 540 |
| gtacgagata tcgggctata gtgcggacac gattgcacca tttctggtgc aacgaaggtg | 600 |
| agcatgtatg gacaggtcag tgtgactcaa gtcgatagtc caagtaggtt atcgactcgc | 660 |
| atagctcaat gactgtcatc gccagagtat ctaggtgtct acctcacgaa tcgcgtcgtt | 720 |
| acatttctgt aacgctcata ccgtgctgat ctatgggaca cgtcgcttat tcttgggtca | 780 |
| tgacagttgc cacaaacaag gcacgacctc acacctgcga acttcaagcg ttaggctgac | 840 |
| gttacatgct tgcgtgcact gattcgtttc cgaatcagag acctacgaag ccagagttcg | 900 |
| ttcactatca taagtgcact gatgcatttg tgccaacatt gaaggcatcg agataaacag | 960 |
| ccgtcttaat caagtgagca cctgagatca gcatgattcg tctatttcta gacgaatcaa | 1020 |
| cttccattca ggtgccttgc tacttaagac gggattaact ctcgatgcaa cgtgcattgg | 1080 |
| cacaactcgt gatgtgcact ttcacactgg aacgaactct ggcttcgtag gtctgtttgt | 1140 |
| catttctgac aaactgcacg cactgttagt acgtcagcca cttaaccgaa gttcgtcata | 1200 |
| agtaggtcgt gcgactacga tggcaacttc tacttaccaa gaataagcga cgtgtcccat | 1260 |
| aatggaagtc ggtatgaggt atgactttcg tcatacacgc gattccacaa tgtgacacct | 1320 |
| aacgtttgag gcgatgacct gatacaagct atgcatggtt caaacctact tggactatcg | 1380 |
| acttgagatg atagtacctg tccaactaac agcaccttcg atacctcgtt tccgaggtat | 1440 |
| tcgtgtcctg tgtcaggccc gatattaatg tgtggctaac ccttaggaac gtgtctagtt | 1500 |
| aacaggctct caacgtcatg acgagctcct agtagcaagc gtacgataca ttgtgactgg | 1560 |
| tgtctactgg atttctccag taacccgact ccgactacaa agtcctgact cattcacctc | 1620 |
| tgcgtggtcc cttgtcagtt gagtcgatgg taagtcaatg catcaggaat cgtggttaag | 1680 |
| tcttgtcgat ctgacacact actccgctgt cctgtttcca ggacagacgt gcattagcag | 1740 |
| ttgtggaatc atcagtacag tgacgagtcg ttactgtacg tcagcttgtt tgcgacttgc | 1800 |
| agttaatcga ctgagggtca aacgtgtctg gtgtgtagtc ggactatgtg acgttcattt | 1860 |
| ctgaacgtac cggcttagtc aacactccgt tgatgagtat gacacgaacg agtcattggc | 1920 |
| tcttcgcttc aatgtagcac tgaacttatg atgtttcata cacattacgc tcagcgaact | 1980 |

| | |
|---|---:|
| gctatggcta gtgttcggat cc | 2002 |

<210> SEQ ID NO 3
<211> LENGTH: 2035
<212> TYPE: RNA
<213> ORGANISM: Artificial Sequence
<220> FEATURE:
<223> OTHER INFORMATION: Description of Artificial Sequence: Synthetic
     polynucleotide

<400> SEQUENCE: 3

| | |
|---|---:|
| gggagaggau ccgaacacua gccauagcag uucgcugagc guaaugugua ugaaacauca | 60 |
| uaaguucagu gcuacauuga agcgaagagc caaugacucg uucgugucau acucaucaac | 120 |
| ggaguguuga cuaagccggu acguucaggg agggugaacg ucacauaguc cgacuacaca | 180 |
| ccagacacgu uugaccccuca gucgauuaac ugcaagucgc aaacaagcug acguacagua | 240 |
| acgacucguc acguacuga ugauuccaca acugcuaaug cacgucuguc cuggggaggg | 300 |
| caggacagcg gaguagugug ucagaucgac aagacuuaac cacgauuccu gaugcauuga | 360 |
| cuuaccaucg acucaacuga caagggacca cgcagaggug aaugagucag gacuuuguag | 420 |
| ucggagucgg guuacuggag ggagggucca guagacacca gucacaaugu aucguacgcu | 480 |
| ugcuacuagg agcucgucau gacguugaga gccuguuaac uagacacguu ccuaaggguu | 540 |
| agccacacau uaauaucggg ccugacacag gacacgaaua ccucggggag ggcgagguau | 600 |
| cgaaggugcu guuaguugga cagguacuau caucucaagu cgauaguccca aguagguuug | 660 |
| aaccaugcau agcuuguauc aggucaucgc cucaaacguu aggugucaca uuguggaauc | 720 |
| gcguguauga cgggaggggu cauaccucau accgacuucc auuaugggac acgucgcuua | 780 |
| uucuugguaa guagaaguug ccaucguagu cgcacgaccu acuuaugacg aacuucgguu | 840 |
| aaguggcuga cguacuaaca gugcgugcag uuugucaggg agggugacaa acagaccuac | 900 |
| gaagccagag uucguuccag ugugaaagug cacaucacga guugugccaa ugcacguugc | 960 |
| aucgagaguu aaucccgucu uaaguagcaa ggcaccugaa uggaaguuga uucgucuaga | 1020 |
| aauagacgaa ucaugcugau cucaggugcu cacuugauua agacggcugu uuaucucgau | 1080 |
| gccuucaaug uuggcacaaa ugcaucagug cacuuaugau agugaacgaa cucuggcuuc | 1140 |
| guaggucucu gauucgggga gggcgaauca gugcacgcaa gcauguaacg ucagccuaac | 1200 |
| gcuugaaguu cgcaggugug aggucgugcc uguuugugg caacgucau gacccaagaa | 1260 |
| uaagcgacgu gucccauaga ucagcacggu augagcguua cagggagggu guaacgacgc | 1320 |
| gauucgugag guagacaccu agauacucug gcgaugacag ucauugagcu augcgagucg | 1380 |
| auaaccuacu uggacuaucg acuugaguca cacgaccug uccauacaug cucaccuucg | 1440 |
| uugcaccagg gagguggug caaucguguc cgcacuauag cccgauaucu cguacaggcu | 1500 |
| aaccucguua cucgugucua guuaacaggc ucucaacucu acuuagagcu ccuaucaagu | 1560 |
| gacguacgau uaccucacac uggugucucg aucaggagg gugaucgaac ccgacucaag | 1620 |
| auuugaaguc cugugaguau gaccucugcg uggucccuug ucaguuaugg uucagguaag | 1680 |
| ucacucguga uggaaucgua agcguuacuu gucgauuaua gugccuacuc cgaucuucag | 1740 |
| gggagggcug aagaucgug caucuugauc aguggaauca ucaguacagu gacgagcuua | 1800 |
| ggaaguacgu caggacuacg acgacuugca uaaacaggac ugagggagag uaucgucugg | 1860 |
| ugcaaaucuu gacauugugu gcuacaggga ggguguagca accggcuuag ucaacacucc | 1920 |
| guugaacuca uucacacgaa cgcugauaca gcucuucgaa cgugcauagc acugacacac | 1980 |

```
cuguguuuca uuguacgagc gcucagcgug aucaaguggc uaguguucgc ucgag          2035
```

<210> SEQ ID NO 4
<211> LENGTH: 2038
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4

```
gggagagagc ucgagcgaac acuagccacu ugaucacgcu gagcgcucgu acaaugaaac       60
acaggugugu cagugcuaug cacguucgaa gagcuguauc agcguucgug ugaaugaguu      120
caacggagug uugacuaagc cgguugcuac acccuccug uagcacacau agucaagauu       180
ugcaccagac gauacucucc cucagcccug uuuaugcaag ucgucguagu ccugacguac      240
uccuaagcu cgucacugua cugaugauuc cacugaucaa gaugcacgua ucuucagccc       300
uccccgaag aucggaguag gcacuauaau cgacaaguaa cgcuuacgau uccaucacga       360
gugacuuacc ugaaccauaa cugacaaggg accacgcaga ggucauacuc acaggacuuc      420
aaaucuugag ucgggucga ucaccccccc ugaucgagac accaguguga gguaaucgua      480
cgucacuuga uaggagcucu aaguagaguu gagagccugu aacuagaca cgaguaacga      540
gguuagccug uacgagauau cgggcuauag ugcggacacg auugcaccac ccucccgggu    600
gcaacgaagg ugagcaugua uggacagguc agugugacuc aagucgauag uccaaguagg     660
uuaucgacuc gcauagcuca augacugucu cgccagagu aucuagguguc uaccucacg      720
aaucgcgucg uuacacccuc ccguaacgc ucauaccgug cugaucuaug ggacacgucg      780
cuuauucuug ggucaugaca guugccacaa acaaggcacg accucacacc ugcgaacuuc     840
aagcguuagg cugacguuac augcuugcgu gcacugauuc gcccucccg aaucagagac      900
cuacgaagcc agaguucguu cacuaucaua agugcacuga ugcauuugug ccaacauuga     960
aggcaucgag auaaacagcc gucuuaauca agugagcacc ugagaucagc augauucguc     1020
uauuucuaga cgaaucaacu uccauucagg ugccuugcua cuuaagacgg gauuaacucu    1080
cgaugcaacg ugcauuggca caacucguga ugugcacuuu cacacuggaa cgaacucugg    1140
cuucguaggu cuguuuguca cccucccuga caaacugcac gcacuguuag uacgucagcc    1200
acuuaaccga aguucgucau aaguaggucg ugcgacuacg auggcaacuu cuacuuacca    1260
agaauaagcg acgugucccca uauggaagu cgguaggagg uaugaccccu cccgucauac    1320
acgcgauucc acaaugugac accuaacguu ugaggcgaug accugauaca agcuaugcau    1380
gguucaaacc uacuuggacu aucgacuuga gaugauagua ccugccaac uaacagcacc     1440
uucgauaccu cgcccucccc gagguauucg ugucccugugu caggcccgau auuaaugugu    1500
ggcuaacccu uaggaacgug ucuaguuaac aggcucucaa cgucaugacg agcuccuagu    1560
agcaagcgua cgaucauug ugacggugu cuacuggacc cucccuccag uacccgacu        1620
ccgacuacaa aguccugacu cauucaccuc ugcgugguccc cuugucaguu gagucgaugg    1680
uaagucaaug caucaggaau cgugguuaag ucugucgau cugacacacu acuccgcugu     1740
ccugcccucc ccaggacaga cgucauuag cagugugga aucaucagua cagugacgag     1800
ucguuacugu acgucagcuu guuugcgacu ugcaguuaau cgacgagggu caaacgugu     1860
cuggugugua gucggacuau ugacgcuuca cccuccccuga acguaccggc uuagucaaca     1920
cuccguugau gaguaugaca cgaacgaguc auuggcucuu cgcuucaaug uagcacugaa    1980
```
cuuaugaugu ucauacaca uuacgcucag cgaacugcua uggcuagugu ucggaucc        2038

<210> SEQ ID NO 5
<211> LENGTH: 2035
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
gggagaggau ccgaacacua gccauagcag uucgcugagc guaaugugua ugaaacauca      60
uaaguucagu gcuacauuga agcgaagagc caaugacucg uucgugucau acucaucaac     120
ggaguguuga cuaagccggu acguucaaaa gaaaugaacg ucacauaguc cgacuacaca     180
ccagacacgu uugacccuca gucgauuaac ugcaagucgc aaacaagcug acguacagua     240
acgacucguc acguacuga ugauuccaca acugcuaaug cacgucuguc cugaaagaaa      300
caggacagcg gaguagugug ucagaucgac aagacuuaac cacgauuccu gaugcauuga     360
cuuaccaucg acucaacuga caagggacca cgcagaggug aaugagucag gacuuuguag     420
ucggagucgg guuacuggaa aagaaaaucca guagacacca gucacaaugu aucguacgcu     480
ugcuacuagg agcucgucau gacguugaga gccuguuaac uagacacguu ccuaaggguu     540
agccacacau uaauaucggg ccugacacag gacacgaaua ccucgaaaga acgagguau      600
cgaaggugcu guuaguugga cagguacuau caucucaagu cgauaguecca aguagguuug     660
aaccaugcau agcuuguauc aggucaucgc cucaaacguu aggugucaca uguggaauc      720
gcguguauga caaagaaagu cauaccucau accgacuucc auuaugggac acgucgcuua     780
uucuuggauaa guagaaguug ccaucguagu cgcacgaccu acuuaugacg aacuucgguu     840
aaguggcuga cguacuaaca gugcgugcag uuugucaaaa gaaaugacaa acagaccuac     900
gaagccagag uucguuccag ugugaaagug cacaucacga guugugccaa ugcacguugc     960
aucgagaguu aaucccgucu uaaguagcaa ggcaccugaa uggaaguuga uucgucuaga    1020
aauagacgaa ucaugcugau cucaggugcu cacuugauua agacggcugu uuaucucgau    1080
gccuucaaug uuggcacaaa ugcaucagug cacuuaugau agugaacgaa cucuggcuuc    1140
guaggucucu gauucgaaag aaacgaauca gugcacgcaa gcauguaacg ucagccuaac    1200
gcuugaaguu cgcaggugug aggucugucc uguuugugg caacgucau gacccaagaa      1260
uaagcgacgu gucccauaga ucagcacggu augagcguua caaagaaau guaacgacgc    1320
gauucgugag guagacaccu agauacucug gcgaugacag ucauugagcu augcgagucg    1380
auaaccuacu uggacuaucg acuugaguca cacgaccug ucauacaug cucaccuucg      1440
uugcaccaaa agaaaugguu caaucguguc cgcacuauag cccgauaucu cguacaggcu    1500
aaccucguua cucgugucua guuaacaggc ucucaacucu acuuagagcu ccuaucaagu    1560
gacguacgau uaccucacac ugguguucg aucaaaagaa augaucgaac ccgacucaag      1620
auuugaaguc cugugaguau gaccucugcg ugguccccuug ucaguuaugg uucagguaag    1680
ucacucguga uggaaucgua agcguuacuu gucgauuaua gugccuacuc cgaucuucag    1740
aaagaaacug aagaucgugu caucuugauc aguggaauca ucaguacagu gacgagcuua    1800
ggaaguacgu caggacuacg acgacuugca uaaacaggac ugagggagag uaucgucugg    1860
ugcaaaucuu gacuauguu gcuacaaaag aaauguagca accggcuuag ucaacacucc     1920
guugaacuca uucacacgaa cgcugauaca gcucuucgaa cgugcauagc acugacacac    1980

```
                                      -continued
cuguguuuca uuguacgagc gcucagcgug aucaaguggc uaguguucgc ucgag         2035

<210> SEQ ID NO 6
<211> LENGTH: 2038
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
gggagagagc ucgagcgaac acuagccacu ugaucacgcu gagcgcucgu acaaugaaac      60
acaggugugu cagugcuaug cacguucgaa gagcuguauc agcguucgug ugaaugaguu     120
caacggagug uugacuaagc cgguugcuac auuucuuuug uagcacacau agucaagauu     180
ugcaccagac gauacucucc cucagcccug uuuaugcaag ucgucguagu ccugacguac     240
uuccuaagcu cgucacugua cugaugauuc cacugaucaa gaugcacgua ucuucaguuu     300
cuuucugaag aucggaguag gcacuauaau cgacaaguaa cgcuuacgau uccaucacga     360
gugacuuacc ugaaccauaa cugacaaggg accacgcaga ggucauacuc acaggacuuc     420
aaaucuugag ucgggaucga ucauuucuuu ugaucgagac accaguguga gguaaucgua     480
cgucacuuga uaggagcucu aaguagaguu gagagccugu aacuagaca cgaguaacga      540 gguuagccug uacgagauau cgggcuauag ugcggacacg auugcaccau ucuuuuggu      600 gcaacgaagg ugagcaugua uggacagguc agugugacuc aagucgauag uccaaguagg     660
uuaucgacuc gcauagcuca augacuguca ucgccagagu aucuaggugu cuacccacg      720 aaucgcgucg uuacauuucu uuuguaacgc ucauaccgug cugaucuaug ggacacgucg     780
cuuauucuug ggucaugaca guugccacaa acaaggcacg accucacacc ugcgaacuuc     840
aagcguuagg cugacguuac augcuugcgu gcacugauuc guuucuuucg aaucagagac     900
cuacgaagcc agaguucguu cacuaucaua agugcacuga ugcauuugug ccaacauuga     960
aggcaucgag auaaacagcc gucuuaauca agugagcacc ugagaucagc augauucguc    1020
uauuucuaga cgaaucaacu uccauucagg ugccuugcua cuuaagacgg gauuaacucu    1080
cgaugcaacg ugcauuggca caacucguga ugugcacuuu cacacuggaa cgaacucugg    1140
cuucguaggu cuguuuguca uuucuuuuga caaacugcac gcacuguuag uacgucagcc    1200
acuuaaccga aguucgucau aaguaggucg ugcgacuacg auggcaacuu cuacuuacca    1260
agaauaagcg acgugucccca uauggaagu cgguagagg uaugacuuuc uuugucauac     1320
acgcgauucc acaaugugac accuaacguu ugaggcgaug accugauaca agcuaugcau    1380
gguucaaacc uacuuggacu aucgacuuga gaugauagua ccugccaac uaacagcacc     1440 uucgauaccu cguucuuuc gagguauucg uguccugugu caggcccgau auuaaugugu    1500
ggcuaacccu uaggaacgug ucuaguuaac aggcucucaa cgucaugacg agcuccuagu    1560
agcaagcgua cgaucauug ugacgguggu cuacuggauu ucuuuccag uaacccgacu      1620 ccgacuacaa aguccugacu cauucaccuc ugcgugguccc uugucaguu gagucgaugg    1680 uaagucaaug caucaggaau cgugguuaag ucugucgau cugacacacu acuccgcugu     1740
ccuguuucuu ucaggacaga cgugcauuag cagugugga aucaucagua cagugacgag    1800
ucguuacugu acgucagcuu guuugcgacu ugcaguuaau cgacgagggu caaacgugu     1860 cuggugugua gucggacuau gugacguuca uuucuuuuga acguaccggc uuagucaaca    1920
cuccguugau gaguaugaca cgaacgaguc auuggcucuu cgcuucaaug uagcacugaa    1980
```

| | |
|---|---|
| cuuaugaugu uucauacaca uuacgcucag cgaacugcua uggcuagugu ucggaucc | 2038 |

<210> SEQ ID NO 7
<211> LENGTH: 2310
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7

| | |
|---|---|
| gggagagagc ucgagcgaac acuagccacu ugaucacucg ugcuucucgu acauggaagc | 60 |
| ccaggugugg agauaagguc uuagguuuuc cuaagaugag cguuaacgu gcaucuugac | 120 |
| ucugauacaa uuccauagac ucauucaugu cgcauaccuc uguuucaga gguaaccacg | 180 |
| gguguagucg acugcguagu caaacgucga ucuacagcua aucgaggcuu ucuccaucgu | 240 |
| uuucgaugga augauucggc aaacuaggac acgagaguaa cgaaggaaug uacaaucgac | 300 |
| ucgacauuca accagcuuuu gcugguugga ucgucgugu caggcguug uccacuuaac | 360 |
| caguagaccc uaaacaguca cugacgacua ugcuuuugca uaguuaugu acaaugcauc | 420 |
| auguacgagg agucgaugcc auauagagag uaugcacgug agagacgaac uuuuguucgu | 480 |
| cuugacuuac uaccucacua ugcuagauca agugaucggg auucauaag uguuaagggc | 540 |
| aucgcuauuu uuagcgaucg caagugguc ugaucacgac cauauagaag ucauggaaac | 600 |
| ugaucaagua gauggugugg cuuguuuuca agccacuugc guaugucaug acaaagccuu | 660 |
| aguagcaaga ugggacuugc acguucucau uggcgcauag guuuccuau gcuucaggag | 720 |
| uuacaugcug uaccucaaug guucauccau gccgcgacua cagcagcaac aaugaucguu | 780 |
| uucgaucauu caugggguca guguugacgug aaucguaacg cuuaugaacc acuaguuugc | 840 |
| aggguuguau augcguuuuc gcauaucacu ccacuggccu aauucgauac cuuccuaagc | 900 |
| uccgcgaccu gacacaguua gcucugucga acuuuuguuc gacaaggcac uuacuaucau | 960 |
| guucgauaca gaguaucuga cugugugau cauaagcaau ggccacagcu uuugcugugg | 1020 |
| accagcagua cuaacagcuu aagagaguca uuguguuaug ucgugaggua cagcucacgu | 1080 |
| cagaucuuuu gaucugacug gucgaaucua cguacugguu caauaaugug ucguaaucgg | 1140 |
| aucagcauga uucgucuauu ucuagacgaa ucaacuucca ucgauuacgu guacgaguug | 1200 |
| aaccagguca ugacuucgac caaccaccug uuuucaggug gugugagcug acauugugga | 1260 |
| cauaacaugu ucagcucuu aagagcaugu aacugcuggu aacgacguuu cgucguucc | 1320 |
| auugcuucuc gugaucacag ucaacguuug aguaucgaac ucacacugaa gugccucugg | 1380 |
| uauguuuuca uaccaggagc uaacgcacua uagucgcgga gucguuacug guaucgaauu | 1440 |
| aggccagugg agugcuuuag cuuuugcuaa agacaacccu gucguagucu gguucauggu | 1500 |
| uaagucgauu cacgaugaua guacccuaug gaucuuacuu uuguaagauc guugcugcac | 1560 |
| aaucuucggc auggaaucga cucugaggua ccuguuagua cuccgaaau gucacuuuug | 1620 |
| ugacaugcca augagguuca augagucca uucacuugau aaggcuuuua cguagaauac | 1680 |
| gcaacuacua acuuuuguua guagaccauc uauagcaguu guuccauga cuucauaug | 1740 |
| gucguaugga aguccacuug cgugaacgau uuuucguuca gcccuuaacc acaccugaau | 1800 |
| cccgacuugc uacucuagca uacacaaugu guaagucagg cucugguuuu ccagagcccu | 1860 |
| cacgguggaau gagucuauau ggcugaacca ucucgacaa ucacgagugu accauaguau | 1920 |
| gaguuuucuc auaccgucag ugagauuagc uggucuacua agcguuagga caacgcuaua | 1980 |

-continued

| | |
|---|---|
| gugccgacga ucucuagucg uuuucgacua gaaaugucga gucgauugua cauuccucuu | 2040 |
| aggaacucgu gucgacuacg accgaaucau aguaaccuuu ugguuacuga aagccuccug | 2100 |
| uuuagguaga ucggauacuc ucuacgcagu aagauugucc cgugguagau ccucuuuuga | 2160 |
| ggaucuugcg acaucauacu cacuauggaa ucaaugacua gucaagacau ugaacaaacg | 2220 |
| cucaagucau cuuuugauga cuccuuaucu cacuuaugag gcuuccaaca cauuaaagca | 2280 |
| cgagaacugc uauggcuagu guucggaucc | 2310 |

<210> SEQ ID NO 8
<211> LENGTH: 2088
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 8

| | |
|---|---|
| gggagagagc ucgagcgaac acuagccacu ugaucaacug dacauacauu guguucaugc | 60 |
| cuguagucga ucugaauggc acuauaucca uaaacacacg ucgcugcgua ggacuacgac | 120 |
| gaaaaugaga guuccacag cauacauacu cagauagugg ucauaagucu gcugugcauc | 180 |
| gagaacagaa gaaguagcaa ggagcucauc acagucguuu ucgacugugc aguuguagau | 240 |
| uagcuaccgg uugaugaaac cauuaaugaa gcccacccgg acugauuucc uaagaacucu | 300 |
| ugugauacuc uccuugguua gucauugcgg gagugaacac auuagugaac augaagccau | 360 |
| aaugcgauga cuuccaugga gcaaacacaa uguagaaacu caaugguuca gccggauucu | 420 |
| aagucguuuu cgacuuagga uaguagggag auggacgauu cggacuuaac cuagcuugua | 480 |
| caaucuuauc uaggcacauu gaacuagaag gguaaugugu ggaccuuucu acuuugucaa | 540 |
| uauccgucau gacucaggga cugaaugagu gcugaucgca gugugaccau ccccggguuu | 600 |
| cauagccugg ggaaaacaag cccuuacagu agcacuuuug ugcuaccguu cggccuguu | 660 |
| uaguuugcag aacuaacagu gccaaaguac uuaugacucc cuugauauag acuaugcuua | 720 |
| ggucaugaca ggagcugcug auacaggaac caaucucgug augaguaacc uauagugcaa | 780 |
| cuacuucaua cgcauguaac aaagguuaag ugccgacuuc aagucgaugu gccgacagua | 840 |
| acacuuuugu guuacucaua cuuguagcag uuucacagaa ucuacacaua cucuggaaug | 900 |
| gaagugcgug uguuugcacg uugcugauug aucacgagac aagggaacua guuugucaau | 960 |
| uucacaagca ccuacgacgu cuuaggaagu aagucgacua ucaucccuug uuccuguuag | 1020 |
| uaagcacugu caagugauac ugcucuauuu cuagagcagu acuugcuacc agugcuuuac | 1080 |
| augcugaaca agggucacac ugcgacuuac aguaacgaac gucguaggug cuugugaaau | 1140 |
| ugaucguagu cuucccuugu augcaucaca aucagcguuc aaugaacaca cgcugcugau | 1200 |
| cuccagagua uguguagauu cugugaugau caagcaagua ugcugcguag uuuucuacgc | 1260 |
| aggucggcac ugaaccauga agucggcuaa cgcuuuuugu uacaugcgua ugaaguaguu | 1320 |
| ugugucaggg uuacucugau gcauauuggu ucccaaugac ucagcuccuu cuacguacua | 1380 |
| agcauagucu auaucaaggg agcaggugug acuuuggcaa gcauguaucu gcaaaagcua | 1440 |
| aucgaccgaa cgucgucgu uuucgaccga guaagggcu uguuucccc aggcuccgua | 1500 |
| ugacggggau ggaugauagu cgaucagcug aguaugaguc ccugauacgu agaggauauu | 1560 |
| gacaaaguag aaagguccug uacgagcccu ucuaaacgug caugccuaga ucgacuacaa | 1620 |
| caagcuaaag cguuaccgaa ucguccaucu cccuacuauc gucacaacuu uuguugugac | 1680 |

-continued

| | |
|---|---|
| aauccggcau cgacuuugag uuucuuaccu cacuuugcuc cgaucagcac aucgcauuau | 1740 |
| ggcuucaugu ucaccucgua caucacuccc guguaucaga accaagguca aacguacaag | 1800 |
| aguuucguua cuaucagucc ggguggggcuu cauuaauuca uacggcaacc ggucuaaaca | 1860 |
| guacaacugc guuacccuuu uggguaacga ugagcucuca cuugauucuu cguuucucga | 1920 |
| ugcacagcag cacaccugcc acuaucacuc auucuaugcu gugacguuug acauuucgc | 1980 |
| aaacuagcua cgcagcgacg uguguuuaug gacugacaca cauucagaua agauugggc | 2040 |
| augaagugag guaaugucca guaacugcua uggcuagugu ucggaucc | 2088 |

<210> SEQ ID NO 9
<211> LENGTH: 1838
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

| | |
|---|---|
| gggagaggau ccgaacacua gccauagcag uucgcugagc guaaugugua ugaaacauca | 60 |
| uaaguucagu gcuacauuga agcgaagagc caaugacucg uucgugucau acucaucaac | 120 |
| ggaguguuga cuaagccgaa aaaacauagu ccgacuacac accagacacg uuugacccuc | 180 |
| agucgauuaa cugcaagucg caaacaagcu gacguacagu aacgacucgu cacuguacug | 240 |
| augauuccac aacugcuaau gcacgaaaaa aggaguagug ugucagaucg acaagacuua | 300 |
| accacgauuc cugaugcauu gacuuaccau cgacucaacu gacaagggac cacgcagagg | 360 |
| ugaaugaguc aggacuuugu agucggaguc ggaaaaaaca ccagucacaa uguaucguac | 420 |
| gcuugcuacu aggagcucgu caugacguug agagccuguu aacuagacac guuccuaagg | 480 |
| guuagccaca cauuaauauc gggccugaca caggacacga aaaagaagg ugcuguuagu | 540 |
| uggacaggua cuaucaucuc aagucgauag uccaaguagg uuugaaccau gcauagcuug | 600 |
| uaucagguca ucgccucaaa cguuaggugu cacauuguug aaucgcaaaa aacauaccga | 660 |
| cuuccauuau gggacacguc gcuuauucuu gguaaguaga aguugccauc guagucgcac | 720 |
| gaccuacuua ugacgaacuu cgguuaagug gcugacguac aaacagugcg ugcaaaaaag | 780 |
| accuacgaag ccagaguucg uuccagugug aaagugcaca ucacgaguug ugccaaugca | 840 |
| cguugcaucg agaguuaauc ccgucuuaag uagcaaggca ccugaaugga aguugauucg | 900 |
| ucuagaaaua gacgaaucau gcugaucuca ggugcucacu ugauuaagac ggcuguuuau | 960 |
| cucgaugccu ucaauguugg cacaaaugca ucagugcacu uauguauagug aacgaacucu | 1020 |
| ggcuucguag gucaaaaaag cacgcaagca guaacguca gccuaacgcu ugaaguucgc | 1080 |
| aggugugagg ucgugccuug uuuguggcaa cugucaugac ccaagaauaa gcgacguguc | 1140 |
| ccauagauca gcacgguaug aaaaaagcga uucgugaggu agacaccuag auacucuggc | 1200 |
| gaugacaguc auugacuaug gcgagucgau aaccuacuug gacuaucgac uugagucaca | 1260 |
| cugaccuguc cauacaugcu caccuucaaa aaacguguucc gcacuauagc ccgauaucuc | 1320 |
| guacaggcua acccguuuac ucgugucuag uuaacaggcu cucaacucua cuuugagcuc | 1380 |
| cuaucaagug acguacgauu acccacacu ggugaaaaaa ccgacucaag auuugaaguc | 1440 |
| cugugaguau gaccucugcg uggucccuug ucaguuaugg uucagguaag ucacucguga | 1500 |
| uggaaucgua agcguuacuu gucgauuaua gugccuacuc caaaaaacgu gcaucuugau | 1560 |
| caguggaauc aucaguacag ugacgagcuu aggaaguacg ucaggacuac gacgacugc | 1620 |

| | |
|---|---|
| auaaacagga cugagggaga guaucgucug gugcaaaucu ugacuaugaa aaaacggcuu | 1680 |
| agucaacacu ccguugaacu cauucacacg aacgcugaua cagcucuucg aacgugcaua | 1740 |
| gcacugacac accuguguuu cauuguacga gcgcucagcg ugaucaagug gcuaguguuc | 1800 |
| gcucgagcuc ucucccuuua gugaggguua auuaagcu | 1838 |

<210> SEQ ID NO 10
<211> LENGTH: 1838
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| gggagagagc ucgagcgaac acuagccacu ugaucacgcu gagcgcucgu acaaugaaac | 60 |
| acaggugugu cagugcuaug cacguucgaa gagcuguauc agcguucgug ugaaugaguu | 120 |
| caacggagug uugacuaagc cguuuuuuca uagucaagau ugcaccaga cgauacucuc | 180 |
| ccucaguccu guuuaugcaa gucgucguag uccugacgua cuuccuaagc ucgucacugu | 240 |
| acugaugauu ccacugauca agaugcacgu uuuuuggagu aggcacuaua ucgacaagu | 300 |
| aacgcuuacg auuccaucac gagugacuua ccugaaccau aacugacaag ggaccacgca | 360 |
| gaggucauac ucacaggacu ucaaaucuug agucgguuuu ucaccagug ugagguaauc | 420 |
| guacgucacu ugauaggagc ucuaaguaga guugagagcc uguuaacuag acacgaguaa | 480 |
| cgagguuagc cuguacgaga uaucgggcua uagugcggac acguuuuuug aaggugagca | 540 |
| uguauggaca ggucagugug acucaagucg auaguccaag uagguuaucg acucgcauag | 600 |
| cucaaugacu gucaucgcca gaguaucuag gugucuaccu cacgaaucgc uuuuuucaua | 660 |
| ccgugcugau cuaugggaca cgucgcuuau ucuuggguca ugacaguugc cacaaacaag | 720 |
| gcacgaccuc acaccugcga acuucaagcg uuaggcugac guuacaugcu ugcgugcuuu | 780 |
| uuugaccuac gaagccagag uucguucacu aucauaagug cacugaugca uuugugccaa | 840 |
| cauugaaggc aucgagauaa acagccgucu uaaucaagug agcaccugag aucagcauga | 900 |
| uucgucuauu ucuagacgaa ucaacuucca ucaggugcc uugcuacuua agacgggauu | 960 |
| aacucucgau gcaacgugca uuggcacaac ucgugaugug cacuuucaca cuggaacgaa | 1020 |
| cucuggcuuc uaggucuuu uuugcacgca cguuuaguac gucagccacu uaaccgaagu | 1080 |
| ucgucauaag uaggucgugc gacuacgaug gcaacuucua cuuaccaaga auaagcgacg | 1140 |
| ugucccauaa uggaagucgg uauguuuuuu gcgauuccac aaugugacac cuaacguuug | 1200 |
| aggcgaugac cugauacaag cuaugcaugg uucaaaccua cuuggacuau cgacuugaga | 1260 |
| ugauaguacc uguccaacua acagcaccuu cuuuuuucgu guccuguguc aggcccgaua | 1320 |
| uuaaugugug gcuaacccuu aggaacgugu cuaguuaaca ggcucucaac gucaugacga | 1380 |
| gcuccuagua gcaagcguac gauacauugu gacuggugu uuuuccgacu ccgacuacaa | 1440 |
| aguccugacu cauucaccuc ugcguggucc cuugucaguu gagucgaugg uaagucaaug | 1500 |
| caucaggaau cgugguuaag ucuugucgau cugacacacu accucuuuuu ucgugcauua | 1560 |
| gcaguugugg aaucaucagu acagugacga gucguuacug uacgcagcu uguugcgac | 1620 |
| uugcaguuaa ucgacugagg gucaaacgug ucggugugu agucggacua uguuuuucg | 1680 |
| gcuuagucaa cacuccguug augaguauga cacgaacgag ucauggcuc uucgcuucaa | 1740 |
| uguagcacug aacuuaugau guuucauaca cauuacgcuc agcgaacugc uauggcuagu | 1800 |

| | |
|---|---:|
| guucggaucc ucucccuaua gugagucgua uuagaauu | 1838 |

<210> SEQ ID NO 11
<211> LENGTH: 2632
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---:|
| gggagagagc ucgagcgaac acuagacuug aucacuucgu uuagcgaaau cgacucugga | 60 |
| uaguacauug aacgugacuc cucauaagug cuuugaagua augugguaggc uauagaucag | 120 |
| cacggucacu uaacauuagg caacgcuacu caauguuuuc auugagugcu acacugucau | 180 |
| gacugugcau gacuugcuac aguuuguccu gauacauaca gaucccgacu acagugcgac | 240 |
| agauuagcuu gccuucaugu uugccguuuu cggcaaacca cacgcauugc agaugcgcca | 300 |
| cgacuuagga agaaugcaug acuuaaccac aucagaugau gcaucccgau agacauacuc | 360 |
| aagacuaguu accucacuag caaccgggug cgauguucaa agcuacgucg uuuucgacgu | 420 |
| agcauggcgc uacaugcuua aagaauaacg uuugaaggcg gcauauagug cauauggccg | 480 |
| augaaaccgg uggcuaaguu gacuuuuucg agagaacagg guuucccug uucguagugg | 540 |
| uacacucagg uauaaaagag ugcuaucucu aaucugauaa cuggccacug guggauaucuc | 600 |
| gguuugauga cuacgacauu guucacauauc auaaugcuag ccuguucaca ccgacagucu | 660 |
| caauguuuuc auugagagua cgagugaacg uccacuuauc ugaugauagu uugaucucac | 720 |
| uaacagcgau agccugugag guacaauauc cuacguagau ccucuuggug cugaucccaa | 780 |
| agucuuaucg agaucucaua guuaaccagu uuucugguua agagagcgac cucguacaac | 840 |
| cuauacguag caaggcgacu gacgaaugag ucgggguuau caaacguaag uuaggccuag | 900 |
| uuuggacauu cauacaugag uuuucucaug uagggcagug aguugauaug ccaccuaga | 960 |
| uaccaaaucc ucucugacac aguuucaugu augcaucaac ccuucgaguc auugguuauc | 1020 |
| accacuuaug auauauccca gucagucguu cgaucgucug cguguuuuca cgcagagaau | 1080 |
| ugcgcugcac guucauguau uugaguucgg aagauagcua acgcuucacg uggggguuuc | 1140 |
| auauagugc guguagacuc aggaucgacg ugauguuuuc aucacgugua gguaagucac | 1200 |
| cauauuuugg aaauagcacu guguuguua caggagaguc cguaauuccu aagcacgucu | 1260 |
| ucuguuuagg uuuggagcga gucgauaccu gcgaccgcua ugaucaaggu cuccaucuau | 1320 |
| uucuagaugg agacuagcag uuuagcgguc gcaggugaa ccaugcucca aacagcuaau | 1380 |
| caagacgugu cguuacuuua cggacuaguc aacucaacac acuccugaug uuccaaaaua | 1440 |
| uggugacuua ccuacccuau aucuuuugau auaggcgauc cugcaguuau ccgacacuau | 1500 |
| ccguaugacc cacguggguu aagugcuauc uucaagauug uaauacaugg uucaauggcg | 1560 |
| caauucgaca uuacuuuugu aauguccgau cgaacgacug acuggauau acaggugugg | 1620 |
| gugauaacug uaucagcgaa ggguaucacg agacaugaaa cgcacuauaa gaggauugac | 1680 |
| accuaaggug gacauaucaa cucacugccc gaugcaucuu uugaugcauc ugaaugcuc | 1740 |
| guagucgccu aacuugauac ucuuaaccac gugaguaugg ucagucgcuc acuugaguau | 1800 |
| agguacacau uagucgcucu ccaaagcacu uuugugcuuu gcuaugagau cucgauaaga | 1860 |
| cuuuggaugg aaguccaaga ggagucauga cggauauuga cauugugagg cuaucgagca | 1920 |
| uguagagauc aacaguguga cagauaagug gacguucacu cguacacacc accuuuuggu | 1980 |

| | |
|---|---:|
| ggugucuguc ggugugaaca ggcuagcauu ucacacugga acaaugcaaa cuagaucaaa | 2040 |
| ccguaggugu cccaguggca gucuacaaga uuagagcauc aggacuuuua uaccugagug | 2100 |
| uaccacuacu ugcuagcuuu ugcuagcaau cucgaaaacu ccuguauagc caccucauac | 2160 |
| ggcggccaua uugugucagu gccgccuaga guaucuauuc uuuacuguua gugcgccaug | 2220 |
| gugacuucuu uugaagucac cuuugaacau cgcaccaggu ugcuacacaa uguacuaguc | 2280 |
| uacucauucu cuaucgggcu cgugauucug auguaagcgu acaugcauu caguaacgau | 2340 |
| cguggcgcau cugcaaugcg guggaguca ucuuuugaug acucaugaag gcacuaaaca | 2400 |
| gugucgcaca caaucuugga ucuguacaau gacugacaaa cuucaaguga ucaugcacau | 2460 |
| cuacguaagu guagcugcgc accuuuuggu gcgcaagcgu ugccuaaugu uaagugaccg | 2520 |
| acuuccauua uagccuugua cgagcuucaa agccacaccu gggagucaca acgugcauac | 2580 |
| uauccaaugg uucauucgcu aaacgaagaa cugcuaucua guguucggau cc | 2632 |

<210> SEQ ID NO 12
<211> LENGTH: 1684
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12

| | |
|---|---:|
| gggagauuac ucauaagggc uggcuugguu cacuaggagc uaguugggua gcccgucacc | 60 |
| agugcguaca gcccguucau ccgcuuugcg auugcucaca caacgcuucg aguuuacccg | 120 |
| uucugcgauu gaucgaaaga ucaggacauc gacggugaa cucgaguugg gaagugagcg | 180 |
| aucgcaagcg aucgaaacgg aaaacucgcu gcuuaccgua ugaauaggag guaccuucug | 240 |
| ccgguagucg uucguucagu aagcgagcu cgaaagagcu uaguaguug aacggacgac | 300 |
| uaacuuagau cguagagacc gaggcauacg guuccuugaa aaaggacgca augaccucgg | 360 |
| uuucuacggu cuaaguaaau caauaucacc acuacuaccu augccacgaa aacccauugc | 420 |
| cgaggaucca caauggugcu cacgcguuua uguagcauuu ugagcgggau cgguugagag | 480 |
| aaaucucaug gaguuacgcu caagaugcua gcacacgccg agccauaga gauggauccu | 540 |
| gcuucgaaag aagcuccuac ggucucuaug ggucugguu gugccuagcu cguagcucua | 600 |
| acuccaauca ugguggaaaa ugaguagucc aucgcagagu auucggccug ugagcguugu | 660 |
| uacggauuug cugcagcgga uggaguuuau gcgaaagcau agacucucga ucgcgcagca | 720 |
| gauccguauu cccaaccaca ggucgaauac cgaugccgg acugcucaaa aagagcgggg | 780 |
| uuagcaugcg uugccaucuc aacaucuccg uacugcacuc uacaugacaa guacgagggu | 840 |
| aucuuguucg ugagaucguu caugguagca cgcagcuucg gcugaggagc gauccacaac | 900 |
| gcucuagaaa uagagcuggu gacaucgcuc uucagccgcu ccuaggugcu aucaugaacc | 960 |
| cuuaugagaa caaaaagucg cguggccccc aaugccuaga gcuaaaugcg aaaggugcaa | 1020 |
| gcuacgcaca gcgucugaua aggcgaguga aacucgucu aguucgucu ugugcguggc | 1080 |
| uugccgcgau uccauuuagu ucaggucgu cuaucccaug cgacaaaaag auauccuccc | 1140 |
| ucugaccaug uagcgugcag ugcggagaag aggugugaga cgcgcaugcu gcguugaaaa | 1200 |
| acgcucgaaa accgucucau accucucucc gugauaucag uaggauucgu cagaggcgca | 1260 |
| ugaaaaugcg guacuuguga auccugcuga uauuacggag uguugaggug gcaaguuuuc | 1320 |
| gaaaccucgc ucccaccgug auaccgaucc gagcuauag cuagcauaaa ugcgugagua | 1380 |

| | |
|---|---|
| ccauugccgu aggacggcga ugggnuugccu cagacgcagc ccuaguuauc uaccuuucga | 1440 |
| uccuuggcca cuucauuggg gacuucgaaa gaaguauaga cgaaaguggc uaaggaugaa | 1500 |
| ucgcgagaua auuagggcua gacgaacggc aaaaaacgug guauagcagc uuacggugau | 1560 |
| guugauuucc ggcaggaggu acuuccuauu ucauugcgaa gcggcgagaa aagcugugcg | 1620 |
| cacguugugg gggcuacuca acuagaagcu gcugaaccga gccagcgauc ucacguaauc | 1680 |
| uccc | 1684 |

```
<210> SEQ ID NO 13
<211> LENGTH: 6337
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
```

| | |
|---|---|
| gggagaggau ccaacaugga gugcggauau gguucgcuaa gggauccccu gaaugcgaac | 60 |
| ucuaucaacu gucgauaccu ggagacgaug cugaucgacc ugucaugggc gaaaaccuau | 120 |
| accgauguaa acuccguaua ucauuuugc ucuaguccag uccuggaggu acuucggaa | 180 |
| aaaaguaccg caguggugaa gcgugucccuc cauacaccuc cgcaagguau ucacuuuugu | 240 |
| gaucauaguu augguguau gaggauaugc acuucacuau gcagaugga uauagaguc | 300 |
| cgugggcaga ugucagcgaa ccgcgaagac ucgcaaugaa aaaacgagug aagggcgucu | 360 |
| uggcgcguco uugucucacc caacugggu guggunagag cuugacucug ggauaugacc | 420 |
| aucugguca cuaauuuagg acugcccuaa ccucccuaau ggaugcgggu gauaaguucu | 480 |
| gaaugucacg uuugcaaaua gcccuuaaug uccccguacu guggcacgag caaaaaaccu | 540 |
| uacaccuaag gcgauacuca cuucaacugu guguaucaca uuaggugccu acgguaaacu | 600 |
| caucgcuag uucugggacu guuucgucu guuugaacgu uauaauagaca cgauaccugg | 660 |
| uucuaccauu cgccgaucca uuuggucuuc gaaaaaacga gggagaauca cucuaucaaa | 720 |
| gaugcaccuc guagcgagug aguggaacuu cauaaaggga agucauggcc ggucagacuu | 780 |
| cuggcacuga uaugcaacau caguacaguc uuaaguucca gccgaaagug cgguuggcau | 840 |
| cucuuaggac acagagcgau uuuggacugg uagcugaccg caugaaaaaa ggaacgacgu | 900 |
| gucgaaaggu cccggnuagua gcucccucau uccacuuggc uaaacguuca acacguaucg | 960 |
| aguugguuua gguaguucgc agacgcacaa acgaaggcag guaaaacuug gcaaguugcg | 1020 |
| ucgugggcacg ucauaccagu guugaaaaaa cggcuaugua gugucuagcu gucauaccc | 1080 |
| guacccaucu gauugguugca ggaugauuag gucgaaacga aguucucugau cugaggucgu | 1140 |
| cugaagcuaa guauaccug gcuaacuuga cuaacucgua ucauacucua gcuuucucac | 1200 |
| auucugugcu caaaaucugc auugacugca acgguccaaa aaagcgaccu ucugugugaa | 1260 |
| uaugaauacu aagcgggagu ugaagaauag cucacagaca gacacaaccu acaaaaugaa | 1320 |
| ugagcagucc guguaagcuc gcauugcuca cuucagccuu cgggcgcuau agccauuauu | 1380 |
| augauccaac ucgaucgaaa aaaggacua cguagauuug gccgacacca gauugcccgu | 1440 |
| accgacaaug cgguuucuuu guaaacuggg cacuuacgau cauagggagc ugguuacgaa | 1500 |
| cggcauccga caggaaucua gcucgaugca ugggauagua cuguccacau ccagccgucc | 1560 |
| cagagauagg uagauuggga aaaaacgauc gguacgauc ucuggugucu gacaaacacc | 1620 |
| uccgcacuca uuugagcaug agccaaugua uaaguugcac cagaaucgcu cugguaguc | 1680 |

```
uaacaucugc aacaucuuaa gggcagucau gacuacugac cguagucggc uagagcaccg   1740
ugaggccaaa ugauccucca gaaaaaagca cugaguugac accauccgag aguauggagc   1800
acuagcuauc augacgaggu ucccaguuga agucagaauc uugauggacg aagccuacua   1860
cuaccgcug uugguacaug gauaagauug gcuuaguagg ucauccaaga cugggccuug   1920
gaaaaaacca cgguuuguga ccaugaucgu cccaugcaua cugaaaucau cacuaguugc   1980
ggaguacgag ucgagcugug cagugcaaac uaaucccuuu cggcggucac auagccuga    2040
acgccguccu uaucaccgaa aucuuccaac aaagcauggc ucguauaggu gcccagucga   2100
cuacuggaua cuggaaaaaa cggacuuuag acagcacccu caaucuauga ucgguccagu   2160
gguuaguucg uuucugcgag uuuaccuugc aucaggauau gacaccucgg guguugaagc   2220
cugaauagag agccgguucg aucuuguguc uacugaacgc aguguagcgu uagcaaaaaa   2280
gacacuaucc ugaagcacgc uauguucgua auucagccga cucgcauuau ugcuggagcu   2340
ucagcucggc cuugacugag ugcacucagg cauaucaguc aacacagcaa cuuccuacga   2400
cuguccuaaa ucaacacugc uagucacgug ugucuaucgu cucgaccugc aagcaugggu   2460
gucgucgaaa aaagcucacg cuguacaacc uucaccccau agugauagcc acagaaaagc   2520
cucugaacac caaccagacg gucgaaaaga aauguaagcu cacgcgucu ggugcguuga    2580
caagaagacc cauuaugagc uuacgugcuc ucacguaggc acuauccaaa aaaggaguaa   2640
aggcgaacgu ucgcagcagu uuacucggug guuuaucucu gaggucacgu cgaccuaagu   2700
cccaugauga cguccagaca accuucccuu gcuuccaagg cuuuggaggu augcuagagu   2760
caagaauuac ucugcaucga gucaucaagc auucaguacu auuagauugg agcacgacac   2820
aaaaaagcau cuucaauuag gcuuaucuga gacaucuggu caggucaccg aguaccagau   2880
gucgguagaa ccaaagauga cauaacagug aucaaccgca acuuacugua cccuacacga   2940
gauauguccg cuauagcguc aaacgcaggu acugcgaugg aaaaaacagc aguagcacag   3000
gcuuaacauc aaucgguggu ucaccucuau agggcuagag ugacggguau cgguuaugac   3060
aguguugcag ucagcaggug cauugucuuc gucgagcagu aagcggauag acaagggucg   3120
acuuggucua uuaucaugua acacuccauu accggucua gaaauagacc agguaccacu    3180
acauuacaug aagcuucgc aagucgacag gcuauaaucc gcuucaaaug gaacgaagac    3240
acgacuuaag cugacugggu augacucaua accgugcugu ugcacucuag uuggaucag    3300
gugaccaguu acgcuauguu aagccugugc uacugcugaa aaaaccaucg cgcauugucc   3360
guuugacaug cgauaggaca uauccaacca ucgguacagu cguaauacgu ugaucaccca   3420
cucaccaucu uuguacaggu agacaucugg acaagccaga ccugacguaa acguucagau   3480
aaguagcgaa caagaugcaa aaaaguguncg ugcuccaauc uaauaguaga guagacuuga   3540
ugaccaucua ucgaguaauu cacagugaaa gcauaccgug ucuaucuugg aagcucaacu   3600
caguguucgu uuaccugcca ugggacuacu ccauccguga ccugcugaag uaaccaccga   3660
uguugagucu gcgaacguuc gccuuuacuc caaaaaagga uaguuaugau cggagagcac   3720
accauuguau aaugggugau cagagcaacg cacguacaua ugugagcuua gucugaccuu   3780
cgaccgcacu cguuguguuc agaaagaugg uuguggcuaa gcaaccaggg ugaaggacag   3840
uugacgugag caaaaaacga cgacacccau gcuugcaggu ccacagacaa gacacacucc   3900
ucauacagug uugacgucac gaagucuag ucccagaaug uguugacaac ggacucugag    3960
ugccuaaacc aaaggccgag gaaauuggcc agcaaucuca uucaucggcu gaagagacgu   4020
uauagcgugc uucaggauag ugucaaaaaa gcuaacgauu ccgucguuc agugcucuuu    4080
```

```
cgaucgaacc uagccaggau ucaggccgug cuuaccgagg uguagacugu agaugcaagu    4140
aucgcaggca gaaacguagg gaggacugga ccuacgacuc auugagggu gacagguaag    4200 uccgaaaaaa ccaguaucca guagucgacu gggcuauugc uggagccaug gaauaccuga    4260
agauuuccau aucgcggacg gcgccuaaug uuaugugacc uuguaugagg auuagucaag    4320
uggacacagc ucguuaucgc uuccgcaacg cuauucuauu ucaguacucu uucaacgauc    4380
augguccaca accguggaaa aaaccaaggc augguggacgg augaccauca cuugcaaucu    4440
uauagaaagc ucaacagcau ccuuaucuag gcuucgagag augcgauucu gaucauugga    4500
gggaaccuca cgugacaagc uagugagaug auuucucgga guacggagu ucagugcaaa    4560 aaacuggagg aucauuuggc cucacggcca agguaccgac uacucaccac ugucaugacu    4620
agucaaggga uguugcgccu uagggacaua ccacuuggua ccggugcau cgacacgauu    4680 ggcucacaug ugacugagug cgcacacaga gucagacag ucgucuacag uaccgaucga    4740
aaaaacccaa ucuaccuuag acgacgacg cuggccaguc uuaguacuau ugaaagaguc    4800
gagcuagcua cacugcggau gccaccgucu cccagcuccc gccuacguua agugccacuc    4860
aacaaaagaa accaguaccu gggucgggga gcguaacugu cggccaaauc uacguaguac    4920
caaaaaacga ucgacccuau agauaauaau guaucgcaug cccgaagcag agauagagca    4980
augcacaaug guacggacug aaugcgaguu uguagggaa agagcgucug ugauagugau    5040
gucaacuccc caagugauuu cauauugagg guuaggucg caaaaaagga ccguugcagu    5100
caaugcagau gucacaugca gaaugugcca uguacgagua ugaagcgaua auagucaagu    5160
ggcucucuua uuacuuccaa uuucacgacc ucacuucuug uacuucguug auggaguauc    5220
auccugucgu guagagaugg gucaacagca ugacagcuag acacuacaua gccgaaaaaa    5280
caacacucaa cacuggugcc acgaguauua cggccaaguu gacgucaucu ucguuugaua    5340
uguaccgaac uacacucagu cacucgauac uaagcacgcg uuuagcuugc acugaugagg    5400
gaggauaagg agggaccuua cuuauacucg uuccaaaaaa caugcgguca gcuaccaguc    5460
caaguaccaa gugugucca uccaucaaca accgcaucau acaauggaac uuacauaucc    5520
ucugauguua guccguugug ccagaacauu ucuuggccau gaugaguuga uaugaaguuu    5580
guuauguucg cuacguuaag ucgcuuugau agagugauuc ucccucgaaa aaacgaagac    5640
acugcucguc ggcgaauuac cuguacaggu aucuccaaag cuauaacguu aacgagugcg    5700
aaacaggaag uugccuagac gaucugcgau acguaggcau ucaggacgau acacacucca    5760
augaugagua ucagauguua uguaaggaaa aaagcucgug ccacaguacg gaacaccuu     5820 gacuuauuug caagucauga uuucagaacg cgauaugcgc auccauaacu aaccuuaggg    5880
caucgugacg uuaugaccg gcuuuccau aucccuucac ugcgcucuaa ccuacucggu     5940
guugggugua uagccuacgc gccaagacgc ccuucacucg aaaaaacauu gcguaauaga    6000
ccgguucgcu acguuuaccc cacggaucga ugcaucacau cuguguugc uagugcauag    6060 ugacuagcac ccauaagagu cguaacaaaa gucuuuguug ugcggaggua aucaucugac    6120 acgcuggucca guagcgguac aaaaaaaccga aguaaccucc aggacuggau accuggaaa     6180 ugaauagugu caacuuacau cgcagcaaua uuucgcccag cugucuacga ucagcugucu    6240
gugcagguau cguuguacag uagaguucgu cuacucggaa ucccuccuaa uugcauaucc    6300 guguagugg uuggauccuc ucgagcucuc ccuuuag                              6337
```

<210> SEQ ID NO 14

<211> LENGTH: 929
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

| | | | | | |
|---|---|---|---|---|---|
| gaattctaat | acgactcact | atagggagag | gatccgaaca | ctagccatag | cagttcgctg | 60 |
| agcgtaatgt | gtatgaaaca | tcataagttc | agtgctacat | tgaagcgaag | agccaatgac | 120 |
| tcgttcgtgt | catactcatc | aacggagtgt | tgactaagcc | gaaaaaacat | agtccgacta | 180 |
| cacaccagac | acgtttgacc | ctcagtcgat | taactgcaag | tcgcaaacaa | gctgacgtac | 240 |
| agtaacgact | cgtcactgta | ctgatgattc | cacaactgct | aatgcacgaa | aaaggagta | 300 |
| gtgtgtcaga | tcgacaagac | ttaaccacga | ttcctgatgc | attgacttac | catcgactca | 360 |
| actgacaagg | gaccacgcag | aggtgaatga | gtcaggactt | tgtagtcgga | gtcggaaaaa | 420 |
| acaccagtca | caatgtatcg | tacgcttgct | actaggagct | cgtcatgacg | ttgagagcct | 480 |
| gttaactaga | cacgttccta | agggttagcc | acacattaat | atcgggcctg | acacaggaca | 540 |
| cgaaaaaaga | aggtgctgtt | agttggacag | gtactatcat | ctcaagtcga | tagtccaagt | 600 |
| aggtttgaac | catgcatagc | ttgtatcagg | tcatcgcctc | aaacgttagg | tgtcacattg | 660 |
| tggaatcgca | aaaacatac | cgacttccat | tatgggacac | gtcgcttatt | cttggtaagt | 720 |
| agaagttgcc | atcgtagtcg | cacgacctac | ttatgacgaa | cttcggttaa | gtggctgacg | 780 |
| tactaacagt | gcgtgcaaaa | aagacctacg | aagccagagt | tcgttccagt | gtgaaagtgc | 840 |
| acatcacgag | ttgtgccaat | gcacgttgca | tcgagagtta | atcccgtctt | aagtagcaag | 900 |
| gcacctgaat | ggaagttgat | tcgtctaga | | | | 929 |

<210> SEQ ID NO 15
<211> LENGTH: 939
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

| | | | | | |
|---|---|---|---|---|---|
| tctagaaata | gacgaatcat | gctgatctca | ggtgctcact | tgattaagac | ggctgtttat | 60 |
| ctcgatgcct | tcaatgttgg | cacaaatgca | tcagtgcact | tatgatagtg | aacgaactct | 120 |
| ggcttcgtag | gtcaaaaaag | cacgcaagca | tgtaacgtca | gcctaacgct | tgaagttcgc | 180 |
| aggtgtgagg | tcgtgccttg | tttgtggcaa | ctgtcatgac | ccaagaataa | gcgacgtgtc | 240 |
| ccatagatca | gcacggtatg | aaaaaagcga | ttcgtgaggt | agacacctag | atactctggc | 300 |
| gatgacagtc | attgagctat | gcgagtcgat | aacctacttg | gactatcgac | ttgagtcaca | 360 |
| ctgacctgtc | catacatgct | caccttcaaa | aaacgtgtcc | gcactatagc | ccgatatctc | 420 |
| gtacaggcta | acctcgttac | tcgtgtctag | ttaacaggct | ctcaactcta | cttagagctc | 480 |
| ctatcaagtg | acgtacgatt | acctcacact | ggtgaaaaaa | ccgactcaag | atttgaagtc | 540 |
| ctgtgagtat | gacctctgcg | tggtcccttg | tcagttatgg | ttcaggtaag | tcactcgtga | 600 |
| tggaatcgta | agcgttactt | gtcgattata | gtgcctactc | caaaaaacgt | gcatcttgat | 660 |
| cagtggaatc | atcagtacag | tgacgagctt | aggaagtacg | tcaggactac | gacgacttgc | 720 |
| ataaacagga | ctgagggaga | gtatcgtctg | gtgcaaatct | tgactatgaa | aaaacggctt | 780 |
| agtcaacact | ccgttgaact | cattcacacg | aacgctgata | cagctcttcg | aacgtgcata | 840 |

```
gcactgacac acctgtgttt cattgtacga gcgctcagcg tgatcaagtg gctagtgttc    900
gctcgagctc tctcccttta gtgagggtta attaagctt                           939

<210> SEQ ID NO 16
<211> LENGTH: 3185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gaattctaat acgactcact atagggagag gatccaacat ggagtgcgga tatggttcgc     60
taagggattc cctgaatgcg aactctatca actgtcgata cctggagacg atgctgatcg    120
acctgtcatg ggcgaaaacc tataccgatg taaactccgt atattcattt tgctctagtc    180
cagtcctgga ggttacttcg gaaaaaagta ccgcagtggt gaagcgtgtc ctccatacac    240
ctccgcaagg tattcacttt tgtgatcata gttatgggtg tatgaggata tgcacttcac    300
tatgcagatg tgagatagat gtccgtgggc agatgtcagc gaaccgcgaa gactcgcaat    360
gaaaaaacga gtgaagggcg tcttggcgcg tccttgtctc acccaactgg cttgtggtta    420
gagcttgact ctgggatatg accatcttgg tcactaattt aggactgccc taacctccct    480
aatggatgcg ggtgataagt tctgaatgtc acgtttgcaa atagcccttaa atgttcccgt    540 actgtggcac gagcaaaaaa ccttacacct aaggcgatac tcacttcaac tgtgtgtatc    600
acattaggtg cctacggtaa actcatcgtc tagttctggg actgtttcgt ctggttgaac    660
gttataatag acacgatacc tggttctacc attcgccgat ccatttggtc ttcgaaaaaa    720
cgagggagaa tcactctatc aaagatgcac ctcgtagcga gtgagtggaa cttcataaag    780
ggaagtcatg gccggtcaga cttctggcac tgatatgcaa catcagtaca gtcttaagtt    840
ccagccgaaa gtgcggttgg catctcttag gacacagagc gatttggac tggtagctga     900 ccgcatgaaa aaaggaacga cgtgtcgaaa ggtcccggta gtagctccct cattccactt    960
ggctaaacgt tcaacacgta tcgagttggt ttaggtagtt cgcagacgca caaacgaagg   1020
caggtaaaac ttggcaagtt gcgtcgtggc acgtcatacc agtgttgaaa aaacggctat   1080
gtagtgtcta gctgtcaata cccgtaccca tctgatggtt gcaggatgat taggtcgaaa   1140
cgaagtctct gatctgaggt cgtctgaagc taagtaatac ctggctaact tgactaactc   1200
gtactcatac tcagctttct cacattctgt gctcaaaatc tgcattgact gcaacggtcc   1260
aaaaaagcga ccttctgtgt gaatatgaat actaagcggg agttgaagaa tagctcacag   1320
acagacacaa cctacaaaat gaatgagcag tccgtgtaag ctcgcattgc tcacttcagc   1380
cttcgggcgc tatagccatt attatgatcc aactcgatcg aaaaaaggta ctacgtagat   1440
ttggccgaca ccagattgcc cgtaccgaca atgcggtttc tttgtaaact gggcacttac   1500
gatcataggg agctggttac gaacggcatc cgacaggaat ctagctcgat gcatgggata   1560
gtactgtcca catccagccg tcccagagat aggtagattg gaaaaaacg atcggtactg   1620 atctctggtg tctgacaaac acctccgcac tcatttgagc atgagccaat gtataagttg   1680
caccagaatc gctctggtat gtctaacatc tgcaacatct taagggcagt catgactact   1740
gaccgtagtc ggctagagca ccgtgaggcc aaatgatcct ccagaaaaaa gcactgagtt   1800
gacaccatcc gagagtatgg agcactagct atcatgacga ggttcccagt tgaagtcaga   1860
atcttgatgg acgaagccta ctactacctg ctgttggtac atggataaga ttggcttagt   1920
```

| | |
|---|---:|
| aggtcatcca agactgggcc ttggaaaaaa ccacggtttg tgaccatgat cgtcccatgc | 1980 |
| atactgaaat catcactagt tgcggagtac gagtcgagct gtgcagtgca aactaatccc | 2040 |
| tttcggcggt cacatagtcc tgaacgccgt ccttatcacc gaaatcttcc aacaaagcat | 2100 |
| ggctcgtata ggtgcccagt cgactactgg atactggaaa aaacggactt tagacagcac | 2160 |
| cctcaatcta tgatcggtcc agtggttagt tcgtttctgc gagtttacct tgcatcagga | 2220 |
| tatgacacct cgggtgttga agcctgaata gagagccggt tcgatcttgt gtctactgaa | 2280 |
| cgcagtgtag cgttagcaaa aagacacta tcctgaagca cgctatgttc gtaattcagc | 2340 |
| cgactcgcat tattgctgga gcttcagctc ggccttgact gagtgcactc aggcatatca | 2400 |
| gtcaacacag caacttccta cgactgtcct aaatcaacac tgctagtcac gtgtgtctat | 2460 |
| cgtctcgacc tgcaagcatg ggtgtcgtcg aaaaaagctc acgctgtaca accttcaccc | 2520 |
| catagtgata gccacagaaa agcctctgaa caccaaccag acggtcgaaa agaaatgtaa | 2580 |
| gctcactgcg tctggtgcgt tgacaagaag acccattatg agcttacgtg ctctcacgta | 2640 |
| ggcactatcc aaaaaaggag taaaggcgaa cgttcgcagc agtttactcg gtggtttatc | 2700 |
| tctgaggtca cgtcgaccta agtcccatga tgacgtccag acaaccttcc cttgcttcca | 2760 |
| aggctttgga ggtatgctag agtcaagaat tactctgcat cgagtcatca agcattcagt | 2820 |
| actattagat tggagcacga cacaaaaaag catcttcaat taggcttatc tgagacatct | 2880 |
| ggtcaggtca ccgagtacca gatgtcggta gaaccaaaga tgacataaca gtgatcaacc | 2940 |
| gcaacttact gtaccctaca cgagatatgt ccgctatagc gtcaaacgca ggtactgcga | 3000 |
| tggaaaaaac agcagtagca caggcttaac atcaatctgg tggtcacctc tatagggcta | 3060 |
| gagtgacggg tatcggttat gacagtgttg cagtcagcag gtgcattgtc ttcgtcgagc | 3120 |
| agtaagcgga tagacaaggg tcgacttggt ctattatcat gtaacactcc attacctggt | 3180 |
| ctaga | 3185 |

<210> SEQ ID NO 17
<211> LENGTH: 3199
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

| | |
|---|---:|
| tctagaaata gaccaggtac cactacatta catgaagtct tcgcaagtcg acaggctata | 60 |
| atccgcttca aatggaacga agacacgact taagctgact gggtatgact cataaccgtg | 120 |
| ctgttgcact ctaggttgga tcaggtgacc agttacgcta tgttaagcct gtgctactgc | 180 |
| tgaaaaaacc atcgcgcatt gtccgtttga catgcgatag gacatatcca accatcggta | 240 |
| cagtcgtaat acgttgatca cccactcacc atctttgtac aggtagacat ctggacaagc | 300 |
| cagacctgac gtaaacgttc agataagtag cgaacaagat gcaaaaagt gtcgtgctcc | 360 |
| aatctaatag tagagtagac ttgatgacca tctatcgagt aattcacagt gaaagcatac | 420 |
| cgtgtctatc ttggaagctc aactcagttg tctgttacct gccatgggac tactccatcc | 480 |
| gtgacctgct gaagtaacca ccgatgttga gtctgcgaac gttcgccttt actccaaaaa | 540 |
| aggatagtta tgatcggaga gcacaccatt gtataatggg tgatcagagc aacgcacgta | 600 |
| catatgtgag cttagtctga ccttcgaccg cactcgttgt gttcagaaag atggttgtgg | 660 |
| ctaagcaacc agggtgaagg acagttgacg tgagcaaaaa acgacgacac ccatgcttgc | 720 |

```
aggtccacag acaagacaca ctcctcatac agtgttgacg tcacgaagtc gtagtcccag    780
aatgtgttga caacggactc tgagtgccta aaccaaaggc cgaggaaatt ggccagcaat    840
ctcattcatc ggctgaagag acggtatagc gtgcttcagg atagtgtcaa aaaagctaac    900
gattcctgtc gttcagtgct ctttcgatcg aacctagcca ggattcaggc cgtgcttacc    960
gaggtgtaga ctgtagatgc aagtatcgca ggcagaaacg tagggaggac tggacctacg   1020
actcattgag ggttgacagg taagtccgaa aaaccagta tccagtagtc gactgggcta    1080
ttgctggagc catggaatac ctgaagattt ccatatcgcg gacggcgcct aatgttatgt    1140
gaccttgtat gaggattagt caagtggaca cagctcgtta tcgcttccgc aacgctattc   1200
tatttcagta ctcttttcaac gatcatggtc acaaaccgtg gaaaaaacca aggcatgtgg   1260
acggatgacc atcacttgca atcttataga aagctcaaca gcatccttat ctaggcttcg   1320
agagatgcga ttctgatcat tggagggaac ctcacgtgac aagctagtga gatgatttct   1380
cggatgtacg gagttcagtg caaaaaactg gaggatcatt tggcctcacg gccaaggtac   1440
cgactactca ccactgtcat gactagtcaa gggatgttgc gccttaggga cataccactt   1500
ggtacctggt gcatcgacac gattggctca catgtgactg agtgcgcaca cagatgtcag   1560
acagtcgtct acagtaccga tcgaaaaaac ccaatctacc ttagacgacg acggctggcc   1620
agtcttagta ctattgaaag agtcgagcta gctacactgc ggatgccacc gtctcccagc   1680
tcccgcctac gttaagtgcc actcaacaaa agaaaccagt acctgggtac gggagcgtaa   1740
ctgtcggcca aatctacgta gtaccaaaaa acgatcgacc ctatagataa taatgtatcg   1800
catgcccgaa gcagagatag agcaatgcac aatggtacgg actgaatgcg agttttgtag   1860
ggaaagagcg tctgtgatag tgatgtcaac tccccaagtg atttcatatt gaggtgttag   1920
gtcgcaaaaa aggaccgttg cagtcaatgc agatgtcaca tgcagaatgt gccatgtacg   1980
agtatgaagc gataatagtc aagtggctct cttattactt ccaatttcac gacctcactt   2040
cttgtacttc gttgatggag tatcatcctg tcgtgtagag atgggtcaac agcatgacag   2100
ctagacacta catagccgaa aaaacaaac tcaacactgg tgccacgagt attacggcca   2160
agttgacgtc atcttcgttt gatatgtacc gaactacact cagtcactcg atactaagca   2220
cgcgtttagc ttgcactgat gagggaggat aaggagggac cttacttata ctcgttccaa   2280
aaaacatgcg gtcagctacc agtccaagta ccaagtgtgt cctatccatc aacaaccgca   2340
tcatacaatg gaacttacat atcctctgat gttagtccgt tgtgccagaa catttcttgg   2400
ccatgatgag ttgatatgaa gtttgttatg ttcgctacgt taagtcgctt tgatagagtg   2460
attctccctc gaaaaaacga agacactgct cgtcggcgaa ttacctgtac aggtatctcc   2520
aaagctataa cgttaacgag tgcgaaacag gaagttgcct agacgatctg cgatacgtag   2580
gcattcagga cgatacacac tccaatgatg agtatcagat gttatgtaag gaaaaaagct   2640
cgtgccacag tacgggaaca ccttgactta tttgcaagtc atgatttcag aacgcgatat   2700
gcgcatccat aactaacctt agggcatcgt gacgttagtg accggctttt ccatatccct   2760
tcactgtgct ctaacctact cggtgttggg tgtatagcct acgcgccaag acgcccttca   2820
ctcgaaaaaa cattgcgtaa tagaccggtt cgctacgttt accccacgga tcgatgcatc   2880
acatctgtgg ttgctagtgc atagtgacta gcacccataa gagtcgtaac aaaagtcttt   2940
gttgtgcgga ggtaatcatc tgacacgctg tcagtagcg gtacaaaaaa ccgaagtaac   3000
ctccaggact ggataccttg gaaatgaata gtgtcaactt acatcgcagc aatatttcgc   3060
```

-continued

```
ccagctgtct acgatcagct gtctgtgcag gtatcgttgt acagtagagt tcgtctactc    3120
ggaatccctc ctaattgcat atccgtgtag tgggttggat cctctcgagc tctcccttta    3180
gtgagggtta attaagctt                                                  3199
```

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Cys Thr Lys Asp Asn Asn Leu Leu Gly Arg Phe Glu Leu Ser Gly Gly
1               5                   10                  15

Gly Ser Lys Lys Lys Lys Lys Lys Lys Lys Lys Lys
            20                  25
```

<210> SEQ ID NO 19
<211> LENGTH: 14
<212> TYPE: PRT
<213> ORGANISM: Homo sapiens

<400> SEQUENCE: 19

```
Thr Lys Asp Asn Asn Leu Leu Gly Arg Phe Glu Leu Ser Gly
1               5                   10
```

<210> SEQ ID NO 20
<211> LENGTH: 14
<212> TYPE: PRT
<213> ORGANISM: Mus sp.

<400> SEQUENCE: 20

```
Thr Arg Asp Asn Asn Leu Leu Gly Arg Phe Glu Leu Ser Gly
1               5                   10
```

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Lys Lys Lys Lys Lys Lys Lys Lys Lys Lys
1               5                   10
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-15 residues

<400> SEQUENCE: 22

```
Lys Lys Lys Lys Lys Lys Lys Lys Lys Lys Lys Lys Lys Lys Lys
1               5                   10                  15
```

RNA NANOSTRUCTURES AND METHODS OF MAKING AND USING RNA NANOSTRUCTURES

CROSS-REFERENCE TO RELATED APPLICATIONS

This patent application is a National Stage Application under 35 U.S.C. § 371 of International Application No. PCT/US2018/048973 filed on Aug. 30, 2018, which claims the benefit of priority of each of the following: U.S. Application Ser. No. 62/552,183 filed Aug. 30, 2017, U.S. Application Ser. No. 62/596,697 filed Dec. 8, 2017, U.S. Application Ser. No. 62/594,473 filed Dec. 4, 2017, U.S. Application Ser. No. 62/594,471 filed Dec. 4, 2017, U.S. Application Ser. No. 62/625,965 filed Feb. 2, 2018, U.S. Application Ser. No. 62/630,020 filed Feb. 13, 2018 and U.S. Application Ser. No. 62/637,807 filed Mar. 2, 2018, the disclosures of each of which are incorporated herein by reference in their entirety. The following applications are herein incorporated by reference: U.S. Application Ser. No. 62/552,183 filed Aug. 30, 2017, U.S. Application Ser. No. 62/594,473 filed Dec. 4, 2017, U.S. Application Ser. No. 62/594,471 filed Dec. 4, 2017, U.S. Application Ser. No. 62/625,965 filed Feb. 2, 2018, U.S. Application Ser. No. 62/630,020 filed Feb. 13, 2018 and U.S. Application Ser. No. 62/637,807 filed Mar. 2, 2018.

GOVERNMENT FUNDING

This invention was made with government support under N000141512689 awarded by the Office of Naval Research. The government has certain rights in the invention.

SEQUENCE LISTING

The instant application contains a Sequence Listing which has been filed electronically in ASCII format and is hereby incorporated by reference in its entirety. Said ASCII copy, created on May 21, 2020, is named G8118-00605_SL.txt and is 56,059 bytes in size.

BACKGROUND

Self-folding of an information-carrying polymer into a compact particle with defined structure and function (for example, folding of a polypeptide into a protein) is foundational to biology and offers attractive potential as a synthetic strategy. Over the past three decades, nucleic acids have been used to create a variety of complex nanoscale shapes and devices. In particular, multiple DNA strands have been designed to self-assemble into user-specified structures, with or without the help of a long scaffold strand. In recent years, RNA has also emerged as a unique, programmable material. However, these nanostructures often contain dozens or hundreds of distinct components and often have undesirable defects such as missing or incorrectly incorporated or synthesized component strands. Additionally, due to the number of components, these nanostructures are often not replicable or cost-efficient.

Accordingly, new types of nucleic acid nanostructures are needed. In particular, new types of RNA nanostructures are needed.

SUMMARY

Certain embodiments provide an RNA nanostructure comprising at least one single-stranded RNA (ssRNA) molecule, wherein the ssRNA molecule forms at least one paranemic cohesion crossover, and wherein the RNA nanostructure has immunomodulatory properties (e.g., immunostimulatory). As used herein, the term "single stranded RNA" or "ssRNA" refers to an RNA molecule that under denaturing conditions is single-stranded. Under alternative conditions, the RNA molecule may self-form into a secondary structure (e.g., a complex secondary structure).

Certain embodiments provide an RNA nanostructure comprising at least one single-stranded RNA (ssRNA) molecule, wherein the at least one ssRNA molecule comprises a plurality of regions of double helices and at least one paranemic crossover operably linked between two regions of double helices, and wherein the RNA nanostructure has immunomodulatory properties (e.g., immuno-stimulatory).

Certain embodiments provide an RNA nanostructure comprising one single-stranded RNA (ssRNA) molecule, wherein the ssRNA molecule forms at least one paranemic cohesion crossover, and wherein the RNA nanostructure has immunomodulatory (e.g., immuno-stimulatory) properties.

Certain embodiments provide an RNA nanostructure comprising one single-stranded RNA (ssRNA) molecule, wherein the ssRNA molecule comprises a plurality of regions of double helices and at least one paranemic crossover operably linked between two regions of double helices, and wherein the RNA nanostructure has immunomodulatory (e.g., immuno-stimulatory) properties.

Certain embodiments provide an RNA nanostructure comprising at least one single-stranded RNA (ssRNA) molecule, wherein the RNA nanostructure comprises at least two structural repeating units, wherein each structural repeating unit is 33 nucleotides in length, and wherein each structural repeating unit comprises, in order:

a first region of a double helix wherein the first region is between 3 and 9 nucleotides in length or between 12 and 20 nucleotides in length, a first paranemic cohesion crossover of between 3 and 5 nucleotides in length or between 7 and 20 nucleotides of length, a second region of a double helix wherein the second region is between 3 and 9 nucleotides in length or between 12 and 20 nucleotides in length, and a second paranemic cohesion crossover of between 3 and 5 nucleotides in length or between 7 and 20 nucleotides of length.

Certain embodiments provide an RNA nanostructure comprising at least one single-stranded RNA (ssRNA) molecule, wherein the RNA nanostructure comprises at least two structural repeating units of 33 nucleotides in length, and wherein each structural repeating unit comprises, in order: a first double helix 8 nucleotides in length, a first paranemic cohesion crossover 8 nucleotides in length, a second double helix 9 nucleotides in length, and a second paranemic cohesion crossover 8 nucleotides in length.

Certain embodiments provide an RNA nanostructure comprising a nucleic acid sequence having at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

Certain embodiments provide a single strand of RNA rationally designed to self-assemble into an RNA nanostructure comprising at least one paranemic cohesion crossover, wherein the RNA nanostructure has immunomodulatory (e.g., immuno-stimulatory) properties.

Certain embodiments provide a complex comprising an RNA nanostructure described herein, and at least one diagnostic agent operably linked to the RNA nanostructure.

Certain embodiments provide a complex comprising an RNA nanostructure described herein, and at least one therapeutic agent operably linked to the RNA nanostructure.

Certain embodiments provide a method of inducing an immune response in a subject (e.g., a mammal, such as a human), comprising administering to the subject an effective amount of an RNA nanostructure, complex or composition as described herein.

Certain embodiments provide a method of enhancing/increasing pro-inflammatory cytokines in a subject (e.g., a mammal, such as a human), comprising administering to the subject a therapeutically effective amount of an RNA nanostructure, complex or composition as described herein. Certain embodiments provide a method of activating immune cells by specific triggering of TLR3 signaling pathway in a subject (e.g., a mammal, such as a human), comprising administering to the subject a therapeutically effective amount of an RNA nanostructure, complex or composition as described herein.

Certain embodiments provide a method of slowing or suppressing tumor growth in a subject, comprising administering to the subject a therapeutically effective amount of an RNA nanostructure, complex or composition as described herein.

Certain embodiments provide a method of elevating levels of anti-tumor proinflammatory cytokines in a subject, comprising administering to the subject a therapeutically effective amount of an RNA nanostructure, complex or composition as described herein.

Certain embodiments provide a method to decrease levels of anti-inflammatory cytokines in a subject comprising administering to the subject a therapeutically effective amount of an RNA nanostructure, complex or composition as described herein.

Certain embodiments provide a method of treating a disease or disorder in a subject, comprising administering to the subject a therapeutically effective amount of an RNA nanostructure, complex or composition as described herein.

In certain embodiments, the disease or disorder to be treated is a hyperproliferative disorder, including tumors, cancers, and neoplastic tissue, along with pre-malignant and non-neoplastic or non-malignant hyperproliferative disorders.

Certain embodiments provide the use of an RNA nanostructure, complex or composition as described herein for the manufacture of a medicament for inducing an immune response in a subject (e.g., a mammal, such as a human).

Certain embodiments provide an RNA nanostructure, complex or composition as described herein for inducing an immune response.

Certain embodiments provide the use of an RNA nanostructure, complex or composition as described herein for the manufacture of a medicament for treating a disease or disorder in a subject.

Certain embodiments provide an RNA nanostructure, complex or composition as described herein for the prophylactic or therapeutic treatment a disease or disorder.

Certain embodiments provide a kit comprising an RNA nanostructure, complex or composition as described herein and instructions for administering the RNA nanostructure/composition to a subject to induce an immune response or to treat a disease or disorder.

Certain embodiments also provide processes that are useful for preparing an RNA nanostructure described herein.

In some embodiments, the methods comprise incubating one or more RNA molecules under conditions that result in the formation of a nanostructure.

BRIEF DESCRIPTION OF THE FIGURES

FIG. 9. Ex vivo splenocyte stimulation: CD86 activation in Dendritic cell. RNA origami activate antigen presenting cells (DC and plasmacytoid DC (pDC)). Mean fluorescence intensity of CD86 in each cell population is plotted.

FIG. 10. Cytokine release in ex vivo splenocyte cell culture supernatant upon stimulation. RNA-Rec induces the production of IFN-alpha and IFN-beta from simulated solenocytes. Type I interferons produce in vitro from stimulated splenocytes.

FIG. 11. Serum cytokine in mice injected with RNA origami. Similar to the finding on in vitro stimulation, an intravenous injection of RNA origami through retro-orbital route resulted in a transient elevation of IFNa/b.

FIGS. 32A-32G. Inhibition of macrophage uptake of RNA OG by DS and GpC. A, B and C: RAW 264.7 cells were pre-incubated with or without inhibitors for 30 minutes, i.e., Dextran Sulfate (DS: 200 ug/mL) or GpC oligonucleotide (GpC: 50 ug/mL), and then treated with AF488-labeled RNA OG (bright) for 60 minutes (5 ug/mL). The nuclei were stained with Hoechst and imaged with a confocal microscope, in which the top panels show all channels for the samples whereas the bottom panels show only AF488 channel. D, E and F: The three samples shown on the left (i.e., samples A, B and C) were treated with RNAse III to remove externally bound RNA OG. The bright spheres in the RNAse treated samples (indicated with arrows) are artifacts caused by the RNAse buffer since the spheres were also present in the sample treated with the RNAse buffer without nuclease. The cells without an incubation with AF488-labeled RNA OG is shown in G.

FIGS. 35A-35D. A. Anti-tumor effect of RNA-OG. Kaplan-Meier survival curve displaying mice from multiple independent experiments. Mice from three independent experiments received 5×10⁵ CT26-iRFP cells via IP injection. Mice began receiving 4 biweekly IP treatments of 100 μL of PBS or 16 μg of RNA-OG in 100 μL PBS on day 1, 3, or 5 for RNA-OG and day 1 for PBS. Tumor progression was monitored via the fluorescent intensity of iRFP. B-D. Lack of anti-tumor immunity in RNA-OG treated mice that were depleted of CD8 and NK cells. B. A schematic to show treatment schedules in various groups. In vivo depletion of CD8 or NK cells was achieved by injecting monoclonal antibodies (Mab) specific to CD8 or NK cells, respectively. The antibodies were injected on the same day of, but 4 hrs post tumor injection. RNA-OG was administered one day post the antibody treatment (100 ug/dose for total four doses). An irrelevant IgG was included as a negative control for CD8/NK depletion. C. Tumor growth in the PBS control mice. D. Tumor growth in mice treated with RNA-OG with or without targeted depletion of CD8 or NK cells.

FIG. 45. Testing of the effectiveness of the RNA origami on A20-iRFP lymphoma tumors in vivo in mice. Each line represents an individual mouse. Control=PBS group.

FIGS. 46A-46B. Lack of anti-tumor immunity in RNA-OG treated mice that were depleted of CD8 and NK cells. A. Schematic to show the depletion of CD8 or NK cells using anti-CD8 or anti-NK monoclonal antibodies, respectively. The antibody was injected on the same day of, but 4 hrs post tumor injection. RNA-OG was administered one day post antibody treatment (100 ug/dose for total four doses). An irrelevant IgG was included as a negative control for CD8/NK depletion. B. Tumor growth monitored by measuring iRFP fluorescence intensity in mice receiving various treatments.

FIG. 47. Other RNA origami shapes.

FIG. 63. PolyIC-H induced both TLR3 and MDA5/RIG pathways. The latter has been implicated to toxicity.

DETAILED DESCRIPTION

Figure 1A:
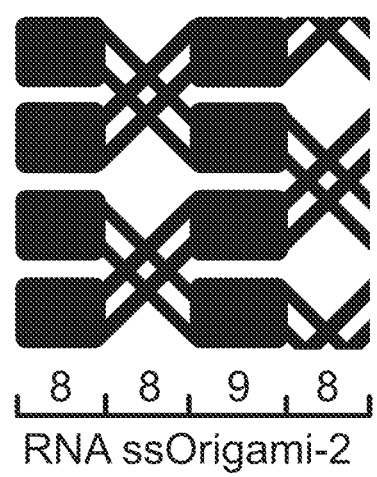
FIGS. 1A-1E. RNA ssOrigami. (A) Design schematics for 8-8-9-8 RNA ssOrigami design. Helical domains and locking domains are represented as rectangles and crosses, respectively. The bottom axis shows the length of each domain in quantity of base pairs. (B) Schematic showing the synthesis of both sense and antisense RNA ssOrigami structures. (C to E) Schematics (top) and AFM images (bottom) of a 1868-nt rectangle-shaped (C and D) and a 6337-nt 9×9 rhombus-shaped (E) RNA ssOrigami using the 8-8-9-8 design in (A). Both the sense strand (D) and antisense strand (E) rectangle ssOrigami are constructed following the workflow depicted in (B).

Described herein are two- and three-dimensional RNA nanostructures comprising at least one single-stranded RNA (ssRNA) molecule, wherein the ssRNA molecule forms at least one paranemic cohesion crossover, as well as methods of making and using such nanostructures. Generally, the RNA molecule(s) is rationally designed to fold into an any user-defined shape (e.g., an arbitrarily desired shape or a shape designed with a specific function or structural purpose) using simple base pairing rules through intrinsic self-complementarity, which guides the nucleic acid folding process. More specifically, the RNA is rationally designed to assemble into a "chain" that includes a hairpin loop as well as paired regions (e.g., "regions of a double helix") and unpaired regions (e.g., portions of the "paranemic cohesion crossovers" or portions of peripheral loop regions located at one or more ends of a double helix within the RNA nanostructure), which direct the nucleic acid chain to further assemble into the final nanostructure. In certain embodiments, the nanostructures have high structural complexity while maintaining knotting simplicity (e.g., an unknotted structure or a structure having a crossing number of zero).

As described herein, certain RNA nanostructures have also been shown to have immunomodulatory properties. For example, certain RNA nanostructures have also been shown to have immuno-stimulatory properties, and as such may be used as an adjuvant (e.g., an anti-cancer adjuvant) (see, the Examples). Additionally, certain RNA nanostructures described herein may be used as anti-tumor agents and/or other beneficial uses, including but not limited to therapeutic, diagnostic, and drug delivery purposes. Of note, certain RNA nanostructures described herein possess certain desirable properties:

1. High stability (e.g., in both cold storage and when subjected to nucleases), and therefore, applicability to in vivo applications;
2. Scalable quantity for human application with relatively low cost;
3. Safety: an RNA nanostructure described herein may selectively stimulate the pathway that is required for an induction of adaptive cellular immunity (anti-cancer or anti-viral), but not the pathway that triggers a cytokine storm (as shown in the cytokine profile analysis);
4. Intrinsic nanoparticle structure for better internalization by immune cells, without additional packaging to promote phagocytosis, in contrast to the processes involved in polyIC, dsRNA or the synthetic oligo-DNA-RNA hybrid (i.e., ARNAX); and/or
5. Well-defined structure and uniformity for reproducibility. This in in contrast to the heterogeneous population of polyIC (low vs. high molecular weight), which have different functional activities.

RNA Nanostructures

Certain embodiments provide an RNA nanostructure comprising at least one single-stranded RNA (ssRNA) molecule, wherein the ssRNA molecule forms at least one paranemic cohesion crossover. As described herein, certain RNA nanostructures have immunomodulatory properties; such RNA nanostructures are configured to exhibit the immunomodulatory properties (e.g., immuno-stimulatory). As used herein, the term "immunomodulatory properties" refers to the ability of the RNA nanostructure to modify the immune response or the functioning of the immune system (e.g., by stimulating or inhibiting the expression or activity of immune system cells). As used herein, the term "is configured to exhibit" a particular property means that the referenced subject matter is configured to exhibit and does exhibit the referenced property.

Accordingly, certain embodiments provide an RNA nanostructure described herein having immuno-stimulatory properties. Thus, certain embodiments provide an RNA nanostructure comprising at least one single-stranded RNA (ssRNA) molecule, wherein the ssRNA molecule forms at least one paranemic cohesion crossover, and wherein the RNA nanostructure has immuno-stimulatory properties.

Certain other embodiments provide an RNA nanostructure described herein having immuno-inhibitory properties. Thus, certain embodiments provide an RNA nanostructure comprising at least one single-stranded RNA (ssRNA) molecule, wherein the ssRNA molecule forms at least one paranemic cohesion crossover, and wherein the RNA nanostructure has immuno-inhibitory properties.

Certain embodiments also provide an RNA nanostructure comprising at least one single-stranded RNA (ssRNA) molecule, wherein the at least one ssRNA molecule comprises a plurality of regions of double helices and at least one paranemic crossover operably linked between two regions of double helices, and wherein the RNA nanostructure has immunomodulatory (e.g., immuno-stimulatory) properties.

As used herein, the term "RNA nanostructure" refers to a nanoscale structure made of RNA, wherein the RNA has a designed sequence and is folded into a structure with geometrical features, and wherein the nanostructure can serve as a structural and/or functional element. In certain embodiments, the RNA within the nanostructure acts both as a structural and functional element. As used herein, the term "RNA nanostructure" and "RNA origami" may be used interchangeably.

As used herein, the term "paranemic cohesion crossover" refers to a multi-stranded (e.g., 2, 3, 4 strands) nucleic acid complex comprising a central dyad axis that relates flanking parallel double helices (one example of which is described in Zhang et al. J. Am Chem. Soc. 2002). The strands within the crossover may be held together by Watson-Crick base pairing interactions or other non-canonical binding interactions. For example, in certain embodiments, selective crossovers may operably link regions of adjacent parallel double helices. Hence, reciprocal crossover points flank the central dyad axis at major or minor groove separation. In one embodiment, the paranemic cohesion crossover is a four-stranded nucleic acid complex comprising a central dyad axis that relates two flanking parallel or anti-parallel double helices. As used herein, the term "paranemic cohesion crossover" and "locking domain" may be used interchangeably.

As described herein, RNA nanostructures comprising at least one ssRNA molecule (e.g., one or more oligonucleotides/polynucleotides) may be prepared using methods described herein, as well as, with respect to certain embodiments, using techniques known in the art. The assembly of such RNA nanostructures may be based on base-pairing principles or other non-canonical binding interactions. For example, while no specific RNA sequence is required, regions of complementary within a single RNA molecule or between multiple RNA molecules may be used for assembly. Persons of ordinary skill in the art will readily understand and appreciate that the optimal sequence for any given RNA nanostructure will depend on the desired or intended shape, size, nucleic acid content, and intended use of such RNA structure. In certain embodiments, wherein the nanostructure comprises more than one ssRNA molecule (e.g. two or more oligonucleotides/polynucleotides), each ssRNA molecule may have a region that is complementary to a region on another ssRNA molecule to enable hybridization of the strands and assembly of the nanostructure. In certain other embodiments, wherein the nanostructure consists of a single ssRNA molecule (i.e., a single unimolecular RNA oligonucleotide/polynucleotide), regions within the molecule may be complementary to certain other regions within the molecule to enable hybridization and assembly of the nanostructure.

RNA nanostructures produced in accordance with the present disclosure are typically nanometer-scale structures (e.g., having length scale of 1 to 1000 nanometers), although, in some instances, the term "nanostructure" herein may refer to micrometer-scale structures (e.g., assembled from more than one nanometer-scale or micrometer-scale structure). In some embodiments, a RNA nanostructure described herein has a length scale of 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm or 1 to 50 nm. In some embodiments, a RNA nanostructure described herein has a length scale of greater than 1000 nm. In some embodiments, a RNA nanostructure described herein has a length scale of 1 micrometer to 2 micrometers.

In certain embodiments, the RNA nanostructure comprises, consists essentially of, or consists of multiple ssRNA molecules (e.g., more than one oligonucleotide/polynucleotide strands, such as two or more ssRNA molecules). In certain embodiments, the RNA nanostructure comprises two or more ssRNA molecules, which are capable of self-assembling (or configured to self-assemble) into a nanostructure. In certain embodiments, the RNA nanostructure is assembled from two or more ssRNA molecules through paranemic cohesion crossovers. Thus, in certain embodiments, the RNA nanostructure comprises two or more ssRNA molecules, wherein the ssRNA molecules self-assemble to form at least one paranemic cohesion crossover.

In certain embodiments, the RNA nanostructure comprises, consists essentially of, or consists of a single ssRNA molecule (i.e., one unimolecular oligonucleotide/polynucleotide strand). In certain embodiments, the RNA nanostructure is assembled using one ssRNA molecule (e.g., in certain embodiments one and only one, exactly one, or greater than zero and less than two). In certain embodiments, the RNA nanostructure is comprised of one ssRNA molecule, which is capable of self-assembling into a nanostructure. In certain embodiments, the RNA nanostructure consists of one ssRNA molecule, which is capable of self-assembling into a nanostructure. In certain embodiments, the RNA nanostructure is assembled from one ssRNA molecule through paranemic cohesion crossovers. Thus, in certain embodiments, the RNA nanostructure comprises one single-stranded RNA (ssRNA) molecule, wherein the ssRNA molecule forms at least one paranemic cohesion crossover.

The length of each RNA strand within an RNA nanostructure is variable and depends on, for example, the type, size, geometric, and/or intended use of nanostructure to be formed. It is to be understood, that if a particular RNA nanostructure comprises more than one ssRNA molecule, the length of each RNA molecule can be selected independently of one another. In certain embodiments, the at least one ssRNA molecule (i.e., oligonucleotide or RNA strand) is about 10 nucleotides in length to about 200,000 nucleotides in length, the at least one ssRNA molecule (i.e., oligonucleotide or RNA strand) is about 10 nucleotides in length to about 100,000 nucleotides in length, the at least one ssRNA molecule (i.e., oligonucleotide or RNA strand) is about 10 nucleotides in length to about 90,000 nucleotides in length, about 10 to about 80,000 nucleotides in length, about 10 to about 70,000 nucleotides in length, about 10 to about 60,000 nucleotides in length, about 10 to about 50,000 nucleotides in length, about 10 to about 40,000 nucleotides in length, about 10 to about 30,000 nucleotides in length, about 10 to about 25,000 nucleotides in length, or about 10 to about 20,000 nucleotides in length. In certain embodiments, the at least one ssRNA molecule (i.e., oligonucleotide or RNA strand) is about 15 nucleotides in length to about 20,000 nucleotides in length, the ssRNA molecule (i.e., oligonucleotide or RNA strand) is about 15 nucleotides in length to about 10,000 nucleotides in length, about 15 to about 7500 nucleotides in length, about 3000 to about 7000 nucleotides in length, about 5000 to about 7000 nucleotides in length, about 1500 to about 6500 nucleotides in length, about 1000 to about 7000 nucleotides in length, about 5500 to about 6500 nucleotides in length, about 15 to about 5000 nucleotides in length, about 15 to about 4000 nucleotides in length, about 15 to about 3000 nucleotides in length, about 250 to about 3000 nucleotides in length, about 500 to about 3000 nucleotides in length, about 1000 to about 3000 nucleotides in length, or about 1500 to about 2500 nucleotides in length.

In certain embodiments, the ssRNA molecule (i.e., oligonucleotide or RNA strand) is about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, about 10000, about 10100, about 10200, about 10300, about 10400, about 10500, about 10600, about 10700, about 10800, about 10900, about 11000, about 11000, about 11100, about 11200, about 11300, about 11400, about 11500, about 11600, about 11700, about 11800, about 11900, about 12000, about 12100, about 12200, about 12300, about 12400, about 12500, about 12600, about 12700, about 12800, about 12900 nucleotides in length, about 13000 nucleotides in length, about 14000 nucleotides in length, about 15000 nucleotides in length, about 16000 nucleotides in length, about 17000 nucleotides in length, about 18000 nucleotides in length, about 19000 nucleotides in length, about 20000 nucleotides in length, about 25000 nucleotides in length, about 30000 nucleotides in length, about 35000 nucleotides in length, about 40000 nucleotides in length, about 45000 nucleotides in length, about 50000 nucleotides in length, about 75000 nucleotides in length, about 100000 nucleotides in length, about 125000 nucleotides in length, about 150000 nucleotides in length, about 175000 nucleotides in length or about 200000 nucleotides in length.

In certain embodiments, an ssRNA molecule used in an RNA nanostructure described herein is synthesized de novo using any number of procedures well known in the art. For example, the cyanoethyl phosphoramidite method (Beaucage, S. L., and Caruthers, M. H., Tet. Let. 22:1859, 1981) or the nucleoside H-phosphonate method (Garegg et al., Tet. Let. 27:4051-4054,1986; Froehler et al., Nucl. Acid. Res. 14:5399-5407, 1986; Garegg et al., Tet. Let. 27:4055-4058, 1986, Gaffney et al., Tet. Let. 29:2619-2622,1988). These chemistries can be performed by a variety of automated oligonucleotide synthesizers available in the market, including the use of an in vitro transcription method.

An ssRNA molecule used in an RNA nanostructure described herein may comprise one or more modifications. Such modifications include, but are not limited to, base modifications, sugar modifications, and backbone modifications. The ssRNA molecule may contain natural or synthetic nucleotides (e.g., modified nucleotides). For example, in certain embodiments, the ssRNA nanostructure comprises one or more modified nucleotides (e.g., one or more inosine residues). ssRNA molecules described herein may have a homogenous backbone (e.g., entirely phosphodiester or entirely phosphorothioate) or a heterogeneous (or chimeric) backbone.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. The synthetic nucleotide base-pairs are also described by Eric Kool (Stanford), Floyd Romesburg (Scripps Research Inst.) or Steven Benner (Florida) and may be used. Backbone modifications are similarly known in the art, and include, chemical modifications to the phosphate linkage (e.g., phosphorodiamidate, phosphorothioate (PS), N3'phosphoramidate (NP), boranophosphate, 2',5'phosphodiester, amide-linked, phosphonoacetate (PACE), morpholino, peptide nucleic acid (PNA) and inverted linkages (5'-5' and 3'-3' linkages)) and sugar modifications (e.g., 2'-O-Me, UNA, LNA).

In certain embodiments, the at least one ssRNA molecule does not comprise a transcription termination sequence (e.g., in the middle of the strand). In certain embodiments, the at least one ssRNA molecule does not comprise an AUCUGUU sequence.

In certain embodiments, an RNA nanostructure described herein has knotting simplicity. In the field of nucleic acid topology, "knotting" refers to nucleic acid that is intertwined many times and tied into knots (see, e.g., Buck D, Proceedings of Symposia in Applied Mathematics 2009; 66: 1-33; Rybenkov V V et al. Proc Natl Acad Sci USA. 1993; 90(11): 5307-5311). Knotting simplicity enables the RNA molecule(s) to avoid being kinetically trapped during the folding process, which can prevent proper folding into a user-defined target shape. Thus, in some embodiments, the crossing number of the nanostructure is zero and the nanostructure is unknotted. A crossing number is a knot invariant that shows the smallest number of crossings in any diagram of the knot, representing the topological complexity of a knot.

Double Helices and Paranemic Crossovers

As described herein, certain embodiments provide an RNA nanostructure comprising at least one single-stranded RNA (ssRNA) molecule, wherein the ssRNA molecule forms at least one paranemic cohesion crossover. Accordingly, the RNA nanostructure may comprise single stranded regions (e.g., a portion of a paranemic cohesion crossover or a loop region) and double-stranded regions (e.g., double helices), which are the result of binding interactions between various sequences in the ssRNA molecule(s). Thus, as used herein, the term "double stranded region" refers to a region in the RNA nanostructure in which two adjacent RNA sequences are base paired to one another. As used herein, the term "single stranded region" refers to a region in the RNA nanostructure having a sequence that is not base paired to a second sequence.

In certain embodiments, at least about 20% of the assembled RNA nanostructure is comprised of double stranded regions. In certain embodiments, at least about, e.g., 25%, 30%, 35%, 40%, 45%, 50%, 55%, 60%, 65%, 70%, 75%, 80%, 85%, 90%, 95% of the assembled RNA nanostructure is comprised of double stranded regions. In certain embodiment, about 60-99% of the RNA nanostructure is comprised of double stranded regions and about 1-40% of the RNA nanostructure is comprised of single stranded regions. In certain embodiments, a majority if the structure is comprised of double stranded regions (e.g., ~95%) and only a small portion of the structure is comprised of single stranded regions (e.g., ~5%).

In certain embodiments, an RNA nanostructure described herein comprises at least one paranemic cohesion crossover. In certain embodiments, the RNA nanostructure comprises a plurality of paranemic cohesion crossovers. As used herein, the term "plurality" means two or more. For example, in certain embodiments, the RNA nanostructure comprises at least one to about 200 paranemic cohesion crossovers. In certain embodiments, the RNA nanostructure comprises one paranemic cohesion crossover. In certain embodiments, the RNA nanostructure comprises between about 1 to about 2000 paranemic cohesion crossovers. In certain embodiments, the RNA nanostructure comprises between about 1 to about 1500 paranemic cohesion crossovers. In certain embodiments, the RNA nanostructure comprises between about 1 to about 1000 paranemic cohesion crossovers. In certain embodiments, the RNA nanostructure comprises between about 1 to about 500 paranemic cohesion crossovers. In certain embodiments, the RNA nanostructure comprises between about 1 to about 200 paranemic cohesion crossovers. In certain embodiments, the RNA nanostructure comprises 2000 paranemic cohesion crossovers. In certain embodiments, the RNA nanostructure comprises 1800 paranemic cohesion crossovers. In certain embodiments, the RNA nanostructure comprises 1600 paranemic cohesion crossovers. In certain embodiments, the RNA nanostructure comprises 1400 paranemic cohesion crossovers. In certain embodiments, the RNA nanostructure comprises 1200 paranemic cohesion crossovers. In certain embodiments, the RNA nanostructure comprises 1000 paranemic cohesion crossovers. In certain embodiments, the RNA nanostructure comprises 800 paranemic cohesion crossovers. In certain embodiments, the RNA nanostructure comprises 600 paranemic cohesion crossovers. In certain embodiments, the RNA nanostructure comprises 400 paranemic cohesion crossovers. In certain embodiments, the RNA nanostructure comprises 200 paranemic cohesion crossovers. In certain embodiments, the RNA nanostructure comprises 1-175 paranemic cohesion crossovers. In certain embodiments, the RNA nanostructure comprises 1-150 paranemic cohesion crossovers. In certain embodiments, the RNA nanostructure comprises 1-125 paranemic cohesion crossovers. In certain embodiments, the RNA nanostructure comprises 1-100 paranemic cohesion crossovers. In certain embodiments, the RNA nanostructure comprises 1-75 paranemic cohesion crossovers. In certain embodiments, the RNA nanostructure comprises 1-50 paranemic cohesion crossovers. In certain embodiments, the RNA nanostructure comprises 1-25 paranemic cohesion crossovers. In certain embodiments, the RNA nanostructure comprises 1-20 paranemic cohesion crossovers. In certain embodiments, the RNA nanostructure comprises 1-15 paranemic cohesion crossovers. In certain embodiments, the RNA nanostructure comprises 1-10 paranemic cohesion crossovers. In certain embodiments, the RNA nanostructure comprises 9 paranemic cohesion crossovers. In certain embodiments, the RNA nanostructure comprises 8 paranemic cohesion crossovers. In certain embodiments, the RNA nanostructure comprises 7 paranemic cohesion crossovers. In certain embodiments, the RNA nanostructure comprises 6 paranemic cohesion crossovers. In certain embodiments, the RNA nanostructure comprises 5 paranemic cohesion crossovers. In certain embodiments, the RNA nanostructure comprises 4 paranemic cohesion crossovers. In certain embodiments, the RNA nanostructure comprises 3 paranemic cohesion crossovers. In certain embodiments, the RNA nanostructure comprises 2 paranemic cohesion crossovers. In certain embodiments, the RNA nanostructure comprises at least 12 to about 100 paranemic cohesion crossovers. In certain embodiments, the RNA nanostructure comprises at least 20 to about 80 paranemic cohesion crossovers. In certain embodiments, the RNA nanostructure comprises at least 40 to about 60 paranemic cohesion crossovers.

The single strand regions that contribute to a paranemic cohesion crossover are typically located in the same layer or plane. It should be understood, however, that single-strand regions of the paranemic cohesion crossovers of one layer may bind pair with single strand regions of paranemic cohesion crossovers of another layer to "lock" multiple layers together. The length of a given paranemic cohesion crossover may vary. Additionally, all of the paranemic cohesion crossovers in a nanostructure, or in a single layer of a nanostructure, need not be the same length relative to one another, although in some embodiments, they are. The number and relative lengths of the paranemic cohesion crossovers may depend on the desired shape and size (e.g., any desired and/or arbitrary shape or size) of the nanostructure.

In certain embodiments, the paranemic cohesion crossover has a length of about 4 to 15 nucleotides (or base pairs). In some embodiments, a paranemic cohesion crossover has a length of 4, 5, 6, 7, 8, 9, 10, 11, 12, 13, 14 or 15 nucleotides (or base pairs). In some embodiments, a paranemic cohesion crossover has a length of 8 nucleotides (or base pairs). It should be understood that, where this application references a "length" of a structure in nucleotides (e.g., 8 nucleotides in "length"), the length of the structure can interchangeably be described (for purposes of describing its "length") in terms of base pairs (e.g., 8 base pairs would be the same "length" as 8 nucleotides).

In certain embodiments, the paranemic cohesion crossover comprises 16 base pairings. In certain embodiments, the at least one paranemic cohesion crossover comprises between about 2 to about 14 GC base pairs. In certain embodiments, the at least one paranemic cohesion crossover comprises between about 2, 3, 4, 5, 6, 7, 8, 9, 10, 11, 12, 13, and 14 GC base pairs.

In certain embodiments, the at least ssRNA molecule comprises a sequence that forms internal loops that remain unpaired prior to forming the at least paranemic cohesion crossover.

In certain embodiments, an RNA nanostructure described herein comprises two or more double helices (e.g., a plurality of double helices). As used herein, the term "double helix" refers to a paired region of an RNA strand that forms a helix.

As used herein, the term "region of a double helix" refers to a subunit, region, or domain within a referenced "double helix." The terms "region of a double helix" and "helical domain" may be used interchangeably. The single strand regions that contribute to a paired helix are typically located in the same layer. The length of a double helix or a region of a double helix may vary. Additionally, all of the double helices or regions of a double helix in a nanostructure, or in a single layer of a nanostructure, need not be the same length relative to one another, although in some embodiments, they are. The number and relative lengths of the double helices or regions of a double helix may depend on the desired shape (e.g., any arbitrary shape) of the nanostructure. In some embodiments, a double helix or a region of a double helix has a length of 5 to 100 nucleotides. For example, a double helix or a region of a double helix may have a length of 5 to 90, 5 to 80, 5 to 70, 5 to 60, 5 to 50, 5 to 40, 5 to 30, 5 to 25, 5 to 20, or 5 to 15. In certain embodiments, a double helix or a region of a double helix has a length of 5, 6, 7, 8, 9, 10, 11, 12, 13, 14 or 15 nucleotides. In certain embodiments, a region of a double helix has a length of 8 nucleotides. In certain embodiments, a region of a double helix has a length of 9 nucleotides. In certain embodiments, a RNA nanostructure comprises a plurality of regions of double helices having a length of 8 nucleotides and a plurality of regions of double helices having a length of 9 nucleotides.

In certain embodiments, the ssRNA molecule comprises at least two parallel double helices. In certain embodiments, the ssRNA molecules comprises 2, 3, 4, 5, 6, 7, 8, 9, 10, 11, 12, 13, 14, 15, 16, 17, 18, 19, or 20 double helices (e.g., parallel double helices). In some embodiments, the nanostructure contains only parallel crossovers.

In some embodiments, the nanostructure contains continuous π-π stacking along greater than 50% (e.g., greater than 60%, greater than 70%, greater than 80%, greater than 85%, greater than 90%, greater than 95%, or greater than 98%) of the double helices or of regions of the double helices of the nanostructure.

In certain embodiments, an RNA nanostructure described herein further comprises at least one loop region (e.g., a peripheral loop region located at an end of one of the double helices included within the RNA nanostructure). In certain embodiments, loop regions connect one end of a double helix to another end of a double helix. Typically, loops regions are relatively short and are located on the edges of an RNA nanostructure. In certain embodiments, the loop regions are located on two edges (e.g., in a nanostructure shaped as a rectangle). In certain embodiments, the RNA nanostructure comprises 2 or more loop regions (e.g., a plurality of loop regions). In certain embodiments, the RNA nanostructure comprises between about 1 to about 100 loop regions. In certain embodiments, the RNA nanostructure comprises between about 1 to about 90 loop regions. In certain embodiments, the RNA nanostructure comprises between about 1 to about 80 loop regions. In certain embodiments, the RNA nanostructure comprises between about 1 to about 70 loop regions. In certain embodiments, the RNA nano structure comprises between about 1 to about 60 loop regions. In certain embodiments, the RNA nanostructure comprises between about 1 to about 50 loop regions. In certain embodiments, the RNA nanostructure comprises between about 1 to about 40 loop regions. In certain embodiments, the RNA nanostructure comprises between about 1 to about 30 loop regions. In certain embodiments, the RNA nanostructure comprises between about 1 to about 20 loop regions. In certain embodiments, the RNA nanostructure comprises between about 1 to about 15 loop regions. In certain embodiments, the RNA nanostructure comprises 1, 2, 3, 4, 5, 6, 7, 8, 9, 10, 11, 12, 13, 14 or 15 loop regions.

The length of a loop region may vary. Additionally, all the loop regions in a nanostructure, or in a single layer of a nanostructure, need not be the same length relative to one another, although in some embodiments, they are. In certain embodiments, the loop region has a length of about 2 to about 100 nucleotides. In certain embodiments, the loop region has a length of about 2 to about 50 nucleotides. In certain embodiments, the loop region is between about 2 to about 25 nucleotides in length. In certain embodiments, the loop region is between about 2 to about 20 nucleotides in length. In certain embodiments, the loop region is between about 2 to about 15 nucleotides in length. In certain embodiments, the loop region is between about 2 to about 10 nucleotides in length. In certain embodiments, the loop region is between about 3 to about 10 nucleotides in length. In certain embodiments, the loop region is about 4 nucleotides in length. In certain embodiments, the loop region is about 5 nucleotides in length. In certain embodiments, the loop region is about 6 nucleotides in length. In certain embodiments, the loop region is about 7 nucleotides in length. In certain embodiments, the loop region is about 8 nucleotides in length. In certain embodiments, the loop region is about 9 nucleotides in length. In certain embodiments, the loop region is about 10 nucleotides in length.

In certain embodiments, the loop region is "G rich" (i.e., a majority of the nucleotides within the loop region are G). In certain embodiments, the loop region is "C rich" (i.e., a majority of the nucleotides within the loop region are C). In certain embodiments, the loop region is "A rich" (i.e., a majority of the nucleotides within the loop region are A). In certain embodiments, the loop region is "U rich" (i.e., a majority of the nucleotides within the loop region are U). In certain embodiments, the loop region comprises or consists of the sequence 'UUUC'. In certain embodiments, the loop region comprises or consists of the sequence 'GGGAGGG'. In certain embodiments, the loop region comprises or consists of the sequence 'CCCUCCC'. In certain embodiments, the loop region comprises or consists of the sequence 'AAAGAAA'. In certain embodiments, the loop region comprises or consists of the sequence 'UUUCUUU'.

In certain embodiments, regions of double helices and paranemic cohesion crossovers can be, but are not necessarily, arranged in an alternating pattern. For example, in a two-layer nanostructure, each layer may have regions of double helices separated by paranemic cohesion crossovers (internally) or double helices (of which regions of double helices are a part) may be separated by loop regions (peripherally). In certain embodiments, at least two regions of a double helix of an RNA nanostructure described herein may be separated from each other by a (or at least one) paranemic cohesion crossover and/or at least two double helices of an RNA nanostructure may be linked or coupled by at least one paranemic cohesion crossover. In some embodiments, 10%, 20%, 30%, 40%, 50%, 60%, 70%, 80%, 90%, 95%, 98%, or 100% of the regions of double helices of an RNA nanostructure may be separated from each other by a (or at least one) paranemic cohesion crossover.

Accordingly, in certain embodiments, the RNA nanostructure comprises a structural repeating unit. In certain embodiments, the structural unit is repeated 2 or more times. Thus, in certain embodiments, the structural unit is repeated a plurality of times within an RNA nanostructure described herein. In certain embodiments, the structural repeating unit comprises, in order: a first region of a double helix, a first paranemic cohesion crossover, a second region of a double helix, and a second paranemic cohesion crossover. In certain embodiments, the structural repeating unit is 33 total base pairs (bp) in length.

In certain embodiments, the RNA nanostructure is based on the 8-8-9-8 design, as described in Example 1. In this design, the RNA nanostructure comprises a structural repeating unit of 33 bp, which contains two regions of a double helix (one 8 nucleotide region of a double helix and one 9 nucleotide region of a double helix), interspersed with two 8 nucleotide paranemic cohesion crossovers. Thus, in certain embodiments, an RNA nanostructure described herein comprises a structural repeating unit comprising, in order, a first region of a double helix that is 8 nucleotides in length, a first paranemic cohesion crossover that is 8 nucleotides in length, a second region of a double helix that is 9 nucleotides in length, and a second paranemic cohesion crossover that is 8 nucleotides in length. Certain embodiments also provide an RNA nanostructure comprising at least one single-stranded RNA (ssRNA) molecule, wherein the RNA nanostructure comprises at least two structural repeating units of 33 nucleotides in length, and wherein each structural repeating unit comprises, in order: a first region of a double helix 8 nucleotides in length, a first paranemic cohesion crossover 8 nucleotides in length, a second region of a double helix 9 nucleotides in length, and a second paranemic cohesion crossover 8 nucleotides in length.

In certain embodiments, an RNA nanostructure comprises at least one single-stranded RNA (ssRNA) molecule, wherein the RNA nanostructure comprises at least two structural repeating units of 33 nucleotides in length. In certain embodiments, each structural repeating unit comprises, in order: a first region of a double helix wherein the first region is 9 or fewer nucleotides in length, 8 or fewer nucleotides in length, 7 or fewer nucleotides in length, or 6 or fewer nucleotides in length; a first paranemic cohesion crossover of 7 or greater nucleotides in length, 8 or greater nucleotides in length, 9 or greater nucleotides in length, or 10 or greater nucleotides in length; a second region of a double helix wherein the second region is 10 or fewer nucleotides in length, 9 or fewer nucleotides in length, 8 or fewer nucleotides in length, 7 or fewer nucleotides in length, or 6 or fewer nucleotides in length, and a second paranemic cohesion crossover of 7 or greater nucleotides in length, 8 or greater nucleotides in length, 9 or greater nucleotides in length, or 10 or greater nucleotides in length.

In certain embodiments, an RNA nanostructure described herein does not comprise a structural repeating unit having a 10-6-11-6 design (i.e., containing two regions of a double helix (one 10 nucleotide region of a double helix and one 11 nucleotide region of a double helix), interspersed with two 6 nucleotide paranemic cohesion crossovers.

Certain embodiments provide an immunomodulatory (e.g., immuno-stimulatory) biopolymer having a three-dimensional structure, comprising:

$$(HD_1\text{-}LD_1\text{-}HD_2\text{-}LD_2)_n$$

wherein n is selected from 2 to 100, 2 to 500, 2 to 1000, 2 to 1500, 2 to 2000, 2 to 2500, 2 to 3000, or 2 to 3500, 2 to 4000, 2 to 4500, 2 to 5000, 2 to 5500, or 2 to 6000; wherein $HD_1$ and $HD_2$ are each an RNA helical domain; wherein $LD_1$ and $LD_2$ are each an RNA locking domain; and further wherein the three-dimensional structure comprises at least one paranemic cohesion crossover. As discussed herein, the term "helical domain" is used interchangeably with the term "a region of a double helix". Additionally, the term "locking domain" is used interchangeably with the term "paranemic cohesion crossover".

In certain embodiments, $HD_1$ and $HD_2$ independently comprise from about 5 to about 50 ribonucleotides. In certain embodiments, $HD_1$ and $HD_2$ independently comprise from about 5 to about 40 ribonucleotides. In certain embodiments, $HD_1$ and $HD_2$ independently comprise from about 5 to about 30 ribonucleotides. In certain embodiments, $HD_1$ and $HD_2$ independently comprise from about 5 to about 25 ribonucleotides. In certain embodiments, $HD_1$ and $HD_2$ independently comprise from about 5 to about 20 ribonucleotides. In certain embodiments, $HD_1$ and $HD_2$ independently comprise from about 5 to about 15 ribonucleotides. In certain embodiments, $HD_1$ and $HD_2$ independently comprise from about 5 to about 10 ribonucleotides. In certain embodiments, $HD_1$ comprises about 8 ribonucleotides. In certain embodiments, $HD_2$ comprises about 9 ribonucleotides.

In certain embodiments, $LD_1$ and $LD_2$ independently comprise from about 4 to about 15 ribonucleotides. In certain embodiments, $LD_1$ and $LD_2$ independently comprise from about 4 to about 12 ribonucleotides. In certain embodiments, $LD_1$ and $LD_2$ independently comprise from about 4, 5, 6, 7, 8, 9, 10, 11 or 12 ribonucleotides. In certain embodiments, $LD_1$ comprises about 8 ribonucleotides. In certain embodiments, $LD_2$ comprises about 8 ribonucleotides.

In certain embodiments, $(HD_1\text{-}LD_1\text{-}HD_2\text{-}LD_2)_1$ is 33 ribonucleotides.

In certain embodiments, wherein the immunomodulatory (e.g., immuno-stimulatory) biopolymer having a three-dimensional structure, comprising:

$$(HD_1\text{-}LD_1\text{-}HD_2\text{-}LD_2)_n$$

wherein n is selected from 2 to 100, 2 to 500, 2 to 1000, 2 to 1500, 2 to 2000, 2 to 2500, 2 to 3000, 2 to 3500, 2 to 4000, 2 to 4500, 2 to 5000, 2 to 5500, or 2 to 6000; wherein $HD_1$ and $HD_2$ are each an RNA helical domain; wherein $LD_1$ and $LD_2$ are each an RNA locking domain; the three-dimensional structure is not: $HD_1$ is 10 ribonucleotides; $LD_1$ is 6 ribonucleotides; $HD_2$ is 11 ribonucleotides; and $LD_2$ is 6 ribonucleotides.

Certain embodiments provide a biopolymer having a three-dimensional structure, comprising:

$$(HD_1\text{-}LD_1\text{-}HD_2\text{-}LD_2)_n$$

wherein n is selected from 2 to 100, 2 to 500, 2 to 1000, 2 to 1500, 2 to 2000, 2 to 2500, 2 to 3000, 2 to 3500, 2 to 4000, 2 to 4500, 2 to 5000, 2 to 5500, or 2 to 6000; wherein $HD_1$ and $HD_2$ are each an RNA helical domain; wherein $LD_1$ and $LD_2$ are each an RNA locking domain; provided that the three-dimensional structure is not: $HD_1$ is 10 ribonucleotides; $LD_1$ is 6 ribonucleotides; $HD_2$ is 11 ribonucleotides; and $LD_2$ is 6 ribonucleotides.

Layers within an RNA Nanostructure

An RNA (e.g., a ssRNA molecule) may be designed to assemble into a double-stranded chain, resembling a large hairpin structure. That hairpin structure then assembles to form a structure containing paired double helices (or regions thereof) and paranemic cohesion crossovers. A "layer" of an RNA nanostructure, as used herein, refers to a planar arrangement of a portion of the RNA chain. In certain embodiments, an RNA nanostructure comprises 2 or more layers. For example, an RNA nanostructure may contain 2, 3, 4, 5, 6, 7, 8, 9, 10, or more layers, depending on the desired shape of the nanostructure.

In certain embodiments, the paranemic cohesion crossovers direct the RNA chain to further assemble into the final structure. The paranemic cohesion crossovers within the bottom layer are designed to (or configured or sequence-coded to) base pair with their corresponding paranemic cohesion crossovers within the top layer, but without traversing through each other. Thus, in certain embodiments, a nanostructure comprises a first layer comprising a plurality of double helices and a plurality of paranemic cohesion crossovers, wherein at least two regions of double helices of the first layer are separated from each other by a paranemic cohesion crossover, and a second layer comprising a plurality of double helices and a plurality of paranemic cohesion crossovers, wherein at least two regions of double helices of the second layer are separated from each other by a paranemic cohesion crossover, wherein a paranemic cohesion crossover of the first layer is hybridized to a paranemic cohesion crossover of the second layer.

RNA Nanostructure Shapes

The RNA nanostructures described herein are programmable structures, which may be designed to assemble into various sizes, shapes, nucleic acid contents, and configurations.

In certain embodiments, the shape of the RNA nanostructure can include or exclude a polyhedron, a tube, a spheroid, or an elliptoid. In certain embodiments, the polyhedron can include or exclude a rectangle, diamond, tetrahedron, or triangle. In certain embodiments, the shape of the RNA nanostructure is, for example, a rectangle, a diamond, a tetrahedron, a triangle, or any other user-defined geometric shape. Persons of ordinary skill in the art will, after having studied the teachings herein, appreciate and understand that these teachings are not limited to any specific RNA nanostructure shape, but rather can be applied to generate any desired shape by programming (or generating) the RNA molecule with the requisite sequence that will cause the molecule to self-assemble through pairing interactions into the desired shape.

In certain embodiments, the shape of the RNA nanostructure is a rectangle. In certain embodiments, the RNA nanostructure is an RNA rectangle nanostructure, self-assembled from one single-stranded RNA molecule through paranemic cohesion crossover. In certain embodiments, the rectangle RNA nanostructure comprises at least one loop region (e.g., 13 loops regions). In certain embodiments, the loop regions comprise or consist of a sequence selected from the group consisting of UUUC, GGGAGGG, CCCUCCC, AAAGAAA and UUUCUUU. In certain embodiments, at least 25% of the loop regions may comprise or consist of UUUC, of GGGAGGG, of CCCUCCC, of AAAGAAA or of UUUCUUU. In certain embodiments, at least 50% of the loop regions may comprise or consist of UUUC, of GGGAGGG, of CCCUCCC, of AAAGAAA or of UUUC-UUU. In certain embodiments, at least 75% of the loop regions may comprise or consist of UUUC, of GGGAGGG, of CCCUCCC, of AAAGAAA or of UUUCUUU. In certain embodiments, all of the loop regions may comprise or consist of UUUC, of GGGAGGG, of CCCUCCC, of AAAGAAA or of UUUCUUU.

Figure 39:
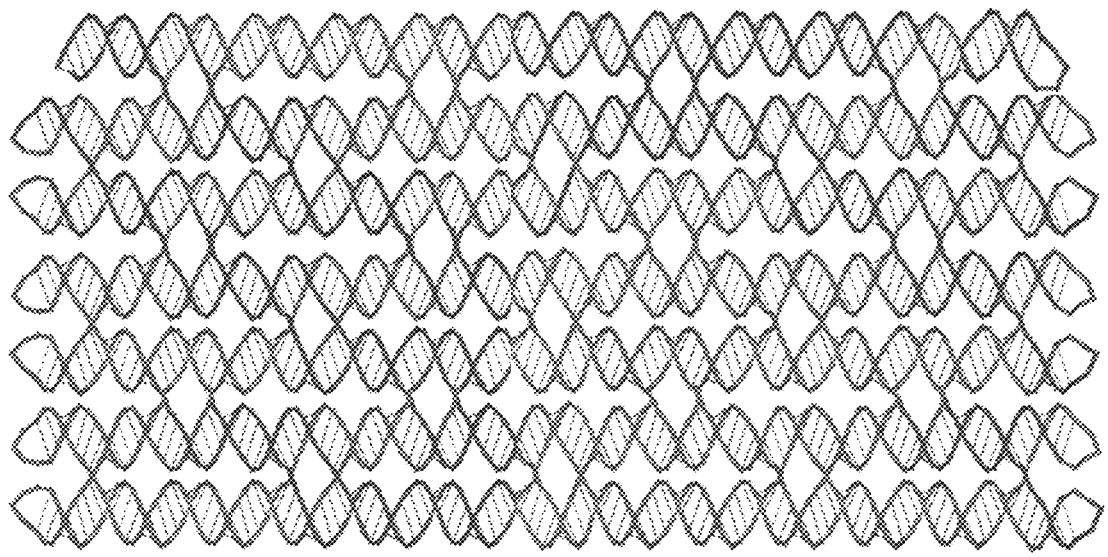
FIG. 39. RNA rectangle origami #1 (see, e.g., SEQ ID NO: 1).

In certain embodiments, the RNA nanostructure is a rectangle RNA nanostructure comprising a nucleic acid sequence having at least about 60% sequence identity to SEQ ID NO:1 (see, e.g., FIG. 39 and Example 2). In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1. Thus, in certain embodiments, the RNA nanostructure comprises SEQ ID NO:1. In certain embodiments, the RNA nanostructure consists of SEQ ID NO:1.

In certain embodiments, the UUUC tetraloops in SEQ ID NO:1 are replaced with alternative loop regions, such as G-rich loop sequences, C-rich loop sequences, A-rich loop sequences or other U-rich loop sequences.

Accordingly, in certain embodiments, the loop regions in SEQ ID NO:1 are replaced with G-rich loops:

```
                                               (SEQ ID NO: 3)
5'GGGAGAGGAUCCGAACACUAGCCAUAGCAGUUCGCUGAGCGUAAUGUGU

AUGAAACAUCAUAAGUUCAGUGCUACAUUGAAGCGAAGAGCCAAUGACUCG

UUCGUGUCAUACUCAUCAACGGAGUGUUGACUAAGCCGGUACGUUCAGGGA

GGGUGAACGUCACAUAGUCCGACUACACACCAGACACGUUUGACCCUCAGU

CGAUUAACUGCAAGUCGCAAACAAGCUGACGUACAGUAACGACUCGUCACU

GUACUGAUGAUUCCACAACUGCUAAUGCACGUCUGUCCUGGGGAGGGCAGG

ACAGCGGAGUAGUGUGUCAGAUCGACAAGACUUAACCACGAUUCCUGAUGC

AUUGACUUACCAUCGACUCAACUGACAAGGGACCACGCAGAGGUGAAUGAG

UCAGGACUUUGUAGUCGGAGUCGGGUUACUGGAGGGAGGGUCCAGUAGACA

CCAGUCACAAUGUAUCGUACGCUUGCUACUAGGAGCUCGUCAUGACGUUGA

GAGCCUGUUAACUAGACACGUUCCUAAGGGUUAGCCACACAUUAAUAUCGG

GCCUGACACAGGACACGAAUACCUCGGGGAGGGCGAGGUAUCGAAGGUGCU

GUUAGUUGGACAGGUACUAUCAUCUCAAGUCGAUAGUCCAAGUAGGUUUGA

ACCAUGCAUAGCUUGUAUCAGGUCAUCGCCUCAAACGUUAGGUGUCACAUU

GUGGAAUCGCGUGUAUGACGGGAGGGGUCAUACCUCAUACCGACUUCCAUU

AUGGGACACGUCGCUUAUUCUUGGUAAGUAGAAGUUGCCAUCGUAGUCGCA

CGACCUACUUAUGACGAACUUCGGUUAAGUGGCUGACGUACUAACAGUGCG

UGCAGUUUGUCAGGGAGGGUGACAAACAGACCUACGAAGCCAGAGUUCGUU

CCAGUGUGAAAGUGCACAUCACGAGUUGUGCCAAUGCACGUUGCAUCGAGA

GUUAAUCCCGUCUUUAAGUAGCAAGGCACCUGAAUGGAAGUUGAUUCGUCUA

GAAAUAGACGAAUCAUGCUGAUCUCAGGUGCUCACUUGAUUAAGACGGCUG

UUUAUCUCGAUGCCUUCAAUGUUGGCACAAAUGCAUCAGUGCACUUAUGAU

AGUGAACGAACUCUGGCUUCGUAGGUCUCUGAUUCGGGGAGGGCGAAUCAG

UGCACGCAAGCAUGUAACGUCAGCCUAACGCUUGAAGUUCGCAGGUGUGAG

GUCGUGCCUUGUUUGUGGCAACUGUCAUGACCCAAGAAUAAGCGACGUGUC

CCAUAGAUCAGCACGGUAUGAGCGUUACAGGGAGGGUGUAACGACGCGAUU

CGUGAGGUAGACACCUAGAUACUCUGGCGAUGACAGUCAUUGAGCUAUGCG

AGUCGAUAACCUACUUGGACUAUCGACUUGAGUCACACUGACCUGUCCAUA

CAUGCUCACCUUCGUUGCACCAGGGAGGGUGUGCAAUCGUGUCCGCACUA

UAGCCCGAUAUCUCGUACAGGCUAACCUCGUUACUCGUGUCUAGUUAACAG

GCUCUCAACUCUACUUAGAGCUCCUAUCAAGUGACGUACGAUUACCUCACA

CUGGUGUCUCGAUCAGGGAGGGUGAUCGAACCCGACUCAAGAUUUGAAGUC

CUGUGAGUAUGACCUCUGCGUGGUCCCUUGUCAGUUAUGGUUCAGGUAAGU

CACUCGUGAUGGAAUCGUAAGCGUUACUUGUCGAUUAUAGUGCCUACUCCG

AUCUUCAGGGGAGGGCUGAAGAUACGUGCAUCUUGAUCAGUGGAAUCAUCA

GUACAGUGACGAGCUUAGGAAGUACGUCAGGACUACGACGACUUGCAUAAA

CAGGACUGAGGGAGAGUAUCGUCUGGUGCAAAUCUUGACUAUGUGUGCUAC

AGGGAGGGUGUAGCAACCGGCUUAGUCAACACUCCGUUGAACUCAUUCACA

CGAACGCUGAUACAGCUCUUCGAACGUGCAUAGCACUGACACACCUGUGUU

UCAUUGUACGAGCGCUCAGCGUGAUCAAGUGGCUAGUGUUCGCUCGAG 3'
```

Thus, in certain embodiments, the RNA nanostructure is a rectangle RNA nanostructure comprising a nucleic acid sequence having at least about 60% sequence identity to SEQ ID NO:3. In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:3. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:3. Thus, in certain embodiments, the RNA nanostructure comprises SEQ ID NO:3. In certain embodiments, the RNA nanostructure consists of SEQ ID NO:3.

In certain embodiments, the loop regions in SEQ ID NO:1 are replaced with C-rich loops:

```
                                               (SEQ ID NO: 4)
5'GGGAGAGAGCUCGAGCGAACACUAGCCACUUGAUCACGCUGAGCGCUCG

UACAAUGAAACACAGGUGUGUCAGUGCUAUGCACGUUCGAAGAGCUGUAUC

AGCGUUCGUGUGAAUGAGUUCAACGGAGUGUUGACUAAGCCGGUUGCUACA

CCCUCCCUGUAGCACACAUAGUCAAGAUUUGCACCAGACGAUACUCUCCCU
```

-continued

CAGUCCUGUUUAUGCAAGUCGUCGUAGUCCUGACGUACUUCCUAAGCUCGU
CACUGUACUGAUGAUUCCACUGAUCAAGAUGCACGUAUCUUCAGCCCUCCC
CUGAAGAUCGGAGUAGGCACUAUAAUCGACAAGUAACGCUUACGAUUCCAU
CACGAGUGACUUACCUGAACCAUAACUGACAAGGGACCACGCAGAGGUCAU
ACUCACAGGACUUCAAAUCUUGAGUCGGGUUCGAUCACCCUCCCUGAUCGA
GACACCAGUGUGAGGUAAUCGUACGUCACUUGAUAGGAGCUCUAAGUAGAG
UUGAGAGCCUGUUAACUAGACACGAGUAACGAGGUUAGCCUGUACGAGAUA
UCGGGCUAUAGUGCGGACACGAUUGCACCACCCUCCCUGGUGCAACGAAGG
UGAGCAUGUAUGGACAGGUCAGUGUGACUCAAGUCGAUAGUCCAAGUAGGU
UAUCGACUCGCAUAGCUCAAUGACUGUCAUCGCCAGAGUAUCUAGGUGUCU
ACCUCACGAAUCGCGUCGUUACACCCUCCCUGUAACGCUCAUACCGUGCUG
AUCUAUGGGACACGUCGCUUAUUCUUGGGUCAUGACAGUUGCCACAAACAA
GGCACGACCUCACACCUGCGAACUUCAAGCGUUAGGCUGACGUUACAUGCU
UGCGUGCACUGAUUCGCCCUCCCCGAAUCAGAGACCUACGAAGCCAGAGUU
CGUUCACUAUCAUAAGUGCACUGAUGCAUUUGUGCCAACAUUGAAGGCAUC
GAGAUAAACAGCCGUCUUAAUCAAGUGAGCACCUGAGAUCAGCAUGAUUCG
UCUAUUUCUAGACGAAUCAACUUCCAUUCAGGUGCCUUGCUACUUAAGACG
GGAUUAACUCUCGAUGCAACGUGCAUUGGCACAACUCGUGAUGUGCACUUU
CACACUGGAACGAACUCUGGCUUCGUAGGUCUGUUUGUCACCCUCCCUGAC
AAACUGCACGCACUGUUAGUACGUCAGCCACUUAACCGAAGUUCGUCAUAA
GUAGGUCGUGCGACUACGAUGGCAACUUCUACUUACCAAGAAUAAGCGACG
UGUCCCAUAAUGGAAGUCGGUAUGAGGUAUGACCCCUCCCGUCAUACACGC
GAUUCCACAAUGUGACACCUAACGUUUGAGGCGAUGACCUGAUCAAGCUA
UGCAUGGUUCAAACCUACUUGGACUAUCGACUUGAGAUGAUAGUACCUGUC
CAACUAACAGCACCUUCGAUACCUCGCCCUCCCCGAGGUAUUCGUGUCCUG
UGUCAGGCCCGAUAUUAAUGUGUGGCUAACCCUUAGGAACGUGUCUAGUUA
ACAGGCUCUCAACGUCAUGACGAGCUCCUAGUAGCAAGCGUACGAUACAUU
GUGACUGGUGUCUACUGGACCCUCCCUCCAGUAACCCGACUCCGACUACAA
AGUCCUGACUCAUUCACCUCUGCGUGGUCCCUUGUCAGUUGAGUCGAUGGU
AAGUCAAUGCAUCAGGAAUCGUGGUUAAGUCUUGUCGAUCUGACACACUAC
UCCGCUGUCCUGCCCUCCCCAGGACAGACGUGCAUUAGCAGUUGUGGAAUC
AUCAGUACAGUGACGAGUCGUUACUGUACGUCAGCUUGUUUGCGACUUGCA
GUUAAUCGACUGAGGGUCAAACGUGUCUGGUGUGUAGUCGGACUAUGUGAC
GUUCACCCUCCCUGAACGUACCGGCUUAGUCAACACUCCGUUGAUGAGUAU
GACACGAACGAGUCAUUGGCUCUUCGCUUCAAUGUAGCACUGAACUUAUGA
UGUUUCAUACACAUUACGCUCAGCGAACUGCUAUGGCUAGUGUUCGGAUCC
3'

Thus, in certain embodiments, the RNA nanostructure is a rectangle RNA nanostructure comprising a nucleic acid sequence having at least about 60% sequence identity to SEQ ID NO:4. In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:4. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:4. Thus, in certain embodiments, the RNA nanostructure comprises SEQ ID NO:4. In certain embodiments, the RNA nanostructure consists of SEQ ID NO:4.

In certain embodiments, the loop regions in SEQ ID NO:1 are replaced with A-rich loops:

(SEQ ID NO: 5)
5'GGGAGAGGAUCCGAACACUAGCCAUAGCAGUUCGCUGAGCGUAAUGUGU
AUGAAACAUCAUAAGUUCAGUGCUACAUUGAAGCGAAGAGCCAAUGACUCG
UUCGUGUCAUACUCAUCAACGGAGUGUUGACUAAGCCGGUACGUUCAAAAG
AAAUGAACGUCACAUAGUCCGACUACACACCAGACACGUUUGACCCUCAGU
CGAUUAACUGCAAGUCGCAAACAAGCUGACGUACAGUAACGACUCGUCACU
GUACUGAUGAUUCCACAACUGCUAAUGCACGUCUGUCCUGAAAGAAACAGG
ACAGCGGAGUAGUGUGUCAGAUCGACAAGACUUAACCACGAUUCCUGAUGC
AUUGACUUACCAUCGACUCAACUGACAAGGGACCACGCAGAGGUGAAUGAG
UCAGGACUUUGUAGUCGGAGUCGGGUUACUGGAAAAGAAAUCCAGUAGACA
CCAGUCACAAUGUAUCGUACGCUUGCUACUAGGAGCUCGUCAUGACGUUGA
GAGCCUGUUAACUAGACACGUUCCUAAGGGUUAGCCACACAUUAAUAUCGG
GCCUGACACAGGACACGAAUACCUCGAAAGAAACGAGGUAUCGAAGGUGCU
GUUAGUUGGACAGGUACUAUCAUCUCAAGUCGAUAGUCCAAGUAGGUUUGA
ACCAUGCAUAGCUUGUAUCAGGUCAUCGCCUCAAACGUUAGGUGUCACAUU
GUGGAAUCGCGUGUAUGACAAAGAAAGUCAUACCUCAUACCGACUUCCAUU
AUGGGACACGUCGCUUAUUCUUGGUAAGUAGAAGUUGCCAUCGUAGUCGCA
CGACCUACUUAUGACGAACUUCGGUUAAGUGGCUGACGUACUAACAGUGCG
UGCAGUUUGUCAAAAGAAAUGACAAACAGACCUACGAAGCCAGAGUUCGUU
CCAGUGUGAAAGUGCACAUCACGAGUUGUGCCAAUGCACGUUGCAUCGAGA
GUUAAUCCCGUCUUAAGUAGCAAGGCACCUGAAUGGAAGUUGAUUCGUCUA
GAAAUAGACGAAUCAUGCUGAUCUCAGGUGCUCACUUGAUUAAGACGGCUG
UUUAUCUCGAUGCCUUCAAUGUUGGCACAAAUGCAUCAGUGCACUUAUGAU
AGUGAACGAACUCUGGCUUCGUAGGUCUCUGAUUCGAAAGAAACGAAUCAG
UGCACGCAAGCAUGUAACGUCAGCCUAACGCUUGAAGUUCGCAGGUGUGAG
GUCGUGCCUUGUUUGUGGCAACUGUCAUGACCCAAGAAUAAGCGACGUGUC
CCAUAGAUCAGCACGGUAUGAGCGUUACAAAAGAAAUGUAACGACGCGAUU
CGUGAGGUAGACACCUAGAUACUCUGGCGAUGACAGUCAUUGAGCUAUGCG
AGUCGAUAACCUACUUGGACUAUCGACUUGAGUCACACUGACCUGUCCAUA
CAUGCUCACCUUCGUUGCACCAAAAGAAAUGGGUGCAAUCGUGUCCGCACUA
UAGCCCGAUAUCUCGUACAGGCUAACCUCGUUACUCGUGUCUAGUUAACAG
GCUCUCAACUCUACUUAGAGCUCCUAUCAAGUGACGUACGAUUACCUCACA

-continued

CUGGUGUCUCGAUCAAAAGAAAUGAUCGAACCCGACUCAAGAUUUGAAGUC

CUGUGAGUAUGACCUCUGCGUGGUCCCUUGUCAGUUAUGGUUCAGGUAAGU

CACUCGUGAUGGAAUCGUAAGCGUUACUUGUCGAUUAUAGUGCCUACUCCG

AUCUUCAGAAAGAAACUGAAGAUACGUGCAUCUUGAUCAGUGGAAUCAUCA

GUACAGUGACGAGCUUAGGAAGUACGUCAGGACUACGACGACUUGCAUAAA

CAGGACUGAGGGAGAGUAUCGUCUGGGUGCAAAUCUUGACUAUGUGUGCUAC

AAAAGAAAUGUAGCAACCGGCUUAGUCAACACUCCGUUGAACUCAUUCACA

CGAACGCUGAUACAGCUCUUCGAACGUGCAUAGCACUGACACACCUGUGUU

UCAUUGUACGAGCGCUCAGCGUGAUCAAGUGGCUAGUGUUCGCUCGAG 3'

Thus, in certain embodiments, the RNA nanostructure is a rectangle RNA nanostructure comprising a nucleic acid sequence having at least about 60% sequence identity to SEQ ID NO:5. In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:5. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:5. Thus, in certain embodiments, the RNA nanostructure comprises SEQ ID NO:5. In certain embodiments, the RNA nanostructure consists of SEQ ID NO:5.

In certain embodiments, the loop regions in SEQ ID NO:1 are replaced with U-rich loops:

(SEQ ID NO: 6)
5'GGGAGAGAGCUCGAGCGAACACUAGCCACUUGAUCACGCUGAGCGCUCG

UACAAUGAAACACAGGUGUGUCAGUGCUAUGCACGUUCGAAGAGCUGUAUC

AGCGUUCGUGUGAAUGAGUUCAACGGAGUGUUGACUAAGCCGGUUGCUACA

UUUCUUUUGUAGCACACAUAGUCAAGAUUUGCACCAGACGAUACUCUCCCU

CAGUCCUGUUUAUGCAAGUCGUCGUAGUCCUGACGUACUUCCUAAGCUCGU

CACUGUACUGAUGAUUCCACUGAUCAAGAUGCACGUAUCUUCAGUUUCUUU

CUGAAGAUCGGAGUAGGCACUAUAAUCGACAAGUAACGCUUACGAUUCCAU

CACGAGUGACUUACCUGAACCAUAACUGACAAGGGACCACGCAGAGGUCAU

ACUCACAGGACUUCAAAUCUUGAGUCGGGUUCGAUCAUUUCUUUUGAUCGA

GACACCAGUGUGAGGUAAUCGUACGUCACUUGAUAGGAGCUCUAAGUAGAG

UUGAGAGCCUGUUAACUAGACACGAGUAACGAGGUUAGCCUGUACGAGAUA

UCGGGCUAUAGUGCGGACACGAUUGCACCAUUUCUUUUGGUGCAACGAAGG

UGAGCAUGUAUGGACAGGUCAGUGUGACUCAAGUCGAUAGUCCAAGUAGGU

UAUCGACUCGCAUAGCUCAAUGACUGUCAUCGCCAGAGUAUCUAGGUGUCU

ACCUCACGAAUCGCGUCGUUACAUUUCUUUUGUAACGCUCAUACCGUGCUG

AUCUAUGGGACACGUCGCUUAUUCUUGGGUCAUGACAGUUGCCACAAACAA

GGCACGACCUCACACCUGCGAACUUCAAGCGUUAGGCUGACGUUACAUGCU

UGCGUGCACUGAUUCGUUUCUUUCGAAUCAGAGACCUACGAAGCCAGAGUU

CGUUCACUAUCAUAAGUGCACUGAUGCAUUUGUGCCAACAUUGAAGGCAUC

GAGAUAAACAGCCGUCUUAAUCAAGUGAGCACCUGAGAUCAGCAUGAUUCG

UCUAUUUCUAGACGAAUCAACUUCCAUUCAGGUGCCUUGCUACUUAAGACG

GGAUUAACUCUCGAUGCAACGUGCAUUGGCACAACUCGUGAUGUGCACUUU

CACACUGGAACGAACUCUGGCUUCGUAGGUCUGUUUGUCAUUUCUUUUGAC

AAACUGCACGCACUGUUAGUACGUCAGCCACUUAACCGAAGUUCGUCAUAA

GUAGGUCGUGCGACUACGAUGGCAACUUCUACUUACCAAGAAUAAGCGACG

UGUCCCAUAAUGGAAGUCGGUAUGAGGUAUGACUUUCUUUGUCAUACACGC

GAUUCCACAAUGUGACACCUAACGUUUGAGGCGAUGACCUGAUACAAGCUA

UGCAUGGUUCAAACCUACUUGGACUAUCGACUUGAGAUGAUAGUACCUGUC

CAACUAACAGCACCUUCGAUACCUCGUUUCUUUCGAGGUAUUCGUGUCCUG

UGUCAGGCCCGAUAUUAAUGUGUGGCUAACCCUUAGGAACGUGUCUAGUUA

ACAGGCUCUCAACGUCAUGACGAGCUCCUAGUAGCAAGCGUACGAUACAUU

GUGACUGGUGUCUACUGGAUUUCUUUUCCAGUAACCCGACUCCGACUACAA

AGUCCUGACUCAUUCACCUCUGCGUGGUCCCUUGUCAGUUGAGUCGAUGGU

AAGUCAAUGCAUCAGGAAUCGUGGUUAAGUCUUGUCGAUCUGACACACUAC

UCCGCUGUCCUGUUUCUUUCAGGACAGACGUGCAUUAGCAGUUGUGGAAUC

AUCAGUACAGUGACGAGUCGUUACUGUACGUCAGCUUGUUUGCGACUUGCA

GUUAAUCGACUGAGGGUCAAACGUGUCUGGUGUGUAGUCGGACUAUGUGAC

GUUCAUUUCUUUUGAACGUACCGGCUUAGUCAACACUCCGUUGAUGAGUAU

GACACGAACGAGUCAUUGGCUCUUCGCUUCAAUGUAGCACUGAACUUAUGA

UGUUUCAUACACAUUACGCUCAGCGAACUGCUAUGGCUAGUGUUCGGAUCC 3'

Thus, in certain embodiments, the RNA nanostructure is a rectangle RNA nanostructure comprising a nucleic acid sequence having at least about 60% sequence identity to SEQ ID NO:6. In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:6. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:6. Thus, in certain embodiments, the RNA nanostructure comprises SEQ ID NO:6. In certain embodiments, the RNA nanostructure consists of SEQ ID NO:6.

Figure 40:
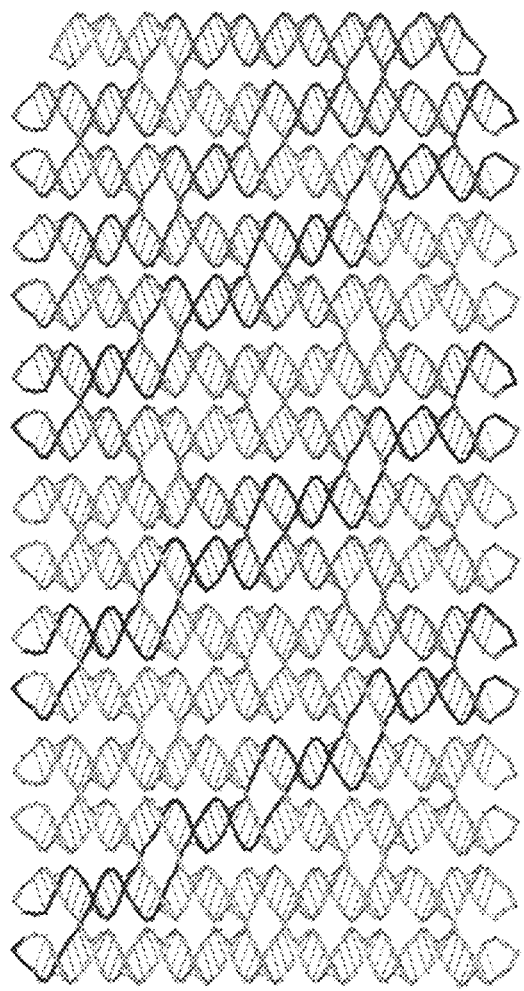
FIG. 40. RNA rectangle origami #2 (see, e.g., SEQ ID NO: 7).

In certain embodiments, the RNA nanostructure is a rectangle RNA nanostructure comprising a nucleic acid sequence having at least about 60% sequence identity to SEQ ID NO:7 (see, e.g., FIG. 40):

(SEQ ID NO: 7)
5'GGGAGAGAGCUCGAGCGAACACUAGCCACUUGAUCACUCGUGCUUCUCG
UACAUGGAAGCCCAGGUGUGGAGAUAAGGUCUUAGGUUUUCCUAAGAUGAG
CGUUUAACGUGCAUCUUGACUCUGAUACAAUUCCAUAGACUCAUUCAUGUC
GCAUACCUCUGUUUUCAGAGGUAACCACGGGUGUAGUCGACUGCGUAGUCA
AACGUCGAUCUACAGCUAAUCGAGGCUUUCUCCAUCGUUUUCGAUGGAAUG
AUUCGGCAAACUAGGACACGAGAGUAACGAAGGAAUGUACAAUCGACUCGA
CAUUCAACCAGCUUUUGCUGGUUGGAUCGUCGUGUGUCAGGCGUUGUCCAC
UUAACCAGUAGACCCUAAACAGUCACUGACGACUAUGCUUUUGCAUAGUUA
UGGUACAAUGCAUCAUGUACGAGGAGUCGAUGCCAUAUAGUGAGUAUGCAC
GUGAGAGACGAACUUUUGUUCGUCUUGACUUACUACCUCACUAUGCUAGAU
CAAGUGAUCGGGAUUUCAUAAGUGUUAAGGGCAUCGCUAUUUUUAGCGAUC
GCAAGUGGUGCUGAUCACGACCAUAUAGAAGUCAUGGAAACUGAUCAAGUA
GAUGGUGUGGCUUGUUUUCAAGCCACUUGCGUAUGUCAUGACAAAGCCUUA
GUAGCAAGAUGGGACUUGCACGUUCUCAUUGGCGCAUAGGUUUUCCUAUGC
UUCAGGAGUUACAUGCUGUACCUCAAUGGUUCAUCCAUGCCGCGACUACAG
CAGCAACAAUGAUCGUUUUCGAUCAUUCAUAGGGUCAGUGUGACGUGAAUC
GUAACGCUUAUGAACCACUAGUUUGCAGGGUUGUAUAUGCGUUUUCGCAUA
UCACUCCACUGGCCUAAUUCGAUACCUUCCUAAGCUCCGCGACCUGACACA
GUUAGCUCUGUCGAACUUUUGUUCGACAAGGCACUUACUAUCAUGUUCGAU
ACAGAGUAUCUGACUGUGUGAUGCAUAAGCAAUGGCCACAGCUUUUGCUGU
GGACCAGCAGUACUAACAGCUUAAGAGAGUCAUUGUGUUAUGUCGUGAGGU
ACAGCUCACGUCAGAUCUUUUGAUCUGACUGGUCGAAUCUACGUACUGGUU
CAAUAAUGUGUCGUAAUCGGAUCAGCAUGAUUCGUCUAUUUCUAGACGAAU
CAACUUCCAUCGAUUACGUGUACGAGUUGAACCAGGUCAUGACUUCGACCA
ACCACCUGUUUUCAGGUGGUGUGAGCUGACAUUGUGGACAUAACAUGUAUC
AGCUCUUAAGAGCAUGUAACUGCUGGUAACGACGUUUUCGUCGUUCCAUUG
CUUCUCGUGAUCACAGUCAACGUUUGAGUAUCGAACUCACACUGAAGUGCC
UCUGGUAUGUUUCAUACCAGGAGCUAACGCACUAUAGUCGCGGAGUCGUU
ACUGGUAUCGAAUUAGGCCAGUGGAGUGCUUUAGCUUUUGCUAAAGACAAC
CCUGUCGUAGUCUGGUUCAUGGUUAAGUCGAUUCACGAUGAUAGUACCCUA
UGGAUCUUACUUUUGUAAGAUCGUUGCUGCACAAUCUUCGGCAUGGAAUCG
ACUCUGAGGUACCUGUUAGUACUCCUGAAAUGUCACUUUUGUGACAUGCCA
AUGAGGUUCAAUGAGUCCCAUUCACUUGAUAAGGCUUUUACGUAGAAUACG
CAACUACUAACUUUUGUUAGUAGACCAUCUAUAGCAGUUGUUUCCAUGACU
UCUAUAUGGUCGUAUGGAAGUCCACUUGCGUGAACGAUUUUUCGUUCAGCC
CUUAACCACACCUGAAUCCCGACUUGCUACUCUAGCAUACACAAUGUGUAA
GUCAGGCUCUGGUUUUCCAGAGCCCUCACGUGGAAUGAGUCUAUAUGGCUG
AACCAUCUCGUACAAUCACGAGUGUACCAUAGUAUGAGUUUUCUCAUACCG
UCAGUGAGAUUAGCUGGUCUACUAAGCGUUAGGACAACGCUAUAGUGCCGA
CGAUCUCUAGUCGUUUCGACUAGAAAUGUCGAGUCGAUUGUACAUUCCUC

UUAGGAACUCGUGUCGACUACGACCGAAUCAUAGUAACCUUUUGGUUACUG
AAAGCCUCCUGUUUAGGUAGAUCGGAUACUCUCUACGCAGUAAGAUUGUCC
CGUGGUAGAUCCUCUUUUGAGGAUCUUGCGACAUCAUACUCACUAUGGAAU
CAAUGACUAGUCAAGACAUUGAACAAACGCUCAAGUCAUCUUUUGAUGACU
CCUUAUCUCACUUAUGAGGCUUCCAACACAUUAAAGCACGAGAACUGCUAU
GGCUAGUGUUCGGAUCC 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:7. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:7. Thus, in certain embodiments, the RNA nanostructure comprises SEQ ID NO:7. In certain embodiments, the RNA nanostructure consists of SEQ ID NO:7.

Figure 41:
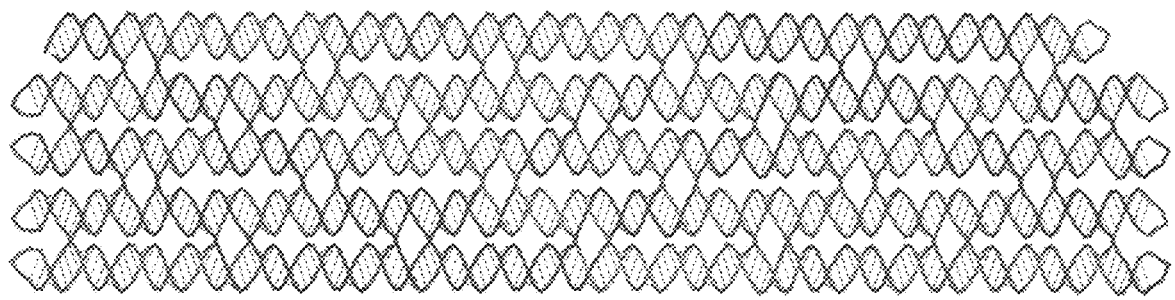
FIG. 41. RNA rectangle origami #3 (see, e.g., SEQ ID NO: 8).

In certain embodiments, the RNA nanostructure is a rectangle RNA nanostructure comprising a nucleic acid sequence having at least about 60% sequence identity to SEQ ID NO:8 (see, e.g., FIG. 41):

(SEQ ID NO: 8)
5'GGGAGAGAGCUCGAGCGAACACUAGCCACUUGAUCAACUGGACAUACAU
UGUGUUCAUGCCUGUAGUCGAUCUGAAUGGCACUAUAUCCAUAAACACACG
UCGCUGCGUAGGACUACGACGAAAAUGAGAGUAUCCACAGCAUACAUACUC
AGAUAGUGGUCAUAAGUCUGCUGUGCAUCGAGAACAGAAGAAGUAGCAAGG
AGCUCAUCACAGUCGUUUCGACUGUGCAGUUGUAGAUUAGCUACCGGUUG
AUGAAACCAUUAAUGAAGCCCACCCGGACUGAUUUCCUAAGAACUCUUGUG
AUACUCUCCUUGGUUAGUCAUUGCGGGAGUGAACACAUUAGUGAACAUGAA
GCCAUAAUGCGAUGACUUCCAUGGAGCAAACACAAUGUAGAAACUCAAUGG
UUCAGCCGGAUUCUAAGUCGUUUUCGACUUAGGAUAGUAGGGAGAUGGACG
AUUCGGACUUAACCUAGCUUGUACAAUCUUAUCUAGGCACAUUGAACUAGA
AGGGUAAUGUGUGGACCUUUCUACUUUGUCAAUAUCCGUCAUGACUCAGGG
ACUGAAUGAGUGCUGAUCGCAGUGUGACCAUCCCCGGGUUUCAUAGCCUGG
GGAAAACAAGCCCUUACAGUAGCACUUUUGUGCUACCGUUCGGUCCUGUUU
AGUUUGCAGAACUAACAGUGCCAAAGUACUUAUGACUCCCUUGAUAUAGAC
UAUGCUUAGGUCAUGACAGGAGCUGCUGAUACAGGAACCAAUCUCGUGAUG
AGUAACCUAUAGUGCAACUACUUCAUACGCAUGUAACAAAGGUUAAGUGCC
GACUUCAAGUCGAUGUGCCGACAGUAACACUUUUGUGUUACUCAUACUUGU
AGCAGUUUCACAGAAUCUACACAUACUCUGGAAUGGAAGUGCGUGUGUUUG
CACGUUGCUGAUUGAUCACGAGACAAGGGAACUAGUUUGUCAAUUUCACAA
GCACCUACGACGUCUUAGGAAGUAAGUCGACUAUCAUCCCUUGUUCCUGUU

-continued

AGUAAGCACUGUCAAGUGAUACUGCUCUAUUUCUAGAGCAGUACUUGCUAC

CAGUGCUUUACAUGCUGAACAAGGGUCACACUGCGACUUACAGUAACGAAC

GUCGUAGGUGCUUGUGAAAUUGAUCGUAGUCUUCCCUUGUAUGCAUCACAA

UCAGCGUUCAAUGAACACACGCUGCUGAUCUCCAGAGUAUGUGUAGAUUCU

GUGAUGAUCAAGCAAGUAUGCUGCGUAGUUUUCUACGCAGGUCGGCACUGA

ACCAUGAAGUCGGCUAACGCUUUUUGUUACAUGCGUAUGAAGUAGUUUGUG

UCAGGGUUACUCUGAUGCAUAUUGGUUCCCAAUGACUCAGCUCCUUCUACG

UACUAAGCAUAGUCUAUAUCAAGGGAGCAGGUGUGACUUUGGCAAGCAUGU

AUCUGCAAAAGCUAAUCGACCGAACGUCGGUCGUUUUCGACCGAUGUAAGG

GCUUGUUUUCCCCAGGCUCCGUAUGACGGGGAUGGAUGAUAGUCGAUCAGC

UGAGUAUGAGUCCCUGAUACGUAGAGGAUAUUGACAAAGUAGAAAGGUCCU

GUACGAGCCCUUCUAAACGUGCAUGCCUAGAUCGACUACAACAAGCUAAAG

CGUUACCGAAUCGUCCAUCUCCCUACUAUCGUCACAACUUUUGUUGUGACA

AUCCGGCAUCGACUUUGAGUUUCUUACCUCACUUUGCUCCGAUCAGCACAU

CGCAUUAUGGCUUCAUGUUCACCUCGUACAUCACUCCCGUGUAUCAGAACC

AAGGUCAAACGUACAAGAGUUUCGUUACUAUCAGUCCGGGUGGGCUUCAUU

AAUUCAUACGGCAACCGGUCUAAACAGUACAACUGCGUUACCCUUUUGGGU

AACGAUGAGCUCUCACUUGAUUCUUCUGUUCUCGAUGCACAGCAGCACACC

UGCCACUAUCACUCAUUCUAUGCUGUGACGUUUGACAUUUUCGCAAACUAG

CUACGCAGCGACGUGUGUUUAUGGACUGACACACAUUCAGAUAAGAUUGUG

GCAUGAAGUGAGGUAAUGUCCAGUAACUGCUAUGGCUAGUGUUCGGAUCC

3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8. Thus, in certain embodiments, the RNA nanostructure comprises SEQ ID NO:8. In certain embodiments, the RNA nanostructure consists of SEQ ID NO:8.

In certain embodiments, the RNA nanostructure is a rectangle RNA nanostructure comprising a nucleic acid sequence having at least about 60% sequence identity to SEQ ID NO:9 (see, e.g., Example 1, sense version):

(SEQ ID NO: 9)
5'GGGAGAGGAUCCGAACACUAGCCAUAGCAGUUCGCUGAGCGUAAUGUGU

AUGAAACAUCAUAAGUUCAGUGCUACAUUGAAGCGAAGAGCCAAUGACUCG

UUCGUGUCAUACUCAUCAACGGAGUGUUGACUAAGCCGAAAAAACAUAGUC

CGACUACACACCAGACACGUUUGACCCUCAGUCGAUUAACUGCAAGUCGCA

-continued

AACAAGCUGACGUACAGUAACGACUCGUCACUGUACUGAUGAUUCCACAAC

UGCUAAUGCACGAAAAAAGGAGUAGUGUGUCAGAUCGACAAGACUUAACCA

CGAUUCCUGAUGCAUUGACUUACCAUCGACUCAACUGACAAGGGACCACGC

AGAGGUGAAUGAGUCAGGACUUUGUAGUCGGAGUCGGAAAAAACACCAGUC

ACAAUGUAUCGUACGCUUGCUACUAGGAGCUCGUCAUGACGUUGAGAGCCU

GUUAACUAGACACGUUCCUAAGGGUUAGCCACACAUUAAUAUCGGGCCUGA

CACAGGACACGAAAAAAGAAGGUGCUGUUAGUUGGACAGGUACUAUCAUCU

CAAGUCGAUAGUCCAAGUAGGUUUGAACCAUGCAUAGCUUGUAUCAGGUCA

UCGCCUCAAACGUUAGGUGUCACAUUGUGGAAUCGCAAAAAACAUACCGAC

UUCCAUUAUGGGACACGUCGCUUAUUCUUGGUAAGUAGAAGUUGCCAUCGU

AGUCGCACGACCUACUUAUGACGAACUUCGGUUAAGUGGCUGACGUACUAA

CAGUGCGUGCAAAAAAGACCUACGAAGCCAGAGUUCGUUCCAGUGUGAAAG

UGCACAUCACGAGUUGUGCCAAUGCACGUUGCAUCGAGAGUUAAUCCCGUC

UUAAGUAGCAAGGCACCUGAAUGGAAGUUGAUUCGUCUAGAAAUAGACGAA

UCAUGCUGAUCUCAGGUGCUCACUUGAUUAAGACGGCUGUUUAUCUCGAUG

CCUUCAAUGUUGGCACAAAUGCAUCAGUGCACUUAUGAUAGUGAACGAACU

CUGGCUUCGUAGGUCAAAAAAGCACGCAAGCAUGUAACGUCAGCCUAACGC

UUGAAGUUCGCAGGUGUGAGGUCGUGCCUUGUUUGUGGCAACUGUCAUGAC

CCAAGAAUAAGCGACGUGUCCCAUAGAUCAGCACGGUAUGAAAAAAGCGAU

UCGUGAGGUAGACACCUAGAUACUCUGGCGAUGACAGUCAUUGAGCUAUGC

GAGUCGAUAACCUACUUGGACUAUCGACUUGAGUCACACUGACCUGUCCAU

ACAUGCUCACCUUCAAAAAACGUGUCCGCACUAUAGCCCGAUAUCUCGUAC

AGGCUAACCUCGUUACUCGUGUCUAGUUAACAGGCUCUCAACUCUACUUAG

AGCUCCUAUCAAGUGACGUACGAUUACCUCACACUGGUGAAAAAACCGACU

CAAGAUUUGAAGUCCUGUGAGUAUGACCUCUGCGUGGUCCCUUGUCAGUUA

UGGUUCAGGUAAGUCACUCGUGAUGGAAUCGUAAGCGUUACUUGUCGAUUA

UAGUGCCUACUCCAAAAAACGUGCAUCUUGAUCAGUGGAAUCAUCAGUACA

GUGACGAGCUUAGGAAGUACGUCAGGACUACGACGACUUGCAUAAACAGGA

CUGAGGGAGAGUAUCGUCUGGUGCAAAUCUUGACUAUGAAAAAACGGCUUA

GUCAACACUCCGUUGAACUCAUUCACACGAACGCUGAUACAGCUCUUCGAA

CGUGCAUAGCACUGACACACCUGUGUUUCAUUGUACGAGCGCUCAGCGUGA

UCAAGUGGCUAGUGUUCGCUCGAGCUCUCUCCCUUUAGUGAGGGUUAAUUA

AGCU 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:9. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:9. Thus, in certain embodiments, the RNA nanostructure comprises SEQ ID NO:9. In certain embodiments, the RNA nanostructure consists of SEQ ID NO:9.

In certain embodiments, the RNA nanostructure is a rectangle RNA nanostructure comprising a nucleic acid sequence having at least about 60% sequence identity to SEQ ID NO:10 (see, e.g., Example 1, anti-sense version):

(SEQ ID NO: 10)
5'GGGAGAGAGCUCGAGCGAACACUAGCCACUUGAUCACGCUGAGCGCUCG

UACAAUGAAACACAGGUGUGUCAGUGCUAUGCACGUUCGAAGAGCUGUAUC

AGCGUUCGUGUGAAUGAGUUCAACGGAGUGUUGACUAAGCCGUUUUUUCAU

AGUCAAGAUUUGCACCAGACGAUACUCUCCCUCAGUCCUGUUUAUGCAAGU

CGUCGUAGUCCUGACGUACUUCCUAAGCUCGUCACUGUACUGAUGAUUCCA

CUGAUCAAGAUGCACGUUUUUGGAGUAGGCACUAUAAUCGACAAGUAACG

CUUACGAUUCCAUCACGAGUGACUUACCUGAACCAUAACUGACAAGGGACC

ACGCAGAGGUCAUACUCACAGGACUUCAAAUCUUGAGUCGGUUUUUUCACC

AGUGUGAGGUAAUCGUACGUCACUUGAUAGGAGCUCUAAGUAGAGUUGAGA

GCCUGUUAACUAGACACGAGUAACGAGGUUAGCCUGUACGAGAUAUCGGGC

UAUAGUGCGGACACGUUUUUUGAAGGUGAGCAUGUAUGGACAGGUCAGUGU

GACUCAAGUCGAUAGUCCAAGUAGGUUAUCGACUCGCAUAGCUCAAUGACU

GUCAUCGCCAGAGUAUCUAGGUGUCUACCUCACGAAUCGCUUUUUUCAUAC

CGUGCUGAUCUAUGGGACACGUCGCUUAUUCUUGGGUCAUGACAGUUGCCA

CAAACAAGGCACGACCUCACACCUGCGAACUUCAAGCGUUAGGCUGACGUU

ACAUGCUUGCGUGCUUUUUUGACCUACGAAGCCAGAGUUCGUUCACUAUCA

UAAGUGCACUGAUGCAUUUGUGCCAACAUUGAAGGCAUCGAGAUAAACAGC

CGUCUUAAUCAAGUGAGCACCUGAGAUCAGCAUGAUUCGUCUAUUUCUAGA

CGAAUCAACUUCCAUUCAGGUGCCUUGCUACUUAAGACGGGAUUAACUCUC

GAUGCAACGUGCAUUGGCACAACUCGUGAUGUGCACUUUCACACUGGAACG

AACUCUGGCUUCGUAGGUCUUUUUUGCACGCACUGUUAGUACGUCAGCCAC

UUAACCGAAGUUCGUCAUAAGUAGGUCGUGCGACUACGAUGGCAACUUCUA

CUUACCAAGAAUAAGCGACGUGUCCCAUAAUGGAAGUCGUAUGUUUUUUG

CGAUUCCACAAUGUGACACCUAACGUUUGAGGCGAUGACCUGAUACAAGCU

AUGCAUGGUUCAAACCUACUUGGACUAUCGACUUGAGAUGAUAGUACCUGU

CCAACUAACAGCACCUUCUUUUUUCGUGUCCUGUGUCAGGCCCGAUAUUAA

UGUGUGGCUAACCCUUAGGAACGUGUCUAGUUAACAGGCUCUCAACGUCAU

GACGAGCUCCUAGUAGCAAGCGUACGAUACAUUGUGACUGGUGUUUUUUCC

GACUCCGACUACAAAGUCCUGACUCAUUCACCUCUGCGUGGUCCCUUGUCA

GUUGAGUCGAUGGUAAGUCAAUGCAUCAGGAAUCGUGGUUAAGUCUUGUCG

AUCUGACACACUACUCCUUUUUCGUGCAUUAGCAGUUGUGGAAUCAUCAG

UACAGUGACGAGUCGUUACUGUACGUCAGCUUGUUUGCGACUUGCAGUUAA

UCGACUGAGGGUCAAACGUGUCGGUGUGUAGUCGGACUAUGUUUUUUCGG

CUUAGUCAACACUCCGUUGAUGAGUAUGACACGAACGAGUCAUUGGCUCUU

CGCUUCAAUGUAGCACUGAACUUAUGAUGUUUCAUACACAUUACGCUCAGC

GAACUGCUAUGGCUAGUGUUCGGAUCCUCUCCCUAUAGUGAGUCGUAUUAG

AAUU 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:10. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:10. Thus, in certain embodiments, the RNA nanostructure comprises SEQ ID NO:10. In certain embodiments, the RNA nanostructure consists of SEQ ID NO:10.

In certain embodiments, the shape of the RNA nanostructure is a diamond.

Figure 42:
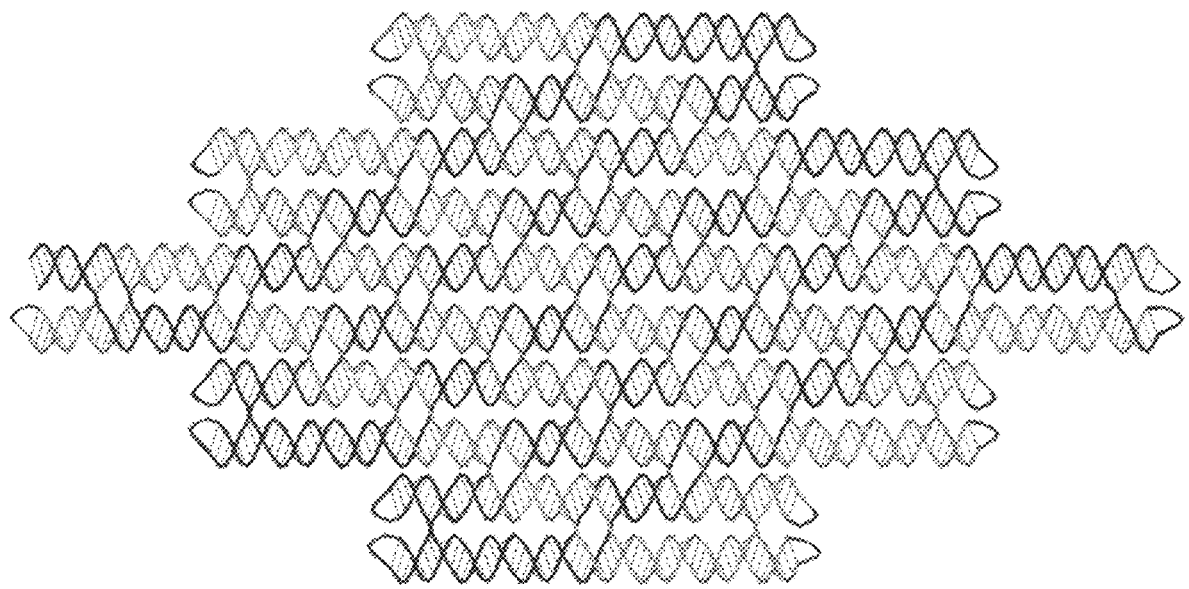
FIG. 42. RNA diamond origami #4 (see, e.g., SEQ ID NO: 11).

In certain embodiments, the RNA nanostructure is a diamond RNA nanostructure comprising a nucleic acid sequence having at least about 60% sequence identity to SEQ ID NO:11 (see, e.g., FIG. 42):

(SEQ ID NO: 11)
5' GGGAGAGAGCUCGAGCGAACACUAGACUUGAUCACUUCGUUUAGCGA

AAUCGACUCUGGAUAGUACAUUGAACGUGACUCCUCAUAAGUGCUUUGA

AGUAAUGUGUAGGCUAUAGAUCAGCACGGUCACUUAACAUUAGGCAACG

CUACUCAAUGUUUCAUUGAGUGCUACACUGUCAUGACUGUGCAUGACU

UGCUACAGUUUGUCCUGAUACAUACAGAUCCCGACUACAGUGCGACAGA

UUAGCUUGCCUUCAUGUUUGCCGUUUCGGCAAACCACACGCAUUGCAG

AUGCGCCACGACUUAGGAAGAAUGCAUGACUUAACCACAUCAGAUGAUG

CAUCCCGAUAGACAUACUCAAGACUAGUUACCUCACUAGCAACCUGGUG

CGAUGUUCAAAGCUACGUCGUUUUCGACGUAGCAUGGCGCUACAUGCUU

AAAGAAUAACGUUUGAAGGCGGCAUAUAGUGCAUAUGGCCGAUGAAACC

GGUGGCUAAGUUGACUUUUUCGAGAGAACAGGGUUUUCCCUGUUCGUAG

UGGUACACUCAGGUAUAAAAGAGUGCUAUCUCUAAUCUGAUAACUGGCC

ACUGGUGGUAUCUCGGUUUGAUGACUACGACAUUGUUCACUAUCAUAAU

GCUAGCCUGUUCACACCGACAGUCUCAAUGUUUUCAUUGAGAGUACGAG

UGAACGUCCACUUAUCUGAUGAUAGUUUGAUCUCACUAACAGCGAUAGC

CUGUGAGGUACAAUAUCCUACGUAGAUCCUCUUGGUGCUGAUCCCAAAG

UCUUAUCGAGAUCUCUAUAGUUAACCAGUUUUCUGGUUAAGAGAGCGACC

UCGUACAACCUAUACGUAGCAAGGCGACUGACGAAUGAGUCGUGGUUAU

CAAACGUAAGUUAGGCCUAGUUUGGACAUUCAUACAUGAGUUUUCUCAU

GUAGGGCAGUGAGUUGAUAUGUCCACCUAAGAUACCAAAUCCUCUCUGAC

ACAGUUUCAUGUAUGCAUCAACCCUUCGAGUCAUUGGUUAUCACCACUU

AUGAUAUAUCCCAGUCAGUCGUUCGAUCGUCUGCGUGUUUUCACGCAGA

GAAUUGCGCUGCACGUUCAUGUAUUUGUAGUCGGAAGAUAGCUAACGCU

-continued

UCACGUGGGGGUUUCAUAUAGUGUCGUGUAGACUCAGGAUCGACGUGAU

GUUUUCAUCACGUGUAGGUAAGUCACCAUAUUUUGGAAAUAGCACUGUG

UGUUGUACAGGAGAGUCCGUAAUUCCUAAGCACGUCUUCUGUUUAGGUU

UGGAGCGAGUCGAUACCUGCGACCGCUAUGAUCAAGGUCUCCAUCUAUU

UCUAGAUGGAGACUAGCAGUUUAGCGGUCGCAGGUUGAACCAUGCUCCA

AACAGCUAAUCAAGACGUGUCGUUACUUUACGGACUAGUCAACUCAACA

CACUCCUGAUGUUCAAAAUAUGGUGACUUACCUACCCUAUAUCUUUUG

AUAUAGGCGAUCCUGCAGUUAUCCGACACUAUCCGUAUGACCCACGUGG

GUUAAGUGCUAUCUUCAAGAUUGUAAUACAUGGUUCAAUGGCGCAAUUC

GACAUUACUUUUGUAAUGUCCGAUCGAACGACUGACUGGGAUAUACAGG

UGUGGGUGAUAACUGUAUCAGCGAAGGGUAUCACGAGACAUGAAACGCA

CUAUAAGAGGAUUGACACCUAAGGUGGACAUAUCAACUCACUGCCCGAU

GCAUCUUUUGAUGCAUCUGAAUGUCUCGUAGUCGCCUAACUUGAUACUC

UUAACCACGUGAGUAUGGUCAGUCGCUCACUUGAGUAUAGGUACACAUU

AGUCGCUCUCCAAAGCACUUUUGUGCUUUGCUAUGAGAUCUCGAUAAGA

CUUUGGAUGGAAGUCCAAGAGGAGUCAUGACGGAUAUUGACAUUGUGAG

GCUAUCGAGCAUGUAGAGAUCAACAGUGUGACAGAUAAGUGGACGUUCA

CUCGUACACACCACCUUUUGGUGGUGUCUGUCGGUGUGAACAGGCUAGC

AUUUCACACUGGAACAAUGCAAACUAGAUCAAACCGUAGGUGUCCCAGU

GGCAGUCUACAAGAUUAGAGCAUCAGGACUUUUAUACCUGAGUGUACCA

CUACUUGCUAGCUUUUGCUAGCAAUCUCGAAAACUCCUGUAUAGCCACC

UCAUACGGCGGCCAUAUUGUGUCAGUGCCGCCUAGAGUAUCUAUUCUUU

ACUGUUAGUGCGCCAUGGUGACUUCUUUUGAAGUCACCUUUGAACAUCG

CACCAGGUUGCUACACAAUGUACUAGUCUACUCAUUCUCUAUCGGGCUC

GUGAUUCUGAUGUAAGCGUUACAUGCAUUCAGUAACGAUCGUGGCGCAU

CUGCAAUGCGUGUGGAGUCAUCUUUUGAUGACUCAUGAAGGCACUAAAC

AGUGUCGCACACAAUCUUGGAUCUGUACAAUGACUGACAAACUUCAAGU

GAUCAUGCACAUCUACGUAAGUGUAGCUGCGCACCUUUUGGUGCGCAAG

CGUUGCCUAAUGUUAAGUGACCGACUUCCAUUAUAGCCUUGUACGAGCU

UCAAAGCCACACCUGGGAGUCACAACGUGCAUACUAUCCAAUGGUUCAU

UCGCUAAACGAAGAACUGCUAUCUAGUGUUCGGAUCC 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:11. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:11. Thus, in certain embodiments, the RNA nanostructure comprises SEQ ID NO:11. In certain embodiments, the RNA nanostructure consists of SEQ ID NO:11.

In certain embodiments, the shape of the RNA nanostructure is a tetrahedron. In certain embodiments, the RNA nanostructure is a tetrahedron RNA nanostructure comprising a nucleic acid sequence having at least about 60% sequence identity to SEQ ID NO:12:

(SEQ ID NO: 12)
5' GGGAGAUUACUCAUAAGGGCUGGCUUGGUUCACUAGGAGCUAGUUGG

GUAGCCCGUCACCAGUGCGUACAGCCCGUUCAUCCGCUUUGCGAUUGCU

CACACAACGCUUCGAGUUUACCCGUUCUGCGAUUGAUCGAAAGAUCAGG

ACAUCGACGGGUGAACUCGAGUUGGGAAGUGAGCGAUCGCAAGCGAUCG

AAACGAAAACUCGCUGCUUACCGUAUGAAUAGGAGGUACCUUCUGCCG

GUAGUCGUUCGUUCAGUAAGCUGAGCUCGAAAGAGCUGUAGUAGUUGAA

CGGACGACUAACUUAGAUCGUAGAGACCGAGGCAUACGGUUCCUUGAAA

AAGGACGCAAUGACCUCGGUUUCUACGGUCUAAGUAAAUCAAUAUCACC

ACUACUACCUAUGCCACGAAAACCCAUUGCCGAGGAUCCACAAUGGUGC

UCACGCGUUUAUGUAGCAUUUUGAGCGGGAUCGGUUGAGAGAAAUCUCA

UGGAGUUACGCUCAAGAUGCUAGCACACGCCGAGCCUAUAGAGAUGGAU

CCUGCUUCGAAAGAAGCUCCUACGGUCUCUAUGGGCUCGGUGUGUGCCU

AGCUCGUAGCUCUAACUCCAAUCAUGGUGGAAAAUGAGUAGUCCAUCGC

AGAGUAUUCGGCCUGUGAGCGUUGUUACGGAUUUGCUGCAGCGGAUGGA

GUUUAUGCGAAAGCAUAGACUCUCGAUCGCGCAGCAGAUCCGUAUUCCC

AACCACAGGUCGAAUACCGAUGUCCGGACUGCUCAAAAAGAGCGGGGUU

AGCAUGCGUUGCCAUCUCAACAUCUCCGUACUGCACUCUACAUGACAAG

UACGAGGGUAUCUUGUUCGUGAGAUCGUUCAUGGUAGCACGCAGCUUCG

GCUGAGGAGCGAUCCACAACGCUCUAGAAAUAGAGCUGGUGACAUCGCU

CUUCAGCCGCUCCUAGGUGCUAUCAUGAACCCUUAUGAGAACAAAAAGU

CGCGUGGGCCCCAAUGCCUAGAGCUAAAUGCGAAAGGUGCAAGCUACGC

ACAGCGUCUGAUAAGGCGAGUGAAAACUCGUCUUAGUUCGUCUUGUGCG

UGGCUUGCCGCGAUUCCAUUUAGUUCUAGGUCGUCUAUCCCAUGCGACA

AAAAGAUAUCCUCCCUCUGACCAUGUAGCGUGCAGUGCGGAGAAGAGGU

GUGAGACGCGCAUGCUGCGUUGAAAAACGCUCGAAAACCGUCUCAUACC

UCUCUCCGUGAUAUCAGUAGGAUUCGUCAGAGGCGCAUGAAAAUGCGGU

ACUUGUGAAUCCUGCUGAUAUUACGGAGUGUUGAGGUGGCAAGUUUUCG

AAACCUCGCUCCCACCGUGAUACCGAUCCGAGCUAUGAGCUAGCAUAAA

UGCGUGAGUACCAUUGCCGUAGGACGGCGAUGGGUUGCCUCAGACGCAG

CCCUAGUUAUCUACCUUUCGAUCCUUGGCCACUUCAUUGGGGACUUCGA

AAGAAGUAUAGACGAAAGUGGCUAAGGAUGAAUCGCGAGAUAAUUAGGG

CUAGACGAACGGCAAAAAACGUGGUAUAGCAGCUUACGGUGAUGUUGAU

UUCCGGCAGGAGGUACUUCCUAUUUCAUUGCGAAGCGGCGAGAAAAGCU

GUGCGCACGUUGUGGGGGCUACUCAACUAGAAGCUGCUGAACCGAGCCA

GCGAUCUCACGUAAUCUCCC 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:12. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:12. Thus, in certain embodiments, the RNA nanostructure comprises SEQ ID NO:12. In certain embodiments, the RNA nanostructure consists of SEQ ID NO:12.

In certain embodiments, the shape of the RNA nanostructure is a rhombus. In certain embodiments, the RNA nanostructure is a rhombus RNA nanostructure comprising a nucleic acid sequence having at least about 60% sequence identity to SEQ ID NO:13 (see, e.g., Example 1):

```
                                          (SEQ ID NO: 13)
5' GGGAGAGGAUCCAACAUGGAGUGCGGAUAUGGUUCGCUAAGGGAUUC

CCUGAAUGCGAACUCUAUCAACUGUCGAUACCUGGAGACGAUGCUGAUC

GACCUGUCAUGGGCGAAAACCUAUACCGAUGUAAACUCCGUAUAUUCAU

UUUGCUCUAGUCCAGUCCUGGAGGUUACUUCGGAAAAAAGUACCGCAGU

GGUGAAGCGUGUCCUCCAUACACCUCCGCAAGGUAUUCACUUUUGUGAU

CAUAGUUAUGGGGUGUAUGAGGAUAUGCACUUCACUAUGCAGAUGUGAGA

UAGAUGUCCGUGGGCAGAUGUCAGCGAACCGCGAAGACUCGCAAUGAAA

AAACGAGUGAAGGGCGUCUUGGCGCGUCCUUGUCUCACCCAACUGGCUU

GUGGUUAGAGCUUGACUCUGGGAUAUGACCAUCUUGGUCACUAAUUUAG

GACUGCCCUAACCUCCCUAAUGGAUGCGGGUGAUAAGUUCUGAAUGUCA

CGUUUGCAAAUAGCCCUUAAUGUUCCCGUACUGUGGCACGAGCAAAAAA

CCUUACACCUAAGGCGAUACUCACUUCAACUGUGUGUAUCACAUUAGGU

GCCUACGGUAAACUCAUCGUCUAGUUCUGGGACUGUUUCGUCUGGUUGA

ACGUUAUAAUAGACACGAUACCUGGUUCUACCAUUCGCCGAUCCAUUUG

GUCUUCGAAAAACGAGGGAGAAUCACUCUAUCAAAGAUGCACCUCGUA

GCGAGUGAGUGGAACUUCAUAAAGGGAAGUCAUGGCCGGUCAGACUUCU

GGCACUGAUAUGCAACAUCAGUACAGUCUUAAGUUCCAGCCGAAAGUGC

GGUUGGCAUCUCUUAGGACACAGAGCGAUUUUGGACUGGUAGCUGACCG

CAUGAAAAAAGGAACGACGUGUCGAAAGGUCCCGGUAGUAGCUCCCUCA

UUCCACUUGGCUAAACGUUCAACACGUAUCGAGUUGGUUUAGGUAGUUC

GCAGACGCACAAACGAAGGCAGGUAAAACUUGGCAAGUUGCGUCGUGGC

ACGUCAUACCAGUGUUGAAAAAACGGCUAUGUAGUGUCUAGCUGUCAAU

ACCCGUACCCAUCUGAUGGUUGCAGGAUGAUUAGGUCGAAACGAAGUCU

CUGAUCUGAGGUCGUCUGAAGCUAAGUAAUACCUGGCUAACUUGACUAA

CUCGUACUCAUACUCAGCUUUCUCACAUUCUGUGCUCAAAAUCUGCAUU

GACUGCAACGGUCCAAAAAAGCGACCUUCUGUGUGAAUAUGAAUACUAA

GCGGGAGUUGAAGAAUAGCUCACAGACAGACACAACCUACAAAAUGAAU

GAGCAGUCCGUGUAAGCUCGCAUUGCUCACUUCAGCCUUCGGGCGCUAU
```

```
-continued

AGCCAUUAUUAUGAUCCAACUCGAUCGAAAAAAGGUACUACGUAGAUUU

GGCCGACACCAGAUUGCCCGUACCGACAAUGCGGUUUCUUUGUAAACUG

GGCACUUACGAUCAUAGGGAGCUGGUUACGAACGGCAUCCGACAGGAAU

CUAGCUCGAUGCAUGGGAUAGUACUGUCCACAUCCAGCCGUCCCAGAGA

UAGGUAGAUUGGGAAAAAACGAUCGGUACUGAUCUCUGGUGUCUGACAA

ACACCUCCGCACUCAUUUGAGCAUGAGCCAAUGUAUAAGUUGCACCAGA

AUCGCUCUGGUAUGUCUAACAUCUGCAACAUCUUAAGGGCAGUCAUGAC

UACUGACCGUAGUCGGCUAGAGCACCGUGAGGCCAAAUGAUCCUCCAGA

AAAAAGCACUGAGUUGACACCAUCCGAGAGUAUGGAGCACUAGCUAUCA

UGACGAGGUUCCCAGUUGAAGUCAGAAUCUUGAUGGACGAAGCCUACUA

CUACCUGCUGUUGGUACAUGGAUAAGAUUGGCUUAGUAGGUCAUCCAAG

ACUGGGCCUUGGAAAAAACCACGGUUUGUGACCAUGAUCGUCCCAUGCA

UACUGAAAUCAUCACUAGUUGCGGAGUACGAGUCGAGCUGUGCAGUGCA

AACUAAUCCCUUUCGGCGGUCACAUAGUCCUGAACGCCGUCCUUAUCAC

CGAAAUCUUCCAACAAAGCAUGGCUCGUAUAGGUGCCCAGUCGACUACU

GGAUACUGGAAAAAACGGACUUUAGACAGCACCCUCAAUCUAUGAUCGG

UCCAGUGGUUAGUUCGUUUCUGCGAGUUUACCUUGCAUCAGGAUAUGAC

ACCUCGGGUGUUGAAGCCUGAAUAGAGAGCCGGUUCGAUCUUGUGUCUA

CUGAACGCAGUGUAGCGUUAGCAAAAAAGACACUAUCCUGAAGCACGCU

AUGUUCGUAAUUCAGCCGACUCGCAUUAUUGCUGGAGCUUCAGCUCGGC

CUUGACUGAGUGCACUCAGGCAUAUCAGUCAACACAGCAACUUCCUACG

ACUGUCCUAAAUCAACACUGCUAGUCACGUGUGUCUAUCGUCUCGACCU

GCAAGCAUGGGUGUCGUCGAAAAAAGCUCACGCUGUACAACCUUCACCC

CAUAGUGAUAGCCACAGAAAAGCCUCUGAACACCAACCAGACGGUCGAA

AAGAAAUGUAAGCUCACUGCGUCUGGUGCGUUGACAAGAAGACCCAUUA

UGAGCUUACGUGCUCUCACGUAGGCACUAUCCAAAAAAGGAGUAAAGGC

GAACGUUCGCAGCAGUUUACUCGGUGGUUUAUCUCUGAGGUCACGUCGA

CCUAAGUCCCAUGAUGACGUCCAGACAACCUUCCCUUGCUUCCAAGGCU

UUGGAGGUAUGCUAGAGUCAAGAAUUACUCUGCAUCGAGUCAUCAAGCA

UUCAGUACUAUUAGAUUGGAGCACGACACAAAAAAGCAUCUUCAAUUAG

GCUUAUCUGAGACAUCUGGUCAGGUCACCGAGUACCAGAUGUCGGUAGA

ACCAAAGAUGACAUAACAGUGAUCAACCGCAACUUACUGUACCCUACAC

GAGAUAUGUCCGCUAUAGCGUCAAACGCAGGUACUGCGAUGGAAAAAAC

AGCAGUAGCACAGGCUUAACAUCAAUCUGGUGGUCACCUCUAUAGGGCU

AGAGUGACGGGUAUCGGUUAUGACAGUGUUGCAGUCAGCAGGUGCAUUG

UCUUCGUCGAGCAGUAAGCGGAUAGACAAGGGUCGACUUGGUCUAUUAU

CAUGUAACACUCCAUUACCUGGUCUAGAAAUAGACCAGGUACCACUACA

UUACAUGAAGUCUUCGCAAGUCGACAGGCUAUAAUCCGCUUCAAAUGGA

ACGAAGACACGACUUAAGCUGACUGGGUAUGACUCAUAACCGUGCUGUU

GCACUCUAGGUUGGAUCAGGUGACCAGUUACGCUAUGUUAAGCCUGUGC

UACUGCUGAAAAAACCAUCGCGCAUUGUCCGUUUGACAUGCGAUAGGAC
```

-continued

AUAUCCAACCAUCGGUACAGUCGUAAUACGUUGAUCACCCACUCACCAU

CUUUGUACAGGUAGACAUCUGGACAAGCCAGACCUGACGUAAACGUUCA

GAUAAGUAGCGAACAAGAUGCAAAAAGUGUCGUGCUCCAAUCUAAUAG

UAGAGUAGACUUGAUGACCAUCUAUCGAGUAAUUCACAGUGAAAGCAUA

CCGUGUCUAUCUUGGAAGCUCAACUCAGUUGUCUGUUACCUGCCAUGGG

ACUACUCCAUCCGUGACCUGCUGAAGUAACCACCGAUGUUGAGUCUGCG

AACGUUCGCCUUUACUCCAAAAAAGGAUAGUUAUGAUCGGAGAGCACAC

CAUUGUAUAAUGGGUGAUCAGAGCAACGCACGUACAUAUGUGAGCUUAG

UCUGACCUUCGACCGCACUCGUUGUGUUCAGAAAGAUGGUUGUGGCUAA

GCAACCAGGGUGAAGGACAGUUGACGUGAGCAAAAAACGACGACACCCA

UGCUUGCAGGUCCACAGACAAGACACACUCCUCAUACAGUGUUGACGUC

ACGAAGUCGUAGUCCCAGAAUGUGUUGACAACGGACUCUGAGUGCCUAA

ACCAAAGGCCGAGGAAAUUGGCCAGCAAUCUCAUUCAUCGGCUGAAGAG

ACGGUAUAGCGUGCUUCAGGAUAGUGUCAAAAAAGCUAACGAUUCCUGU

CGUUCAGUGCUCUUUCGAUCGAACCUAGCCAGGAUUCAGGCCGUGCUUA

CCGAGGUGUAGACUGUAGAUGCAAGUAUCGCAGGCAGAAACGUAGGGAG

GACUGGACCUACGACUCAUUGAGGGUUGACAGGUAAGUCCGAAAAACC

AGUAUCCAGUAGUCGACUGGGCUAUUGCUGGAGCCAUGGAAUACCUGAA

GAUUUCCAUAUCGCGGACGGCGCCUAAUGUUAUGUGACCUUGUAUGAGG

AUUAGUCAAGUGGACACAGCUCGUUAUCGCUUCCGCAACGCUAUUCUAU

UUCAGUACUCUUUCAACGAUCAUGGUCACAAACCGUGGAAAAAACCAAG

GCAUGUGGACGGAUGACCAUCACUUGCAAUCUUAUAGAAAGCUCAACAG

CAUCCUUAUCUAGGCUUCGAGAGAUGCGAUUCUGAUCAUUGGAGGGAAC

CUCACGUGACAAGCUAGUGAGAUGAUUUCUCGGAUGUACGGAGUUCAGU

GCAAAAAACUGGAGGAUCAUUUGGCCUCACGGCCAAGGUACCGACUACU

CACCACUGUCAUGACUAGUCAAGGGAUGUUGCGCCUUAGGGACAUACCA

CUUGGUACCUGGUGCAUCGACACGAUUGGCUCACAUGUGACUGAGUGCG

CACACAGAUGUCAGACAGUCGUCUACAGUACCGAUCGAAAAAACCCAAU

CUACCUUAGACGACGACGGCUGGCCAGUCUUAGUACUAUUGAAAGAGUC

GAGCUAGCUACACUGCGGAUGCCACCGUCUCCCAGCUCCCGCCUACGUU

AAGUGCCACUCAACAAAAGAAACCAGUACCUGGGUACGGGAGCGUAACU

GUCGGCCAAAUCUACGUAGUACCAAAAAACGAUCGACCCUAUAGAUAAU

AAUGUAUCGCAUGCCCGAAGCAGAGAUAGAGCAAUGCACAAUGGUACGG

ACUGAAUGCGAGUUUGUAGGGAAAGAGCGUCUGUGAUAGUGAUGUCAA

CUCCCCAAGUGAUUCAUAUUGAGGUGUUAGGUCGCAAAAAGGACCGU

UGCAGUCAAUGCAGAUGUCACAUGCAGAAUGUGCCAUGUACGAGUAUGA

AGCGAUAAUAGUCAAGUGGCUCUCUUAUUACUUCCAAUUUCACGACCUC

ACUUCUUGUACUUCGUUGAUGGAGUAUCAUCCUGUCGUGUAGAGAUGGG

UCAACAGCAUGACAGCUAGACACUACAUAGCCGAAAAACAACACUCAA

CACUGGUGCCACGAGUAUUACGGCCAAGUUGACGUCAUCUUCGUUUGAU

-continued

AUGUACCGAACUACACUCAGUCACUCGAUACUAAGCACGCGUUUAGCUU

GCACUGAUGAGGGAGGAUAAGGAGGGACCUUACUUAUACUCGUUCCAAA

AAACAUGCGGUCAGCUACCAGUCCAAGUACCAAGUGUGUCCUAUCCAUC

AACAACCGCAUCUAUCAAUGGAACUUACAUAUCCUCUGAUGUUAGUCCG

UUGUGCCAGAACAUUUCUUGGCCAUGAUGAGUUGAUAUGAAGUUUGUUA

UGUUCGCUACGUUAAGUCGCUUUGAUAGAGUGAUUCUCCCUCGAAAAAA

CGAAGACACUGCUCGUCGGCGAAUUACCUGUACAGGUAUCUCCAAAGCU

AUAACGUUAACGAGUGCGAAACAGGAAGUUGCCUAGACGAUCUGCGAUA

CGUAGGCAUUCAGGACGAUACACACUCCAAUGAUGAGUAUCAGAUGUUA

UGUAAGGAAAAAAGCUCGUGCCACAGUACGGGAACACCUUGACUUAUUU

GCAAGUCAUGAUUUCAGAACGCGAUAUGCGCAUCCAUAACUAACCUUAG

GGCAUCGUGACGUUAGUGACCGGCUUUUCCAUAUCCCUUCACUGUGCUC

UAACCUACUCGUGUUGGGUGUAUAGCCUACGCGCCAAGACGCCCUUCA

CUCGAAAAAACAUUGCGUAAUAGACCGGUUCGCUACGUUUACCCCACGG

AUCGAUGCAUCACAUCUGUGGUUGCUAGUGCAUAGUGACUAGCACCCAU

AAGAGUCGUAACAAAAGUCUUUGUUGUGCGGAGGUAAUCAUCUGACACG

CUGGUCAGUAGCGGUACAAAAAACCGAAGUAACCUCCAGGACUGGAUAC

CUUGGAAAUGAAUAGUGUCAACUUACAUCGCAGCAAUAUUUCGCCCAGC

UGUCUACGAUCAGCUGUCUGUGCAGGUAUCGUUGUACAGUAGAGUUCGU

CUACUCGGAAUCCCUCCUAAUUGCAUAUCCGUGUAGUGGGUUGGAUCCU

CUCGAGCUCUCCCUUUAG 3'

In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:13. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:13. Thus, in certain embodiments, the RNA nanostructure comprises SEQ ID NO:13. In certain embodiments, the RNA nanostructure consists of SEQ ID NO:13.

Certain embodiments also provide a nucleic acid sequence (e.g., a nucleic acid configured to assemble into an RNA nanostructure based on its configured sequence and resulting pairing interactions, wherein the nucleic acid comprises a nucleic acid sequence) having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. In certain embodiments, the nucleic acid sequence has at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. Thus, the nucleic acid comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. In certain embodiments, the nucleic acid consists of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. In certain embodiments, the nucleic acid forms an RNA nanostructure. In certain embodiments, the RNA nanostructure is immunomodulatory. In certain embodiments, the RNA nanostructure is immuno-stimulatory. In certain embodiments, the RNA nanostructure is immuno-inhibitory.

In certain embodiments, the sequences described herein can include or exclude two or three flanking G nucleotides at the 3' or 5' terminate.

RNA Nanostructure Design

Figure 36:
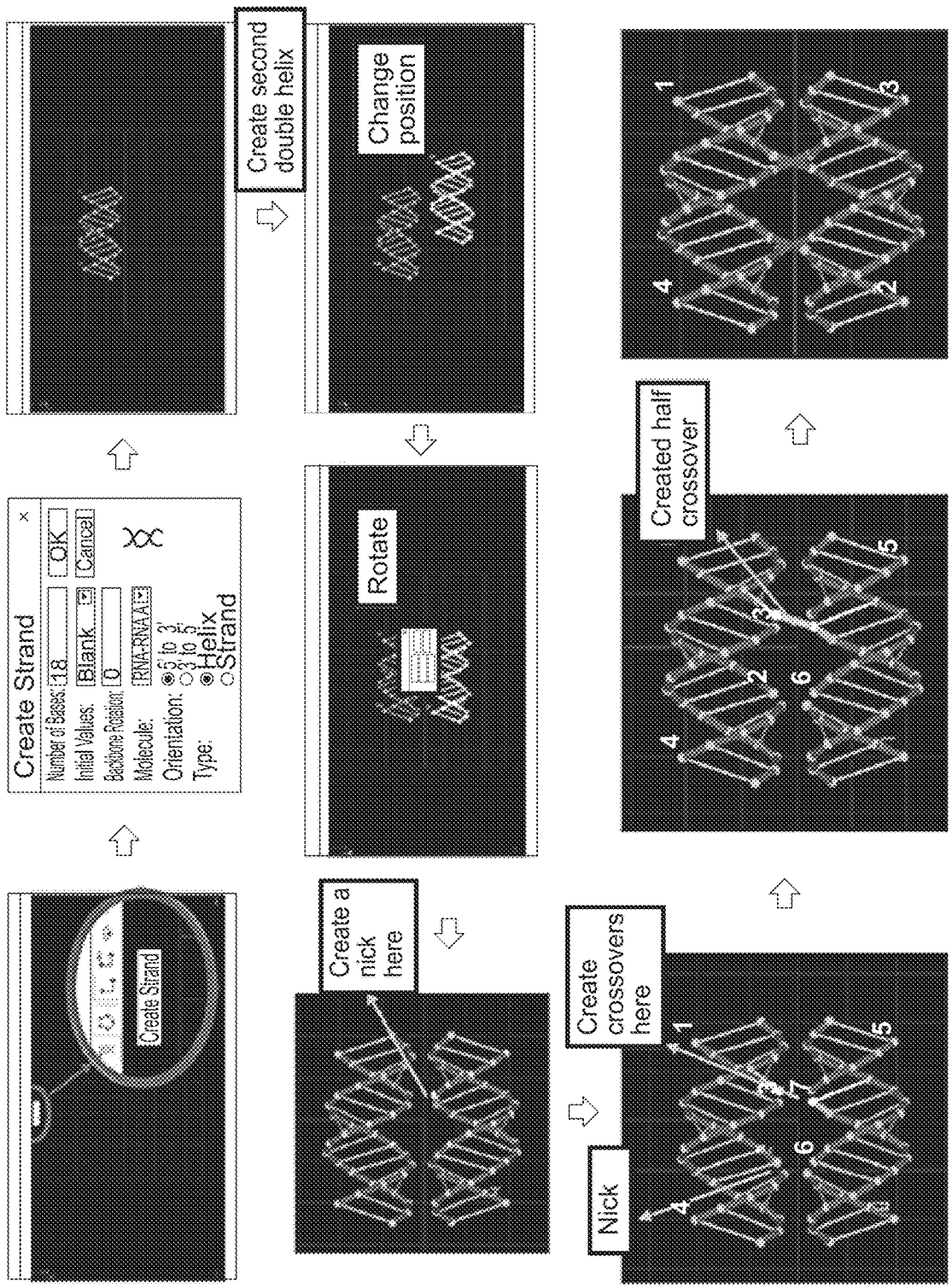
FIG. 36. Computer-aided design process for RNA origami. Step 1: Create an RNA tile as robust building block for any target structure.
Figure 37:
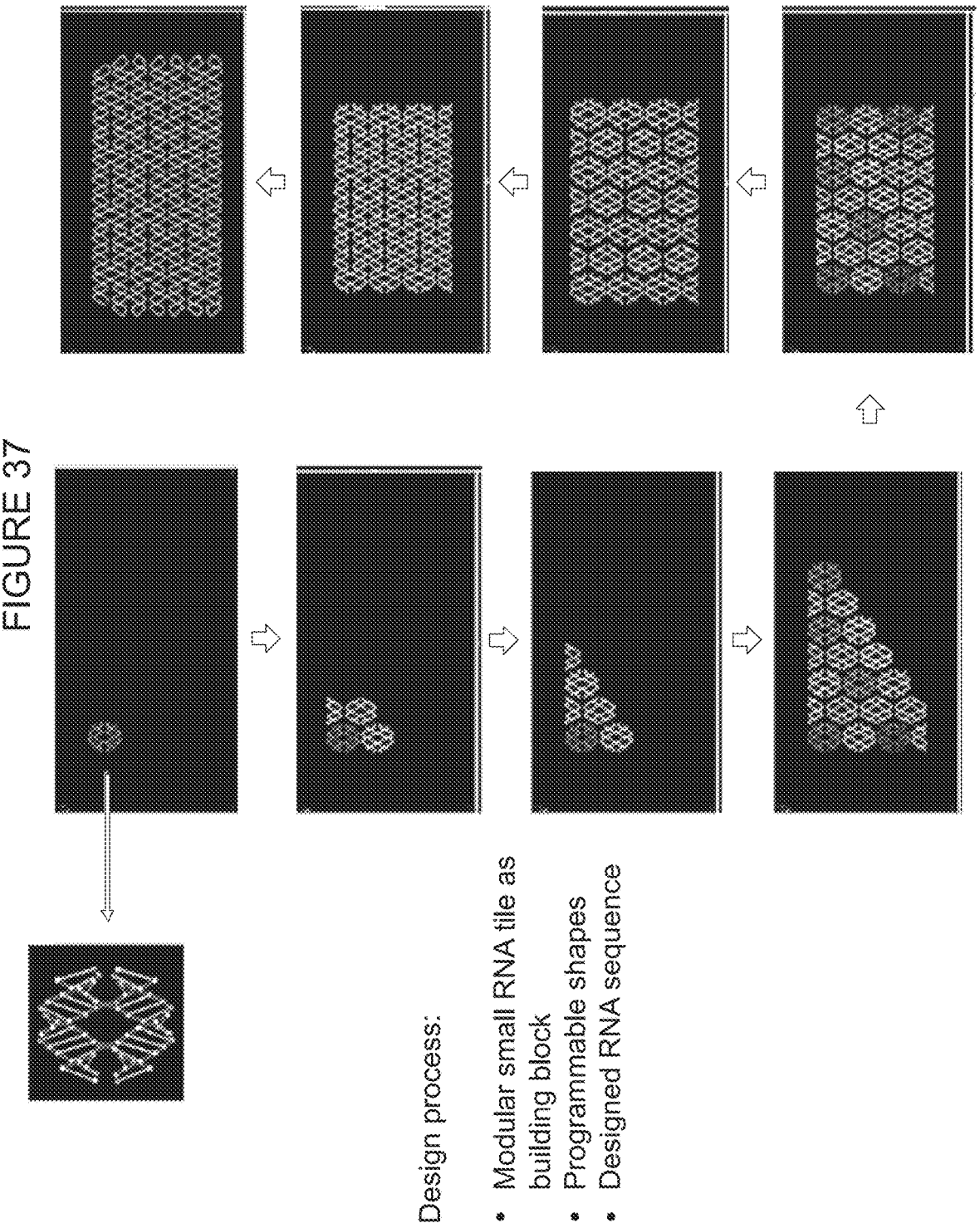
FIG. 37. Computer-aided design process for RNA origami. Step 2: Create target shapes and routing pathway into single-stranded RNA.
Figure 38:
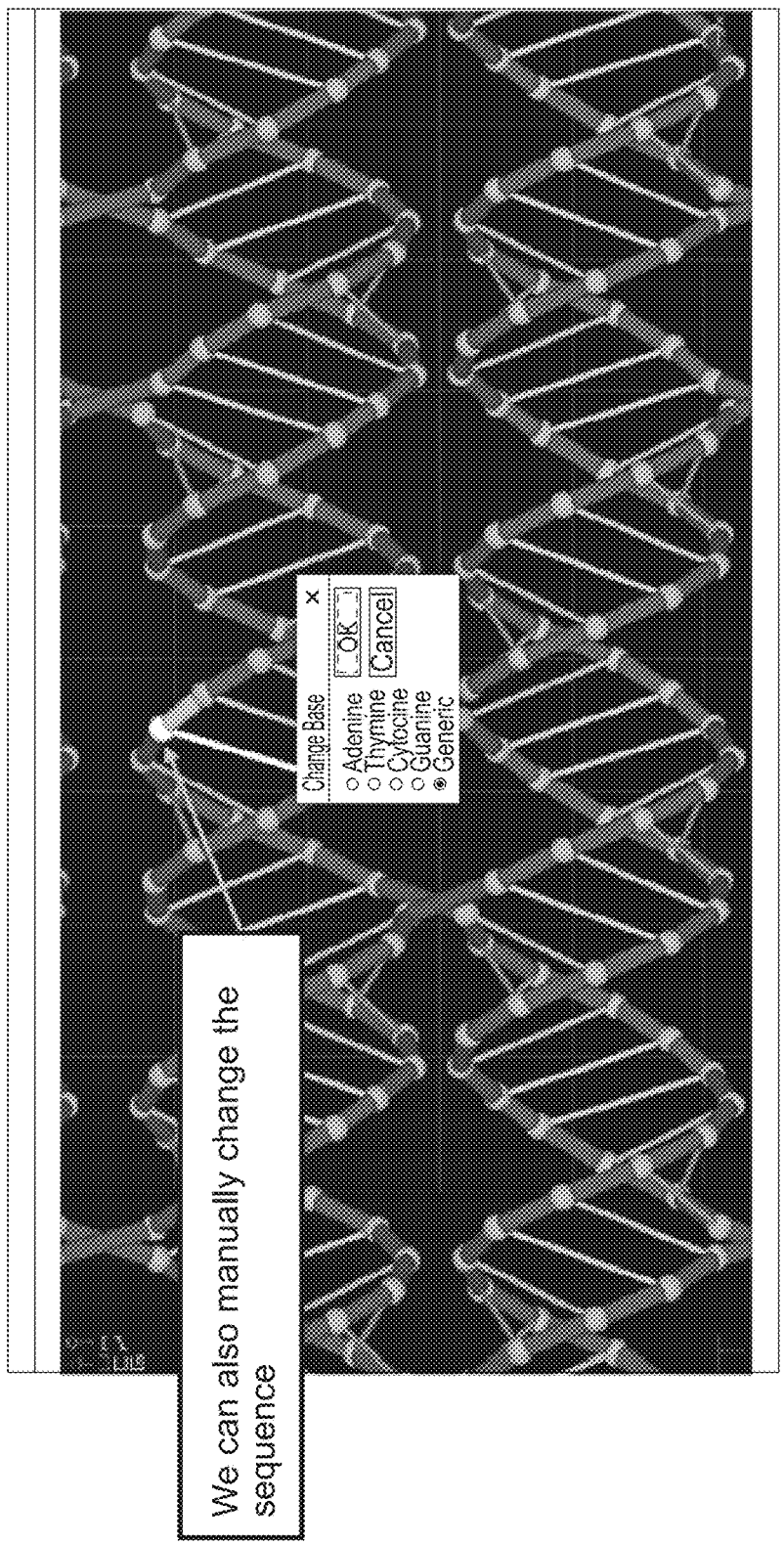
FIG. 38. Computer-aided design process for RNA origami. Design the RNA sequence.

RNA nanostructures may be designed using methods described herein, as well as, in certain embodiments, methods known in the art. For example, RNA nanostructures may be designed using ASU's proprietary Tiamat RNA software, which facilitates the visualization of RNA double helices and structure units (see, e.g., the Examples). Typically, the design process involves (and methods for generating or designing an RNA nanostructure described herein may comprise) the following:

Step 1: Creating an RNA tile (e.g., a structural unit as described herein) as robust building block for any target structures (FIG. 36);

Step 2: Creating one or more target shapes and routing pathway into single-stranded RNA (FIG. 37); and Step 3: Designing or generating the RNA sequence (FIG. 38).

Accordingly, certain embodiments provide a method of designing an RNA nanostructure described herein using a computer-implemented method (e.g., Tiamat RNA software). In certain embodiments, the method comprises: 1) creating an RNA tile as a building block for any target structure (i.e., a structural repeating unit as described herein); 2) creating target shapes and a routing pathway into ssRNA; and 3) designing or generating the RNA sequence.

In certain embodiments, the sequence of the ssRNA is optimized through manual modification. For example, the Tiamat software will typically control the overall GC content of the ssRNA sequence. Therefore, the paranemic cohesion regions may have high or low GC content, which may be further adjusted. For example, a particular paranemic cohesion crossing may have 16 base pairings. In such a scenario, the GC content of the paranemic cohesion crossing may be adjusted to contain about 6 to about 10 GC base pairs (e.g., 6, 7, 8, 9 or 10 GC base pairs).

The paranemic cohesion crossing is formed from two internal loops (where internal loops, here, refers to unpaired regions of the RNA molecule prior to folding). In certain embodiments, the sequence of the at least one ssRNA may be modified to ensure the internal loops remain unpaired before forming the paranemic cohesion crossing. The nucleotide composition will be manually changed so that the internal loops remain unpaired.

The sequence of the ssRNA may also contain a transcription termination sequence (e.g., AUCUGUU). If present, this sequence may be removed and/or modified to a different sequence.

Thus, certain embodiments provide a method of designing an RNA nanostructure using a method described herein.

Certain embodiments also provide a method of producing an RNA nanostructure, the method comprising incubating at least one ssRNA molecule under conditions that result in the formation of the nanostructure (e.g., self-assembly through pairing interactions). In certain embodiments, the conditions are conditions described herein (e.g., in the Examples). In certain embodiments, the ssRNA molecule has a sequence described herein (e.g., any of SEQ ID NOs:1-13).

Certain embodiments provide a method of forming an RNA nanostructure using a method described herein. For example, in certain embodiments, the RNA nanostructure is formed using are conditions described herein (e.g., in the Examples). In certain embodiments, an Echo Chilling Incubator is used for the assembly of an RNA nanostructure described herein. In certain embodiments, a pH range, including but not limited to, about 7.0 to about 8.0 is used. In certain embodiments, ionic conditions, including but not limited to, 50-250 mM of monovalent salt (e.g. NaCl) is used. In certain embodiments, a pH of about 7.4 and 150 mM monovalent salt is used.

Nuclease Resistance

Figure 7:
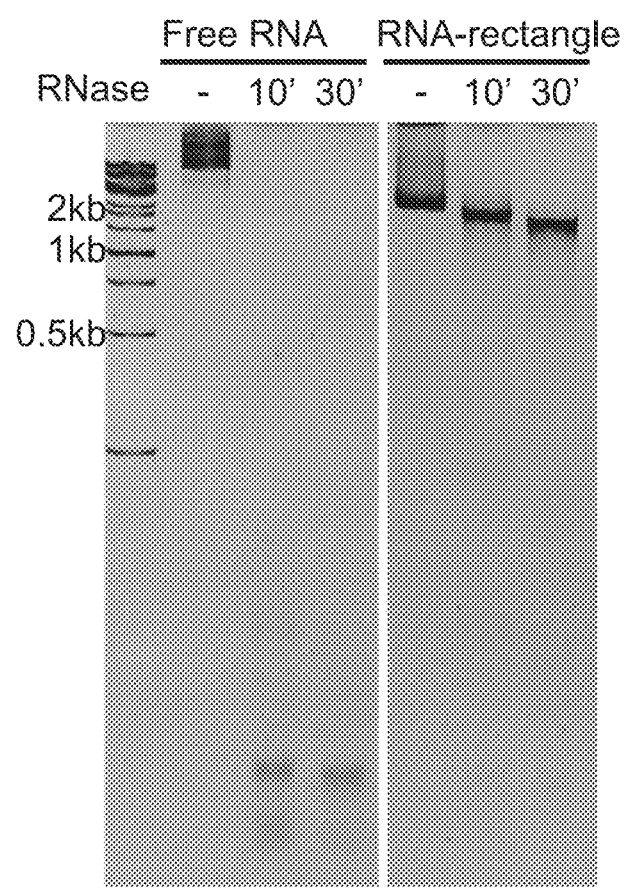
FIG. 7. Nuclease resistance. Self-assembled RNA origami is resistant to RNase I digestion as a result of being configured to have such resistance, while the unassembled RNA molecule can be digested easily by RNase I. Lane 1 represents 1 kb dsDNA marker. 1 μg of unassembled RNA molecule was treated without RNase I (lane 2) or with 1 U of RNase I for 10 min or 30 min (lane 3 and 4) at room temperature. The self-assembled RNA origami was also treated without RNase I (lane 5) or with 1 U RNase I for 10 min or 30 min (lane 6 and 7) at room temperature. Highly stable RNA-rectangle (RNA-Rec) is formed, which has an intact structure even without cations and is resistant to RNase.

In certain embodiments, an RNA nanostructure described herein has increased nuclease resistance (e.g., as compared to a control, such as an unfolded ssRNA molecule comprising the same nucleic acid sequence as the RNA nanostructure) (see, e.g., FIG. 7). In certain embodiments, nuclease resistance of the RNA nanostructure is about 10%, 20%, 30%, 40%, 50%, 60%, 70%, 80%, 90%, 95% or more than a control. Methods of evaluating nuclease resistance are described herein and known in the art. Accordingly, in certain embodiments, the nuclease resistance of an RNA nanostructure described herein is evaluated using an assay described herein.

Immunomodulatory Properties of RNA Nanostructures

A series of in vitro and the in vivo experiments, which are described below and in the Examples, were performed to evaluate the immunomodulatory properties (e.g., immuno-stimulatory) of the RNA nanostructures described herein. These experiments demonstrated that the RNA nanostructures may have immuno-stimulatory (or otherwise immunomodulatory) properties and may be used an adjuvant (e.g., an anti-cancer adjuvant). Additionally, these experiments indicated that the RNA nanostructures described herein can be used as anti-tumor (anti-cancer) agents. Finally, these experiments indicated that the RNA nanostructures described herein have certain advantages over previously known TLR3 ligands.

Double-stranded RNA (dsRNA) is a by-product of viral infection. It is a natural ligand of Toll-like receptor 3 (TLR3) and a potent stimulator for activating innate and adaptive immunity. PolyIC is a synthetic dsRNA analogue and has been widely explored for anti-cancer immunotherapy. PolyIC, however, is associated with high toxicity, primarily due to excessive production of cytokines, which subsequently could lead to cytokinemia.

The adjuvant activity of an RNA-nanostructure (SEQ ID NO:1) was tested in cancer immunotherapy and it was found that repeat injections (e.g., 2, 3, 4, 5, 6, 7, or 8 injections, depending on the tumor load and intrinsic tumor immunogenicity) of the RNA-nanostructure at 16 µg/dose significantly delayed tumor growth. In certain embodiments, the dosage is greater than zero and: less than about 5 mg/kg, less than about 4 mg/kg, less than about 3 mg/kg, less than about 2 mg/kg, less than about 1 mg/kg, or less than about 0.8 mg/kg. In certain embodiments, the dosage is 1 to 10 mg/kg; 1 to 100 mg/kg; 0.1 to 10 mg/kg; or 0.1 to 1 mg/kg. In addition, when the cytokine profiles were analyzed, it was found that the cytokines produced by the mice treated with RNA nanostructure had higher levels of particular cytokines and chemokines required for the generation of effective anti-tumor immunity, but lower levels of cytokines involved in systemic cytokine storm. Thus, RNA nanostructure can be used as effective and safe adjuvants. Further, it was demonstrated that the RNA nanostructures disclosed herein exhibit potent anti-tumor activity, but without apparent toxicity.

TLR3 ligands have multiple modes of action in cancer therapy. They can be used as inducers of apoptosis/neprotosis in cancer cells. They are strong activators for the production of type-I interferon in a wide range of cell types, including host immune cells and cancer cells, via two major pathways: TLR3 (endo-lysosome) and MDA/RIG (present in cytoplasm). TLR3 ligands exhibit synergistic effects in combination with chemotherapeutics, apoptosis enhancers, other TLR ligands, tumor antigens, and checkpoint inhibitors (e.g., anti-PD1, CTLA4 or PD-L1). The same ligands can be used for both murine models and for humans.

Current TLR3 ligands include PolyIC, Poly A:U and ARNAX. There are three types of PolyIC: (1) standard Poly-IC, which is rapidly inactivated by serum; (2) Poly-IC/poly-lysine (polyICLC, Hiltonol, Oncovir), which has been studied in 12 clinical trials for many malignant tumors; and (3) Poly(I:C12 U) (Ampiligen), which has been studied in clinical trials for OVC and peritoneal tumors. PolyIC has been tested in humans since the late 1970s as anti-cancer adjuvants. PolyIC, however, was found to be quickly inactivated by serum. Although its complex with poly-lysine greatly enhances its half-life in circulation and efficacy, complexed polyIC causes intolerable adversity, due to excessive production of cytokines. It is believed that polyIC activates both TLR3 and MDA5/RIG signaling pathways. The latter has been linked to systemic toxicity. Instead, polyIC has been explored as a part of cancer vaccines by mixing with tumor-specific antigens, which were delivered locally. In addition, double-stranded poly A:U was tested in early 1980s in clinical studies. Due to its low efficacy (possibly labile) and poor cellular uptake, the efforts were discontinued.

A third line of study involves ARNAX, which is phosphorothioate ODN-guided dsRNA (sODN-dsRNA) that resembles PolyA:U. It exhibits ODN-mediated cellular uptake (Matsumoto, M. et al. 2015. Nature Communications. 6:6280).

The RNA nanostructures described herein are advantageous over previously known TLR3 ligands for many reasons. For example, they are scalable in terms of quantity for production with relatively low cost. They are well-defined structure and uniformity for reproducibility. The particulate size and intrinsic nanoparticle structure is superior for better internalization by immune cells without additional packaging to promote phagocytosis, in contrast to the processes involved in polyIC, dsRNA or the synthetic oligo-DNA-RNA hybrid (i.e., ARNAX). They are highly stable so as to be feasible for in vivo applications. The RNA nanostructures described herein have better safety as they may selectively activate a pathway (TLR3) that is required for an induction of adaptive cellular immunity (anti-cancer or anti-viral), but not MDA5/RIG pathway, and therefore are less likely to induce cytokine storm. Accordingly, in certain embodiments, the RNA nanostructure are configured to selectively activate the TLR3 pathway while not activating the MDA5 and/or RIG pathways. They have well-defined structure and uniformity for reproducibility, unlike heterogenous population of polyIC (low vs high molecular weight) with different functional activities. Thus, they have better stability, uptake, homogeneity, selectivity and low toxicity.

The results from in vitro and the in vivo experiments showed promising outcomes for RNA nanostructures as a therapeutic anti-cancer adjuvant. In vitro studies highlighted that the RNA nanostructure was able to elicit various immune cells to promote the innate and adaptive immune response and provoke the release of immuno-active cytokines, all of which can mostly be attributed to the RNA nanostructure's initiation of the TLR3 pathway. All of these components were evident in the comparisons done with Poly(I:C), which has already been established as an immuno-adjuvant. As seen in Table 1, the comparison between Poly(I:C) and the RNA nanostructure was promising.

TABLE 1

Summary of the In Vitro Effects of RNA Origami Compared to Poly (I:C)

| | Control (PBS) | HMW Poly (I:C) | RNA Nanostructure |
|---|---|---|---|
| TLR3 Pathway Stimulation (HEK-blue) | | | |
| | − | ++ | ++ |
| RIG-I and MDA5 Pathway Stimulation (A549 WT-MAVS and KO-MAVS) | | | |
| | − | ++ | − |
| Macrophage Line (RAW-264.7) Activation | | | |
| | − | + | ++ |
| Ex Vivo Lymphocyte Stimulation | | | |
| T-Cells (CD69) | − | + | ++ |
| B-Cells (CD69) | − | ++ | ++ |
| cDC | − | + | ++ |
| pDC | − | ++ | ++ |
| B-cells (APC) | − | ++ | ++ |
| Macrophages | − | + | ++ |
| Ex Vivo Cytokine Production | | | |
| CCL5 | − | + | + |
| CXLC10 | − | ++ | ++ |
| IFNα | − | − | + |
| IFNβ | − | − | + |
| IFNγ | − | − | + |
| Serum Cytokines | | | |
| CCL2 | − | ++ | − |
| CCL5 | − | + | − |
| CXLC10 | − | ++ | ++ |
| IFNα | − | ++ | − |
| IFNβ | − | ++ | − |

Note.
(+) indicated at least a one-fold difference than the control. (++) indicated two-fold or greater difference than the control. (−) indicated little to no difference to the control.

In many instances, the RNA nanostructure performed better than Poly(I:C). One example functional difference between Poly(I:C) and the RNA nanostructure, in vitro, was the PRRs that they activated (Poly(I:C) can interact with RIG-I and MDA5 and RNA nanostructure could not). The RNA nanostructure's inability to activate these might play in its favor due to these features of Poly(I:C) possibly contributing to the toxicity levels that are reported with it when used at high concentrations. This could be due to the overexpression of certain immune responses which end up being toxic to the host, thus giving the RNA nanostructures disclosed herein a more favorable appeal over Poly(I:C). These positive outcomes from the in vitro studies helped lead to the in vivo studies.

The in vivo studies with the RNA nanostructure showed that it could be used as an effective therapeutic in treating cancer (e.g., in the designed PM model, as one illustrative example). As summarized in Table 2, the RNA nanostructure effected the growth of the cancer, especially if the treatments were performed earlier on (primarily day one treated).

TABLE 2

Summary of the In Vivo Effects of RNA Origami

|  | Control (PBS) | HMW Poly (I:C) | RNA Nanostructure |
|---|---|---|---|
| CT26 Tumor Growth | | | |
| Day 1 | ++ | − | − |
| Day 3 | ++ | N/A | − |
| Day 5 | ++ | N/A | + |
| IFNγ in Murine Model Serum (ELISPOT) | | | |
|  | + | ++ | ++ |
| In Vivo Murine Model Ascites Cytokine Profile | | | |
| IFNγ | + | N/A | ++ |
| TNFα | + | N/A | ++ |
| TGFbβ1 | ++ | N/A | + |
| TGFβ2 | ++ | N/A | + |
| IL-10 | ++ | N/A | − |
| IL-4 | ++ | N/A | − |
| MDSC Presence in Murine Model | | | |
| Splenocytes | ++ | N/A | + |
| Peritoneal Cells | ++ | N/A | − |

Note.
(+) indicated at least a one-fold difference than the control. (++) indicated two-fold or greater difference than the control. (−) indicated little to no difference to the control. N/A indicated that the category was not a part to the study.

In several cases, it proved that the RNA nanostructure elicited an immune response that prevented the growth of the CT26 cell, where they were eliminated before detection could be achieved from the imager. In other cases, clear tumor regression was observable. The tumor development was initially seen both visually by the enlarging of the abdominal region and by the fluorescent detection from the imager, but as time went on and the mice were treated, the tumor eventually regressed. Additionally, it showed that the RNA nanostructure could lead to tumor growth delay, usually in the delayed treatment studies (day three and day five treated). This was seen in comparison to the PBS group which had the mice reach their endpoint much faster that the mice treated with the RNA nanostructure, thus demonstrating the potential effects the stimulation of the immune system had on tumor progression. This was only further supported by the results from tests observing immune-suppressive cells and anti-inflammatory cytokines. The RNA nanostructure treated mice showed that MDSC were present at reduced levels as well as cytokines such as TGFbβ1, TGFβ2, IL-10, and IL-4, which are known to regulate and suppress immune-stimulation. Even more validation for the RNA nanostructure's aptitude to interact with the immune system was seen with both the tumor re-challenge group and the adoptive transfer group. Both cases presented how it is the adaptive immune system that is attacking the cancer by either preventing the CT26 cancer cells from growing when reinjected into a previously RNA nanostructure treated mouse, or the ability of RNA nanostructure treated splenocytes to recognize the cancer and prevent it from growing in a new host that is also immunocompromised. Furthermore, this nude group of mice also showed the development of immunity to the CT26 cancer cells, meaning that the RNA nanostructure could lead to the development of memory T-cells against the cancer line. Finally, the in vivo trials also supported some of the findings in the initial in vitro studies by illustrating that the RNA nanostructure could stimulate T-cells, promote the secretion of the similar cytokines found in the in vitro studies, and cause the production of IFN-gamma, a vital cytokine that helps upregulate the both the innate and adaptive immune system.

Accordingly, certain embodiments provide an RNA nanostructure that is immuno-stimulatory. As used herein, an immuno-stimulatory RNA nanostructure stimulates the immune system thereby inducing activation or increasing activity of any components of the immune system. In some aspects, the immune-stimulatory RNA structures described herein stimulate immune cell activation, boost anti-tumor immunity, increase anti-tumor (pro-inflammatory) cytokines and/or reduce immunosuppressive cytokines. For example, in some aspects immuno-stimulatory RNA structures described herein: activate immune cells, e.g., T helper cells, T cells (including CD69+ activated T cells), dendritic cells, natural killer cells, macrophages, reprogram the cytokine microenvironment by, for example, decreasing levels of immunosuppressive cytokines e.g., TGF beta (TGFβ1, TGFβ2, IL10, and IL4 and/or increasing production of anti-tumor (pro-inflammatory) cytokines, for example, interferon gamma and TNF-alpha; inhibit or suppress tumor growth, cause tumor regression and/or induce tumor immunity; stimulate splenic B and T cells; or activate the TLR3-signaling pathway.

In certain embodiments, the RNA nanostructure having immunomodulatory properties comprises a ssRNA molecule comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the RNA nanostructure having immuno-stimulatory properties comprises a ssRNA molecule comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the single stranded RNA molecule is SEQ ID NO:1, as described in Example 2. As described above and in the Examples, this nanostructure may be used as an immune-adjuvant to boost an immune response, including inducing anti-tumor immunity. Advantageously, this adjuvant may be easily scaled up by biochemical production.

In certain embodiments, the immuno-stimulatory activity of an RNA nanostructure as described herein is more potent than the immuno-stimulatory activity of PolyIC.

In certain embodiments, the immunomodulatory properties of the RNA nanostructure may be altered by the shape of the RNA nanostructure. In certain embodiments, the immunomodulatory properties of the RNA nanostructure may be altered by the sequence of the ssRNA (e.g., the nucleotide composition at a loop region).

In certain embodiments, the immuno-stimulatory properties of the RNA nanostructure may be altered by the shape of the RNA nanostructure. In certain embodiments, the immuno-stimulatory properties of the RNA nanostructure may be altered by the sequence of the ssRNA (e.g., the nucleotide composition at a loop region).

In certain embodiments, the RNA nanostructure is an agonist of a pattern recognition receptor. As used herein, the terms "pattern recognition receptor" or "PRR" refer to proteins expressed by cells of the innate immune system, such as dendritic cells, macrophages, monocytes, neutrophils and epithelial cells, to identify two classes of molecules: pathogen-associated molecular patterns (PAMPs), which are associated with microbial pathogens, and damage-associated molecular patterns (DAMPs), which are associated with components of host's cells that are released during cell damage or death. PRRs also mediate the initiation of antigen-specific adaptive immune response and release of inflammatory cytokines. In certain embodiments, the PRR is a toll-like receptor (TLR) (e.g., TLR3 or TLR7).

Certain embodiments provide an RNA nanostructure TLR3 agonist comprising at least one single-stranded RNA (ssRNA) molecule, wherein the ssRNA molecule forms at least one paranemic cohesion crossover, and wherein the RNA nanostructure has immuno-stimulatory properties.

RNA Nanostructure Complexes

In certain embodiments, RNA nanostructures may also serve as a scaffold for the formation of other structures. In certain embodiments, the RNA nanostructures themselves (the base structure) may consist of a single ssRNA molecule folded into a desired shape; however, as described herein the RNA nanostructures may comprise agents or other molecules that are added to or attached to the folded nanostructure.

Accordingly, certain embodiments provide an RNA nanostructure described herein, wherein the RNA nanostructure comprises at least one diagnostic agent operably linked to the RNA nanostructure. Certain embodiments also provide an RNA nanostructure described herein, wherein the RNA nanostructure comprises at least one therapeutic agent operably linked to the RNA nanostructure.

Certain embodiments also provide a complex comprising an RNA nanostructure described herein and at least one diagnostic and/or therapeutic agent operably linked to the RNA nanostructure.

In certain embodiments, one or more agents (e.g., 1, 2, 3, 4, 5, 6, 7, 8, 9, 10 etc.) may be operably linked to the RNA nanostructure, such as diagnostic agents or therapeutic agents. In certain embodiments, at least one diagnostic agent is operably linked to the RNA nanostructure. In certain embodiments, at least one therapeutic agent is operably linked to the RNA nanostructure. In certain embodiments, at least one diagnostic agent and at least one therapeutic agent are operably linked to the RNA nanostructure.

Diagnostic agents are known in the art and include imaging agents, e.g., fluorophores, radioisotopes, and colorimetric indicators.

As used herein, the term "therapeutic agent" includes agents that provide a therapeutically desirable effect when administered to a subject (e.g., a mammal, such as a human). The agent may be of natural or synthetic origin. For example, it may be a nucleic acid, a polypeptide, a protein, a peptide, a radioisotope, saccharide or polysaccharide or an organic compound, such as a small molecule. The term "small molecule" includes organic molecules having a molecular weight of less than about, e.g., 1000 daltons. In one embodiment a small molecule can have a molecular weight of less than about 800 daltons. In another embodiment a small molecule can have a molecular weight of less than about 500 daltons.

In certain embodiments, the therapeutic agent is an immuno-stimulatory agent, a radioisotope, a chemotherapeutic drug (e.g., doxorubicin) or an immuno-therapy agent, such as antibody or an antibody fragment. In certain embodiments, the therapeutic agent is a vaccine, such as a cancer vaccine. In certain embodiments, the therapeutic agent is a tumor targeting agent, such as a monoclonal tumor-specific antibody, a tumor targeting peptide or an aptamer. In certain embodiments, the therapeutic agent is an antibody (e.g., a monoclonal antibody, e.g., an anti-PD1 antibody). In certain embodiments, the therapeutic agent is an antigen (e.g., a tumor associated antigen or a tumor specific antigen). In certain embodiments, the therapeutic agent is a tumor antigen peptide(s).

In certain embodiments, the diagnostic or therapeutic agent is targeting agent, which can specifically target and/or bind a particular cell of interest. Accordingly, such a targeting agent may be used to deliver an RNA nanostructure to a particular type of cell. In certain embodiments, the targeting agent is a tumor targeting agent. As used herein, a tumor targeting agent is an agent that can target and/or bind to a tumor cell. Accordingly, such a tumor targeting agent may be used to deliver an RNA nanostructure to a tumor site. In certain embodiments, a tumor targeting agent is a tumor targeting peptide (TTP).

In certain embodiments, the diagnostic or therapeutic agent is a peptide comprising a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues (SEQ ID NO: 21).

In certain embodiments, the peptide is a tumor targeting peptide (TTP), a tumor antigen peptide, a human cancer peptide, an infectious agent peptide, or calreticulin protein.

In certain embodiments, the infectious agent peptide comprises specific epitopes for CD8+ T cells involved in the immunity against influenza, HIV, HCV, and other infectious agents.

In certain embodiments, the peptide is calreticulin protein. Calreticulin protein allows the RNA-origami to engage interactions between tumor cells and macrophages or dendritic cells for enhanced antigen presentation and stimulation of antigen-specific T cells.

In certain embodiments, the peptide is human cancer peptide NY-ESO-1 or Muc1.

In certain embodiments, the at least one therapeutic agent is a tumor antigen peptide (e.g., a tumor-specific antigen; e.g., for use as a cancer vaccine). Thus, in certain embodiments, a component of an RNA nanostructure complex of the present invention is a tumor-specific antigen. In certain embodiments, the tumor-specific antigen is TKD. It is understood that the tumor-specific antigens may be modified to enhance complex formation, to modulate RNA nanostructure: tumor specific antigen ratios and to operably link one or more agents. In certain embodiments, the tumor-specific antigen is TKD modified to add a C at the N-terminus. In certain embodiments, the tumor-specific antigen is TKD modified to add from 1 to 15 lysine residues (SEQ ID NO: 22) at the C-terminus. In certain embodiments, the tumor-specific antigen is TKD modified to add 10 lysine residues (SEQ ID NO: 21) at the C-terminus. In certain embodiments, the tumor-specific antigen is TKD modified to add a C at the N-terminus and from 1 to 15 lysine (SEQ ID NO: 22) at the C-terminus. In certain embodiments, the tumor-specific antigen is TKD modified to add a C at the N-terminus and 10 lysine (SEQ ID NO: 21) at the C-terminus. In certain embodiments, the peptide is CTKD-K10 (CTKDNNLLGRFELSGGGSK$_{10}$ (SEQ ID NO:18)).

In certain embodiments, the at least one agent is operably linked to the RNA nanostructure through a linkage to a single-stranded linker or "handle" or "antihandle" (short, e.g., 5 to 50 nt single-stranded nucleic acids: a handle is at least partially complementary, and may be wholly complementary, to an antihandle).

The linkage between the agent(s) and the RNA nanostructure is not critical and may be any group that can connect the RNA nanostructure and the agent using known chemistry, provided that is does not interfere with the function of the agent or the RNA nanostructure. Chemistries that can be used to link the agent to an oligonucleotide are known in the art, such as disulfide linkages, amino linkages, covalent linkages, etc. In certain embodiments, aliphatic or ethylene glycol linkers that are well known to those with skill in the art can be used. In certain embodiments phosphodiester, phosphorothioate and/or other modified linkages are used. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate probe, IgG-protein A, antigen-antibody, aptamer-target and the like. In certain embodiments, a first member of the binding pair comprises avidin or streptavidin and a second member of the binding pair comprises biotin.

Compositions and Kits

Certain embodiments also provide a composition comprising an RNA nanostructure described herein and a carrier. Certain embodiments provide a composition comprising an RNA nanostructure complex described herein and a carrier. In certain embodiments, the composition comprises a plurality of RNA nanostructures, and a carrier. In certain embodiments, the composition further comprises at least one therapeutic agent described herein.

In certain embodiments, the composition is pharmaceutical composition and the carrier is a pharmaceutically acceptable carrier.

In certain embodiments, the pharmaceutical composition further comprises at least one therapeutic agent (e.g., a therapeutic agent described herein). In certain embodiments, the at least one therapeutic agent is a chemotherapeutic drug, such as doxorubicin or cyclophosphamide. Certain embodiments also provide a vaccine comprising an RNA nanostructure complex as described herein.

Certain embodiments provide kits for practicing the present methods. Accordingly, certain embodiments provide a kit comprising an RNA nanostructure or RNA nanostructure complex described herein and instructions for administering the RNA nanostructure to induce an immune response (e.g., anti-tumor immunity) or to treat a disease or condition. In certain embodiments, the kit further comprises a therapeutic agent described herein and instructions for administering the therapeutic agent in combination (e.g., simultaneously or sequentially) with the RNA nanostructure or RNA nanostructure complex. Certain embodiments provide a kit comprising a composition described herein and instructions for administering the composition to induce an immune response (e.g., anti-tumor immunity) or to treat a disease or condition. In certain embodiments, the kit further comprises a therapeutic agent described herein and instructions for administering the therapeutic agent in combination (e.g., simultaneously or sequentially) with the composition.

Certain Methods of Use

As described in the Examples, an RNA nanostructure, RNA nanostructure complex or composition described herein may be used as an immune-adjuvant to boost an immune response (e.g., inducing anti-tumor immunity).

Accordingly, certain embodiments provide a method of inducing an immune response in a subject (e.g., a mammal, such as a human), comprising administering to the subject an effective amount of an RNA nanostructure, RNA nanostructure complex, or composition as described herein.

In certain embodiments, the administration increases an immune response by at least about, e.g., 20%, 30%, 40%, 50%, 60%, 70%, 80%, 90%, or more (e.g., as compared to a control). Methods of measuring an immune response are known in the art, for example using an assay described in the Example. The phrase "inducing an immune response" refers to the activation of an immune cell. Methods of measuring an immune response are known in the art, for example using an assay described in the Example. The phrase "effective amount" means an amount of an RNA nanostructure or RNA nanostructure complex described herein that induces an immune response.

Certain embodiments also provide a method of treating a disease or disorder in a subject, comprising administering to the subject a therapeutically effective amount of an RNA nanostructure, RNA nanostructure complex, or a composition as described herein.

Certain embodiments provide a method, wherein the method further comprises administering at least one therapeutic agent to the subject.

The at least one therapeutic agent may be administered in combination with the RNA nanostructure, RNA nanostructure complex or composition. As used herein, the phrase "in combination" refers to the simultaneous or sequential administration of the RNA nanostructure, RNA nanostructure complex or composition and the at least one therapeutic agent. For simultaneous administration, the RNA nanostructure RNA nanostructure complex or composition and the at least one therapeutic agent may be present in a single composition or may be separate (e.g., may be administered by the same or different routes).

Certain embodiments provide an RNA nanostructure, RNA nanostructure complex, or a composition as described herein for use in medical therapy.

Certain embodiments provide the use of an RNA nanostructure, RNA nanostructure complex, or a composition as described herein for the manufacture of a medicament for inducing an immune response in a subject (e.g., a mammal, such as a human).

Certain embodiments provide the use of an RNA nanostructure, RNA nanostructure complex, or a composition as described herein for the manufacture of a medicament for inducing an immune response in a subject (e.g., a mammal, such as a human), in combination with at least one therapeutic agent.

Certain embodiments provide an RNA nanostructure, RNA nanostructure complex, or a composition as described herein for inducing an immune response.

Certain embodiments provide an RNA nanostructure, RNA nanostructure complex, or a composition as described herein for inducing an immune response, in combination with at least one therapeutic agent.

Certain embodiments provide the use of an RNA nanostructure, RNA nanostructure complex, or a composition as described herein for the manufacture of a medicament for treating a disease or disorder in a subject.

Certain embodiments provide the use of an RNA nanostructure, RNA nanostructure complex, or a composition as described herein for the manufacture of a medicament for treating a disease or disorder in a subject, in combination with at least one therapeutic agent.

Certain embodiments provide an RNA nanostructure, RNA nanostructure complex, or a composition as described herein for the prophylactic or therapeutic treatment a disease or disorder.

Certain embodiments provide an RNA nanostructure, RNA nanostructure complex, or a composition as described herein for the prophylactic or therapeutic treatment of a disease or disorder, in combination with at least one therapeutic agent.

In certain embodiments, the disease or disorder is a condition that requires a boost of the host immunity. In certain embodiments, the disease or disorder is a hyperproliferative disorder, such as cancer. In certain embodiments, the disease or disorder is an infectious disease.

In certain embodiments, the cancer is carcinoma, lymphoma, blastoma, sarcoma, or leukemia. In certain embodiments, the cancer is a solid tumor cancer.

In certain embodiments, the cancer is squamous cell cancer, small-cell lung cancer, non-small cell lung cancer, adenocarcinoma of the lung, squamous carcinoma of the lung, cancer of the peritoneum, hepatocellular cancer, renal cell carcinoma, gastrointestinal cancer, gastric cancer, esophageal cancer, pancreatic cancer, glioma, cervical cancer, ovarian cancer, liver cancer, bladder cancer, hepatoma, breast cancer (e.g., endocrine resistant breast cancer), colon cancer, rectal cancer, lung cancer, endometrial or uterine carcinoma, salivary gland carcinoma, kidney cancer, liver cancer, prostate cancer, vulval cancer, thyroid cancer, hepatic carcinoma, melanoma, leukemia, or head and neck cancer. In certain embodiments, the cancer is breast cancer. In certain embodiments, the cancer is colon cancer. In certain embodiments, the cancer is colorectal cancer. In certain embodiments, the cancer is lymphoma.

In certain embodiments, the therapeutic agent is a therapeutic agent described herein. For example, in certain embodiments, the therapeutic agent is an immuno-stimulatory agent, a radioisotope, a chemotherapeutic drug (e.g., doxorubicin) or an immuno-therapy agent, such as antibody or an antibody fragment. In certain embodiments, the therapeutic agent is a vaccine, such as a cancer vaccine. In certain embodiments, the therapeutic agent is a tumor targeting agent, such as a monoclonal tumor-specific antibody or an aptamer. In certain embodiments, the therapeutic agent is an antibody (e.g., a monoclonal antibody, e.g., an anti-PD1 antibody). In certain embodiments, the therapeutic agent is an antigen (e.g., a tumor associated antigen or a tumor specific antigen). In certain embodiments, the therapeutic agent is a tumor antigen peptide(s).

It should be understood that any of the following methods may be used in one or more combinations with any of the other methods described herein.

Certain embodiments provide a method of enhancing/increasing pro-inflammatory cytokines in a subject (e.g., a mammal, such as a human), comprising administering to the subject an effective amount of an RNA nanostructure, complex or composition as described herein.

Certain embodiments provide a method of activating immune cells by specific triggering of toll-like receptor 3 (TLR3) signaling pathway in a subject (e.g., a mammal, such as a human), comprising administering to the subject an effective amount of an RNA nanostructure, complex or composition as described herein.

Certain embodiments provide a method of slowing or suppressing tumor growth in a subject (e.g., a mammal, such as a human) as compared to a control subject, comprising administering to the subject an effective amount of an RNA nanostructure, complex or composition as described herein. In certain embodiments a control subject is a subject that is not administered an effective amount of an RNA nanostructure, complex or composition as described herein.

Certain embodiments provide a method to elevate levels of anti-tumor proinflammatory cytokines in a subject (e.g., a mammal, such as a human) with a tumor as compared to a control subject, comprising administering to the subject an effective amount of an RNA nanostructure, complex or composition as described herein.

Certain embodiments provide a method to decrease levels of anti-inflammatory cytokines in a subject (e.g., a mammal, such as a human) with a tumor as compared to a control subject, comprising administering to the subject an effective amount of an RNA nanostructure, complex or composition as described herein.

Certain embodiments provide an effective amount of an RNA nanostructure, complex or composition as described herein for use in enhancing/increasing pro-inflammatory cytokines in a subject (e.g., a mammal, such as a human).

Certain embodiments provide an effective amount of an RNA nanostructure, complex or composition as described herein for use in activating immune cells by specific triggering of toll-like receptor 3 (TLR3) signaling pathway in a subject (e.g., a mammal, such as a human).

Certain embodiments provide an effective amount of an RNA nanostructure, complex or composition as described herein for use in slowing or suppressing tumor growth in a subject (e.g., a mammal, such as a human) as compared to a control subject.

Certain embodiments provide an effective amount of an RNA nanostructure, complex or composition as described herein for use in elevating levels of anti-tumor proinflammatory cytokines in a subject (e.g., a mammal, such as a human) with a tumor as compared to a control subject.

Certain embodiments provide an effective amount of an RNA nanostructure, complex or composition as described herein for use in decreasing levels of anti-inflammatory cytokines in a subject (e.g., a mammal, such as a human) with a tumor as compared to a control subject.

Administration

As described herein, in certain embodiments, methods may comprise administering an RNA nanostructure described herein, and optionally, a therapeutic agent to a subject. Such compounds (i.e., an RNA nanostructure and/or therapeutic agent) may be formulated as a pharmaceutical composition and administered to a mammalian host, such as a human patient in a variety of forms adapted to the chosen route of administration, i.e., orally or parenterally, by intravenous, intramuscular, intraperitoneal or topical or subcutaneous routes.

Thus, the compounds may be systemically administered, e.g., orally, in combination with a pharmaceutically acceptable vehicle such as an inert diluent or an assimilable edible carrier. They may be enclosed in hard or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars, buffers or sodium chloride may be included. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation include vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound may be conveniently formulated in unit dosage form. Certain embodiments provide a composition comprising a compound formulated in such a unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain Definitions

As used herein, the term "about" means±10%.

"Operably-linked" refers to the association two chemical moieties so that the function of one is affected by the other, e.g., an arrangement of elements wherein the components so described are configured so as to perform their usual function.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The terms "nucleotide sequence" and "nucleic acid sequence" and "nucleic acid strand" refer to a sequence of bases (purines and/or pyrimidines) in a polymer of DNA or RNA, which can be single-stranded or double-stranded, optionally containing synthetic, non-natural or altered nucleotide bases capable of incorporation into DNA or RNA polymers, and/or backbone modifications (e.g., a modified oligomer, such as a morpholino oligomer, phosphorodiamate morpholino oligomer or vivo-mopholino). The terms "oligo", "oligonucleotide" and "oligomer" may be used interchangeably and refer to such sequences of purines and/or pyrimidines. The terms "modified oligos", "modified oligonucleotides" or "modified oligomers" may be similarly used interchangeably, and refer to such sequences that contain synthetic, non-natural or altered bases and/or backbone modifications (e.g., chemical modifications to the internucleotide phosphate linkages and/or to the backbone sugar).

The oligonucleotides described herein may be synthesized using standard solid or solution phase synthesis techniques that are known in the art. In certain embodiments, the oligonucleotides are synthesized using solid-phase phosphoramidite chemistry (U.S. Pat. No. 6,773,885) with automated synthesizers. Chemical synthesis of nucleic acids allows for the production of various forms of the nucleic acids with modified linkages, chimeric compositions, and nonstandard bases or modifying groups attached in chosen places through the nucleic acid's entire length.

Certain embodiments encompass isolated or substantially purified nucleic acid compositions. An "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

By "portion" or "fragment," as it relates to a nucleic acid molecule, sequence or segment, when it is linked to other sequences for expression, is meant a sequence having at least 80 nucleotides, at least 150 nucleotides, or at least 400 nucleotides. If not employed for expressing, a "portion" or "fragment" means at least 9, at least 12, at least 15, or at least 20, consecutive nucleotides, e.g., probes and primers (oligonucleotides), corresponding to the nucleotide sequence of the nucleic acid molecules described herein.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

"Homology" refers to the percent identity between two polynucleotides or two polypeptide sequences. Two RNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleotide sequences: (a) "reference sequence," (b) "comparison window," (c) "sequence identity" (d) "percentage of sequence identity," (e) "substantial identity" and (f) "complementarity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity, including sequence complementarity, between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity or complementarity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001. To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the embodiments described herein, comparison of nucleotide sequences for determination of percent sequence identity may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., PCR Protocols, *A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

The term "complementary" as used herein refers to the broad concept of complementary base pairing between two nucleic acids aligned in an antisense position in relation to each other. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60%, or at least about 80% of corresponding positions in each of the molecules are occupied by nucleotides which normally base pair with each other (e.g., A:T (A:U for RNA) and G:C nucleotide pairs).

As used herein, the term "derived" or "directed to" with respect to a nucleotide molecule means that the molecule has complementary sequence identity to a particular molecule of interest.

The term "subject" as used herein refers to humans, higher non-human primates, rodents, domestic, cows, horses, pigs, sheep, dogs and cats. In certain embodiments, the subject is a human.

The term "therapeutically effective amount," in reference to treating a disease state/condition, refers to an amount of a therapeutic agent that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound, RNA nanostructure or composition described herein that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the RNA nanostructure/therapeutic agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the RNA nanostructure/therapeutic agent may prevent growth and/or kill existing cancer cells, it may be cytostatic and/or cytotoxic. For cancer therapy, efficacy can be measured, for example, by assessing the time to disease progression and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

A "chemotherapeutic agent" is a biological (large molecule) or chemical (small molecule) compound useful in the treatment of cancer, regardless of mechanism of action. Classes of chemotherapeutic agents include, but are not limited to alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted conventional chemotherapy.

The term "synergistic" as used herein refers to a therapeutic combination that is more effective than the additive effects of the two or more single agents. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

This section provides the definitions of the criteria used to determine objective tumor response for target lesions. "Complete response" (CR) is used to mean disappearance of all observable target lesions with pathological lymph nodes (whether target or non-target) having reduction in short axis to less than about 10 mm. "Partial response" (PR) is used to mean at least about a 30% decrease in the sum of diameters of target lesions, taking as reference the baseline sum of diameters. "Progressive disease" (PD) is used to mean at least about a 20% increase in the sum of diameters of target lesions, taking as reference the smallest sum on study (nadir), including baseline. In addition to the relative increase of about 20%, the sum also demonstrates an absolute increase of at least about 5 mm. In certain embodiments, the appearance of one or more new lesions is considered PD. "Stable disease" (SD) is used to mean neither sufficient shrinkage to qualify for PR nor sufficient increase to qualify for PD, taking as reference the smallest sum on study.

Certain Embodiments

Certain embodiments provide a complex comprising an RNA nanostructure and at least one diagnostic and/or therapeutic agent operably linked to the RNA nanostructure.

In certain embodiments, the RNA nanostructure comprises one single-stranded RNA (ssRNA) molecule, wherein the ssRNA molecule forms at least one paranemic cohesion crossover, and wherein the RNA nanostructure has immuno-stimulatory properties.

In certain embodiments, the RNA nanostructure comprises one single-stranded RNA (ssRNA) molecule, wherein the ssRNA molecule comprises a plurality of regions of double helices and at least one paranemic crossover operably linked between two regions of double helices, and wherein the RNA nanostructure has immuno-stimulatory properties.

In certain embodiments, the ssRNA molecule comprises at least two parallel double helices.

In certain embodiments, about 60-99% of the RNA nanostructure is double stranded and about 1-40% of the RNA nanostructure is single stranded.

In certain embodiments, about 95% of the RNA nanostructure is double stranded and about 5% of the RNA nanostructure is single stranded.

In certain embodiments, the RNA nanostructure comprises rectangular origami nanostructure.

In certain embodiments, the RNA nanostructure comprises a nucleic acid sequence about 1500 to about 2500 nucleotides in length.

In certain embodiments, the RNA nanostructure comprises a nucleic acid sequence having at least about 75% sequence identity to SEQ ID NO:1.

In certain embodiments, the RNA nanostructure comprises a nucleic acid sequence having at least about 85% sequence identity to SEQ ID NO:1.

In certain embodiments, the RNA nanostructure comprises a nucleic acid sequence having at least about 90% sequence identity to SEQ ID NO:1.

In certain embodiments, the RNA nanostructure comprises a nucleic acid sequence having at least about 95% sequence identity to SEQ ID NO:1.

In certain embodiments, the RNA nanostructure comprises a nucleic acid sequence having at least about 95% sequence identity to SEQ ID NO:1.

In certain embodiments, the RNA nanostructure comprises SEQ ID NO:1.

In certain embodiments, the RNA nanostructure consists of SEQ ID NO:1.

In certain embodiments, the nucleic acid sequence of the RNA nanostructure is about 1500 to about 2500 nucleotides in length.

In certain embodiments, the RNA nanostructure comprises at least one paranemic cohesion crossover.

In certain embodiments, the diagnostic or therapeutic agent is a peptide that comprises a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues (SEQ ID NO: 21).

In certain embodiments, the peptide is tumor targeting peptide (TTP), a human cancer peptide, an infectious agent peptide, or calreticulin protein.

In certain embodiments, the infectious agent peptide is specific for epitopes for CD8+ T cells involved in the immunity against influenza, HIV, HCV, and other infectious agents.

In certain embodiments, the protein is calreticulin protein. Calreticulin protein allows the RNA-origami to engage interactions between tumor cells and macrophages or dendritic cells for enhanced antigen presentation and stimulation of antigen-specific T cells.

In certain embodiments, the protein is Human cancer peptide NY-ESO-1 or Muc1.

In certain embodiments, the at least one therapeutic agent is a tumor antigen peptide.

In certain embodiments, the TTP is CTKD-K10 (CTKDNNLLGRFELSGGGSK$_{10}$ (SEQ ID NO:18)).

In certain embodiments, a component of an RNA nanostructure complex is a tumor-specific antigen.

In certain embodiments, the tumor-specific antigen is TKD. It is understood that the tumor-specific antigens may be modified to enhance complex formation, to modulate RNA nanostructure: tumor specific antigen ratios and to operably link one or more agents. In certain embodiments, the tumor-specific antigen is TKD modified to add a C at the N-terminus. In certain embodiments, the tumor-specific antigen is TKD modified to add from 1 to 15 lysine residues (SEQ ID NO: 22) at the C-terminus. In certain embodiments, the tumor-specific antigen is TKD modified to add 10 lysine residues (SEQ ID NO: 21) at the C-terminus. In certain embodiments, the tumor-specific antigen is TKD modified to add a C at the N-terminus and from 1 to 15 lysine (SEQ ID NO: 22) at the C-terminus. In certain embodiments, the tumor-specific antigen is TKD modified to add a C at the N-terminus and 10 lysine (SEQ ID NO: 21) at the C-terminus.

Certain embodiments provide a pharmaceutical composition comprising the complex described herein and a pharmaceutically acceptable carrier.

Certain embodiments provide a pharmaceutical composition described herein and further comprising at least one therapeutic agent.

In certain embodiments, the at least one therapeutic agent is a chemotherapeutic drug.

In certain embodiments, the chemotherapeutic drug is doxorubicin.

Certain embodiments provide a method of inducing an immune response a subject (e.g., a mammal, such as a human), comprising administering to the subject an effective amount of a complex or a composition as described herein.

Certain embodiments provide a method of treating a disease or disorder in a subject, comprising administering to the subject a therapeutically effective amount of a complex or a composition as described herein.

In certain embodiments, the disease or disorder is cancer.
In certain embodiments, the cancer is breast cancer.
In certain embodiments, the cancer is colon cancer.
In certain embodiments, the cancer is lymphoma.
In certain embodiments, the method further comprises administering at least one therapeutic agent to the subject.
In certain embodiments, the at least one therapeutic agent is a tumor targeting agent.
In certain embodiments, the tumor-targeting agent is a monoclonal tumor specific antibody or an aptamer.

Certain embodiments provide a method of enhancing/increasing pro-inflammatory cytokines in a subject (e.g., a mammal, such as a human), comprising administering to the subject an effective amount of a complex or a composition as described herein.

Certain embodiments provide a method of activating immune cells by specific triggering of TLR3 signaling pathway in a subject (e.g., a mammal, such as a human), comprising administering to the subject an effective amount of a complex or a composition as described herein.

Certain embodiments provide a method of slowing or suppressing tumor growth in a subject (e.g., a mammal, such as a human) as compared to a control subject, comprising administering to the subject an effective amount of a complex or a composition as described herein.

Certain embodiments provide a method of elevate levels of anti-tumor proinflammatory cytokines in a subject (e.g., a mammal, such as a human) with a tumor as compared to a control subject, comprising administering to the subject an effective amount of a complex or a composition as described herein.

Certain embodiments provide a method to decrease levels of anti-inflammatory cytokines in a subject (e.g., a mammal, such as a human) with a tumor as compared to a control subject, comprising administering to the subject an effective amount of a complex or a composition as described herein.

Certain embodiments provide the use of a complex or a composition as described herein for the manufacture of a medicament for inducing an immune response in a subject (e.g., a mammal, such as a human).

Certain embodiments provide a complex or a composition as described herein for inducing an immune response.

Certain embodiments provide a use of a complex or a composition as described herein for the manufacture of a medicament for treating a disease or disorder in a subject.

Certain embodiments provide a complex or a composition as described herein for the prophylactic or therapeutic treatment a disease or disorder.

Certain embodiments provide a kit comprising a complex or a composition as described herein and instructions for administering the RNA nanostructure/composition to a subject to induce an immune response or to treat a disease or disorder.

In certain embodiments, the kit further comprises at least one therapeutic agent.

In certain embodiments, the RNA nanostructure is a nanostructure as described in the Examples or Figures.

Certain embodiments provide an RNA nanostructure comprising one single-stranded RNA (ssRNA) molecule, wherein the ssRNA molecule forms at least one paranemic cohesion crossover, and wherein the RNA nanostructure has immuno-stimulatory properties.

In certain embodiments, the RNA nanostructure is an RNA rectangle origami nanostructure.

In certain embodiments, the RNA nanostructure comprises a nucleic acid sequence about 1500 to about 2500 nucleotides in length.

Certain embodiments provide an RNA nanostructure comprising a nucleic acid sequence having at least about 75% sequence identity to SEQ ID NO:1.

In certain embodiments, the nucleic acid sequence has at least about 85% sequence identity to SEQ ID NO:1.

In certain embodiments, the nucleic acid sequence has at least about 95% sequence identity to SEQ ID NO:1.

In certain embodiments, the nucleic acid sequence has at least about 99% sequence identity to SEQ ID NO:1.

In certain embodiments, the RNA nanostructure comprises SEQ ID NO:1.

In certain embodiments, the RNA nanostructure consists of SEQ ID NO:1.

In certain embodiments, the nucleic acid sequence is about 1500 to about 2500 nucleotides in length.

In certain embodiments, the RNA nanostructure comprises at least one paranemic cohesion crossover.

In certain embodiments, the RNA nanostructure is an RNA rectangle origami nanostructure.

In certain embodiments, the RNA nanostructure is an agonist of a pattern recognition receptor.

In certain embodiments, at least one diagnostic agent is operably linked to the RNA nanostructure.

In certain embodiments, at least one therapeutic agent is operably linked to the RNA nanostructure.

In certain embodiments, the at least one therapeutic agent is a tumor antigen peptide.

Certain embodiments provide a pharmaceutical composition comprising the RNA nanostructure described herein and a pharmaceutically acceptable carrier.

In certain embodiments, the pharmaceutical composition further comprises at least one therapeutic agent.

In certain embodiments, the at least one therapeutic agent is a chemotherapeutic drug (e.g., doxorubicin).

Certain embodiments provide a method of inducing an immune response a subject (e.g., a mammal, such as a human), comprising administering to the subject an effective amount of an RNA nanostructure as described herein or a composition as described herein.

Certain embodiments provide a method of treating a disease or disorder in a subject, comprising administering to the subject a therapeutically effective amount of an RNA nanostructure as described herein or a composition as described herein.

In certain embodiments, the disease or disorder is cancer.

In certain embodiments, the cancer is breast cancer.

In certain embodiments, the method further comprises administering at least one therapeutic agent to the subject.

In certain embodiments, the at least one therapeutic agent is a tumor targeting agent (e.g., a monoclonal tumor-specific antibody or an aptamer).

Certain embodiments provide a use of an RNA nanostructure as described herein or a composition as described herein for the manufacture of a medicament for inducing an immune response in a subject (e.g., a mammal, such as a human).

Certain embodiments provide an RNA nanostructure as described herein or a composition as described herein for inducing an immune response.

Certain embodiments provide an RNA nanostructure as described herein or a composition as described herein for the manufacture of a medicament for treating a disease or disorder in a subject.

Certain embodiments provide an RNA nanostructure as described herein or a composition as described herein for the prophylactic or therapeutic treatment a disease or disorder.

Certain embodiments provide a kit comprising an RNA nanostructure as described herein or a composition as described herein and instructions for administering the RNA nanostructure/composition to a subject to induce an immune response or to treat a disease or disorder.

In certain embodiments, the kit further comprises at least one therapeutic agent.

In certain embodiments, the RNA nanostructure comprises a nucleic acid sequence about 15 to about 20000 nucleotides in length.

In certain embodiments, the RNA nanostructure comprises a nucleic acid sequence about 1000 to about 12000 nucleotides in length.

In certain embodiments, the RNA nanostructure comprises a nucleic acid sequence about 1000 to about 10000 nucleotides in length.

Certain embodiments provide an RNA nanostructure comprising one single-stranded RNA (ssRNA) molecule, wherein the at least one ssRNA molecule comprises a plurality of regions of double helices and at least one paranemic crossover operably linked between two regions of double helices, and wherein the RNA nanostructure has immuno-stimulatory properties.

In certain embodiments, the ssRNA molecule comprises at least two parallel double helices.

In certain embodiments, the ssRNA molecule comprises at least seven parallel double helices.

In certain embodiments, the RNA nanostructure is a RNA rectangle origami nanostructure.

In certain embodiments, the RNA nanostructure comprises a nucleic acid sequence about 1500 to about 2500 nucleotides in length.

Certain embodiments provide an RNA nanostructure comprising a nucleic acid sequence having at least about 75% sequence identity to SEQ ID NO:1.

In certain embodiments, the nucleic acid sequence has at least about 85% sequence identity to SEQ ID NO:1.

In certain embodiments, the nucleic acid sequence has at least about 95% sequence identity to SEQ ID NO:1.

In certain embodiments, the nucleic acid sequence has at least about 99% sequence identity to SEQ ID NO:1.

In certain embodiments, the RNA nanostructure comprises SEQ ID NO:1.

In certain embodiments, the RNA nanostructure consists of SEQ ID NO:1.

In certain embodiments, the nucleic acid sequence is about 1500 to about 2500 nucleotides in length.

In certain embodiments, the RNA nanostructure comprises at least one paranemic cohesion crossover.

In certain embodiments, the RNA nanostructure is an RNA rectangle origami nanostructure.

In certain embodiments, the RNA nanostructure is an agonist of a pattern recognition receptor.

Certain embodiments provide a complex comprising the RNA nanostructure described herein, and at least one diagnostic agent operably linked to the RNA nanostructure.

Certain embodiments provide a complex comprising the RNA nanostructure described herein, wherein at least one therapeutic agent is operably linked to the RNA nanostructure.

Certain embodiments provide a complex comprising the RNA nanostructure described herein, wherein the at least one therapeutic agent is a tumor antigen peptide.

Certain embodiments provide a pharmaceutical composition comprising the RNA nanostructure or the complex described herein and a pharmaceutically acceptable carrier In certain embodiments, the pharmaceutical composition further comprises at least one therapeutic agent.

In certain embodiments, the at least one therapeutic agent is a chemotherapeutic drug.

In certain embodiments, the chemotherapeutic drug is doxorubicin.

Certain embodiments provide a method of inducing an immune response a subject (e.g., a mammal, such as a human), comprising administering to the subject an effective amount of an RNA nanostructure as described herein or the complex described herein, or a composition described herein.

Certain embodiments provide a method of treating a disease or disorder in a subject, comprising administering to the subject a therapeutically effective amount of an RNA nanostructure as described herein or the complex described herein, or a composition as described herein.

In certain embodiments, the disease or disorder is cancer.

In certain embodiments, the cancer is breast cancer.

In certain embodiments, the cancer is colon cancer.

In certain embodiments, the method further comprises administering at least one therapeutic agent to the subject.

In certain embodiments, the at least one therapeutic agent is a tumor targeting agent.

In certain embodiments, the tumor targeting agent is a monoclonal tumor specific antibody or an aptamer.

Certain embodiments provide a method of enhancing/increasing pro-inflammatory cytokines in a subject (e.g., a mammal, such as a human), comprising administering to the subject an effective amount of an RNA nanostructure as described herein or the complex described herein, or a composition as described herein.

Certain embodiments provide a method of activating immune cells by specific triggering of TLR3 signaling pathway in a subject (e.g., a mammal, such as a human), comprising administering to the subject an effective amount of an RNA nanostructure as described herein or the complex described herein, or a composition as described herein.

Certain embodiments provide a method of slowing or suppressing tumor growth in a subject (e.g., a mammal, such as a human) as compared to a control subject, comprising administering to the subject an effective amount of an RNA nanostructure as described herein or the complex described herein, or a composition as described herein.

Certain embodiments provide a method of elevate levels of anti-tumor proinflammatory cytokines in a subject (e.g., a mammal, such as a human) with a tumor as compared to a control subject, comprising administering to the subject an effective amount of an RNA nanostructure as described herein or the complex described herein, or a composition as described herein.

Certain embodiments provide a method to decrease levels of anti-inflammatory cytokines in a subject (e.g., a mammal, such as a human) with a tumor as compared to a control subject, comprising administering to the subject an effective amount of an RNA nanostructure as described herein or the complex described herein, or a composition as described herein.

Certain embodiments provide a use of an RNA nanostructure as described herein or the complex described herein, or a composition as described for the manufacture of a medicament for inducing an immune response in a subject (e.g., a mammal, such as a human).

Certain embodiments provide an RNA nanostructure as described herein or the complex described herein, or a composition as described herein for inducing an immune response.

Certain embodiments provide a use of an RNA nanostructure as described herein or the complex described herein, or a composition as described herein for the manufacture of a medicament for treating a disease or disorder in a subject.

Certain embodiments provide an RNA nanostructure as described herein or the complex described herein, or a composition as described herein for the prophylactic or therapeutic treatment a disease or disorder.

Certain embodiments provide a kit comprising an RNA nanostructure as described herein or the complex described herein, or a composition as described herein and instructions for administering the RNA nanostructure/composition to a subject to induce an immune response or to treat a disease or disorder.

In certain embodiments, the kit further comprises at least one therapeutic agent.

In certain embodiments, the diagnostic or therapeutic agent is a peptide that comprises a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues (SEQ ID NO: 21).

In certain embodiments, the peptide is tumor targeting peptide (TTP), a human cancer peptide, an infectious agent peptide, or calreticulin protein.

In certain embodiments, the infectious agent peptide is specific epitopes for CD8+ T cells involved in the immunity against influenza, HIV, HCV, and other infectious agents.

In certain embodiments, the protein is calreticulin protein. Calreticulin protein allows the RNA-origami to engage interactions between tumor cells and macrophages or dendritic cells for enhanced antigen presentation and stimulation of antigen-specific T cells.

In certain embodiments, the protein is Human cancer peptide NY-ESO-1 or Muc1.

In certain embodiments, the at least one therapeutic agent is a tumor antigen peptide.

In certain embodiments, the TTP is CTKD-K10 (CTKDNNLLGRFELSGGGSK$_{10}$ (SEQ ID NO:18)).

In certain embodiments, a component of an RNA nanostructure complex of the present invention is a tumor-specific antigen.

In certain embodiments, the tumor-specific antigen is TKD. It is understood that the tumor-specific antigens may be modified to enhance complex formation, to modulate RNA nanostructure: tumor specific antigen ratios and to operably link one or more agents. In certain embodiments, the tumor-specific antigen is TKD modified to add a C at the N-terminus. In certain embodiments, the tumor-specific antigen is TKD modified to add from 1 to 15 lysine residues (SEQ ID NO: 22) at the C-terminus. In certain embodiments, the tumor-specific antigen is TKD modified to add 10 lysine residues (SEQ ID NO: 21) at the C-terminus. In certain embodiments, the tumor-specific antigen is TKD modified to add a C at the N-terminus and from 1 to 15 lysine (SEQ ID NO: 22) at the C-terminus. In certain embodiments, the tumor-specific antigen is TKD modified to add a C at the N-terminus and 10 lysine (SEQ ID NO: 21) at the C-terminus.

Certain embodiments provide an RNA nanostructure comprising at least one single-stranded RNA (ssRNA) molecule, wherein the ssRNA molecule forms at least one paranemic cohesion crossover, and wherein the RNA nanostructure has immunomodulatory (e.g., immuno-stimulatory) properties.

Certain embodiments provide an RNA nanostructure comprising at least one single-stranded RNA (ssRNA) molecule, wherein the at least one ssRNA molecule comprises a plurality of regions of double helices and at least one paranemic crossover operably linked between two regions of double helices, and wherein the RNA nanostructure has immunomodulatory (e.g., immuno-stimulatory) properties.

In certain embodiments, the RNA nanostructure described herein, comprises one ssRNA molecule.

In certain embodiments, the RNA nanostructure described herein, consists of one ssRNA molecule.

In certain embodiments, the at least one ssRNA molecule is about 10 to about 100,000 nucleotides in length.

In certain embodiments, the at least one ssRNA molecule is about 10 to about 20,000 nucleotides in length.

In certain embodiments, the at least one ssRNA molecule is about 10 to about 10,000 nucleotides in length.

In certain embodiments, the at least one ssRNA molecule does not comprise a transcription termination sequence.

In certain embodiments, the at least one ssRNA molecule does not comprise an AUCUGUU sequence.

In certain embodiments, about 60-99% of the RNA nanostructure is comprised of double stranded regions and about 1-40% of the RNA nanostructure is comprised of single stranded regions.

In certain embodiments, about 95% of the RNA nanostructure is comprised of double stranded regions and about 5% of the RNA nanostructure is comprised of single stranded regions.

In certain embodiments, the RNA nanostructure comprises at least two parallel double helices.

In certain embodiments, the RNA nanostructure comprises at least seven parallel double helices.

In certain embodiments, a double helix or a region of a double helix has a length of about 5 to about 50 nucleotides.

In certain embodiments, a double helix or a region of a double helix has a length of about 5 to about 25 nucleotides.

In certain embodiments, a double helix or a region of a double helix has a length of 8 or 9 nucleotides.

In certain embodiments, the RNA nanostructure comprises a plurality of regions of double helices having a length of 8 nucleotides and a plurality of regions of double helices having a length of 9 nucleotides.

In certain embodiments, the RNA nanostructure comprises between about 1 to about 200 paranemic cohesion crossovers.

In certain embodiments, the RNA nanostructure comprises a plurality of paranemic cohesion crossovers.

In certain embodiments, the at least one paranemic cohesion crossover has a length of about 4 to about 15 nucleotides.

In certain embodiments, the at least one paranemic cohesion crossover has a length of about 8 nucleotides.

In certain embodiments, the paranemic cohesion crossover comprises 16 base pairings.

In certain embodiments, the at least one paranemic cohesion crossover comprises between about 6 to about 10 GC base pairs.

In certain embodiments, the at least one ssRNA molecule comprises a sequence that forms internal loops that remain unpaired prior to forming the at least one paranemic cohesion crossover.

In certain embodiments, the RNA nanostructure comprises at least one loop region that connects one double helix to another double helix, and wherein the at least one loop region is located along an edge of the RNA nanostructure.

In certain embodiments, the RNA nanostructure comprises a plurality of loop regions.

In certain embodiments, the at least one loop region has a length of about 2 to about 100 nucleotides.

In certain embodiments, the at least one loop region has a length of about 2 to about 50 nucleotides.

In certain embodiments, the RNA nanostructure comprises a structural repeating unit of 33 nucleotides.

In certain embodiments, the structural repeating unit comprises, in order: a first region of a double helix, a first paranemic cohesion crossover, a second region of a double helix, and a second paranemic cohesion crossover.

In certain embodiments, the first region of a double helix is 8 nucleotides in length, the first paranemic cohesion crossover is 8 nucleotides in length, the second region of a double helix is 9 nucleotides in length, and the second paranemic cohesion crossover is 8 nucleotides in length.

In certain embodiments, the RNA nanostructure comprises:

a first layer comprising a plurality of double helices and a plurality of paranemic cohesion crossovers, wherein at least two regions of double helices of the first layer are separated from each other by a paranemic cohesion crossover; and a second layer comprising a plurality of double helices and a plurality of paranemic cohesion crossovers, wherein at least two regions of double helices in the second layer are separated from each other by a paranemic cohesion crossover; and wherein a paranemic cohesion crossover of the first layer is hybridized to a paranemic cohesion crossover of the second layer.

In certain embodiments, the RNA nanostructure has a crossing number of zero, and wherein the RNA nanostructure is unknotted.

In certain embodiments, the RNA nanostructure comprises only parallel crossovers.

In certain embodiments, the RNA nanostructure comprises continuous $\pi$-$\pi$ stacking along greater than 50% of the double helices of the nanostructure.

In certain embodiments, the RNA nanostructure has a rectangular shape, a diamond shape or a tetrahedron shape.

In certain embodiments, the RNA nanostructure has a rectangular shape.

Certain embodiments provide an RNA nanostructure comprising at least one single-stranded RNA (ssRNA) molecule, wherein the RNA nanostructure comprises at least two structural repeating units of 33 nucleotides in length, and wherein each structural repeating unit comprises, in order: a first region of a double helix 8 nucleotides in length, a first paranemic cohesion crossover 8 nucleotides in length, a second region of a double helix 9 nucleotides in length, and a second paranemic cohesion crossover 8 nucleotides in length.

Certain embodiments provide an RNA nanostructure comprising a nucleic acid sequence having at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the nucleic acid sequence has at least about 85% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the nucleic acid sequence has at least about 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the nucleic acid sequence has at least about 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the RNA nanostructure described herein comprises SEQ ID NO:1.

In certain embodiments, the RNA nanostructure described herein consists of SEQ ID NO:1.

In certain embodiments, the RNA nanostructure described herein comprises at least one paranemic cohesion crossover.

In certain embodiments, the RNA nanostructure has a rectangular, diamond or tetrahedron shape.

In certain embodiments, the RNA nanostructure has immuno-stimulatory properties

In certain embodiments, the RNA nanostructure is an agonist of a pattern recognition receptor.

In certain embodiments, at least one diagnostic agent is operably linked to the RNA nanostructure.

In certain embodiments, at least one therapeutic agent is operably linked to the RNA nanostructure.

Certain embodiments provide a complex comprising an RNA nanostructure described herein, and at least one diagnostic agent operably linked to the RNA nanostructure.

Certain embodiments provide a complex comprising an RNA nanostructure described herein, and at least one therapeutic agent operably linked to the RNA nanostructure.

In certain embodiments, the diagnostic or therapeutic agent is a peptide comprising a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues (SEQ ID NO: 21).

In certain embodiments, the peptide is a tumor targeting peptide (TTP), a human cancer peptide, an infectious agent peptide, tumor antigen peptide or calreticuln protein.

In certain embodiments, the infectious agent peptide comprises specific epitopes for CD8+ T cells involved in the immunity against influenza, HIV, HCV, or other infectious agents.

In certain embodiments, the peptide is calreticuln protein.

In certain embodiments, the peptide is human cancer peptide NY-ESO-1 or Muc1.

In certain embodiments, the peptide is a tumor antigen peptide.

In certain embodiments, the peptide is CTKD-K10 (CTKDNNLLGRFELSGGGSK$_{10}$ (SEQ ID NO:18)).

Certain embodiments provide a pharmaceutical composition comprising an RNA nanostructure or complex described herein and a pharmaceutically acceptable carrier.

In certain embodiments, the pharmaceutical composition described herein further comprises at least one therapeutic agent.

In certain embodiments, the at least one therapeutic agent is a chemotherapeutic drug (e.g., doxorubicin).

Certain embodiments provide a method of inducing an immune response a subject (e.g., a mammal, such as a human), comprising administering to the subject an effective amount of an RNA nanostructure, complex or composition as described herein.

Certain embodiments provide a method of treating a disease or disorder in a subject, comprising administering to the subject a therapeutically effective amount of an RNA nanostructure, complex or composition described herein.

In certain embodiments, the disease or disorder is cancer.

In certain embodiments, the cancer is breast cancer, colorectal cancer or lymphoma.

In certain embodiments, a method described herein, further comprises administering at least one therapeutic agent to the subject.

In certain embodiments, the at least one therapeutic agent is a tumor targeting agent (e.g., a monoclonal tumor-specific antibody or an aptamer).

Certain embodiments provide a method of enhancing/increasing pro-inflammatory cytokines in a subject (e.g., a mammal, such as a human), comprising administering to the subject an effective amount of an RNA nanostructure, complex or composition described herein.

Certain embodiments provide a method of activating immune cells by specific triggering of toll-like receptor 3 (TLR3) signaling pathway in a subject (e.g., a mammal, such as a human), comprising administering to the subject an effective amount of an RNA nanostructure, complex or composition as described herein.

Certain embodiments provide a method of slowing or suppressing tumor growth in a subject (e.g., a mammal, such as a human) as compared to a control subject, comprising administering to the subject an effective amount of an RNA nanostructure, complex or composition as described herein.

Certain embodiments provide a method to elevate levels of anti-tumor proinflammatory cytokines in a subject (e.g., a mammal, such as a human) with a tumor as compared to a control subject, comprising administering to the subject an effective amount of an RNA nanostructure, complex or composition as described herein.

Certain embodiments provide a method to decrease levels of anti-inflammatory cytokines in a subject (e.g., a mammal, such as a human) with a tumor as compared to a control subject, comprising administering to the subject an effective amount of an RNA nanostructure, complex or composition as described herein.

Certain embodiments provide the use of an RNA nanostructure, complex or composition as described herein for the manufacture of a medicament for inducing an immune response in a subject (e.g., a mammal, such as a human).

Certain embodiments provide an RNA nanostructure, complex or composition as described herein for inducing an immune response.

Certain embodiments provide the use of an RNA nanostructure, complex or composition as described herein for the manufacture of a medicament for treating a disease or disorder in a subject.

Certain embodiments provide the RNA nanostructure, complex or composition as described herein for the prophylactic or therapeutic treatment a disease or disorder.

Certain embodiments provide a kit comprising an RNA nanostructure, complex or composition as described herein and instructions for administering the RNA nanostructure, complex or composition to a subject to induce an immune response or to treat a disease or disorder.

In certain embodiments, a kit as described herein, further comprises at least one therapeutic agent.

Certain embodiments provide a single strand of RNA rational-designed to self-assemble into an RNA nanostructure comprising at least one paranemic cohesion crossover, wherein the RNA nanostructure has immuno-stimulatory properties.

Certain embodiments provide a nucleic acid having at least about 75% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

Certain embodiments provide a nucleic acid which has at least about 90% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the nucleic acid forms an RNA nanostructure.

Certain embodiments provide an RNA nanostructure comprising at least one single-stranded RNA (ssRNA) molecule, wherein the RNA nanostructure comprises at least two structural repeating units of 33 nucleotides in length, and wherein each structural repeating unit comprises, in order: a first region of a double helix 8 nucleotides in length, a first paranemic cohesion crossover 8 nucleotides in length, a second region of a double helix 9 nucleotides in length, and a second paranemic cohesion crossover 8 nucleotides in length.

In certain embodiments, the RNA nanostructure described herein, comprises one ssRNA molecule.

In certain embodiments, the RNA nanostructure described herein, consists of one ssRNA molecule.

In certain embodiments, the at least one ssRNA molecule is about 10 to about 100,000 nucleotides in length.

In certain embodiments, the at least one ssRNA molecule is about 10 to about 20,000 nucleotides in length.

In certain embodiments, the at least one ssRNA molecule is about 10 to about 10,000 nucleotides in length.

In certain embodiments, the at least one ssRNA molecule does not comprise a transcription termination sequence.

In certain embodiments, the at least one ssRNA molecule does not comprise an AUCUGUU sequence.

In certain embodiments, about 60-99% of the RNA nanostructure is comprised of double stranded regions and about 1-40% of the RNA nanostructure is comprised of single stranded regions.

In certain embodiments, about 95% of the RNA nanostructure is comprised of double stranded regions and about 5% of the RNA nanostructure is comprised of single stranded regions.

In certain embodiments, the RNA nanostructure comprises at least two parallel double helices.

In certain embodiments, the RNA nanostructure comprises at least seven parallel double helices.

In certain embodiments, the RNA nanostructure comprises between about 2 to about 100 of the structural repeating units.

In certain embodiments, the RNA nanostructure comprises a plurality of the structural repeating units.

In certain embodiments, the RNA nanostructure comprises between about 2 to about 200 paranemic cohesion crossovers.

In certain embodiments, the RNA nanostructure comprises a plurality of paranemic cohesion crossovers.

In certain embodiments, the paranemic cohesion crossover comprises 16 base pairings.

In certain embodiments, the at least one paranemic cohesion crossover comprises between about 6 to about 10 GC base pairs.

In certain embodiments, the at least ssRNA molecule comprises a sequence that forms internal loops that remain unpaired prior to forming the at least paranemic cohesion crossover.

In certain embodiments, the RNA nanostructure comprises at least one loop region (e.g., a peripheral loop region) that connects one end of a double helix to another end of a double helix, and wherein the at least one loop region is located along an edge of the RNA nanostructure.

In certain embodiments, the RNA nanostructure comprises a plurality of loop regions.

In certain embodiments, the at least one loop region has a length of about 2 to about 100 nucleotides.

In certain embodiments, the at least one loop region has a length of about 2 to about 50 nucleotides.

In certain embodiments, the RNA nanostructure of this disclosure comprises: a first layer comprising at least two structural repeating units of 33 nucleotides in length; and a second layer comprising at least two structural repeating units of 33 nucleotides in length;

wherein each structural repeating unit comprises, in order: a first region of a double helix 8 nucleotides in length, a first paranemic cohesion crossover 8 nucleotides in length, a second region of a double helix 9 nucleotides in length, and a second paranemic cohesion crossover 8 nucleotides in length; and wherein a paranemic cohesion crossover of the first layer is hybridized to a paranemic cohesion crossover of the second layer.

In certain embodiments, the RNA nanostructure has a crossing number of zero, and wherein the RNA nanostructure is unknotted.

In certain embodiments, the RNA nanostructure comprises only parallel crossovers.

In certain embodiments, the RNA nanostructure comprises continuous π-π stacking along greater than 50% of the double helices or regions of double helices of the nanostructure.

In certain embodiments, the RNA nanostructure has a rectangular shape, a diamond shape or a tetrahedron shape.

In certain embodiments the RNA nanostructure has a rectangular shape.

Certain embodiments provide an RNA nanostructure comprising a nucleic acid sequence having at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the nucleic acid sequence has at least about 85% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the nucleic acid sequence has at least about 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the nucleic acid sequence has at least about 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

In certain embodiments, the RNA nanostructure of this disclosure comprises SEQ ID NO:1.

In certain embodiments, the RNA nanostructure of this disclosure consists of SEQ ID NO:1.

In certain embodiments, the RNA nanostructure has a rectangular, diamond or tetrahedron shape.

In certain embodiments, the RNA nanostructure has immuno-stimulatory properties.

In certain embodiments, the RNA nanostructure is an agonist of a pattern recognition receptor.

In certain embodiments, at least one diagnostic agent is operably linked to the RNA nanostructure.

In certain embodiments, at least one therapeutic agent is operably linked to the RNA nanostructure.

Certain embodiments provide a complex comprising an RNA nanostructure as described herein, and at least one diagnostic agent operably linked to the RNA nanostructure.

Certain embodiments provide a complex comprising an RNA nanostructure described herein, and at least one therapeutic agent operably linked to the RNA nanostructure.

In certain embodiments, the diagnostic or therapeutic agent is a peptide comprising a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues (SEQ ID NO: 21).

In certain embodiments, the peptide is a tumor targeting peptide (TTP), a human cancer peptide, an infectious agent peptide, tumor antigen peptide, or calreticuln protein.

In certain embodiments, the infectious agent peptide comprises specific epitopes for CD8+ T cells involved in the immunity against influenza, HIV, HCV, and other infectious agents.

In certain embodiments, the peptide is calreticuln protein.

In certain embodiments, the peptide is human cancer peptide NY-ESO-1 or Muc1.

In certain embodiments, the peptide agent is a tumor antigen peptide.

In certain embodiments, the peptide is CTKD-K10 (CTKDNNLLGRFELSGGGSK$_{10}$ (SEQ ID NO:18)).

Certain embodiments provide a pharmaceutical composition comprising the RNA nanostructure or complex described herein and a pharmaceutically acceptable carrier.

In certain embodiments, a pharmaceutical composition described herein further comprises at least one therapeutic agent.

In certain embodiments, the at least one therapeutic agent is a chemotherapeutic drug (e.g., doxorubicin).

Certain embodiments provide a method of inducing an immune response a subject (e.g., a mammal, such as a human), comprising administering to the subject an effective amount of an RNA nanostructure, complex or composition as described herein.

Certain embodiments provide a method of treating a disease or disorder in a subject, comprising administering to the subject a therapeutically effective amount of an RNA nanostructure, complex or composition as described herein.

In certain embodiments, the disease or disorder is cancer.

In certain embodiments, the cancer is breast cancer, colorectal cancer or lymphoma.

In certain embodiments, a method described herein, further comprises administering at least one therapeutic agent to the subject.

In certain embodiments, the at least one therapeutic agent is a tumor targeting agent (e.g., a monoclonal tumor-specific antibody or an aptamer).

Certain embodiments provide a method of enhancing/increasing pro-inflammatory cytokines in a subject (e.g., a mammal, such as a human), comprising administering to the subject an effective amount of an RNA nanostructure, complex or composition as described herein.

Certain embodiments provide a method of activating immune cells by specific triggering of toll-like receptor 3 (TLR3) signaling pathway in a subject (e.g., a mammal, such as a human), comprising administering to the subject an effective amount of an RNA nanostructure, complex or composition as described herein.

Certain embodiments provide a method of slowing or suppressing tumor growth in a subject (e.g., a mammal, such as a human) as compared to a control subject, comprising administering to the subject an effective amount of an RNA nanostructure, complex or composition as described herein.

Certain embodiments provide a method to elevate levels of anti-tumor proinflammatory cytokines in a subject (e.g., a mammal, such as a human) with a tumor as compared to a control subject, comprising administering to the subject an effective amount of an RNA nanostructure, complex or composition as described herein.

Certain embodiments provide a method to decrease levels of anti-inflammatory cytokines in a subject (e.g., a mammal, such as a human) with a tumor as compared to a control subject, comprising administering to the subject an effective amount of an RNA nanostructure, complex or composition as described herein.

Certain embodiments provide the use of an RNA nanostructure, complex or composition as described herein for the manufacture of a medicament for inducing an immune response in a subject (e.g., a mammal, such as a human).

Certain embodiments provide an RNA nanostructure, complex or composition as described herein for inducing an immune response.

Certain embodiments provide the use of an RNA nanostructure, complex or composition as described herein for the manufacture of a medicament for treating a disease or disorder in a subject.

Certain embodiments provide an RNA nanostructure, complex or composition as described herein for the prophylactic or therapeutic treatment a disease or disorder.

Certain embodiments provide a kit comprising an RNA nanostructure, complex or composition as described herein and instructions for administering the RNA nanostructure, complex or composition to a subject to induce an immune response or to treat a disease or disorder.

In certain embodiments, a kit described herein, further comprises at least one therapeutic agent.

Certain embodiments provide a nucleic acid having at least about 75% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the nucleic acid has at least about 90% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

In certain embodiments, the nucleic acid forms an RNA nanostructure.

Certain embodiments provide a method of making an RNA nanostructure using a procedure described herein.

Certain embodiments will now be illustrated by the following non-limiting Examples.

Example 1

Single-Stranded RNA Origami

Self-folding of an information-carrying polymer into a defined structure is foundational to biology and offers attractive potential as a synthetic strategy. Although multicomponent self-assembly has produced complex synthetic nanostructures, unimolecular folding only sees limited progress. Described herein is a framework to design and synthesize a single RNA strand to self-fold into a complex yet unknotted structure that approximates an arbitrary user-prescribed shape. Diverse multi-kilobase single-stranded structures were experimentally constructed, including a ~6000-nt RNA structure. Facile replication of the strand was demonstrated in vitro and in living cells. The work here thus establishes unimolecular folding as a general strategy for constructing complex and replicable nucleic acid nanostructures and expands the design space and material scalability for bottom-up nanotechnology.

Foundational to biological replication, function, and evolution is the transfer of information between sequence-specific polymers (for example, DNA replication, RNA transcription, and protein translation) and the folding of an information-carrying polymer into a compact particle with defined structure and function (for example, protein and RNA folding). Biology's operational principles on the molecular scale motivate synthetic efforts to design replicable, information-bearing polymers that can self-fold into user-prescribed nanoscale shapes.

Using nucleic acids' specific base pairing, complex nanostructures have been created with DNA and RNA (1-27), enabling diverse applications (28-40). Particularly noteworthy are multi-kilobase, megadalton-scale nanoparticles with arbitrary user-prescribed geometry that are self-assembled from hundreds of synthetic DNA strands, with and without the assistance of a central organizing scaffold strand (that is, scaffolded DNA origami (4, 8-10, 13, 20-23) and DNA bricks (14, 15)). In contrast to the remarkable success of structures self-assembled from multiple components, the progress on designing a single-stranded DNA (ssDNA) or RNA (ssRNA) that can self-fold into a defined shape is limited, and only relatively simple shapes were demonstrated (for example, the folding of a 79-nucleotide (nt) DNA strand into a four-arm junction (41), a 146-nt strand into a paranemic crossover (42), a 286-nt DNA strand into a tetrahedron (43), and a 660-nt RNA into a six-helix rectangle tile (44)). In addition, a 1700-nt DNA strand, with the help of five auxiliary strands, was folded into an octahedron structure (3). Notably, the simple ssDNA structures (41-43) as well as the 1700-nt scaffold for the octahedron (3) can be replicated in vitro (3, 41-43), and these simple single-stranded structures were cloned and replicated in living cells (43, 45). The 660-nt RNA structure can be transcribed from DNA template and folds isothermally (44).

The ability to design a nucleic acid polymer that self-folds in a protein-like fashion into a user-prescribed compact shape not only is interesting and important on a fundamental basis but also offers key conceptual advantages in practicality (3, 41-45) over the current paradigm of multicomponent RNA self-assembly. Compared to multi-stranded RNA structures formed via self-assembly, ssRNA nanostructures formed via self-folding offer greater potential of being amplifiable, replicable, and clonable, and hence the opportunity for cost-efficient, large-scale production using enzymatic and biological replication, as well as the possibility for using in vitro evolution to produce sophisticated phenotypes and functionalities. In addition, unimolecular folding process is independent of the reactant concentration and thus, in principle, offers higher formation yield and more robust folding kinetics than multi-stranded structures produced with concentration-dependent intermolecular self-assembly. Furthermore, unlike multi-stranded RNA nanostructures, which typically contain dozens or hundreds of distinct components and often undesirable defects such as missing or incorrectly incorporated or synthesized component strands, a single-stranded structure could, in principle, be synthesized as a homogeneous system with high purity (for example, via enzymatic production of monoclonal strands (46)).

Despite its fundamental importance and practical desirability, as well as the aforementioned promising early efforts (41-45), it remains challenging to develop a general strategy for the design and synthesis of an ssRNA that can fold into a user-prescribed complex, arbitrary shape (for example, comparable in complexity and programmability to scaffolded nucleic acid origami (4)). The key challenge is to achieve structural complexity, programmability, and generality while maintaining the topology simplicity of strand routing (to avoid kinetic traps imposed by knots) and hence ensuring smooth folding.

A general design and synthesis framework for folding a multi-kilobase ssRNA strand into a complex user-prescribed shape is described herein. The key innovation is to use partially complemented RNA strands, which form double stranded regions, and parallel crossover cohesion(s) (3, 47-50) to construct a structurally complex yet knot-free structure that can be folded smoothly from a single strand. These structures are called ssRNA origami, RNA ssOrigami, or ssRNA nanostructures. The versatility of the strategy was experimentally validated by constructing a variety of space-filling, compact shapes (for example, rhombus (i.e. diamond) tetrahedron and rectangle shapes). The space-filling nature of the structure and the unique base-resolution addressability along the strand enables the creation of user-prescribed patterns of protruding hairpins or loops on the structure surface, and such loops can be used as "handles" to attach other moieties. The strategy produces structures with an architecture that is amenable to amplification and replication; it was experimentally demonstrated that a folded RNA ssOrigami structure can be melted and used as a template for amplification by polymerases in vitro and that the RNA ssOrigami strand can be replicated and amplified via clonal production in living cells. The design is also scalable.

RNA has been used to construct synthetic nanostructures (44, 51-54) and offers unique application potentials over DNA structures (for example, functional diversity, economical production via genetic expression, and amenability for intracellular applications) (44). However, whereas multi-kilobase, megadalton-size discrete DNA nanostructures have been demonstrated (for example, via scaffolded origami (4, 8) and DNA bricks (14, 15)), synthetic RNA nanostructures remain comparatively simple: The largest discrete structure demonstrated is the aforementioned 660-nt ssRNA tile (44). As described herein, a variety of multi-kilobase complex RNA ssOrigami structures with user-prescribed shapes were generated (for example, rhombus and rectangle shapes), including a 6000-nt RNA structure that represents a 10-fold increase in complexity for RNA nanotechnology. The generality and adaptability of the RNA ssOrigami architecture is additionally revealed by the successful folding of two identical target shapes by both the sense and antisense RNA strands transcribed from the same dsDNA template.

This work establishes that it is possible to design a multi-kilobase ssRNA to fold into a user-prescribed complex shape. This technology increases the structural complexity for designable RNA nanotechnology. Unimolecular folding, alongside self-assembly (for example, scaffolded nucleic acid origami and nucleic acid bricks), thus represents another fundamental, general, yet practically accessible design strategy for constructing digitally programmable nanostructures and expands the design space and material scalability for bottom-up nanotechnology.

Design of RNA ssOrigami

Although various DNA nanostructures have been created in a multi-stranded format, simply breaking and reconnecting strands from existing origami designs would not solve a key challenge in designing RNA ssOrigami, which is to create an RNA ssOrigami structure with minimal knotting complexity to avoid being kinetically trapped during the folding process.

To precisely quantify the knotting complexity of different ssOrigami models to facilitate the design process, an open-chain linear RNA strand can be converted into a closed loop by connecting its 5' and 3' ends, and then characterize the topological complexity of this closed loop, which can be treated as mathematical knots. Two RNA knots are homotopic if they can be transformed into each other through a continuous deformation, which means that strands cannot be cut during any operation (55). Such rules also apply to ssOrigami because the nucleic acid backbone cannot be cut or intersected during the folding process. The knotting complexity of ssOrigami designs can be approximately described by the crossing number, a knot invariant defined as the smallest number of crossings found in any diagram of the knot (56, 57).

If a knot has a crossing number of zero, then it is topologically equivalent to an unknotted circle (also referred as an unknot). In nature, most of the RNA and protein structures have a crossing number of 0, and only in rare cases, some proteins may have very small crossing number (58-61). On the contrary, ssOrigami designs derived from traditional origami structures (e.g., DNA) tend to result in complex knots with high crossing numbers, which will likely hinder proper folding.

To achieve the ssOrigami structures with small crossing number, the first consideration in ssOrigami design is to choose between antiparallel and parallel crossovers for interhelical cohesion. At every antiparallel crossover position, RNA strands need to run through the central plane that contains all the parallel RNA helical axes, like threading a needle through a piece of fabric. On the contrary, at parallel crossover positions, RNA strands do not go through this plane, which could reduce the knotting complexity of the structure.

Design and Synthesis of RNA ssOrigami

To synthesize long ssRNA molecules, a DNA template with both T7 and T3 promoter sequences was first synthesized as two fragments. The two DNA fragments were subcloned into a vector through Eco RI and Hind III restriction sites and amplified in *E. coli*. The purified plasmids were then linearized by Eco RI and Hind III, and transcribed using T7 RNA polymerase and/or T3 RNA polymerase (see FIG. 1B, which depicts both). The in vitro transcribed RNA molecules were then purified, self-folded from 65° C. to 25° C. with a 1° C. per 15 minutes ramp. The RNA molecules were, characterized with AFM.

Figure 1B:
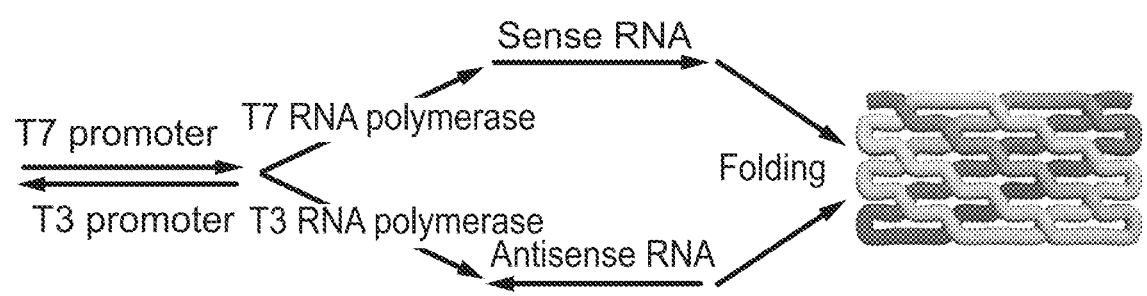
Figure 1C:
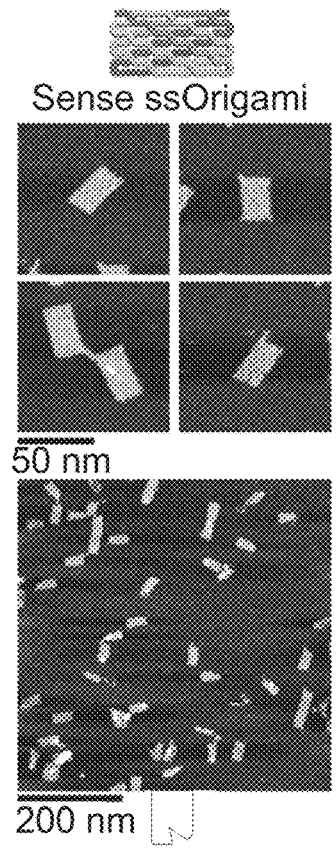
Figure 1D:
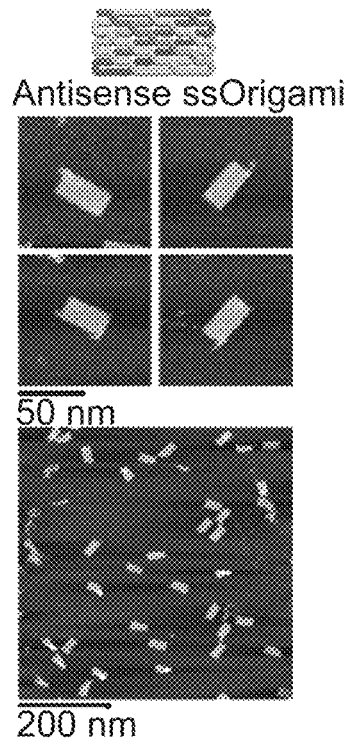
Figure 1E:
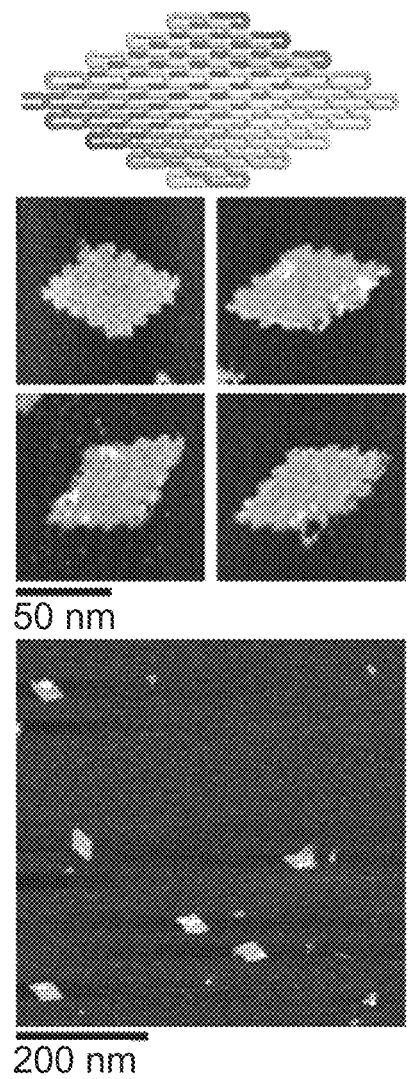

In one embodiment, a design of an 8 nt helical domain, followed by an 8 nt locking domain, followed by a 9 nt helical domain, followed by an 8 nt locking domain (i.e., an 8-8-9-8 structure) was designed, which gives three turns per 33-bp repeating unit (FIG. 1A). Using the 8-8-9-8 design, an 1868-nt rectangle (FIGS. 1, C and D) and a 6337-nt 9×9 rhombus (FIG. 1E) RNA ssOrigami were constructed. The RNA strand for 1868-nt rectangle from both the sense strand (FIG. 1C) and the antisense strand (FIG. 1D) were tested and both produced expected and identical shapes under AFM. The 6337-nt rhombus RNA ssOrigami is 10 times larger than any previous synthetic discrete RNA nanostructure (44).

Discussion ssOrigami structures were constructed from ssRNA with synthetic sequence ranging in length from ~1000 to ~10,000 nt, which represents the largest unimolecular folding of a synthetic nucleic acid structure that has been achieved to date. Compared to the wire-frame DNA octahedron assembled from a 1700-nt scaffold strand and five auxiliary short strands reported in 2004 (3), the RNA ssOrigami uses no auxiliary strands and can be designed to form a wide variety of space-filling compact shapes. Meanwhile, compared to the ssRNA nanostructures reported in 2014 (44), the design strategies can be applied to RNA ssOrigami because it is not limited by RNA kissing-loop interactions (64). As a consequence, ssOrigami is a purely de novo designed structure that does not rely on the availability of highly sequence specific, naturally occurring molecular interaction motifs with defined geometrical arrangements (for example, the RNA kissing loops) and thus promises, in principle, better designability and scalability, as reflected in practice by construction of a 6000-nt ssRNA structure.

Previous work demonstrates the self-assembly of complex structures from hundreds of distinct components (with and without the assistance of a scaffold), and the RNA ssOrigami work here demonstrates the folding of complex structures from a single strand. Therefore, previous multi-component assembly work (scaffolded origami and DNA bricks) and the current unimolecular folding work represent two extremes for engineering synthetic nucleic acid nano-structures, and together promise a vast design space in between.

Materials and Methods

Materials

Restriction endonucleases EcoRI (5,000 units), XhoI (5,000 units) and HindIII (5,000 units), T7 and T3 RNA polymerases (5,000 units), NEB 10-beta competent *E. coli* were purchased from NEW ENGLAND BIO LABS INC. Pureyield plasmid miniprep system and the Wizard SV Gel and PCR Clean-UP System were purchased from Promega (www.promegA.com). RNA Clean and Concentrator-25 was purchased from Zymo Research (www.zymoresearch.com).

DNA and RNA Sequence Design

DNA sequences were designed with the Tiamat software (66). Sequence generation of RNA ssOrigami structures uses the following criteria in the software: (1) Unique sequence limit: 8-10; (2) Repetition limit: 8; (3) G repletion limit: 4; (4) G/C percentage: 0.38-0.5. For ssRNA origami sequences, T7/T3 promoter sequences followed with two or three consecutive Gs were added to the end to facilitate efficient in vitro transcription reactions.

In Vivo Cloning Sample Preparation

The DNA templates for transcribing ssRNAs were divided into two DNA sequences with both T7 and T3 promoter sequences added to the ends, and ordered as gene synthesis products from BioBasic Inc. The two fragments were then subcloned into pUC19 vector using the same restriction sites as ssDNA origami. The final plasmids were linearized by EcoRI and HindIII, and transcribed by T7 or T3 RNA polymerase following manufacturer's instruction (New England Biolabs). The transcription reaction mixture was purified by RNA Clean and Concentrator kit as described in the manufacturer's instruction (Zymo Research). After purification, the ssRNA was annealed using the same program as ssDNA origami.

AFM Imaging

For AFM imaging, the sample (15 mL) was deposited onto a freshly cleaved mica surface (Ted Pella, Inc.) and left to adsorb for 1 minute. 40 mL 1×TAE-Mg2+ and 2-15 mL 100 mM NiCl2 was added onto the mica, and the sample wasscanned on a Veeco 5 Multimode AFM in the Scanasyst in Fluid mode using scanasyst in fluid+ tips (Veeco, Inc.).

Synthesis and Replication of ssRNA for ssOrigami Folding.

Figure 2A:
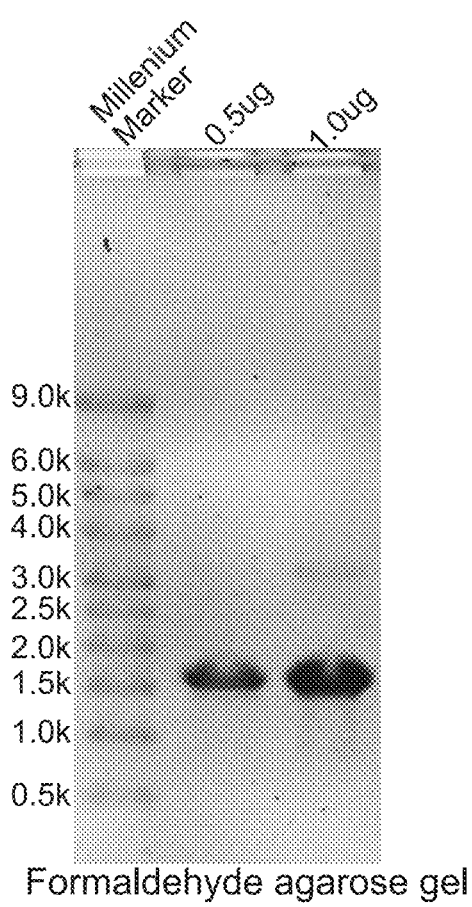
FIGS. 2A-2B. (A) Rectangle ssRNA and (B) 9×9 ssRNA denaturing agarose gel image. The in vitro transcribed RNA was purified and loaded onto the formaldehyde agarose gel.
Figure 2B:
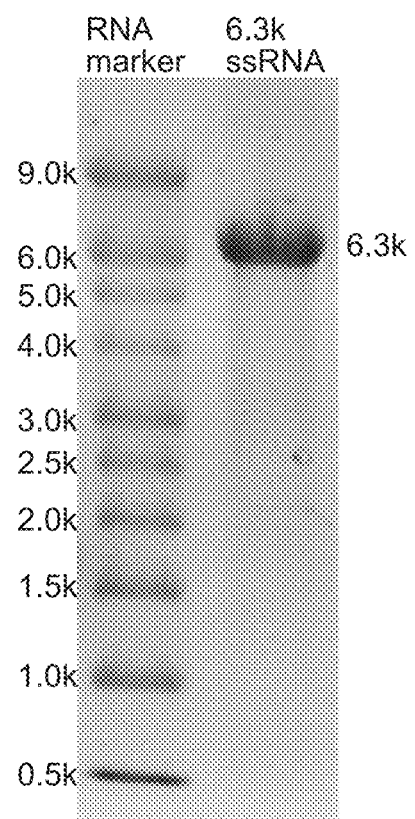

The DNA templates for transcribing ssRNAs were divided into two DNA sequences with both T7 and T3 promoter sequences added to the ends, and ordered as gene synthesis products from BioBasic Inc. The two fragments were then subcloned into pUC19 vector using the same restriction sites as ssDNA origami. The final plasmids were linearized by EcoRI and HindIII, and transcribed by T7 or T3 RNA polymerase following manufacturer's instruction (New England Biolabs). The transcription reaction mixture was purified by RNA Clean & Concentrator kit as described in the manufacturer's instruction (Zymo Research). After purification, the ssRNA was annealed using the same program as ssDNA origami, and characterized by AFM. (FIGS. 2A and 2B).

Melting Study for RNA ssOrigami Structures

Figure 3:
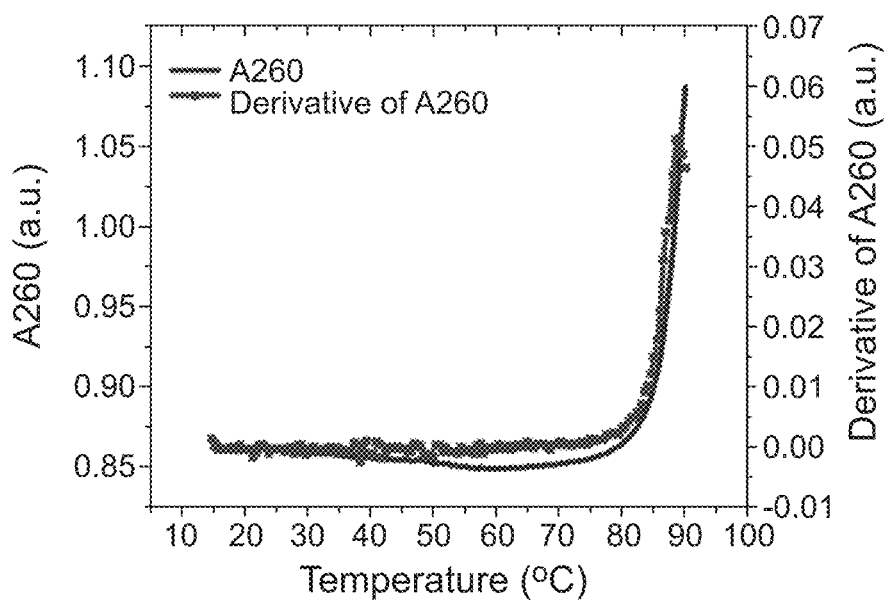
FIG. 3. Melting analysis of the RNA ssOrigami structures from FIG. 1C (8-8-9-8). The plot of raw data (A260 vs. temperature) of heating and cooling curves, as well as the plot of the first derivative of A260 as a function of temperature.

To compare the thermal stability of ssRNA origami, the melting assay was carried out on RNA ssOrigamis 8-8-9-8 by melting the well-formed origamis, and measuring the absorbance changes at 260 nm as a function of temperature in 1×TAE/Mg$^{2+}$ buffer. The samples were heated from 15° C. to 90° C. at a rate of +0.05° C./min. The results of the melting assay for RNA ssOrigami 8-8-9-8 are plotted in FIGS. 3A-B.

Figure 4:
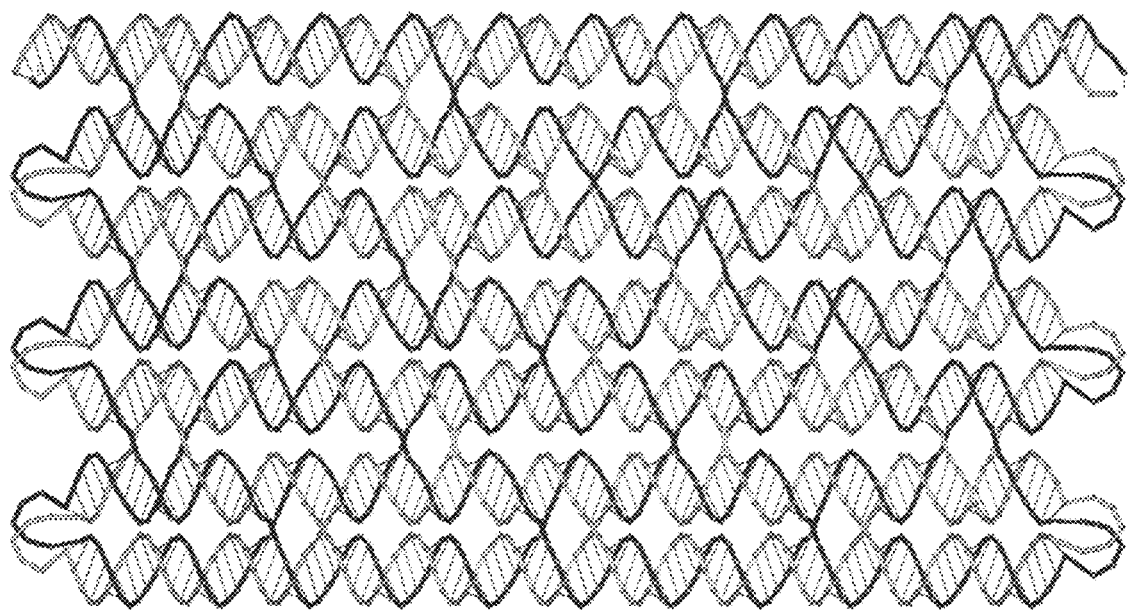
FIG. 4. Design detail of rectangle RNA ssOrigami with 8 bps locking domains. Dark strand is the forward strand and light strand is the reverse strand.

DNA Template Used to Generate the ssRNA Nanostructures 1868-nt Rectangle (see, FIG. 4)

Forward Strand:

(SEQ ID NO: 14)
5' GAATTCTAATACGACTCACTATAGGGAGAGGATCCGAACACTAGCCA

TAGCAGTTCGCTGAGCGTAATGTGTATGAAACATCATAAGTTCAGTGCT

ACATTGAAGCGAAGAGCCAATGACTCGTTCGTGTCATACTCATCAACGG

AGTGTTGACTAAGCCGAAAAAACATAGTCCGACTACACACCAGACACGT

TTGACCCTCAGTCGATTAACTGCAAGTCGCAAACAAGCTGACGTACAGT

AACGACTCGTCACTGTACTGATGATTCCACAACTGCTAATGCACGAAAA

AAGGAGTAGTGTGTCAGATCGACAAGACTTAACCACGATTCCTGATGCA

TTGACTTACCATCGACTCAACTGACAAGGGACCACGCAGAGGTGAATGA

GTCAGGACTTTGTAGTCGGAGTCGGAAAAAACACCAGTCACAATGTATC

GTACGCTTGCTACTAGGAGCTCGTCATGACGTTGAGAGCCTGTTAACTA

GACACGTTCCTAAGGGTTAGCCACACATTAATATCGGGCCTGACACAGG

ACACGAAAAAGAAGGTGCTGTTAGTTGGACAGGTACTATCATCTCAAG

TCGATAGTCCAAGTAGGTTTGAACCATGCATAGCTTGTATCAGGTCATC

GCCTCAAACGTTAGGTGTCACATTGTGGAATCGCAAAAAACATACCGAC

TTCCATTATGGGACACGTCGCTTATTCTTGGTAAGTAGAAGTTGCCATC

GTAGTCGCACGACCTACTTATGACGAACTTCGGTTAAGTGGCTGACGTA

CTAACAGTGCGTGCAAAAAAGACCTACGAAGCCAGAGTTCGTTCCAGTG

TGAAAGTGCACATCACGAGTTGTGCCAATGCACGTTGCATCGAGAGTTA

ATCCCGTCTTAAGTAGCAAGGCACCTGAATGGAAGTTGATTCGTCTAGA

3'

Reverse Strand:

(SEQ ID NO: 15)
5' TCTAGAAATAGACGAATCATGCTGATCTCAGGTGCTCACTTGATTAA

GACGGCTGTTTATCTCGATGCCTTCAATGTTGGCACAAATGCATCAGTG

CACTTATGATAGTGAACGAACTCTGGCTTCGTAGGTCAAAAAAGCACGC

AAGCATGTAACGTCAGCCTAACGCTTGAAGTTCGCAGGTGTGAGGTCGT

GCCTTGTTTGTGGCAACTGTCATGACCCAAGAATAAGCGACGTGTCCCA

TAGATCAGCACGGTATGAAAAAAGCGATTCGTGAGGTAGACACCTAGAT

ACTCTGGCGATGACAGTCATTGAGCTATGCGAGTCGATAACCTACTTGG

ACTATCGACTTGAGTCACACTGACCTGTCCATACATGCTCACCTTCAAA

AAACGTGTCCGCACTATAGCCCGATATCTCGTACAGGCTAACCTCGTTA

CTCGTGTCTAGTTAACAGGCTCTCAACTCTACTTAGAGCTCCTATCAAG

TGACGTACGATTACCTCACACTGGTGAAAAAACCGACTCAAGATTTGAA

GTCCTGTGAGTATGACCTCTGCGTGGTCCCTTGTCAGTTATGGTTCAGG

TAAGTCACTCGTCGATGGAATCGTAAGCGTTACTTGTCGATTATAGTGCC

TACTCCAAAAAACGTGCATCTTGATCAGTGGAATCATCAGTACAGTGAC

GAGCTTAGGAAGTACGTCAGGACTACGACGACTTGCATAAACAGGACTG

AGGGAGAGTATCGTCTGGTGCAAATCTTGACTATGAAAAACGGCTTAG

TCAACACTCCGTTGAACTCATTCACACGAACGCTGATACAGCTCTTCGA

ACGTGCATAGCACTGACACACCTGTGTTTCATTGTACGAGCGCTCAGCG

TGATCAAGTGGCTAGTGTTCGCTCGAGCTCTCTCCCTTTAGTGAGGGTT

AATTAAGCTT 3'

Figure 5:
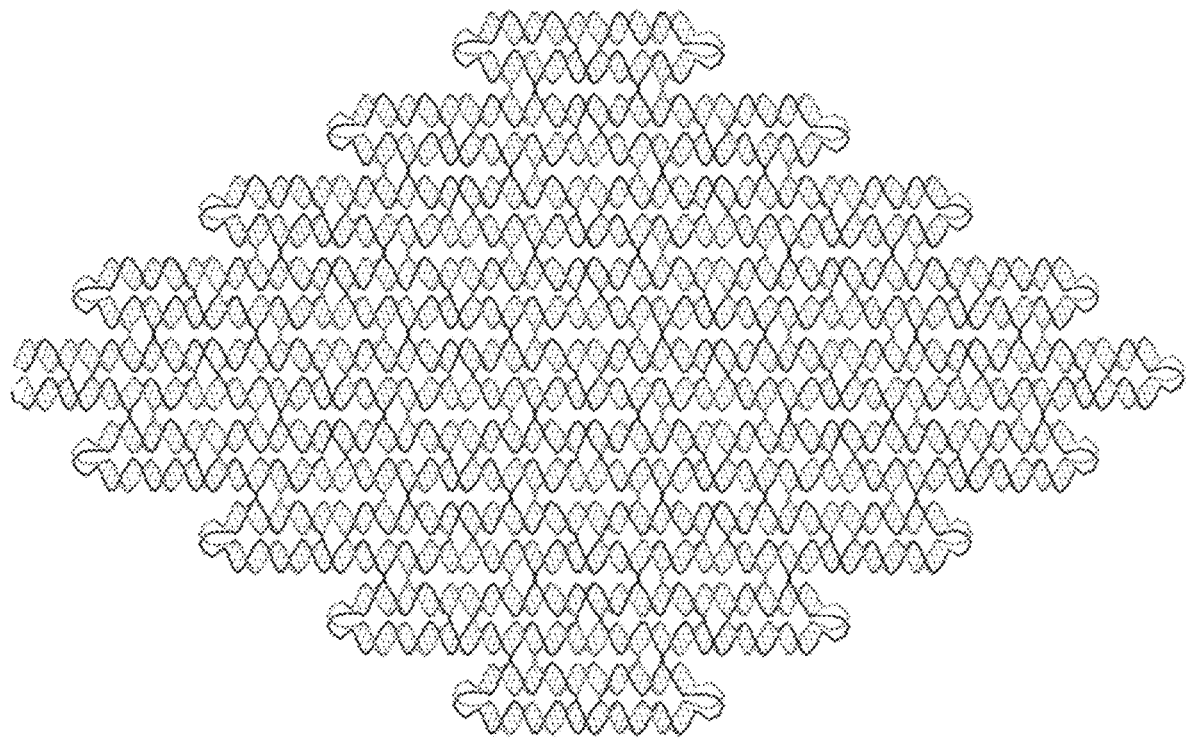
FIG. 5. Design detail of 9×9 RNA ssOrigami containing 6337 nt with 8 bps locking domains. Dark strand is the forward strand and light strand is the reverse strand.

6337-nt 9×9 rhombus (i.e., diamond shape) (see, FIG. 5)
Forward Strand;

(SEQ ID NO: 16)
5' GAATTCTAATACGACTCACTATAGGGAGAGGATCCAACATGGAGTGC

GGATATGGTTCGCTAAGGGATTCCCTGAATGCGAACTCTATCAACTGTC

GATACCTGGAGACGATGCTGATCGACCTGTCATGGGCGAAAACCTATAC

CGATGTAAACTCCGTATATTCATTTTGCTCTAGTCCAGTCCTGGAGGTT

-continued

ACTTCGGAAAAAAGTACCGCAGTGGTGAAGCGTGTCCTCCATACACCTC

CGCAAGGTATTCACTTTTGTGATCATAGTTATGGGTGTATGAGGATATG

CACTTCACTATGCAGATGTGAGATAGATGTCCGTGGGCAGATGTCAGCG

AACCGCGAAGACTCGCAATGAAAAAACGAGTGAAGGGCGTCTTGGCGCG

TCCTTGTCTCACCCAACTGGCTTGTGGTTAGAGCTTGACTCTGGGATAT

GACCATCTTGGTCACTAATTTAGGACTGCCCTAACCTCCCTAATGGATG

CGGGTGATAAGTTCTGAATGTCACGTTTGCAAATAGCCCTTAATGTTCC

CGTACTGTGGCACGAGCAAAAAACCTTACACCTAAGGCGATACTCACTT

CAACTGTGTGTATCACATTAGGTGCCTACGGTAAACTCATCGTCTAGTT

CTGGGACTGTTTCGTCTGGTTAACGTTATAATAGACACGATACCTGGT

TCTACCATTCGCCGATCCATTTGGTCTTCGAAAAAACGAGGGAGAATCA

CTCTATCAAAGATGCACCTCGTAGCGAGTGAGTGGAACTTCATAAAGGG

AAGTCATGGCCGGTCAGACTTCTGGCACTGATATGCAACATCAGTACAG

TCTTAAGTTCCAGCCGAAAGTGCGGTTGGCATCTCTTAGGCACAGAGC

GATTTTGGACTGGTAGCTGACCGCATGAAAAAAGGAACGACGTGTCGAA

AGGTCCCGGTAGTAGCTCCCTCATTCCACTTGGCTAAACGTTCAACACG

TATCGAGTTGGTTTAGGTAGTTCGCAGACGCACAAACGAAGGCAGGTAA

AACTTGGCAAGTTGCGTCGTGGCACGTCATACCAGTGTTGAAAAAACGG

CTATGTAGTGTCTAGCTGTCAATACCCGTACCCATCTGATGGTTGCAGG

ATGATTAGGTCGAAACGAAGTCTCTGATCTGAGGTCGTCTGAAGCTAAG

TAATACCTGGCTAACTTGACTAACTCGTACTCATACTCAGCTTTCTCAC

ATTCTGTGCTCAAAATCTGCATTGACTGCAACGGTCCAAAAAAGCGACC

TTCTGTGTGAATATGAATACTAAGCGGGAGTTGAAGAATAGCTCACAGA

CAGACACAACCTACAAAATGAATGAGCAGTCCGTGTAAGCTCGCATTGC

TCACTTCAGCCTTCGGGCGCTATAGCCATTATTATGATCCAACTCGATC

GAAAAAAGGTACTACGTAGATTTGGCCGACACCAGATTGCCCGTACCGA

CAATGCGGTTTCTTTGTAAACTGGGCACTTACGATCATAGGGAGCTGGT

TACGAACGGCATCCGACAGGAATCTAGCTCGATGCATGGGATAGTACTG

TCCACATCCAGCCGTCCCAGAGATAGGTAGATTGGGAAAAAACGATCGG

TACTGATCTCTGGTGTCTGACAAACACCTCCGCACTCATTTGAGCATGA

GCCAATGTATAAGTTGCACCAGAATCGCTCTGGTATGTCTAACATCTGC

AACATCTTAAGGGCAGTCATGACTACTGACCGTAGTCGGCTAGAGCACC

GTGAGGCCAAATGATCCTCCAGAAAAAAGCACTGAGTTGACACCATCCG

AGAGTATGGAGCACTAGCTATCATGACGAGGTTCCCAGTTGAAGTCAGA

ATCTTGATGGACGAAGCCTACTACTACCTGCTGTTGGTACATGGATAAG

ATTGGCTTAGTAGGTCATCCAAGACTGGGCCTTGGAAAAAACCACGGTT

TGTGACCATGATCGTCCCATGCATACTGAAATCATCACTAGTTGCGGAG

TACGAGTCGAGCTGTGCAGTGCAAACTAATCCCTTTCGGCGGTCACATA

GTCCTGAACGCCGTCCTTATCACCGAAATCTTCCAACAAAGCATGGCTC

GTATAGGTGCCCAGTCGACTACTGGATACTGGAAAAAACGGACTTTAGA

CAGCACCCTCAATCTATGATCGGTCCAGTGGTTAGTTCGTTTCTGCGAG

TTTACCTTGCATCAGGATATGACACCTCGGGTGTTGAAGCCTGAATAGA

GAGCCGGTTCGATCTTGTGTCTACTGAACGCAGTGTAGCGTTAGCAAAA

AAGACACTATCCTGAAGCACGCTATGTTCGTAATTCAGCCGACTCGCAT

TATTGCTGGAGCTTCAGCTCGGCCTTGACTGAGTGCACTCAGGCATATC

AGTCAACACAGCAACTTCCTACGACTGTCCTAAATCAACACTGCTAGTC

ACGTGTGTCTATCGTCTCGACCTGCAAGCATGGGTGTCGTCGAAAAAAG

CTCACGCTGTACAACCTTCACCCCATAGTGATAGCCACAGAAAAGCCTC

TGAACACCAACCAGACGGTCGAAAAGAAATGTAAGCTCACTGCGTCTGG

TGCGTTGACAAGAAGACCCATTATGAGCTTACGTGCTCTCACGTAGGCA

CTATCCAAAAAGGAGTAAAGGCGAACGTTCGCAGCAGTTTACTCGGTG

GTTTATCTCTGAGGTCACGTCGACCTAAGTCCCATGATGACGTCCAGAC

AACCTTCCCTTGCTTCCAAGGCTTTGGAGGTATGCTAGAGTCAAGAATT

ACTCTGCATCGAGTCATCAAGCATTCAGTACTATTAGATTGGAGCACGA

CACAAAAAGCATCTTCAATTAGGCTTATCTGAGACATCTGGTCAGGTC

ACCGAGTACCAGATGTCGGTAGAACCAAAGATGACATAACAGTGATCAA

CCGCAACTTACTGTACCCTACACGAGATATGTCCGCTATAGCGTCAAAC

GCAGGTACTGCGATGGAAAAAACAGCAGTAGCACAGGCTTAACATCAAT

CTGGTGGTCACCTCTATAGGGCTAGAGTGACGGGTATCGGTTATGACAG

TGTTGCAGTCAGCAGGTGCATTGTCTTCGTCGAGCAGTAAGCGGATAGA

CAAGGGTCGACTTGGTCTATTATCATGTAACACTCCATTACCTGGTCTA

GA 3'

Reverse Strand:

(SEQ ID NO: 17)
5' TCTAGAAATAGACCAGGTACCACTACATTACATGAAGTCTTCGCAAG

TCGACAGGCTATAATCCGCTTCAAATGGAACGAAGACACGACTTAAGCT

GACTGGGTATGACTCATAACCGTGCTGTTGCACTCTAGGTTGGATCAGG

TGACCAGTTACGCTATGTTAAGCCTGTGCTACTGCTGAAAAAACCATCG

CGCATTGTCCGTTTGACATGCGATAGGACATATCCAACCATCGGTACAG

TCGTAATACGTTGATCACCCACTCACCATCTTTGTACAGGTAGACATCT

GGACAAGCCAGACCTGACGTAAACGTTCAGATAAGTAGCGAACAAGATG

CAAAAAAGTGTCGTGCTCCAATCTAATAGTAGAGTAGACTTGATGACCA

TCTATCGAGTAATTCACAGTGAAAGCATACCGTGTCTATCTTGGAAGCT

CAACTCAGTTGTCTGTTACCTGCCATGGGACTACTCCATCCGTGACCTG

CTGAAGTAACCACCGATGTTGAGTCTGCGAACGTTCGCCTTTACTCCAA

AAAAGGATAGTTATGATCGGAGAGCACACCATTGTATAATGGGTGATCA

GAGCAACGCACGTACATATGTGAGCTTAGTCTGACCTTCGACCGCACTC

GTTGTGTTCAGAAAGATGGTTGTGGCTAAGCAACCAGGGTGAAGGACAG

TTGACGTGAGCAAAAAACGACGACACCCATGCTTGCAGGTCCACAGACA

AGACACACTCCTCATACAGTGTTGACGTCACGAAGTCGTAGTCCCAGAA

-continued

```
TGTGTTGACAACGGACTCTGAGTGCCTAAACCAAAGGCCGAGGAAATTG

GCCAGCAATCTCATTCATCGGCTGAAGAGACGGTATAGCGTGCTTCAGG

ATAGTGTCAAAAAAGCTAACGATTCCTGTCGTTCAGTGCTCTTTCGATC

GAACCTAGCCAGGATTCAGGCCGTGCTTACCGAGGTGTAGACTGTAGAT

GCAAGTATCGCAGGCAGAAACGTAGGGAGGACTGGACCTACGACTCATT

GAGGGTTGACAGGTAAGTCCGAAAAAACCAGTATCCAGTAGTCGACTGG

GCTATTGCTGGAGCCATGGAATACCTGAAGATTTCCATATCGCGGACGG

CGCCTAATGTTATGTGACCTTGTATGAGGATTAGTCAAGTGGACACAGC

TCGTTATCGCTTCCGCAACGCTATTCTATTTCAGTACTCTTTCAACGAT

CATGGTCACAAACCGTGGAAAAAACCAAGGCATGTGGACGGATGACCAT

CACTTGCAATCTTATAGAAAGCTCAACAGCATCCTTATCTAGGCTTCGA

GAGATGCGATTCTGATCATTGGAGGGAACCTCACGTGACAAGCTAGTGA

GATGATTTCTCGGATGTACGGAGTTCAGTGCAAAAAACTGGAGGATCAT

TTGGCCTCACGGCCAAGGTACCGACTACTCACCACTGTCATGACTAGTC

AAGGGATGTTGCGCCTTAGGGACATACCACTTGGTACCTGGTGCATCGA

CACGATTGGCTCACATGTGACTGAGTGCGCACACAGATGTCAGACAGTC

GTCTACAGTACCGATCGAAAAAACCCAATCTACCTTAGACGACGACGGC

TGGCCAGTCTTAGTACTATTGAAAGAGTCGAGCTAGCTACACTGCGGAT

GCCACCGTCTCCCAGCTCCCGCCTACGTTAAGTGCCACTCAACAAAGA

AACCAGTACCTGGGTACGGGAGCGTAACTGTCGGCCAAATCTACGTAGT

ACCAAAAAACGATCGACCCTATAGATAATAATGTATCGCATGCCCGAAG

CAGAGATAGAGCAATGCACAATGGTACGGACTGAATGCGAGTTTTGTAG

GGAAAGAGCGTCTGTGATAGTGATGTCAACTCCCCAAGTGATTTCATAT

TGAGGTGTTAGGTCGCAAAAAAGGACCGTTGCAGTCAATGCAGATGTCA

CATGCAGAATGTGCCATGTACGAGTATGAAGCGATAATAGTCAAGTGGC

TCTCTTATTACTTCCAATTTCACGACCTCACTTCTTGTACTTCGTTGAT

GGAGTATCATCCTGTCGTGTAGAGATGGGTCAACAGCATGACAGCTAGA

CACTACATAGCCGAAAAAACAACACTCAACACTGGTGCCACGAGTATTA

CGGCCAAGTTGACGTCATCTTCGTTTGATATGTACCGAACTACACTCAG

TCACTCGATACTAAGCACGCGTTTAGCTTGCACTGATGAGGGAGGATAA

GGAGGGACCTTACTTATACTCGTTCCAAAAAACATGCGGTCAGCTACCA

GTCCAAGTACCAAGTGTGTCCTATCCATCAACAACCGCATCATACAATG

GAACTTACATATCCTCTGATGTTAGTCCGTTGTGCCAGAACATTTCTTG

GCCATGATGAGTTGATATGAAGTTTGTTATGTTCGCTACGTTAAGTCGC

TTTGATAGAGTGATTCTCCCTCGAAAAAACGAAGACACTGCTCGTCGGC

GAATTACCTGTACAGGTATCTCCAAAGCTATAACGTTAACGAGTGCGAA

ACAGGAAGTTGCCTAGACGATCTGCGATACGTAGGCATTCAGGACGATA

CACACTCCAATGATGAGTATCAGATGTTATGTAAGGAAAAAAGCTCGTG

CCACAGTACGGGAACACCTTGACTTATTTGCAAGTCATGATTTCAGAAC

GCGATATGCGCATCCATAACTAACCTTAGGGCATCGTGACGTTAGTGAC

CGGCTTTTCCATATCCCTTCACTGTGCTCTAACCTACTCGGTGTTGGGT
```

-continued

```
GTATAGCCTACGCGCCAAGACGCCCTTCACTCGAAAAAACATTGCGTAA

TAGACCGGTTCGCTACGTTTACCCCACGGATCGATGCATCACATCTGTG

GTTGCTAGTGCATAGTGACTAGCACCCATAAGAGTCGTAACAAAAGTCT

TTGTTGTGCGGAGGTAATCATCTGACACGCTGGTCAGTAGCGGTACAAA

AAACCGAAGTAACCTCCAGGACTGGATACCTTGGAAATGAATAGTGTCA

ACTTACATCGCAGCAATATTTCGCCCAGCTGTCTACGATCAGCTGTCTG

TGCAGGTATCGTTGTACAGTAGAGTTCGTCTACTCGGAATCCCTCCTAA

TTGCATATCCGTGTAGTGGGTTGGATCCTCTCGAGCTCTCCCTTTAGTG

AGGGTTAATTAAGCTT 3'
```

Example 1 References and Notes

1. J. Chen, N. C. Seeman, Synthesis from DNA of a molecule with the connectivity of a cube. Nature 350, 631-633 (1991). doi: 10.1038/350631a0; pmid: 2017259
2. E. Winfree, F. Liu, L. Wenzler, N. Seeman, Design and self-assembly of two-dimensional DNA crystals. Nature 394, 539-544 (1998). doi: 10.1038/28998; pmid: 9707114
3. W. Shih, J. Quispe, G. Joyce, A 1.7-kilobase single-stranded DNA that folds into a nanoscale octahedron. Nature 427, 618-621 (2004). doi: 10.1038/nature02307; pmid: 14961116
4. P. Rothemund, Folding DNA to create nanoscale shapes and patterns. Nature 440, 297-302 (2006). doi: 10.1038/nature04586; pmid: 16541064
5. Y. He et al., Hierarchical self-assembly of DNA into symmetric supramolecular polyhedra. Nature 452, 198-201 (2008). doi: 10.1038/nature06597; pmid: 18337818
6. J. Zheng et al., From molecular to macroscopic via the rational design of a self-assembled 3D DNA crystal. Nature 461, 74-77 (2009). doi: 10.1038/nature08274; pmid: 19727196
7. H. Gu, J. Chao, S.-J. Xiao, N. C. Seeman, Dynamic patterning programmed by DNA tiles captured on a DNA origami substrate. Nat. Nanotechnol. 4, 245-248 (2009). doi: 10.1038/nnano.2009.5; pmid: 19350035
8. S. M. Douglas et al., Self-assembly of DNA into nanoscale three-dimensional shapes. Nature 459, 414-418 (2009). doi: 10.1038/nature08016; pmid: 19458720
9. H. Dietz, S. M. Douglas, W. M. Shih, Folding DNA into twisted and curved nanoscale shapes. Science 325, 725-730 (2009). doi: 10.1126/science.1174251; pmid: 19661424
10. E. S. Andersen et al., Self-assembly of a nanoscale DNA box with a controllable lid. Nature 459, 73-76 (2009). doi: 10.1038/nature07971; pmid: 19424153
11. A. Rajendran, M. Endo, Y. Katsuda, K. Hidaka, H. Sugiyama, Programmed two-dimensional self-assembly of multiple DNA origami jigsaw pieces. ACS Nano 5, 665-671 (2011). doi: 10.1021/nn1031627; pmid: 21188996
12. S. Woo, P. W. K. Rothemund, Programmable molecular recognition based on the geometry of DNA nanostructures. Nat. Chem. 3, 620-627 (2011). doi: 10.1038/nchem.1070; pmid: 21778982
13. D. Han et al., DNA origami with complex curvatures in three dimensional space. Science 332, 342-346 (2011). doi: 10.1126/science.1202998; pmid: 21493857

14. B. Wei, M. Dai, P. Yin, Complex shapes self-assembled from single-stranded DNA tiles. Nature 485, 623-626 (2012).doi: 10.1038/nature11075; pmid: 22660323
15. Y. Ke, L. L. Ong, W. M. Shih, P. Yin, Three-dimensional structures self-assembled from DNA bricks. Science 338, 1177-1183 (2012). doi: 10.1126/science.1227268; pmid: 23197527
16. D. Han et al., DNA gridiron nanostructures based on four-arm junctions. Science 339, 1412-1415 (2013). doi: 10.1126/science.1232252; pmid: 23520107
17. R. Iinuma et al., Polyhedra self-assembled from DNA tripods and characterized with 3D DNA-PAINT. Science 344, 65-69 (2014). doi: 10.1126/science.1250944; pmid: 24625926
18. Y. Ke et al., DNA brick crystals with prescribed depths. Nat. Chem. 6, 994-1002 (2014). doi: 10.1038/nchem.2083; pmid: 25343605
19. K. E. Dunn et al., Guiding the folding pathway of DNA origami. Nature 525, 82-86 (2015). doi: 10.1038/nature14860; pmid: 26287459
20. T. Gerling, K. Wagenbauer, A. Neuner, H. Dietz, Dynamic DNA devices and assemblies formed by shape-complementary, non-base pairing 3D components. Science 347, 1446-1452 (2015). doi: 10.1126/science.aaa5372; pmid: 25814577
21. E. Benson et al., DNA rendering of polyhedral meshes at the nanoscale. Nature 523, 441-444 (2015). doi: 10.1038/nature14586; pmid: 26201596
22. F. Zhang et al., Complex wireframe DNA origami nanostructures with multi-arm junction vertices. Nat. Nanotechnol. 10, 779-784 (2015). doi: 10.1038/nnano.2015.162; pmid: 26192207
23. R. Veneziano et al., Designer nanoscale DNA assemblies programmed from the top down. Science 352, 1534 (2016). doi: 10.1126/science.aaf4388; pmid: 27229143
24. N. Avakyan et al., Reprogramming the assembly of unmodified DNA with a small molecule. Nat. Chem. 8, 368-376 (2016). doi: 10.1038/nchem.2451; pmid: 27001733
25. D. Liu, G. Chen, U. Akhter, T. Cronin, Y. Weizmann, Creating complex molecular topologies by configuring DNA four-way junctions. Nat. Chem. 8, 907-914 (2016). doi: 10.1038/nchem.2564; pmid: 27657865
26. G. Tikhomirov, P. Peterson, L. Qian, Programmable disorder in random DNA tilings. Nat. Nanotechnol. 12, 251-259 (2017). doi: 10.1038/nnano.2016.256; pmid: 27893729
27. S. L. Sparvath, C. W. Geary, E. S. Andersen, Computer-aided design of RNA origami structures. Methods Mol. Biol. 1500, 51-80 (2017). doi: 10.1007/978-1-4939-6454-3; pmid: 27813001
28. S. M. Douglas, J. J. Chou, W. M. Shih, DNA-nanotube-induced alignment of membrane proteins for NMR structure determination. Proc. Natl. Acad. Sci. U.S.A. 104, 6644-6648 (2007). doi: 10.1073/pnas.0700930104; pmid: 17404217
29. G. P. Acuna et al., Fluorescence enhancement at docking sites of DNA-directed self-assembled nanoantennas. Science 338, 506-510 (2012). doi: 10.1126/science.1228638; pmid: 23112329
30. A. Kuzyk et al., DNA-based self-assembly of chiral plasmonic nanostructures with tailored optical response. Nature 483, 311-314 (2012). doi: 10.1038/nature10889; pmid: 22422265
31. S. Douglas, I. Bachelet, G. M. Church, A logic-gated nanorobot for targeted transport of molecular payloads. Science 335, 831-834 (2012). doi: 10.1126/science.1214081; pmid: 22344439
32. Z. Jin et al., Metallized DNA nanolithography for encoding and transferring spatial information for graphene patterning. Nat. Commun. 4, 1663 (2013). doi: 10.1038/ncomms2690; pmid: 23575667
33. W. Sun et al., Casting inorganic structures with DNA molds. Science 346, 1258361 (2014). doi: 10.1126/science.1258361; pmid: 25301973
34. J. Fu et al., Multi-enzyme complexes on DNA scaffolds capable of substrate channelling with an artificial swinging arm. Nat. Nanotechnol. 9, 531-536 (2014). doi: 10.1038/nnano.2014.100; pmid: 24859813
35. J. B. Knudsen et al., Routing of individual polymers in designed patterns. Nat. Nanotechnol. 10, 892-898 (2015). doi: 10.1038/nnano.2015.190; pmid: 26322946
36. P. C. Nickels et al., Molecular force spectroscopy with a DNA origami-based nanoscopic force clamp. Science 354, 305-307 (2016). doi: 10.1126/science.aah5974; pmid: 27846560
37. F. Kilchherr et al., Single-molecule dissection of stacking forces in DNA. Science 353, aaf5508 (2016). doi: 10.1126/science. aaf5508; pmid: 27609897
38. T. G. Martin et al., Design of a molecular support for cryo-EM structure determination. Proc. Natl. Acad. Sci. U.S.A. 113, E7456-E7463 (2016). doi: 10.1073/pnas.1612720113; pmid: 27821763
39. A. Gopinath, E. Miyazono, A. Faraon, P. W. K. Rothemund, Engineering and mapping nanocavity emission via precision placement of DNA origami. Nature 535, 401-405 (2016). doi: 10.1038/nature18287; pmid: 27398616
40. N. A. W. Bell, U. F. Keyser, Digitally encoded DNA nanostructures for multiplexed, single-molecule protein sensing with nanopores. Nat. Nanotechnol. 11, 645-651 (2016). doi: 10.1038/nnano.2016.50; pmid: 27043197
41. C. Lin, M. Xie, J. J. L. Chen, Y. Liu, H. Yan, Rolling-circle amplification of a DNA nanojunction. Angew. Chem. Int. Ed. 45, 7537-7539 (2006). doi: 10.1002/anie.200602113; pmid: 17048296
42. C. Lin, X. Wang, Y. Liu, N. C. Seeman, H. Yan, Rolling circle enzymatic replication of a complex multi-crossover DNA nanostructure. J. Am. Chem. Soc. 129, 14475-14481 (2007). doi: 10.1021/ja0760980; pmid: 17963390
43. Z. Li et al., A replicable tetrahedral nanostructure self assembled from a single DNA strand. J. Am. Chem. Soc. 131, 13093-13098 (2009). doi: 10.1021/ja903768f; pmid: 19737020
44. C. Geary, P. W. Rothemund, E. S. Andersen, A single-stranded architecture for cotranscriptional folding of RNA nanostructures. Science 345, 799-804 (2014). doi: 10.1126/science.1253920; pmid: 25124436
45. C. X. Lin, et al, In vivo cloning of artificial DNA nanostructures. Proc. Natl. Acad. Sci. U.S.A. 105, 17626-17631 (2008).doi: 10.1073/pnas.0805416105; pmid: 18927233
46. C. Ducani, C. Kaul, M. Moche, W. M. Shih, B. Hogberg, Enzymatic production of 'monoclonal stoichiometric' single stranded DNA oligonucleotides. Nat. Methods 10, 647-652 (2013). doi: 10.1038/nmeth.2503; pmid: 23727986
47. N. C. Seeman, The design and engineering of nucleic acid nanoscale assemblies. Curr. Opin. Struct. Biol. 6, 519-526 (1996). doi: 10.1016/50959-440X(96)80118-7; pmid: 8794156
48. X. Zhang, H. Yan, Z. Shen, N. Seeman, Paranemic cohesion of topologically-closed DNA molecules. J. Am.

Chem. Soc. 124, 12940-12941 (2002). doi: 10.1021/ja026973b; pmid: 12405808
49. Z. Shen, H. Yan, T. Wang, N. Seeman, Paranemic crossover DNA: A generalized Holliday structure with applications in nanotechnology. J. Am. Chem. Soc. 126, 1666-1674 (2004). doi: 10.1021/ja038381e; pmid: 14871096
50. D. Han, S. Jiang, A. Samanta, Y. Liu, H. Yan, Unidirectional scaffold-strand arrangement in DNA origami. Angew. Chem. Int. Ed. 52, 9031-9034 (2013). doi: 10.1002/anie.201302177; pmid: 23852715
51. L. Jaeger, N. B. Leontis, Tecto-RNA: One-dimensional self-assembly through tertiary interactions. Angew. Chem. Int. Ed. 39, 2521-2524 (2000). doi: 10.1002/1521-3773(20000717)39:14<2521::AIDANIE2521>3.0.CO;2-P; pmid: 10941124
52. A. Chworos et al., Building programmable jigsaw puzzles with RNA. Science 306, 2068-2072 (2004). doi: 10.1126/science.1104686; pmid: 15604402
53. C. J. Delebecque, A. B. Lindner, P. A. Silver, F. A. Aldaye, Organization of intracellular reactions with rationally designed RNA assemblies. Science 333, 470-474 (2011). doi: 10.1126/science.1206938; pmid: 21700839
54. L. Jaeger, A. Chworos, The architectonics of programmable RNA and DNA nanostructures. Curr. Opin. Struct. Biol. 16, 531-543 (2006). doi: 10.1016/j.sbi.2006.07.001; pmid: 16843653
55. J. W. Alexander, G. B. Briggs, On types of knotted curves, in The Annals of Mathematics, Second Series (Annals of Mathematics, 1926), pp. 562-586.
56. J. W. Alexander, Topological invariants of knots and links. Trans. Am. Math. Soc. 30, 275-306 (1928). doi: 10.1090/50002-9947-1928-1501429-1
57. K. Murasugi, Knot Theory and Its Applications (Springer Science and Business Media, 2007).
58. M. L. Mansfield, Are there knots in proteins? Nat. Struct. Mol. Biol. 1, 213-214 (1994). doi: 10.1038/nsb0494-213; pmid: 7656045
59. F. Takusagawa, S. Kamitori, A real knot in protein. J. Am. Chem. Soc. 118, 8945-8946 (1996). doi: 10.1021/ja961147m
60. W. R. Taylor, A deeply knotted protein structure and how it might fold. Nature 406, 916-919 (2000). doi: 10.1038/35022623; pmid: 10972297
61. J. R. Wagner, J. S. Brunzelle, K. T. Forest, R. D. Vierstra, A light sensing knot revealed by the structure of the chromophore binding domain of phytochrome. Nature 438, 325-331 (2005). doi: 10.1038/nature04118; pmid: 16292304
62. H. Lee, E. Popodi, H. Tang, P. L. Foster, Rate and molecular spectrum of spontaneous mutations in the bacterium *Escherichia coli* as determined by whole-genome sequencing. Proc. Natl. Acad. Sci. U.S.A. 109, E2774-E2783 (2012). doi: 10.1073/pnas.1210309109; pmid: 22991466
63. E. D. Demaine, J. O'Rourke, Geometric Folding Algorithms: Linkages, Origami, Polyhedra (Cambridge Univ. Press, 2007).
64. S. Horiya, et al, RNA LEGO: Magnesium-dependent formation of specific RNA assemblies through kissing interactions. Chem. Biol. 10, 645-654 (2003). doi: 10.1016/S1074-5521(03)00146-7; pmid: 12890538
65. More formally, previous scaffolded origami work and the DNA brick work demonstrates the construction of a size n object using O(n) number of components; the unimolecular ssOrigami demonstrates the construction a size n object using 1 component; the 2-strand case represents its construction using O(1) components; the 20-strand case represents its construction using O(√n) components.
66. S. Williams, K. Lund, C. Lin, P. Wonka, S. Lindsay, H. Yan, Tiamat: A three-dimensional editing tool for complex DNA structures, in International Workshop on DNA-Based Computers (Springer, 2008), pp. 90-101.

Example 2

Figure 6:
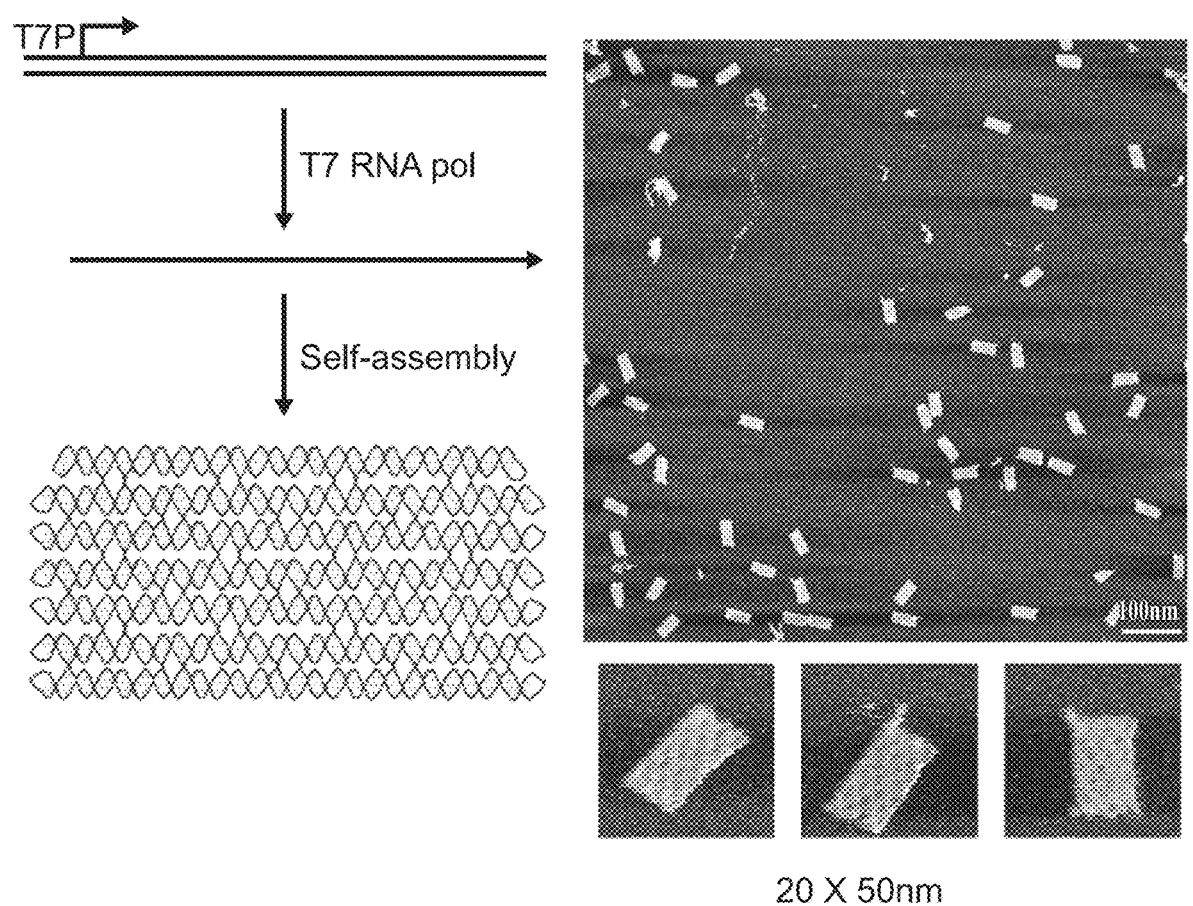
FIG. 6. RNA origami schematics (left panel) and AFM images (right panel). A plasmid containing a ssRNA origami gene was linearized and the ssRNA was in vitro transcribed using T7 RNA polymerase. The purified RNA molecule was self-assembled into the ssRNA rectangle origami nanostructure through paranemic cohesion crossover.
Figure 8:
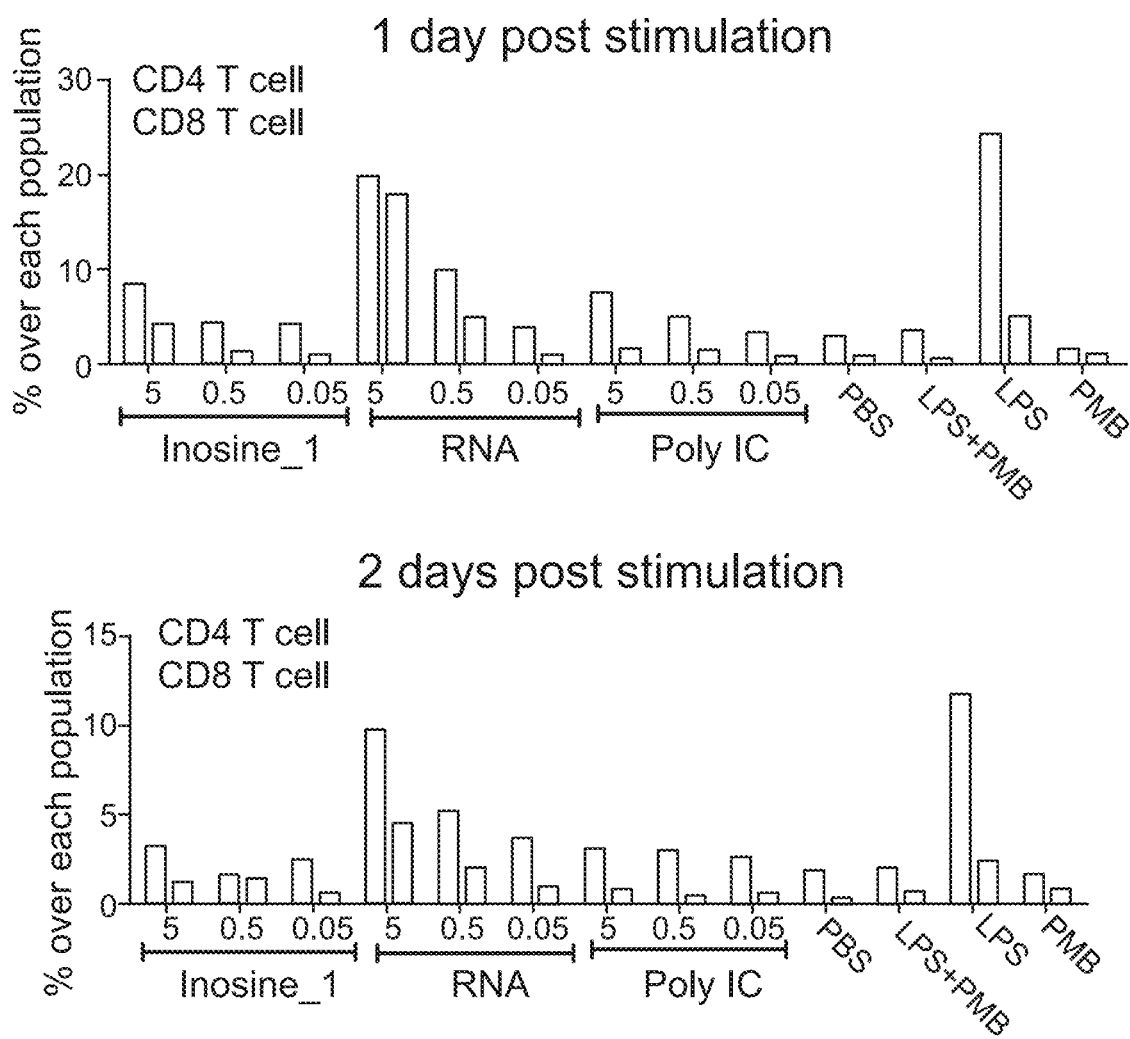
FIG. 8. Ex vivo splenocyte stimulation: CD69 activation in T cell. RNA origami activate both CD8 and CD4 T cells. Percentages of CD69+ cells in CD4 T cells and CD8 T cells are plotted. PBS: phosphate buffer saline, LPS: lipopolysaccharide; PMB: polymyxin B; Inosine_1: inosine-incorporated RNA origami. For each grouping, CD4T cell is shown in the left and CD8 T cell is shown on the right.

RNA origami has the structural characteristics of being capable of forming programmable structures varying in size, shape and configurations (see, e.g., FIG. 47). RNA origami is compact and forms uniformly dispersed nanostructures. As described in FIG. 6, a plasmid containing an ssRNA origami gene was linearized and the ssRNA was in vitro transcribed using T7 RNA polymerase. The purified RNA molecule was then self-assembled into the ssRNA origami nanostructure (RNA-Rec). The RNA origami had an intact structure, even without cations. The properly-folded RNA origami was shown to be resistant to nuclease digestion and contained regions of both dsRNA and ssRNA, which may serve as pathogen associated molecular patterns. Specifically, in vitro RNase digestion experiments were conducted, and the RNA origami was found to exhibit higher nuclease resistance than the unfolded ssRNA with the same sequence as the RNA origami (FIG. 7, 51). In addition, the immunostimulating effects of RNA origami was tested using an ex vivo splenocyte stimulation assay and enhanced stimulatory activity mediated by RNA origami over PolyIC was observed (FIGS. 8-10). Similar to the in vitro findings on stimulation, an intraveneous injection of RNA origami through a retro-orbital route resulted in a transient elevation of IFNa/b in mice (FIG. 11).

Figure 12:
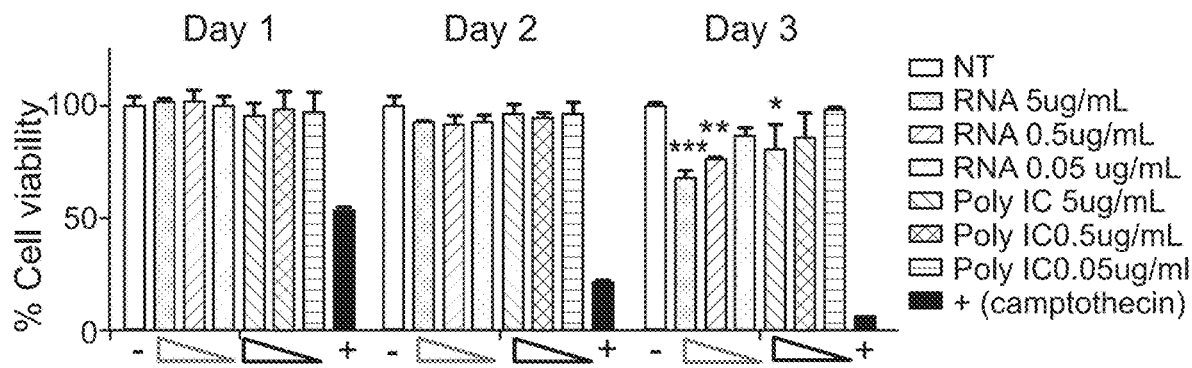
FIG. 12. Influence on tumor cell viabilities. After three days of incubation, RNA origami was found to reduce the viability of 4T1, a mouse breast cancer cell line, in vitro. The delayed inhibitory effect might have been mediated through the production of pro-inflammatory cytokines by the tumor cells after their exposure to RNA origami. RNA origami exerted little or minimal effect on the viability of certain other mouse and human tumor cell lines tested in vitro (not shown). Within each grouping, the following are included from left to right: NT (no treatment), RNA (RNA origami) 5 µg/ml, RNA (RNA origami) 0.5 µg/ml, RNA (RNA origami) 0.05 µg/ml, PolyIC 5 µg/ml, PolyIC 0.5 µg/ml, PolyIC 0.05 µg/ml, +(camptothecin).
Figure 13:
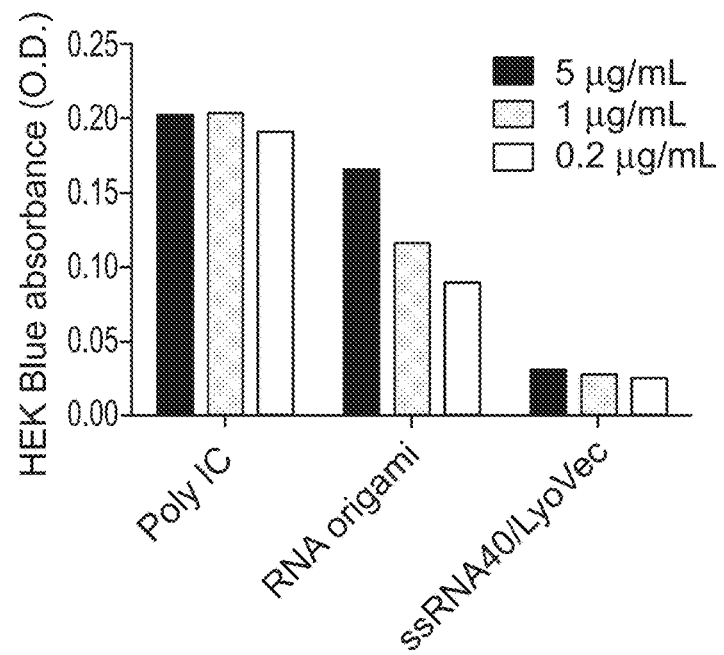
FIG. 13. TLR3 agonist. RNA origami showed as a TLR3 agonist in a reporter cell line, HEK-Blue™-mTLR3 cells, although its activity is not as strong as polyIC.
Figure 14:
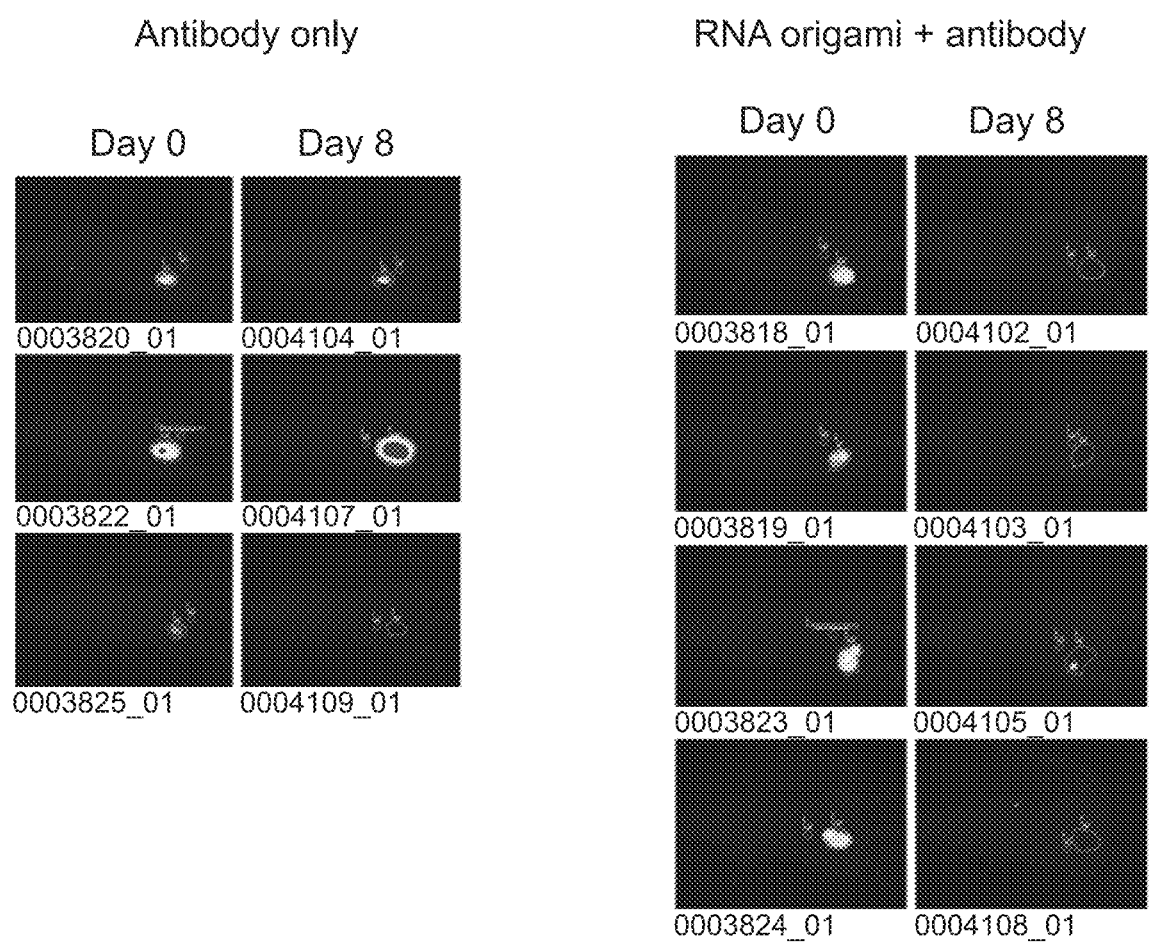
FIG. 14. Anti-tumor immunity in vivo. Track in vivo tumor growth with A20-iRFP model. Antibody only is shown in the left panel and RNA origami+antibody is shown in the right panel. The antibody used was anti-PD1 antibody (Clone 29F.1A12) from Biolegend, primarily for in vivo application (GoInVivo™ Purified anti-mouse CD279 (PD-1) Antibody). The RNA origami is the one depicted in FIG. 6.
Figure 15:
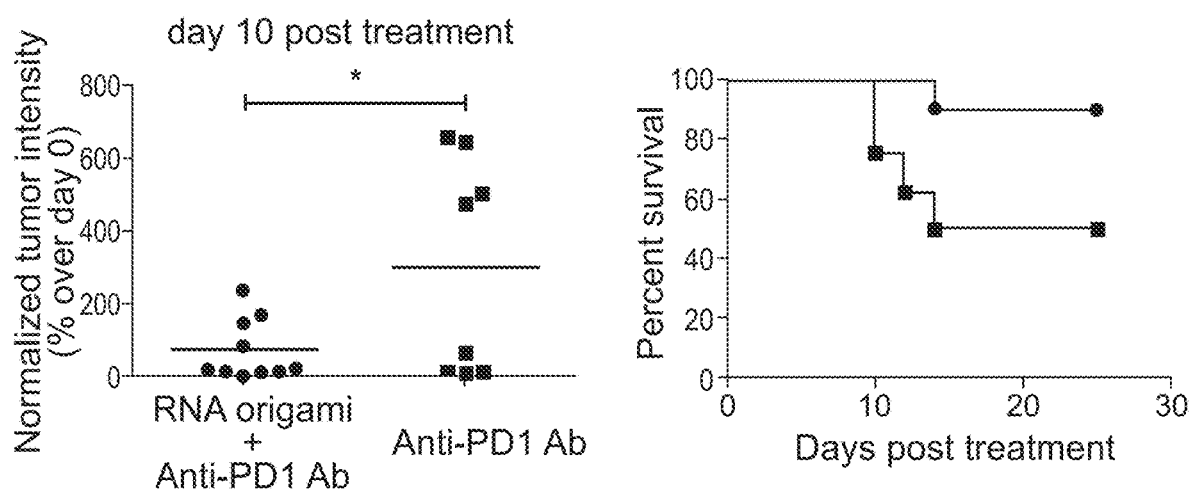
FIG. 15. Tumor reduction upon combination treatment with anti-PD1 antibody and RNA origami. The antibody and RNA origami are the same as was used in FIG. 14. RNA-origami synergizes the anti-tumor activity of checkpoint inhibitors.

Upon prolonged incubation, the RNA origami were also found to reduce the viability of some tumor cells in vitro (FIG. 12). As shown in FIG. 13, the RNA origami acted as a TLR3 agonist in the HEK-Blue™-mTLR3 reporter cell line. Finally, anti-tumor immunity was evaluated in vivo using an A20-iRFP model, which allowed tumor growth to be tracked in vivo (FIGS. 14-15). In these experiments, mice were either administered an anti-PD1 antibody alone or the anti-PD1 antibody in combination with RNA origami. As shown in FIGS. 14 and 15, tumor reduction was observed upon treatment with RNA origami, which was greater than with the administration of antibody alone.

Taken together, these results indicate that the RNA origami can function as agonists of pattern recognition receptors, such as TLR3 and TLR7 in immune cells, and could potentially serve as a new line of adjuvants. By using an established mouse tumor model, this platform may be further explored for the construction of tumor-specific vaccines. Additionally, this RNA origami is conducive to scalable production.

RNA Nanostructure Design

RNA rectangle origami nanostructure and RNA sequence were designed using the Tiamat software (Yanlab.asu.edu/Tiamat.exe), which facilitates the visualization of DNA/RNA helices. Artificial RNA sequence was generated by using the following criteria in the Tiamat software: (1) Unique sequence limit: 8 nt; (2) Repetition limit: 6-8 nt; (3) G repetition limit: 4 nt; (4) GC content: 0.45-0.55. Once sequences were generated, a few nucleotides were adjusted to eliminate the restriction enzyme targeting sequences (e.g. by EcoRI, EcoRV, HindIII and XbaI) for cloning purposes. A T7 promoter sequence followed with three consecutive Gs were manually incorporated onto the 5' end of the DNA template in order to facilitate efficient in vitro transcription reaction. The dsDNA template was synthesized by BioBasic Inc. and cloned into the pUC19 vector through EcoRI and HindIII restriction sites.

RNA Strand Synthesis

The plasmid containing the ssRNA nanostructure gene was linearized by using a HindIII enzyme (New England Biolabs) and the linear plasmid was purified by using a Phenol/chloroform extraction and ethanol precipitation. The in vitro transcription reaction was carried out by using the T7 RiboMAX Express Large Scale RNA Production System (Promega), following the manufacturer's instructions. For inosine containing RNA preparation, additional 5 mM Inosine-5'-triphosphate (TriLink BioTechnologies) was added to the in vitro transcription reaction. The RNA molecules were then purified via a RNA Clean & Concentrator-25 kit (Zymo Research).

RNA Origami Nanostructure Assembly

The purified RNA molecule was diluted to 20-250 nM in 1×PBS buffer (20 mM Sodium phosphate, 130 mM Sodium chloride, pH 7.4). The resulting solution was annealed from 65° C. to 25° C. with a cooling ramp of 1° C. per 20 minutes to form the desired structures.

Atomic Force Microscope Characterization

RNA origami was imaged in "ScanAsyst mode in fluid," using a Dimension FastScan microscope with PEAK-FORCE-HiRs-F-A tips (Bruker Corporation). After annealing, 2 µl of each sample was deposited onto a freshly cleaved mica surface (Ted Pella, Inc.), and left to adsorb for 1 minute. Then, 80 µl of 1×TAE-Mg buffer and 2 µl 100 mM of a $NiCl_2$ solution was added onto the mica, and 40 µl of the same buffer was deposited onto the microscope tip. The samples were then scanned by following the manufacturer's instructions.

Animals

Female BALB/c mice were obtained from Charles River Laboratories and maintained in a pathogen-free animal facility at the Arizona State University Animal Resource Center. All mice were handled in accordance with the Animal Welfare Act and Arizona State University Institutional Animal Care and Use Committee (IACUC). Before experimental treatment, the mice were randomly distributed in cages and allowed to acclimate for at least 1 week prior to vaccination.

Splenocyte Isolation and Stimulation

Mice were euthanized with carbon dioxide asphyxia, and the spleens were removed and sterilized by quickly dipping in 70% ethanol for 1 s before transfer to sterile RPMI-1640 medium supplemented with 10% fetal bovine serum (FBS) in the biosafety cabinet. Spleen was cut on one end, and a thin, sealed L-shaped glass tube was used to push spleen marrows out. The extracted spleen cells were pelleted and washed by spinning at 380×g for 3 min in the sterile RPMI-1640 medium described above, and red blood cells were depleted by ACT lysis buffer (combination of 0.16M $NH_4Cl$ and 0.17 M Tris [pH 7.65] at a volume ratio of 9:1, pH adjusted to 7.2 with 1 M HCl, and filter sterilized). After washing twice in RPMI-1640 medium supplemented with 10% FBS and antibiotics, the splenocytes were seeded in 12-well plates at a density of $4\times10^6$ cells/mL. RNA origami, Inosine-incorporated RNA origami, or other adjuvants are added into each well at desired concentrations (5 µg/mL, 0.5 µg/mL, or 0.05 µg/mL), 50 ng/mL lipopolysaccharide (LPS) was added to the positive control well and Polymyxin B (PMB) is added into each well except for the LPS alone well at final concentration of 100 µg/mL to prevent endotoxin contamination. 24 hours or 48 hours after stimulation, cells were harvested, labelled for surface markers, and analysed by flow cytometry.

Flow Cytometry

Stimulated splenocytes were harvested by spinning down at 380×g for 3 min, and supernatants were saved for cytokine analysis. Pelleted cells were washed once with 1×PBS, and labeled with Zombie Violet viability dye (Biolegend) at room temperature for 15 min. After washing twice in staining buffer (1×PBS, 2% BSA, 0.01% sodium azide), cells were incubated in the following antibody cocktail containing FcR block: (a) FITC anti-mouse CD4, PE anti-mouse CD3, PE/Cy5 anti-mouse CD69, and PE/Cy7 anti-mouse PD1; b) FITC anti-mouse CD11b, PE anti-mouse CD86, PE/Cy5 anti-mouse B220, and PE/Cy7 anti-mouse CD11c. After 30 min incubation at 4° C., cells were washed twice in staining buffer and resuspended in 200 uL staining buffer. Then each sample was analyzed on a FACSAria II instrument at Biodesign Institute, Arizona State University. Live cells were defined as Zombie Violet-low cell population, and CD4 T cells were gated as CD3+CD4+ live cells, CD8 T cells were gated as CD3+CD4− live cells. Percentage of CD69+ cells in CD4 T cell population and CD8 T cell population were plotted for T cell stimulation measurment Plasmacytoid dendritic cells (pDC) were defined as CD11b-CD11c+ B220+ live cells, and conventional dendritic cells (DC) were defined as CD11b+CD11c+ cells. Mean fluorescent intensity of CD86 in each DC cell population is plotted as an indicator of DC stimulation status.

Cytokine Analysis

Cytokine release in ex vivo splenocyte cell culture supernatant was measured by the mouse Procarta IFN 2-plex featured assay of Eve Technologies (catalog no. MTN-02-103). For serum cytokine analysis, 100 uL of RNA origami (25 µg), PolyIC (25 µg) or 1×PBS were i.v. injected to naive mice through retro-orbital route, and mouse serum were collected at 3 hr, 6 hr, and 24 hr post injection by cheek-vein bleeding. Blood was spin down at 7000 rpm for 10 min at 4° C., and measured by the mouse Procarta IFN 2-plex featured assay of Eve Technologies (catalog no. MIFN-02-103).

Cell Viability Test

Viability of cells after incubation with RNA origami was analyzed by MTT assay, (Vybrant® MTT cell proliferation assay kit from Thermo Fisher) following manufacture's protocol. Camptothecin (Sigma-Aldrich, catalog no. C9911) at final concentration of 5 µM served as the positive control, as it is known to induce apoptosis.

TLR3 Agonist Test

A reporter cell line expressing mouse TLR3, HEK-Blue™ mTLR3 cells, was purchased from Invivogen. Agonist activity of RNA origami and other adjuvants were quantified by the absorbance of HEK-Blue medium after co-incubation of these adjuvants with cells, following manufacture's protocol. ssRNA40/LyoVec™ purchased from Invivogen served as negative control.

A20-iFRP-OVA Tumor Model

Figure 16:
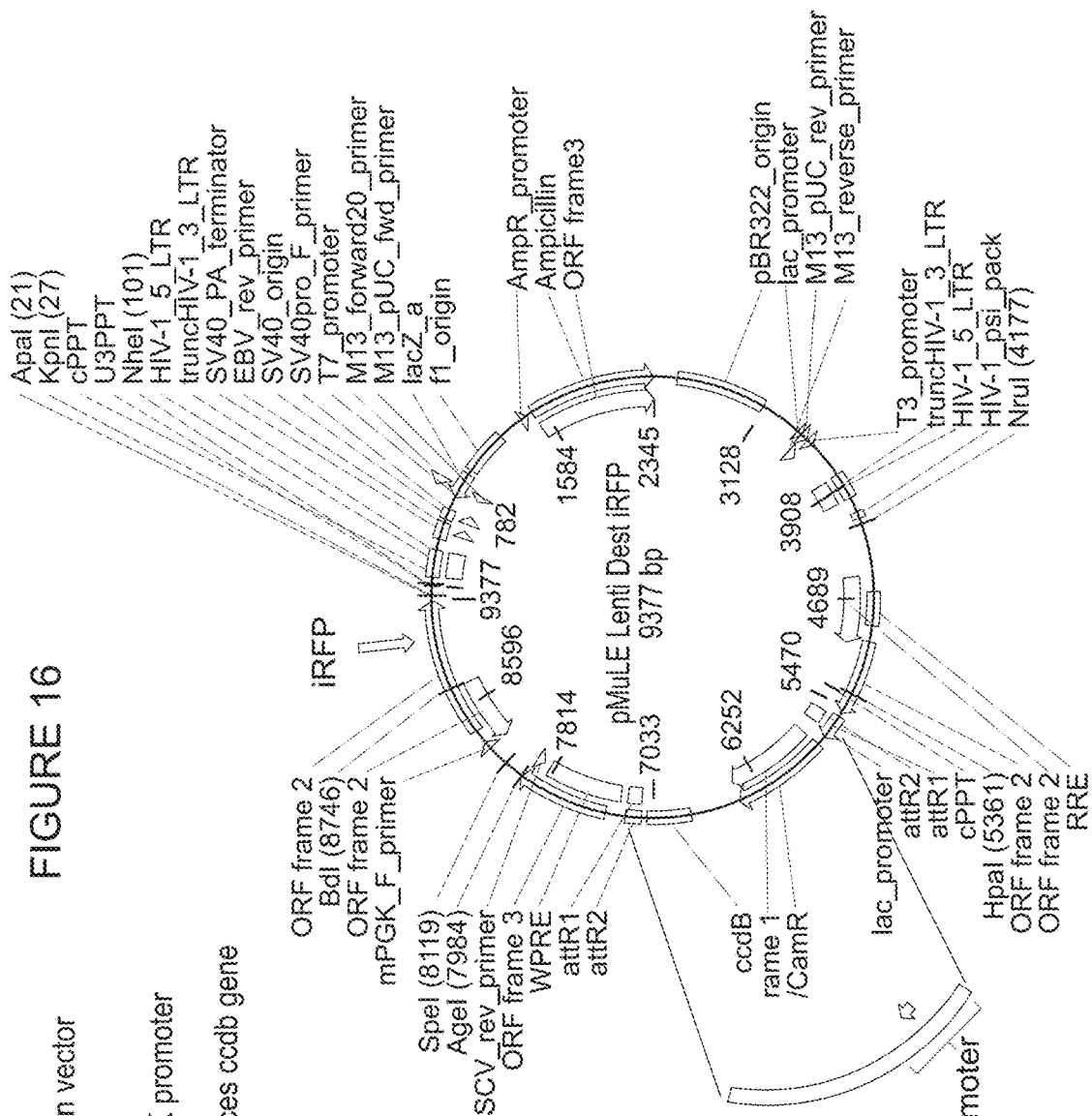
FIG. 16. MuLE (Multiple Leniviral Expression) Destination Vector.

A20, mouse B cell lymphoma cells, were transduced with lentiviral vector that was constructed to express near-infrared fluorescent protein (FIG. 16), iRFP, and oval albumin using LENTI-Smart™ transduction kit from Invivogen by following manufacture's protocols. Cell-sorting was carried out on BD FACSAria II at Biodesign Institute, Arizona State University, to isolate A20-iRFP cells with the top 1% fluorescent intensity for subsequent cell culture. Bright and stable expression of iRFP in A20 cells were confirmed by flow cytometry and Pearl small animal imaging system (LI-COR, San Diego, Calif.). For tumor inoculation, BALB/c mice were shaved at the left flank and injected s.c. with 10×10$^6$ A20-iRFP cells. 7-10 days post injection, mice were imaged under the Pearl small animal imaging system, and mice bearing tumors of similar near-infrared intensities were randomized into different groups for subsequent treatments.

For treatment, mice were injected with 25 ug RNA origami in 50 uL PBS, or 50 uL PBS through intratumor injection on day 0. Anti-PD1 antibody (Biolegend, catalog no. 114108) were injected into mouse tumors on day 2 and day 4, at a dose of 2.5 ug per injection. Tumor growth were tracked every other day and tumor size was quantified by measuring the near-infrared fluorescent intensity using Image Studio™ software from LI-COR.

RNA Nanostructure Sequence

```
                                                    (SEQ ID NO: 1)
5' GGGAGAGAGCUCGAGCGAACACUAGCCACUUGAUCACGCUGAGCGCU
CGUACAAUGAAACACAGGUGUGUCAGUGCUAUGCACGUUCGAAGAGCUG
UAUCAGCGUUCGUGUGAAUGAGUUCAACGGAGUGUUGACUAAGCCGGUU
GCUACAUUUCUGUAGCACACAUAGUCAAGAUUUGCACCAGACGAUACUC
UCCCUCAGUCCUGUUUAUGCAAGUCGUCGUAGUCCUGACGUACUUCCUA
AGCUCGUCACUGUACUGAUGAUUCCACUGAUCAAGAUGCACGUAUCUUC
AGUUUCCUGAAGAUCGGAGUAGGCACUAUAAUCGACAAGUAACGCUUAC
GAUUCCAUCACGAGUGACUUACCUGAACCAUAACUGACAAGGGACCACG
CAGAGGUCAUACUCACAGGACUUCAAAUCUUGAGUCGGGUUCGAUCAUU
UCUGAUCGAGACACCAGUGUGAGGUAAUCGUACGUCACUUGAUAGGAGC
UCUAAGUAGAGUUGAGAGCCUGUUAACUAGACACGAGUAACGAGGUUAG
CCUGUACGAGAUAUCGGGCUAUAGUGCGGACACGAUUGCACCAUUUCUG
GUGCAACGAAGGUGAGCAUGUAUGGACAGGUCAGUGUGACUCAAGUCGA
UAGUCCAAGUAGGUUAUCGACUCGCAUAGCUCAAUGACUGUCAUCGCCA
GAGUAUCUAGGUGUCUACCUCACGAAUCGCGUCGUUACAUUUCUGUAAC
GCUCAUACCGUGCUGAUCUAUGGGACACGUCGCUUAUUCUUGGGUCAUG
ACAGUUGCCACAAACAAGGCACGACCUCACACCUGCGAACUUCAAGCGU
UAGGCUGACGUUACAUGCUUGCGUGCACUGAUUCGUUUCCGAAUCAGAG
ACCUACGAAGCCAGAGUUCGUUCACUAUCAUAAGUGCACUGAUGCAUUU
GUGCCAACAUUGAAGGCAUCGAGAUAAACAGCCGUCUUAAUCAAGUGAG
CACCUGAGAUCAGCAUGAUUCGUCUAUUUCUAGACGAAUCAACUUCCAU
UCAGGUGCCUUGCUACUUAAGACGGGAUUAACUCUCGAUGCAACGUGCA
UUGGCACAACUCGUGAUGUGCACUUUCACACUGGAACGAACUCUGGCUU
CGUAGGUCUGUUUGUCAUUUCUGACAAACUGCACGCACUGUUAGUACGU
CAGCCACUUAACCGAAGUUCGUCAUAAGUAGGUCGUGCGACUACGAUGG
CAACUUCUACUUACCAAGAAUAAGCGACGUGUCCCAUAAUGGAAGUCGG
UAUGAGGUAUGACUUUCGUCAUACACGCGAUUCCACAAUGUGACACCUA
ACGUUUGAGGCGAUGACCUGAUACAAGCUAUGCAUGGUUCAAACCUACU
UGGACUAUCGACUUGAGAUGAUAGUACCUGUCCAACUAACAGCACCUUC
GAUACCUCGUUUCCGAGGUAUUCGUGUCCUGUGUCAGGCCCGAUAUUAA
UGUGUGGCUAACCCUUAGGAACGUGUCUAGUUAACAGGCUCUCAACGUC
AUGACGAGCUCCUAGUAGCAAGCGUACGAUACAUUGUGACUGGUGUCUA
CUGGAUUUCUCCAGUAACCCGACUCCGACUACAAAGUCCUGACUCAUUC
ACCUCUGCGUGGUCCCUUGUCAGUUGAGUCGAUGGUAAGUCAAUGCAUC
AGGAAUCGUGGUUAAGUCUUGUCGAUCUGACACACUACUCCGCUGUCCU
GUUUCCAGGACAGACGUGCAUUAGCAGUUGUGGAAUCAUCAGUACAGUG
ACGAGUCGUUACUGUACGUCAGCUUGUUUGCGACUUGCAGUUAAUCGAC
UGAGGGUCAAACGUGUCUGGUGUGUAGUCGGACUAUGUGACGUUCAUUU
CUGAACGUACCGGCUUAGUCAACACUCCGUUGAUGAGUAUGACACGAAC
GAGUCAUUGGCUCUUCGCUUCAAUGUAGCACUGAACUUAUGAUGUUUCA
UACACAUUACGCUCAGCGAACUGCUAUGGCUAGUGUUCGGAUCC 3'
```

Sequence Encoding RNA Nanostructure

```
                                                    (SEQ ID NO: 2)
5' GGGAGAGAGCTCGAGCGAACACTAGCCACTTGATCACGCTGAGCGCT
CGTACAATGAAACACAGGTGTGTCAGTGCTATGCACGTTCGAAGAGCTG
TATCAGCGTTCGTGTGAATGAGTTCAACGGAGTGTTGACTAAGCCGGTT
GCTACATTTCTGTAGCACACATAGTCAAGATTTGCACCAGACGATACTC
TCCCTCAGTCCTGTTTATGCAAGTCGTCGTAGTCCTGACGTACTTCCTA
AGCTCGTCACTGTACTGATGATTCCACTGATCAAGATGCACGTATCTTC
AGTTTCCTGAAGATCGGAGTAGGCACTATAATCGACAAGTAACGCTTAC
GATTCCATCACGAGTGACTTACCTGAACCATAACTGACAAGGGACCACG
CAGAGGTCATACTCACAGGACTTCAAATCTTGAGTCGGGTTCGATCATT
TCTGATCGAGACACCAGTGTGAGGTAATCGTACGTCACTTGATAGGAGC
TCTAAGTAGAGTTGAGAGCCTGTTAACTAGACACGAGTAACGAGGTTAG
CCTGTACGAGATATCGGGCTATAGTGCGGACACGATTGCACCATTTCTG
GTGCAACGAAGGTGAGCATGTATGGACAGGTCAGTGTGACTCAAGTCGA
TAGTCCAAGTAGGTTATCGACTCGCATAGCTCAATGACTGTCATCGCCA
GAGTATCTAGGTGTCTACCTCACGAATCGCGTCGTTACATTTCTGTAAC
GCTCATACCGTGCTGATCTATGGGACACGTCGCTTATTCTTGGGTCATG
ACAGTTGCCACAAACAAGGCACGACCTCACACCTGCGAACTTCAAGCGT
TAGGCTGACGTTACATGCTTGCGTGCACTGATTCGTTTCCGAATCAGAG
ACCTACGAAGCCAGAGTTCGTTCACTATCATAAGTGCACTGATGCATTT
GTGCCAACATTGAAGGCATCGAGATAAACAGCCGTCTTAATCAAGTGAG
CACCTGAGATCAGCATGATTCGTCTATTTCTAGACGAATCAACTTCCAT
TCAGGTGCCTTGCTACTTAAGACGGGATTAACTCTCGATGCAACGTGCA
TTGGCACAACTCGTGATGTGCACTTTCACACTGGAACGAACTCTGGCTT
CGTAGGTCTGTTTGTCATTTCTGACAAACTGCACGCACTGTTAGTACGT
CAGCCACTTAACCGAAGTTCGTCATAAGTAGGTCGTGCGACTACGATGG
CAACTTCTACTTACCAAGAATAAGCGACGTGTCCCATAATGGAAGTCGG
TATGAGGTATGACTTTCGTCATACACGCGATTCCACAATGTGACACCTA
```

-continued

```
ACGTTTGAGGCGATGACCTGATACAAGCTATGCATGGTTCAAACCTACT

TGGACTATCGACTTGAGATGATAGTACCTGTCCAACTAACAGCACCTTC

GATACCTCGTTTCCGAGGTATTCGTGTCCTGTGTCAGGCCCGATATTAA

TGTGTGGCTAACCCTTAGGAACGTGTCTAGTTAACAGGCTCTCAACGTC

ATGACGAGCTCCTAGTAGCAAGCGTACGATACATTGTGACTGGTGTCTA

CTGGATTTCTCCAGTAACCCGACTCCGACTACAAAGTCCTGACTCATTC

ACCTCTGCGTGGTCCCTTGTCAGTTGAGTCGATGGTAAGTCAATGCATC

AGGAATCGTGGTTAAGTCTTGTCGATCTGACACACTACTCCGCTGTCCT

GTTTCCAGGACAGACGTGCATTAGCAGTTGTGGAATCATCAGTACAGTG

ACGAGTCGTTACTGTACGTCAGCTTGTTTGCGACTTGCAGTTAATCGAC

TGAGGGTCAAACGTGTCTGGTGTGTAGTCGGACTATGTGACGTTCATTT

CTGAACGTACCGGCTTAGTCAACACTCCGTTGATGAGTATGACACGAAC

GAGTCATTGGCTCTTCGCTTCAATGTAGCACTGAACTTATGATGTTTCA

TACACATTACGCTCAGCGAACTGCTATGGCTAGTGTTCGGATCC 3'
```

Example 3

TLR3 and TLR7/8 HEK-293T reporter lines were used to study whether RNA-origami (e.g., SEQ ID NO:1) could activate TLR3-signaling pathway and/or the TLR7 pathway. The results indicated that the RNA-origami could activate TLR3-signaling pathway, but not the TLR7. Unlike dsRNA-mediated activation, the stimulatory activity observed was independent of transfection, which suggests that RNA-origami could be taken up by HEK-293T cells to trigger TLR3-signaling pathway, rather than mediated through cytoplasmic RNA sensors, i.e., MDA5/RIG. Interestingly, although the RNA-origami and polyIC displayed a comparable level of activation in TLR3-reporter line, much more potent activation of splenocytes was found by RNA-origami than polyIC (see, FIG. 8 and FIG. 9). This finding suggests that antigen presenting cells present in the spleen can uptake RNA-origami for the activation of these immune cells.

Figure 17:
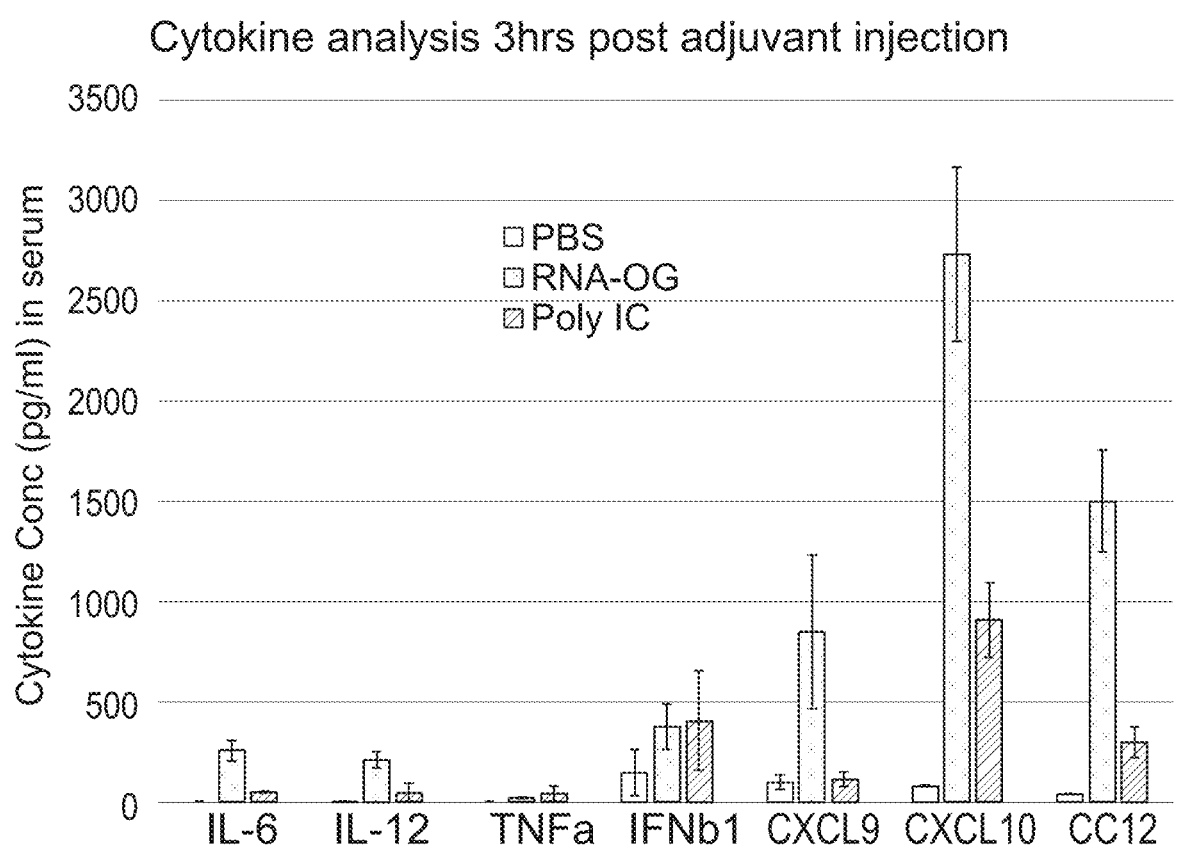
FIG. 17. Cytokines and chemokines three hours after IP treatment. Within each grouping, PBS is shown in the left, RNA-OG in the middle and Poly IC on the right.

Furthermore, the cytokine profiles were examined in mice receiving intraperitoneal injection of RNA origami or low molecular weight polyIC that is in the same size range as the present RNA-origami. Interestingly, it was found that the cytokine profile in RNA-origami mice showed high levels of IL12, chemokines, but low and moderate levels of TNFa and IL6, respectively (FIG. 17). PolyIC used in this example has low molecular weight, whereas the one used in Takeda's report likely are high molecular weight PolyIC, which is associated with high toxicity. (Takeda et al., A TLR3-Specific Adjuvant Relieves Innate Resistance to PD-L1 Blockade without Cytokine Toxicity in Tumor Vaccine Immunotherapy, Cell Rep. 2017 May 30; 19(9):1874-1887.) Nevertheless, the polyIC-LMW did not induce significant elevation of these cytokines, similar to the study reported by Zhou et al. (Zhou, Y., et al. 2012. TLR3 activation efficiency by high or low molecular mass Poly I:C. Innate Immunity. 19:184-192), which shows that high molecular weight (HMW) PolyIC (known as PolyIC-HMW) is more potent in vivo than low molecular weight (LMW) polyIC (polyIC-LMW). In addition, PolyIC-HMW is usually used as vaccination adjuvants and its systemic application is associated with toxicity. Compared to the levels of TNFa and IL-6 shown in Takeda's study, the levels of these cytokines induced by RNA-origami are at the range of those induced by two ARNAX, i.e., have low toxicity. Thus, the present RNA-origami may function more like ARNAX. On the other hand, elevation of three chemokines, CXCL9, CXCL10 and CCL2 are known to play important roles to recruit CD8-T and NK cells to mount anti-tumor immunity.

Figure 18:
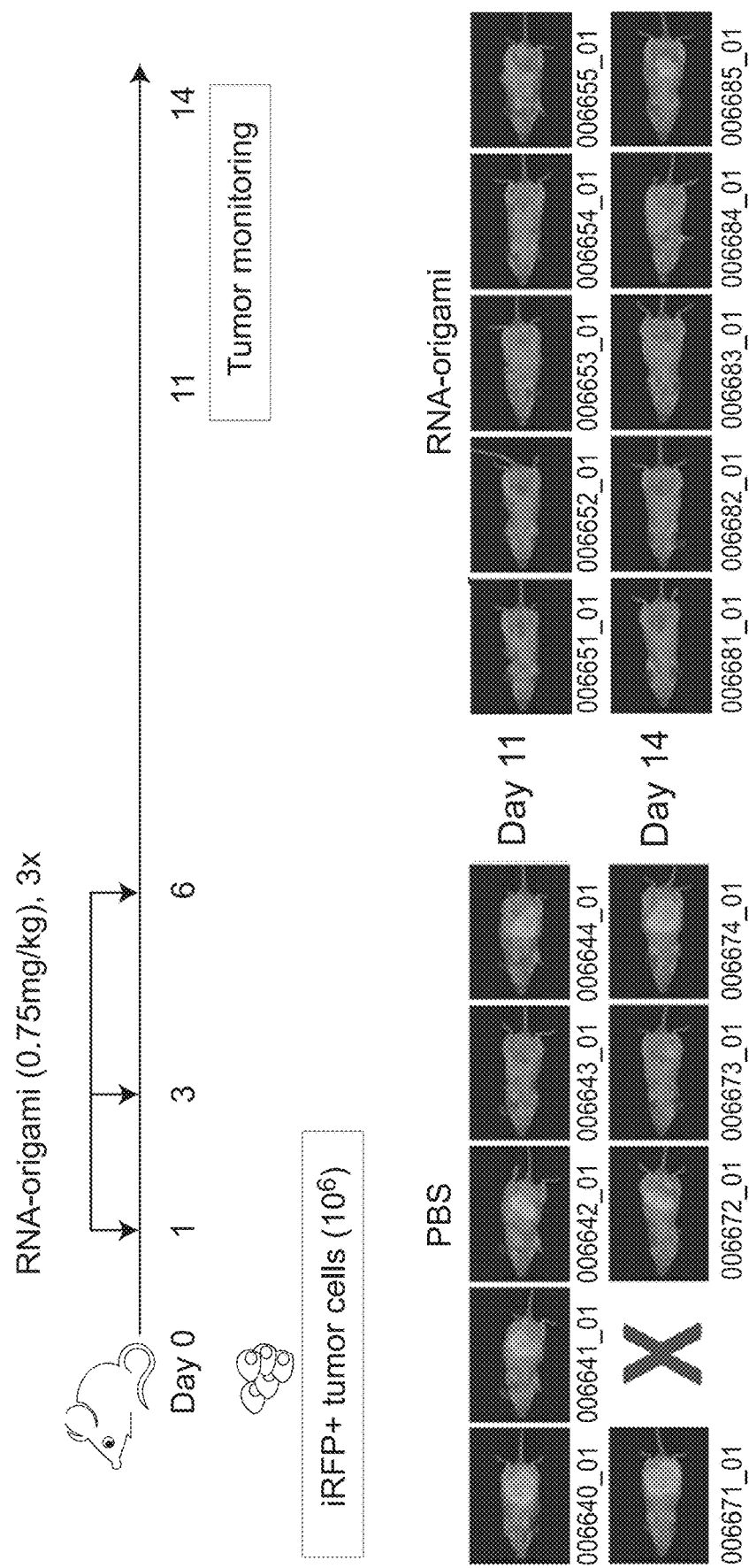
FIG. 18. Inhibition of tumor growth after RNA-origami injection. Mice treated with RNA-origami show significant reduction in tumor growth.
Figure 19:
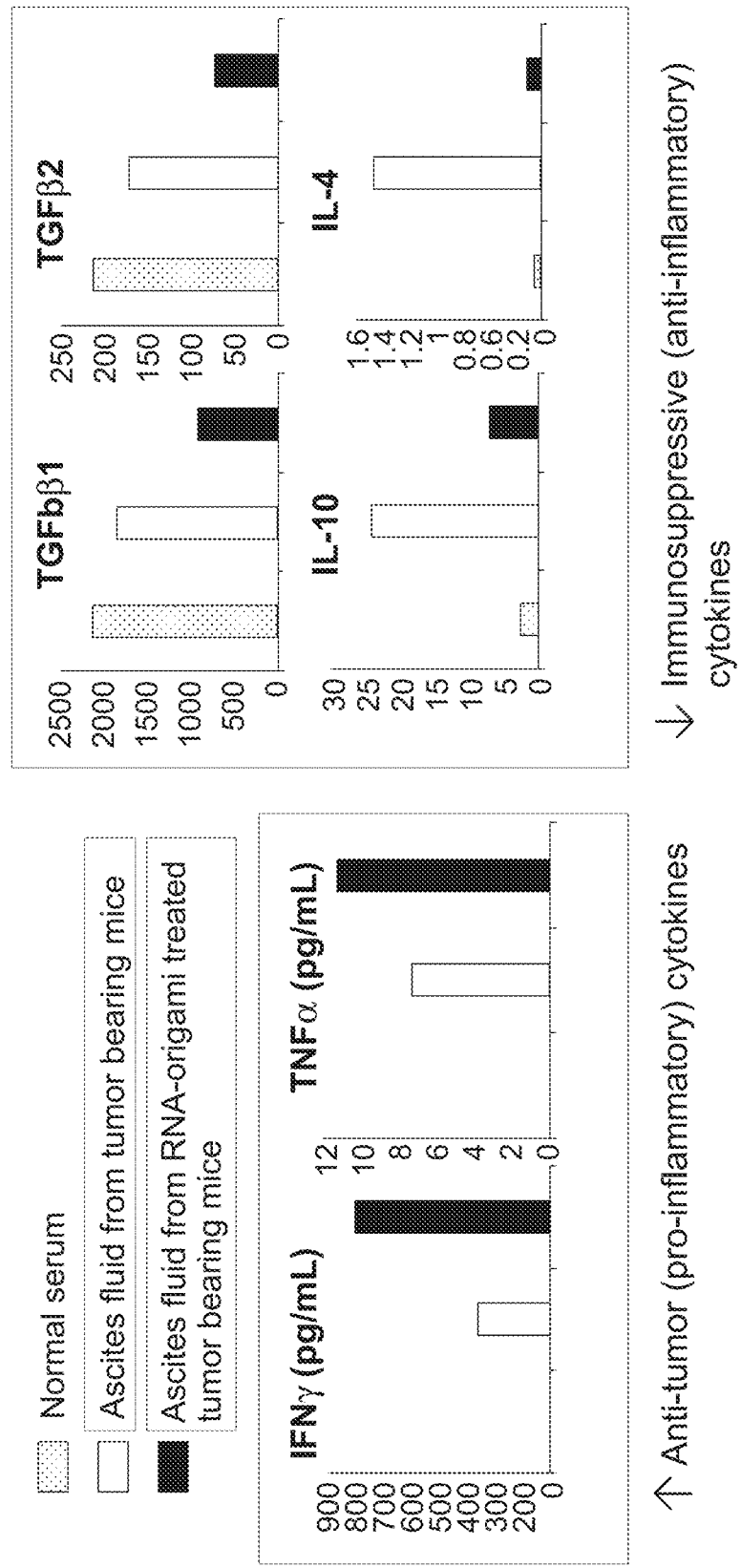
FIG. 19. Role of RNA-origami in re-programming cytokine profiles in tumor-bearing mice. RNA-origami increases pro-inflammatory cytokines and reduces anti-inflammatory cytokines. The high levels of IFNg and TNFa in the bearing-tumor bearing mouse treated with RNA-origami clearly showed strong induction of adaptive anti-tumor immunity.

To determine whether the in vitro stimulation of immune cells can be translated into anti-cancer immune adjuvants, CT26 peritoneal colon carcinoma model was used, which has been explored as a peritoneal metastatic model, to test whether RNA-origami can reduce tumor growth in the peritoneal cavity. To monitor tumor growth in real time, a gene iRFP was introduced into CT26 cells, which codes for a near infrared fluorescence protein, such that the growth of tumor cells is measured by iRFP fluorescence intensity. A higher fluorescence intensity is indicative of a larger tumor mass. Specifically, on day 0, mice received one million CT26-iRFP cells via i.p. injection. The mice were treated with RNA-origami or control PBS on day 1, 3 and 7 at 16 microgram/dose, and tumor cells in peritoneal cavity was monitored by iRFP fluorescence intensity using LI-COR Pearl Small Animal Imaging System. It was found that while the mice injected with PBS developed tumor quickly (with 10-12 days), the mice treated with RNA-origami showed a significant reduction in tumor growth (FIG. 18). Thus, at rather low doses used in the experiment, RNA-origami suppressed tumor growth. When the cytokines produced from ascites fluid that were accumulated within tumor cells present in the peritoneal cavity were analyzed, it was found that the ascites contained very high levels of immunosuppressive cytokines, including TGFb1, TGFb2, IL-10 and IL-4 (FIG. 19). In contrast, for the tumor-bearing mice treated with RNA-origami, they had much lower levels of immunosuppressive cytokines, but elevated levels of anti-tumor proinflammatory cytokines, which correlates with the small tumor load in the treated mice.

Figure 20:
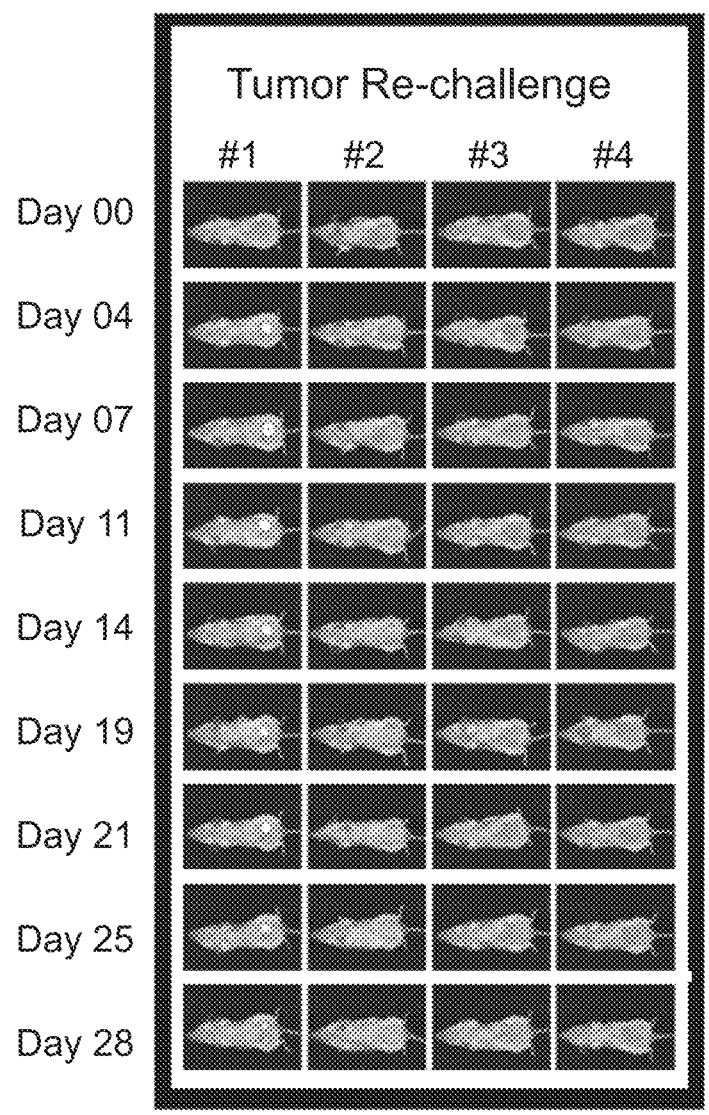
FIG. 20. Re-challenge cancer murine model. Four BALB/c mice that had been injected with CT26 and treated with 16 µg of RNA origami six times starting on day 1 over the course of a month and had regression or no tumor growth were re-injected with 500,000 CT26-iRFP cells (mice #1 and #2 received re-challenge 49 days after final treatment and mice #3 and #4 received re-challenge 36 days after final treatment).

CT26 immunity assessment in murine models. The presence of anti-tumor immunity was tested by re-challenging RNA treated mice that had shown regression. Four mice were used, two mice were tested 49 days after the last RNA origami treatment, and two mice were tested 36 days after last RNA origami treatment. These mice were injected a second time with 500,000 CT26-iRFP cells subcutaneously on the abdomen of the mice. No treatments were given here, and the results are shown in FIG. 20. Out of the four mice, only one grew a tumor, and even this mouse's tumor regressed, illustrating the possibility of a recall response from the T-cells.

Example 4

Self-Assembling RNA-Origami Programmable for Potent and Safe Anti-Cancer Immunotherapy Nucleic acid (NA) nanotechnology has developed tremendously over the past 30 years and numerous DNA and RNA nanostructures have been rationally designed and characterized. Previous studies have demonstrated a few in vivo biological applications of NA nanostructures, mainly serving as drug delivery vehicles and scaffolds for functional molecules such as vaccine design. We previously developed a replicable single-stranded RNA (ssRNA) origami technology which allows a long RNA molecule to be programmed to self-assemble into RNA-origami (RNA-OG) nanostructures that are uniformly dispersed and highly resistant to RNAse and nucleases in the serum or plasma. Inspired by its RNA nature and uniform geometry in nano-meter scale, here we explored its potential serving as an adjuvant to activate immune responses. We demonstrated that the highly-stable RNA-OG stimulates a potent immune response primarily through a Toll-like-receptor 3 (TLR3) pathway. In a murine peritoneal metastasis colon cancer model, the intraperitoneal injected RNA-OG significantly induced tumor retardation or regression. Despite its higher resistance to serum nucleases than polyIC, a well-known double-stranded RNA analog, the RNA-OG treatment did not trigger systemic production of type-I interferons, implicating lower toxicity, and therefore, safer for its in vivo application. Furthermore, the analysis of peritoneal cavity cells retrieved from tumor-bearing mice treated with or without RNA-OG showed that RNA-OG treatment resulted a significant reduction of myeloid derived suppression cells (MDSCs) in the peritoneal tumor environment, which is consistent with the cytokine profile in the mice showing tumor regression. Thus, RNA-OG is able to reprogram the tumor peritoneal environment to reverse immunosuppression. Given its superiority in scalable production, programmability of self-assembly into well-defined nanostructures, and high structural stability, RNA-OG may constitute a new line of adjuvants that are safe and effective for cancer immunotherapy.

Introduction:

Nucleic acid (NA) molecules have been shown to be excellent materials to build nanostructures with precise shapes and geometries[1,2]. In the past decades, novel methods and strategies have been developed for fabricating synthetic architectures based on DNA/RNA self-assembly, such as DNA origami[3], ssDNA tile (SST) nanostructures[4], and single-stranded DNA/RNA origami[5]. To date, numerous 2D and 3D DNA/RNA nanostructures with various geometries were successfully constructed and characterized[5-11]. One major challenge of nanotechnology is to control and organize matter with nanometer precision[12]. With full addressability, the DNA/RNA nanostructures were constructed to host guest molecules (such as DNA, RNA or proteins) successfully and precisely[2]. This leads to a major biological application of DNA/RNA nanostructures as drug delivery vehicles. It was reported that DNA/RNA nanostructures can be efficiently loaded with siRNAs[13], proteins[14], and drugs[15] to be delivered into specific cells or locations to treat cancers. We previously explored another biological application of DNA nanostructure as a synthetic vaccine, which precisely organizes antigens and adjuvants[16].

Besides the above mentioned biological applications of DNA/RNA nanostructures, previous research focuses to employ them in display of certain functional NA molecules, in order to stimulate an immune response. Nucleic acids are well-known to be recognized by several pattern recognition receptors (PRRs) to induce immune activation through innate immunity[17]. When internalized into endosomes, the nucleic acids are recognized by Toll-like-receptors (TLR), including TLR3[18] (for endosomal dsRNA), TLR7/8[19,20] (for endosomal ssRNA), and TLR9[21] (for endosomal CpG DNA). Cytoplasmic receptors, such as retinoic acid-inducible gene I (RIG-I) and Melanoma Differentiation-Associated protein 5 (MDA5), also sense dsRNA and trigger strong immune responses[22]. The CpG DNA is a well characterized and popular immune adjuvant[23]. We previously incorporated it into DNA nanostructures to construct synthetic vaccines[16]. However, one of the disadvantages of CpG DNA is that it does not induce a substantial immune response in Homo sapiens, due to the limited cellular distribution of TLR9 in humans[24]. Polyinosinic-polycytidylic acid (PolyIC), a synthetic dsRNA analog, has been studied and employed as an immune adjuvant for decades[25]. As a ligand for multiple PRRs, it not only activates TLR3 in the endosome, but also stimulates RIG-I and MDA5 in the cytoplasm through the mitochondrial antiviral-signaling protein (MAVS) pathway[26,27]. However, systemic cytokine release upon polyIC administration, which has been attributed to the RIG-I/MDA5 signaling pathway, causes substantial cytotoxicity and adversity, thereby significantly limiting its systemic application clinically[28-29]. A recently developed dsRNA adjuvant, ARNAX, which is a synthetic DNA-dsRNA hybrid molecule consisting of 140 bp dsRNA and a 5' GpC DNA oligo, was reported to only induce TLR3 activation, thus providing a safer immune-stimulatory effect[30]. The ARNAX is still in the early stages of development and construction/identification of stable, potent, and safe RNA adjuvant is still attractive. Our recently developed single-stranded RNA origami (RNA-OG) is a synthetic nanostructure containing compact dsRNA regions[5]. Inspired by the above synthetic RNA adjuvant, we explored the adjuvant potential of our single stranded RNA origami, and its application in cancer immunotherapy.

Self-assembled from a long single-stranded RNA molecule with high yield, the RNA-OG is capable of being conveniently produced in a large quantity with high accuracy, which overcomes the disadvantages of traditional DNA origami nanostructures. The stability tests demonstrated that it exhibits strong RNase I resistance and excellent stability in serum, and holds a long shelf-life. In the in vitro cell stimulation experiments, we discovered that the RNA-OG induces potent immune-stimulatory effects primarily through TLR3 pathway, which behaves similarly to ARNAX[31]. In line with this finding, the cytokine profile analysis indicated that the in vivo administration of RNA-OG does not induce substantial systemic type-I interferon release, suggesting it is a safer immune adjuvant than polyIC. When administered intraperitoneally (IP) into mice with a metastasized colorectal cancer model, the RNA-OG dramatically reduces tumor growth or causes tumor regression. Further analysis also reveals that the RNA-OG treatment changed the peritoneal environment by increasing the production of proinflammatory cytokines (IFNγ and TNFα), but reducing the level of immunosuppressive cytokines (TGFβ, IL10, and IL4) and the number of myeloid derived suppressor cells (MDSCs). Thus, IP administration of RNA-OG could reprogram the tumor microenvironment to reverse tumor-mediated immunosuppression and enhance anti-tumor immunity. Together with its robustness in scalable production, superior structural stability, and good safety profile, the RNA-OG represents a new and promising immune adjuvant for cancer immunotherapy.

Results:

Scalable Production and Excellent Stability of RNA-OG

Figure 21A:
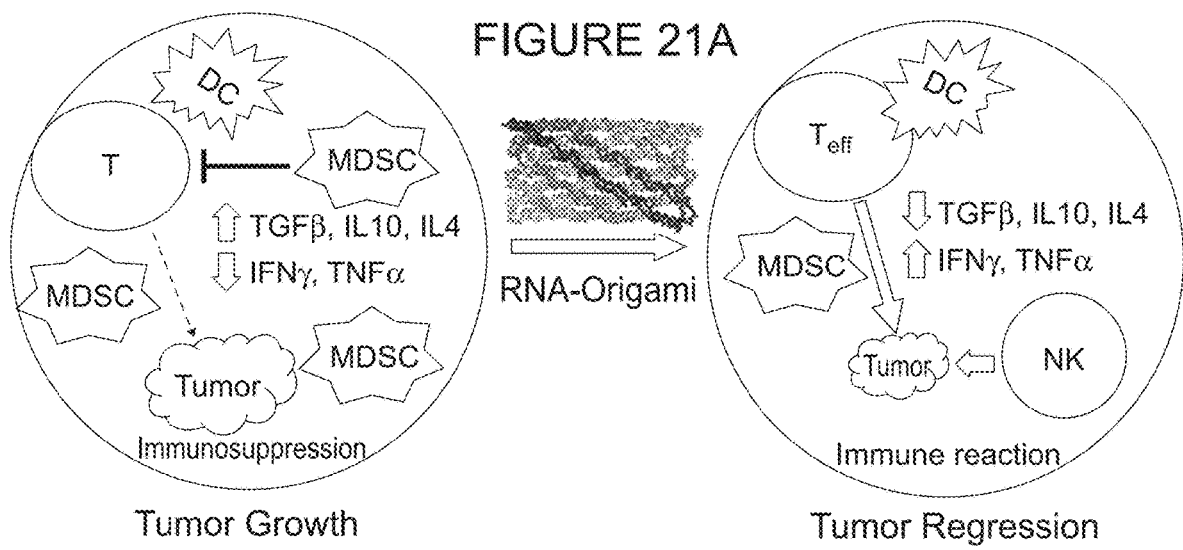
FIGS. 21A-21E. A. RNA-Origamis: TLR3-based adjuvants to induce anti-tumor immunity without a systemic cytokine storm. B-E. Large scale synthesis and characterization of ssRNA origami. B: The left panel shows a schematic of the large-scale synthesis of ssRNA by in vitro transcription and self-assembly into ssRNA origami. The right panel indicates the AFM characterization of the self-assembled ssRNA origami. The inset shows a magnified view of the outlined structure. C RNA OG remain intact after storage at 4° C. for 4 months. The freshly prepared RNA-OG (lane 1) and the 4-month old RNA-OG (lane 2) have similar mobility in the agarose gel (left panel). The AFM image also indicate the integrity of RNA-OG remained (right panel). The inset shows a magnified view of the outlined structure. All scale bars, 50 nm. D: Agarose gel electrophoresis analysis of RNA-OG and PolyIC-H stability in 10% serum. 1 µg of RNA-OG (lane 1) was incubated with 10% mouse serum at 37° C. for 1 hr (lane 2), 2 hr (lane 3) and 16 hr (lane 4). 1 µg of polyIC-H (lane 5), was incubated with 10% serum at 37° C. for 0.5 hr (lane 6), 1 hr (lane 7), 2 hr (lane 8) and 16 hr (lane 9) respectively. M denotes 1 kb marker. E. dsRNA integrity after incubation with 10% human plasma, including RNA-OG (lanes 1-6), polyIC-H (lanes 7-12) and polyAU (lanes 13-18), for 0 hr (lanes 1, 7 and 13); 0.5 hr (lanes 2, 8 and 14); 1 hr (3, 9, and 15); 2 hrs (lanes 4, 10, 16); 4 hrs (lanes 5, 11, and 17); and 18 hrs (6, 12, and 18).
Figure 21B:
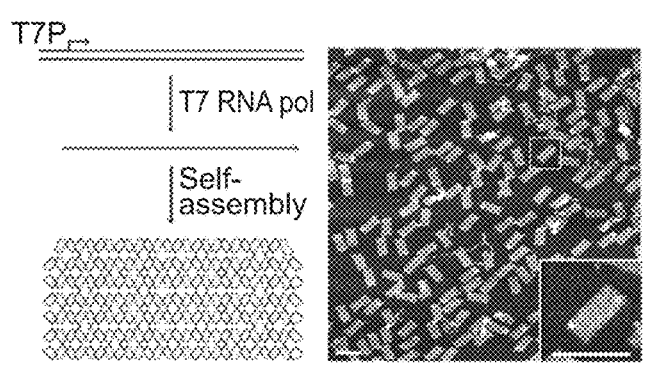
Figure 21C:
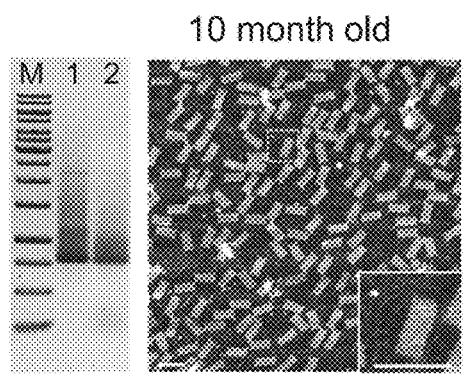
Figure 21D:
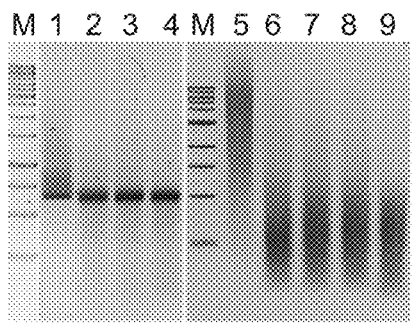
Figure 21E:
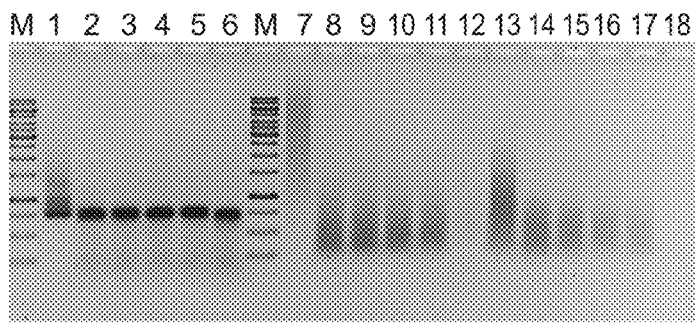
Figure 28:
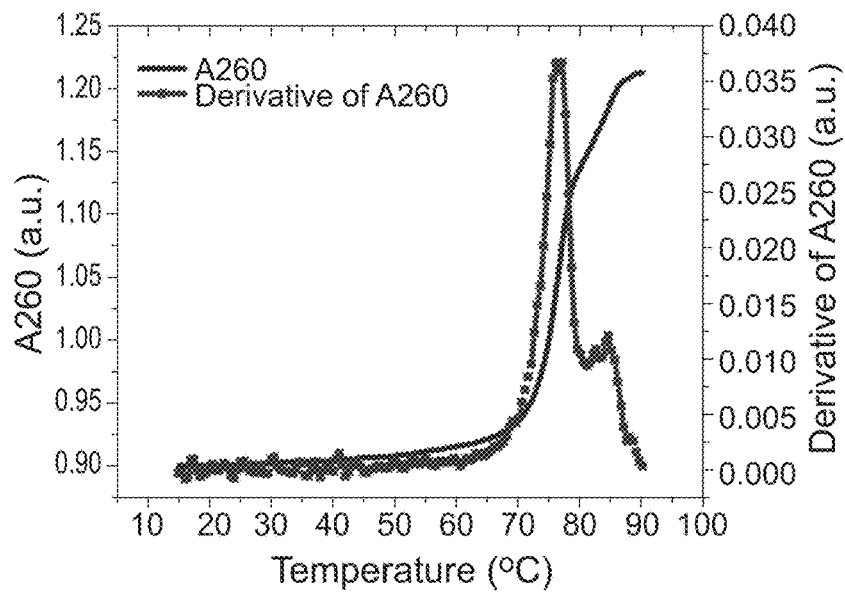
FIG. 28. UV melting curve of the RNA-OG. The UV absorbance of RNA at 260 nm (A260) was plotted as a function of temperature. Two melting transitions were observed by taking the first derivative of A260 vs. temperature. The tall and sharp transition (~76° C.) corresponds to the melting of paranemic cohesion; and the short transition (~84° C.) corresponds to the melting of the remaining hybridized regions.
Figure 29A:
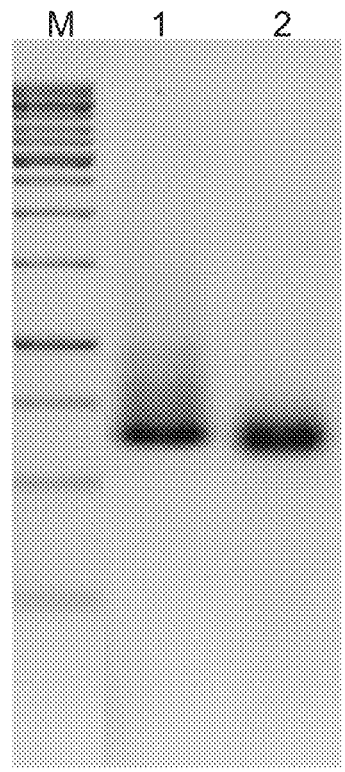
FIGS. 29A-29B. Stability evaluation of RNA-OG. A. RNase I digestion of RNA-OG. 1 μg of RNA-OG (lane 1) was incubated with 1 U of RNase I at room temperature for 20 minutes (lane 2). Unit definition: One unit of the RNase I enzyme catalyzes degradation of 100 ng of *E. coli* rRNA per second into acid-soluble nucleotides at 37° C. B. RNA-OG stability in 50% mouse serum. 1 μg of RNA-OG (lane 1) was incubated with 50% mouse serum at 37° C. for 1 hour (lane 2), 2 hours (lane 3), 4 hours (lane 4) and 20 hours (lane 5). M denotes 1 kb DNA marker.
Figure 29B:
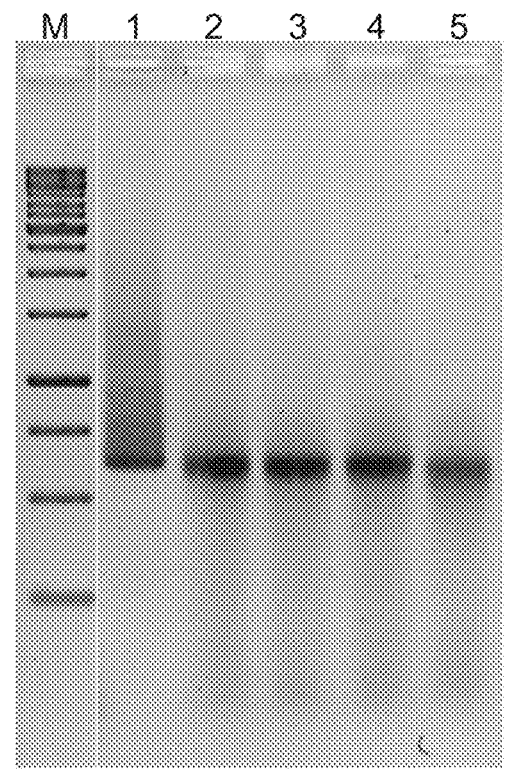

Unlike conventional DNA origami nanostructures which require the assistance of hundreds of short oligonucleotides[3], the ssRNA origami was designed to self-assemble a long ssRNA molecule in a programmable manner. To achieve sequence accuracy and consistency, the DNA template was cloned and replicated in a plasmid DNA. The RNA molecule can be conveniently produced in a large quantity through in vitro transcription reactions (FIG. 21B), with a typical yield over 5 mg per ml transcription mixture. Thus the RNA-OG can easily achieve scalable production with little effort or cost. The uniform RNA-OG was self-assembled via a simple annealing process in 1×PBS buffer without any addition of divalent cations, indicating it is highly thermostable. To prove its thermostability, UV melting assay was employed to measure its melting temperature. Two transition temperatures were observed at ~76° C. and ~84° C., corresponding to the melting of the paranemic cohesion and the remaining hybridized dsRNA regions respectively (Supplementary FIG. 28), similar to our previous findings[5]. With a 76° C. as its first melting temperature without divalent cations in the buffer, the RNA-OG definitely exhibits superior thermostability than DNA origami nanostructures[32]. To demonstrate its overall stability, the assembled RNA-OG was stored at 4° C. for four months, and its integrity remained as shown in the gel electrophoresis as well as AFM images (FIG. 21C). Most DNA origami nanostructures are susceptible to DNase digestion and therefore behave very unstable in the serum[33]. In contrast, the RNA-OG is resistant to RNase I digestion (FIG. 29A) and remains intact in the mouse serum for an overnight incubation (FIG. 21E lanes 1-4 & FIG. 29B). We speculate that such high stability might be attributed to its intrinsic properties: very compact structure without internal nick positions. The polyIC-high molecular weight (PolyIC-H), a well-studied dsRNA immune adjuvant, however, is reduced into lower molecular weight upon 30 min incubation in the mouse serum (FIG. 21D, lane 6). A comprehensive stability comparison was also performed in the human plasma with RNA-OG, polyIC, and polyAU. While RNA-OG remained intact with only a slight down-shift after overnight incubation (FIG. 21E, compare lanes 1-5 to lane 6), both polyIC and polyAU were susceptible to degradation over time and eventually vanished (FIG. 21E, lanes 12&18). In summary, the RNA-OG exhibits extremely high thermostability and excellent enzymatic stability.

In Vitro Stimulation of RNA-OG

Figure 22A:
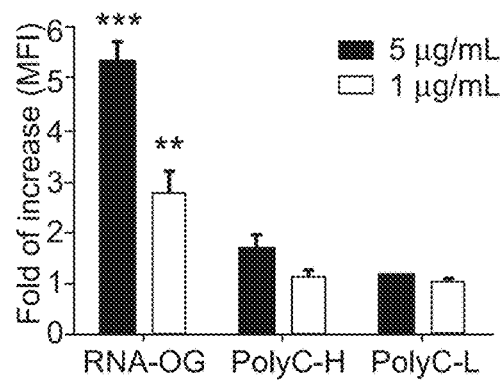
FIGS. 22A-22D. In vitro cell stimulation of RNA-OG. A: RAW 264.7 stimulation with RNA-OG, polyIC-H or polyIC-L at different dosages for 20 hours. CD40-PE mean fluorescence intensity (MFI) was normalized with PBS control group; B: mice splenocyte stimulation with RNA-OG or PolyIC-H. CD86-PE MFI was normalized with PBS group. C: In vitro stimulation of TLR3 reporter cell line, HEK-Blue TLR3, with RNA-OG, PolyIC-H, and PolyIC-L at different dosages for 20 hours; D: In vitro stimulation of A549-Dual and A549-Dual KO-MAVS reporter lines with 3.5 µg/ml of RNA-OG, PolyAU, or polyIC-H.
Figure 22B:
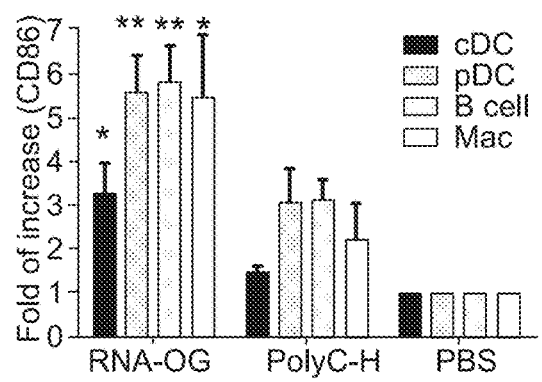
Figure 30:
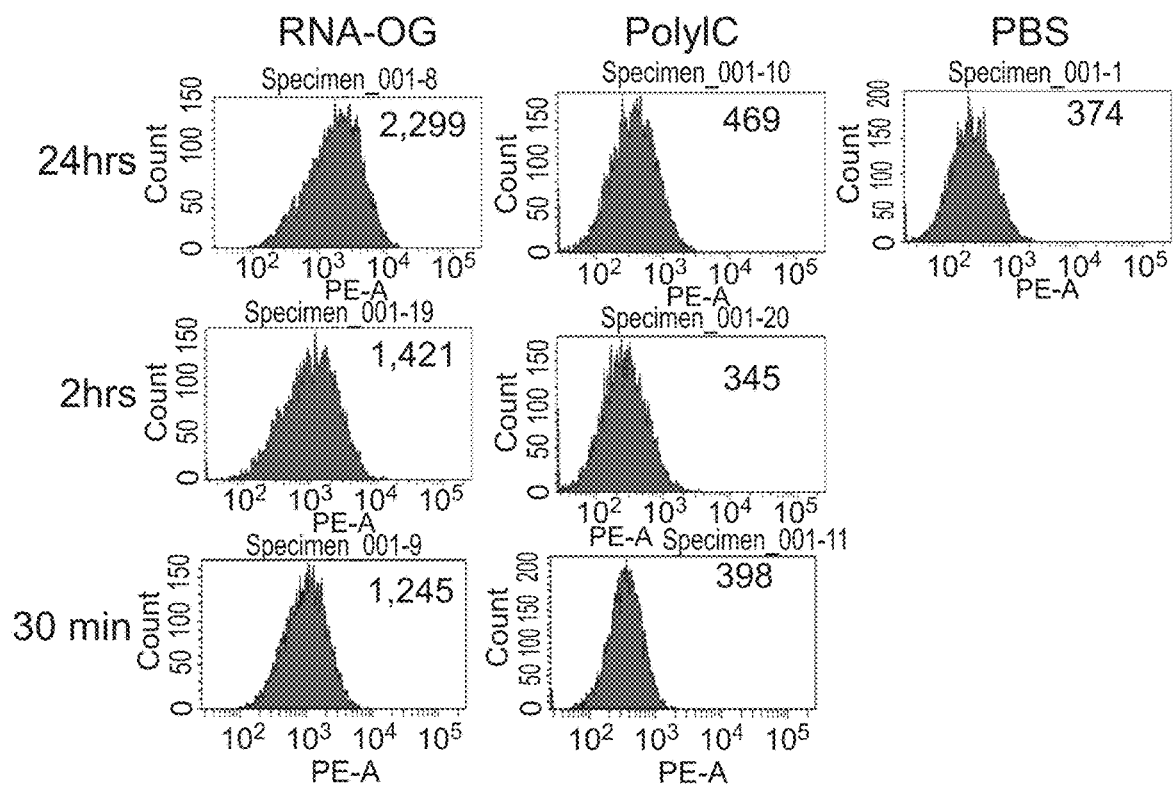
FIG. 30. Rapid stimulation of RAW 264.7 cells with RNA-OG. Murine macrophage cell line, RAW 264.7 cells, were incubated with 5 μg of RNA-OG or PolyIC at 37° C. for various time points. The cells were then stained with PE labeled anti-CD40 antibody and analyzed by FACS. The MFI numbers were shown.
Figure 31:
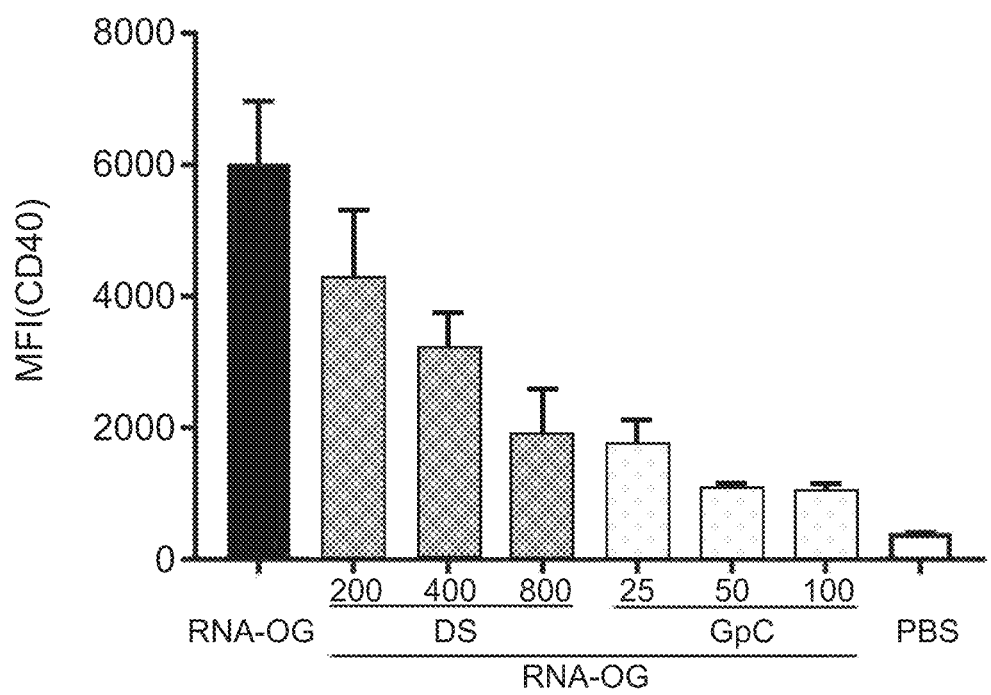
FIG. 31. Inhibition of RNA-OG mediated macrophage activation (CD40) by Dextran sulfate (DS) and GpC. RAW 264.7 cells were pre-incubated with DS or GpC at various concentrations for 30 minutes at 37° C. The numbers listed on top of DS or GpC are inhibitor concentrations utilized (μg/ml). The RNA-OG (5 μg/ml) was added as a stimulator for additional 60 minutes. The cells were stained with PE-labeled anti-CD40 antibody and analyzed by FACS. The CD40 MFI numbers were shown.
Figure 33:
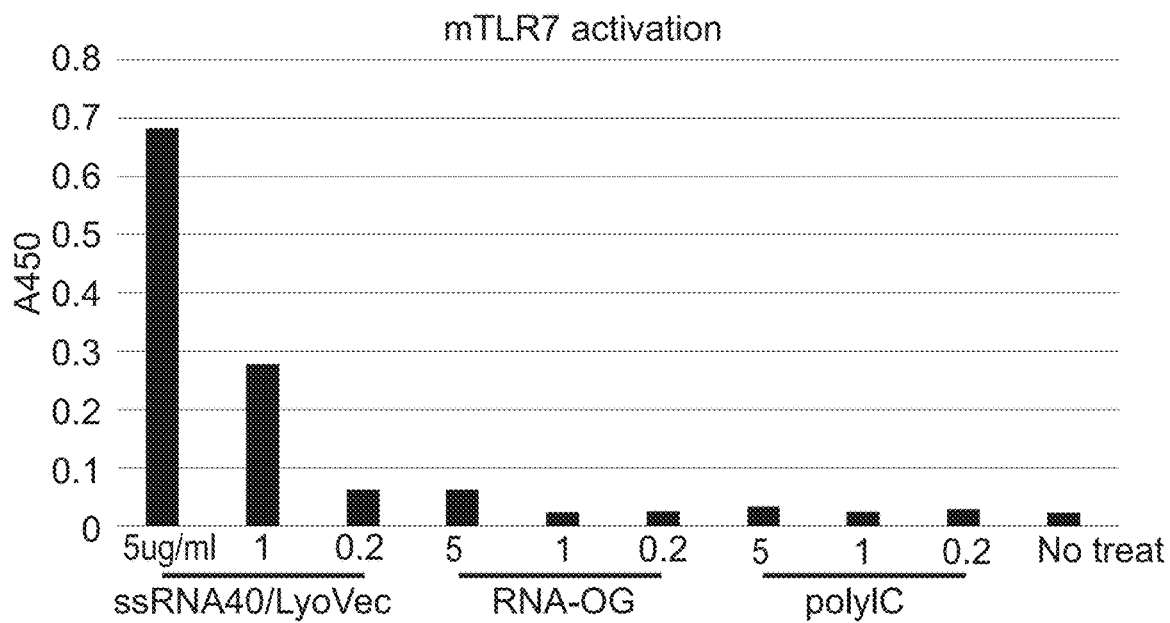
FIG. 33. RNA-OG is not recognized by mTLR7. In vitro stimulation of TLR7 reporter cell line, HEK-Dual mTLR7, with RNA-0G, PolyIC, and ssRNA40 at different dosages for 20 hours.

The well-assembled RNA-OG consists of dsRNA regions as the major structure and a few small single-stranded RNA loops hanging on both sides. Both of these RNA components have the potential to stimulate innate immunity through different receptors. The immuno-stimulating effect of RNA-OG was first examined in a mouse macrophage cell line, RAW 264.7, measuring the upregulation of CD40, a co-stimulatory molecule expressed on the surface of immune cells upon activation[16]. RNA-OG induced more potent activation of the cells than the groups treated with polyIC-H and polyIC low molecular weight (polyIC-L) (FIG. 22A). The stimulation could be detected as early as 30 min post the RNA-OG addition, indicating a rapid interaction of RNA-OG, but not polyIC, with the cells (FIG. 30). The scavenger receptor A has been reported to facilitate cellular uptake of extracellular nucleic acids, including dsRNA and unmethylated CpG oligonucleotides (ODNs). Interestingly, phosphorothioate CpG (B/C type TLR9 agonist) or GpC (TLR9 non-agonist) was found to inhibit polyIC-mediated activation of TLR3, presumably by blocking cellular binding and uptake of polyIC[34-35]. Here, we found that a non-stimulatory phosphorothioate TLR9 ligand, GpC, significantly inhibited RNA-OG-mediated stimulation although it only caused a moderate, but a significant reduction in the cellular interaction and internalization of RNA-OG (FIGS. 31 and 32A-G). Furthermore, we tested the stimulatory activity of RNA-OG on naïve splenocytes. Different cell populations of splenocytes were gated based on the strategy described in Methods, and levels of the co-stimulatory signal molecule, CD86, measured by mean flurescence intensity (MFI), was compared among different types of antigen presenting cells (APCs), B cells, macrophage conventional dendritic cells (cDCs) and plasmacytoid dendritic cells (pDCs). Increased levels of CD86 in these cell types (FIG. 22B) suggests that RNA-OG is effective in activating APCs, which will help initiate the adaptive immunity.

Figure 22C:
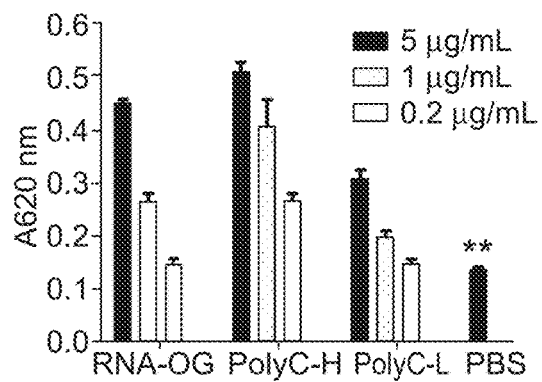
Figure 22D:
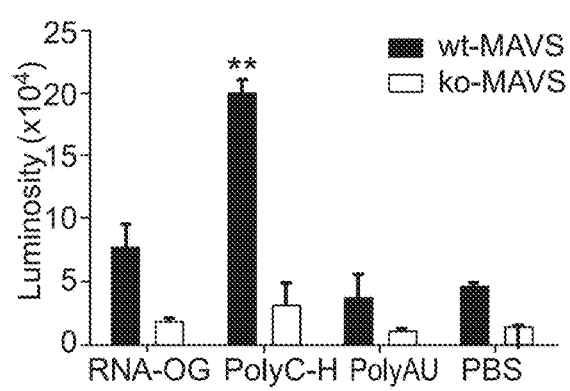

Based on the strong stimulation of immune cells by RNA-OG, we explored the underlying mechanism. As RNA-OG contains dsRNA regions and ssRNA loops, it may work possibly through PRRs that recognize dsRNA or ssRNA. Murine TLR3 and TLR7 reporter cell lines, HEK-Blue™ mTLR3 and HEK-Blue™ mTLR7, respectively, were employed for the evaluation. Similar to polyIC-H and polyIC-L, an incubation with RNA-OG leads to an increased level of reporter signal in HEK-Blue™ mTLR3, but not HEK-Blue™ mTLR7 cells (FIG. 22C), indicating that RNA-OG stimulate cells through TLR3, but not likely TLR7. Another common type of PRR recognizing dsRNA signals includes cytoplasmic RNA sensors RIG-I and MDA5. Here, we used an A549-Dual™ reporter line (with wild type MAVS) and its variant, an A549-Dual™ KO-MAVS cell line, in which MAVS, the signal adaptor in RIG-I/MDA5 pathway, was knocked out, to test whether RNA-OG functions through the MAVS pathway that is downstream of the RIG-1 and MDA-5 sensors. As expected, polyIC, that is known to trigger the RIG-I/MDA5 pathway, induced a strong activation in wild type MAVS A549 reporter line, but not so in KO-MAVS mutant cell line (FIG. 22D). On the other hand, the transfection of RNA-OG only resulted a slight increase in the reporting signal over the control group (FIG. 22D), suggesting that RNA-OG is not a potent agonist of RIG-I/MDA5 dsRNA sensors, which may warrant its less likelihood to inflict systemic cytokine reaction.

Ex Vivo and In Vivo Cytokine Profiles with RNA-OG

Figure 23A:
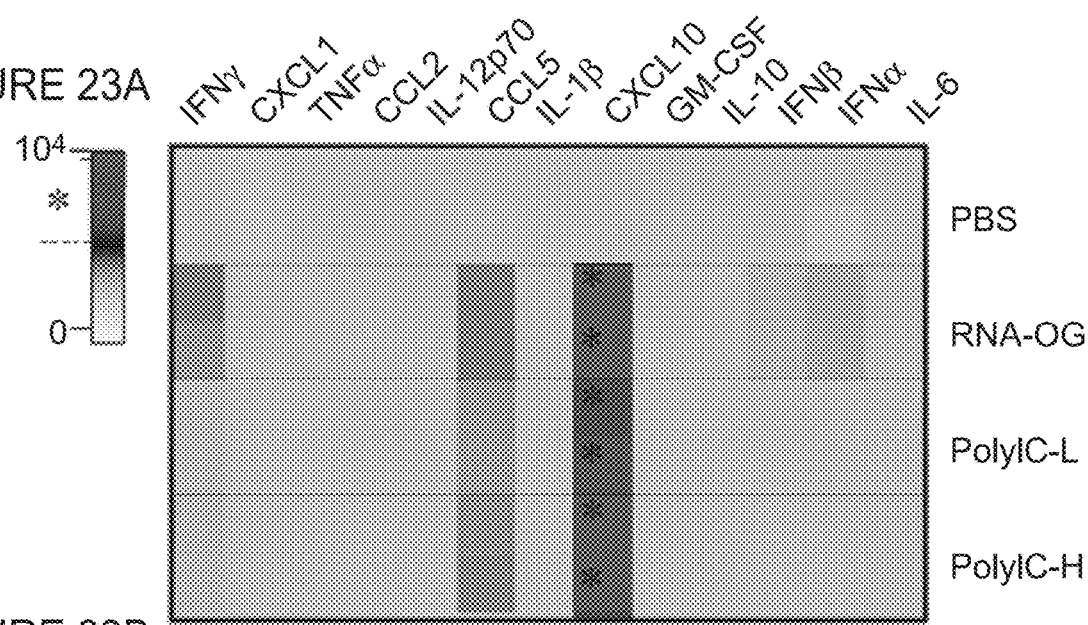
FIGS. 23A-23B. Cytokine profile analysis with RNA-OG and PolyIC treatment. A: Cytokines analysis by splenocytes upon in vitro stimulation with RNA-OG, PolyIC-L and PolyIC-H. B: Cytokine profile of serum taken 3 hrs post intraperitoneal injection from mice treated with RNA-OG, PolyIC-H, or PBS.
Figure 23B:
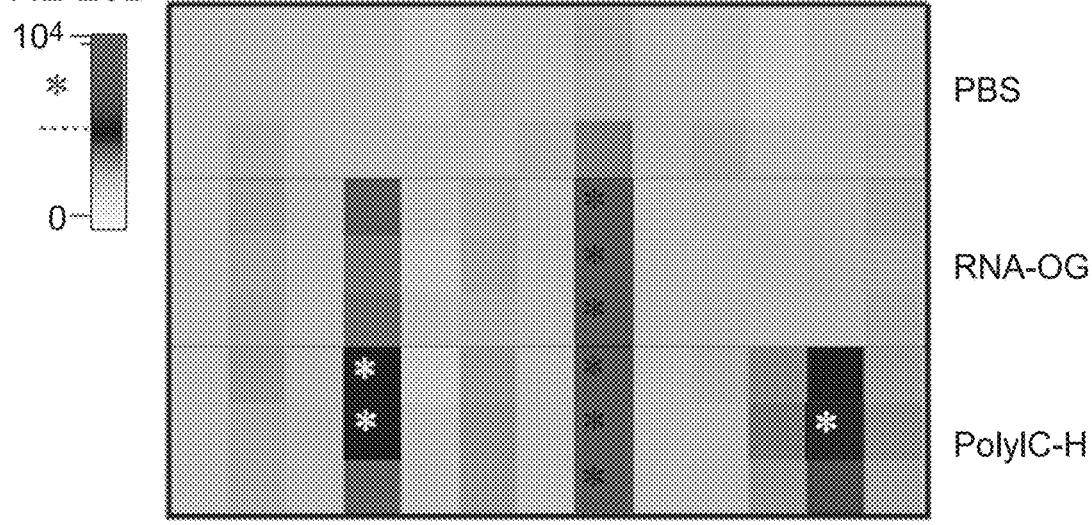

As RNA-OG showed potent stimulation of co-stimulatory molecules in vitro and ex vivo, we next examined the cytokine profile of immune cells after RNA-OG stimulation. Cell cultured supernatant after ex vivo stimulation was collected for cytokine analysis. Consistent with the stimulation profile of splenocytes observed in FIG. 22B, RNA-OG induced higher, although modest, production of type-I IFN than PIC-H and PIC-L (FIG. 23A) from activated immune cells. Interestingly, CXCL10, a chemokine involved in recruiting T cells into tumor environment[36], has been associated with good prognosis in colorectal cancer patients[37]. This chemokine was found elevated by RNA-OG and polyIC to the similar levels both the ex vivo and in vivo stimulation (FIGS. 23A and 23B). Thus, serum CXCL10, in responding to stimulation of RNA-OG and polyIC-H, are likely produced from the immune cells that were found responsive to these stimulators in vitro. In contrast, the slight increase in IFN-α/β seen in the splenocyte culture with RNA-OG (FIG. 23A) was not recapitulated in the serum cytokine analysis (FIG. 23B). Instead, significant elevation of IFN-α/β was observed only in the serum from the mice treated with polyIC-H, but not RNA-OG (FIG. 23B). It has been reported that the polyIC-mediated stimulatory activity varies greatly, depending on the length of polyIC polymer chain and the type of target cells[38, 39]. Nevertheless, as compared to polyIC-H, IP injection of RNA-OG could induce systemic production of CXCL10, but not IFN-α/β. This in vivo cytokine pattern is very similar to those induced by ARNAX and polyAU[40, Gatti, 2013 #79,41], implicating a safe profile of RNA-OG if used in vivo. Next, we explored the potential of RNA-OG in cancer immunotherapy.

Figure 24A:
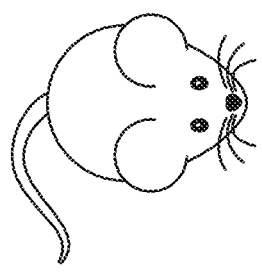
FIGS. 24A-24B. Anti-tumor adjuvant activity of RNA-OG and PolyIC. A. A schematic illustration of tumor injection and treatment schedule. Mice received intraperitoneal (IP) injection of $8 \times 10^5$ CT26-iRFP on day 0. Starting on day 1, the mice received biweekly IP injections of RNA-OG, PolyIC, or PBS, for total four times. B. Tumor progression monitored by Li-Cor Imaging of near infrared fluorescence intensity from CT26-iRFP line that expresses near infrared fluorescence protein (iRFP). Fluorescence images of animals were taken on various days (as indicated in the numbers on the left), in which the images of the mice prior to tumor inoculation serve as background (denoted as pre). Blank rectangles indicate euthanized animals that reached to the end stage.
Figure 24B:
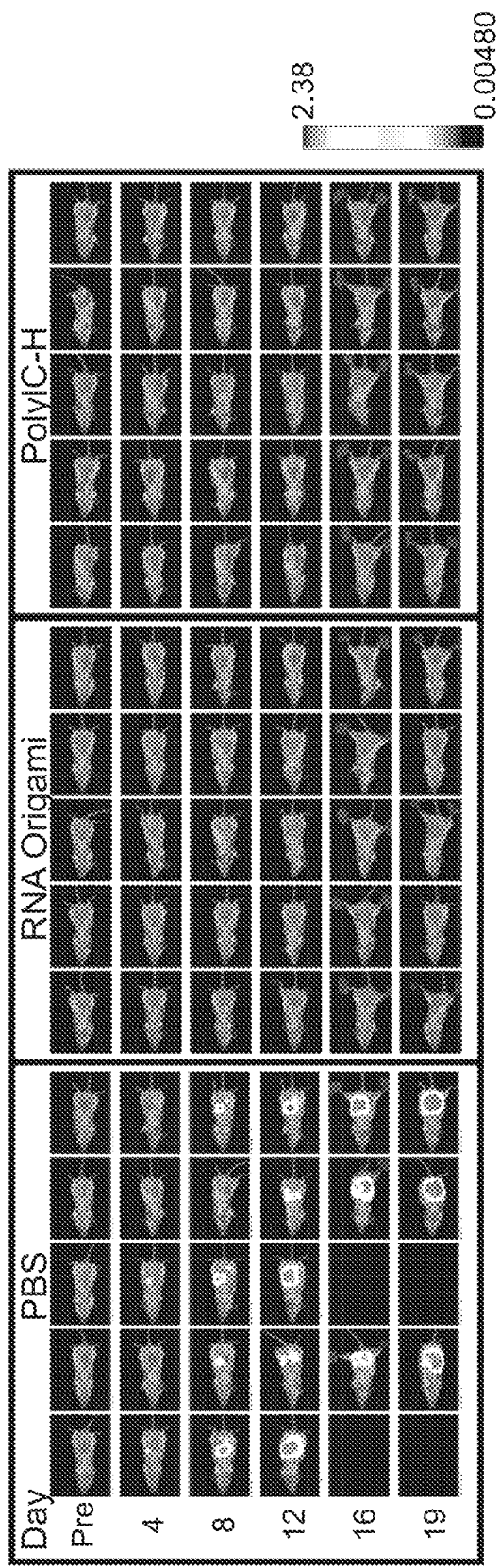
Figure 34A:
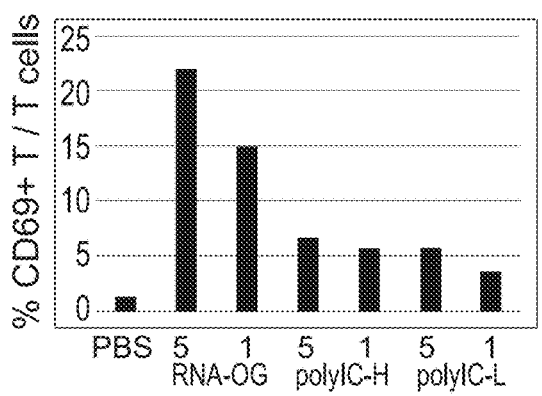
FIGS. 34A-34C. A-B. Increase in CD69+ activated T cells in the splenocyte culture with RNA-OG. The total number of NK cells is increased, in which activated CD69+NK cells are also elevated. C. CT26-iRFP MTT assay with different doses of RNA-OG or PolyIC. Different doses of RNA-OG or PolyIC were utilized to incubate with the CT26-iRFP cells. The cell viability was evaluated through MTT assay.
Figure 34B:
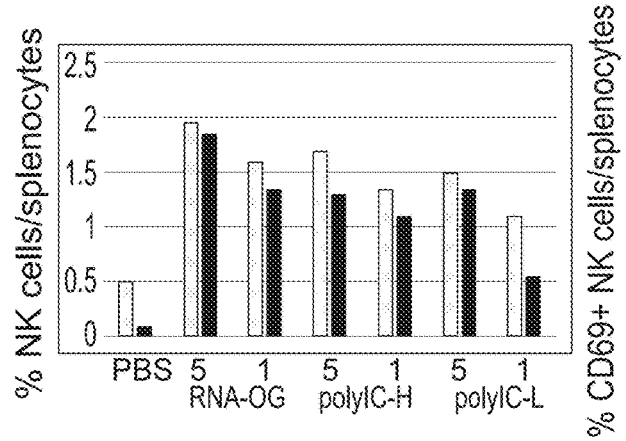

Anti-Tumor Immunity of RNA-OG in a Murine Colorectal Peritoneal Metastatic Model The safety profile of RNA-OG demonstrated in vivo prompted us to test whether RNA-OG via an intraperitoneal administration route can retard tumor progression of peritoneal metastasis (PM) and peritoneal carcinomatosis (PC), since PM/PC is considered advanced stages and fatal diseases with poor prognosis and limited therapeutic options[42]. To test this scenario, we used a synegenic peritoneal metastatic (PM) colon cancer CT26-iRFP model that was engineered to express near infrared fluorescent protein (iRFP), which allows real-time monitoring of tumor growth in whole animals, especially when tumor load is low[43]. Following intraperitoneal administration of CT26-iRFP cells on day 0, the mice received biweekly treatments beginning on day 1 (FIG. 24A). Tumor progression was monitored via the fluorescent intensity of iRFP (FIG. 24B). The PBS-treated control mice began to show visible tumor by day 4 and all had developed tumor by day 12. Control mice reached the endpoint before day 16. In contrast, all RNA-OG and PolyIC treated mice did not develop visible tumor, indicating that the adjuvant activity of both types of nucleic acids was able to induce sufficient activity to halt tumor growth. Thus, despite its inability to induce systemic production of type-I interferon, RNA-OG demonstrates the anti-tumor activity comparable to the one induced PolyIC. To investigate whether the anti-tumor activity observed with RNA-OG was owing to its direct effect on tumor cells, the MTT assay was performed to evaluate RNA-OG mediated cellular toxicity. However, cell viability was not significantly affected by either RNA-OG or polyIC (FIGS. 34A-34B), implying that RNA-OG exerts no direct anti-tumor effect.

Figure 25A:
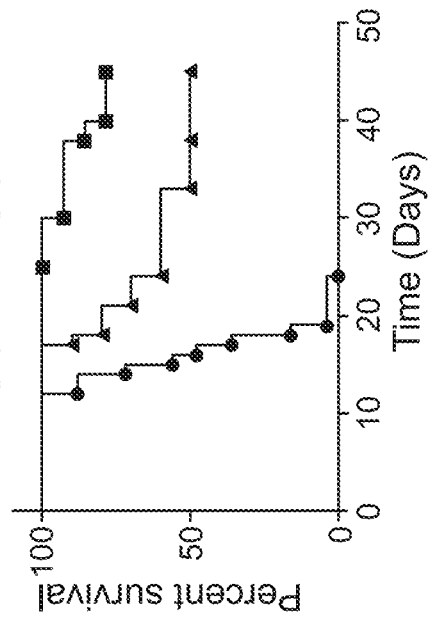
FIGS. 25A-25D. Time-dependent anti-tumor immunity induced by RNA-OG. A. A schematic diagram to show the schedules of tumor inoculation, treatment, and re-challenge of the second dose of tumor cells. B. Tumor progression was monitored by the Li-Cor imaging system in mice receiving treatments illustrated in A. C. Kaplan-Meier survival curve. The graph compiles the survival data of treated mice from several independent experiments, including PBS (●, n=25), RNA-OG injected one day post tumor injection (□, n=15), RNA-OG administered 3-days tumor injection (Δ, n=10). D. Anti-tumor immunity developed in the tumor-bearing mice treated with RNA-OG. The mice survived from the first tumor challenge (shown in B) were immune to the re-challenge of the tumor cells, as they showed no detectable tumor growth (left panel) whereas the naïve control mice developed sizable tumor loads with high fluorescence intensity (right panel). The mouse highlighted with square was sacrificed as a donor for adoptive transfer experiment in FIG. 26.
Figure 25B:
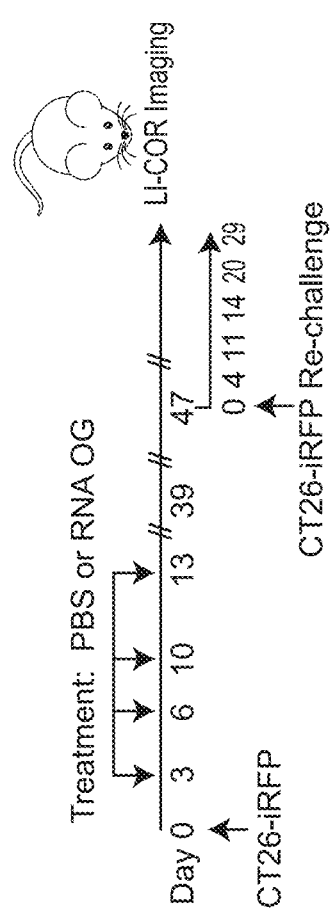
Figure 25C:
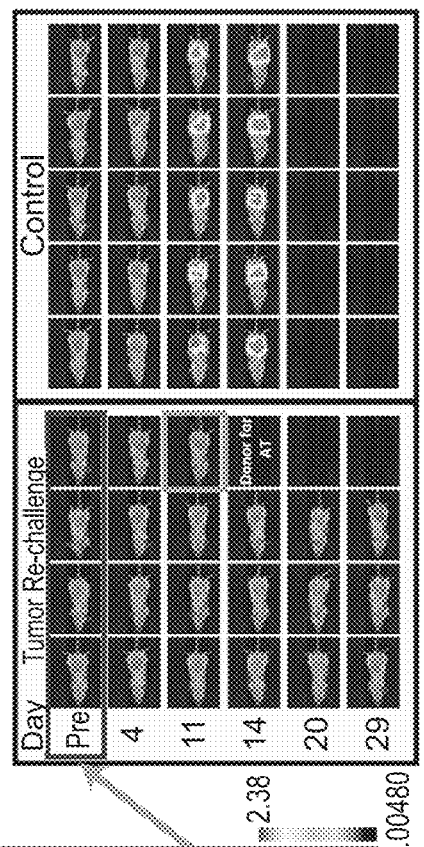
Figure 25D:
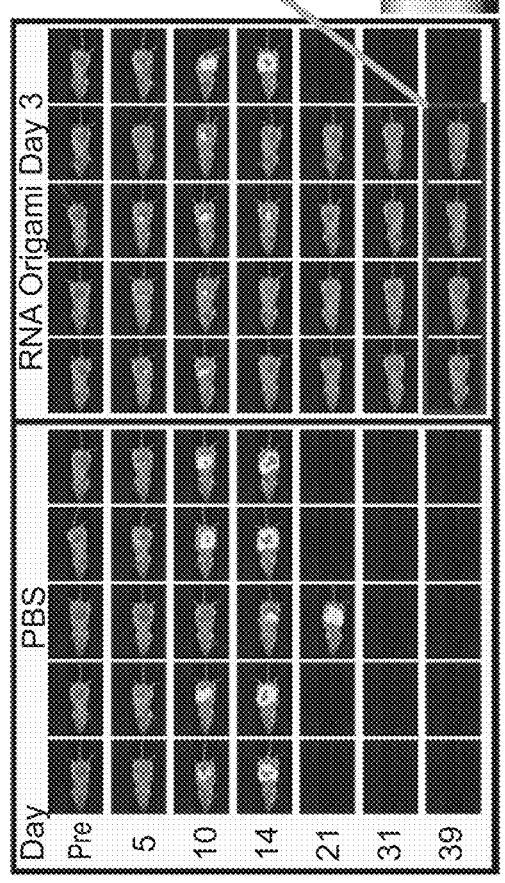
Figure 34C:
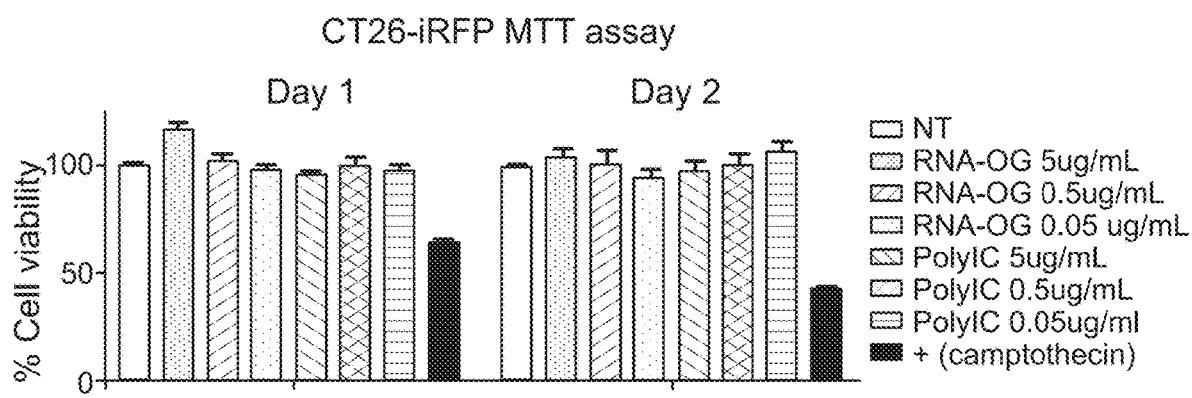
Figure 35A:
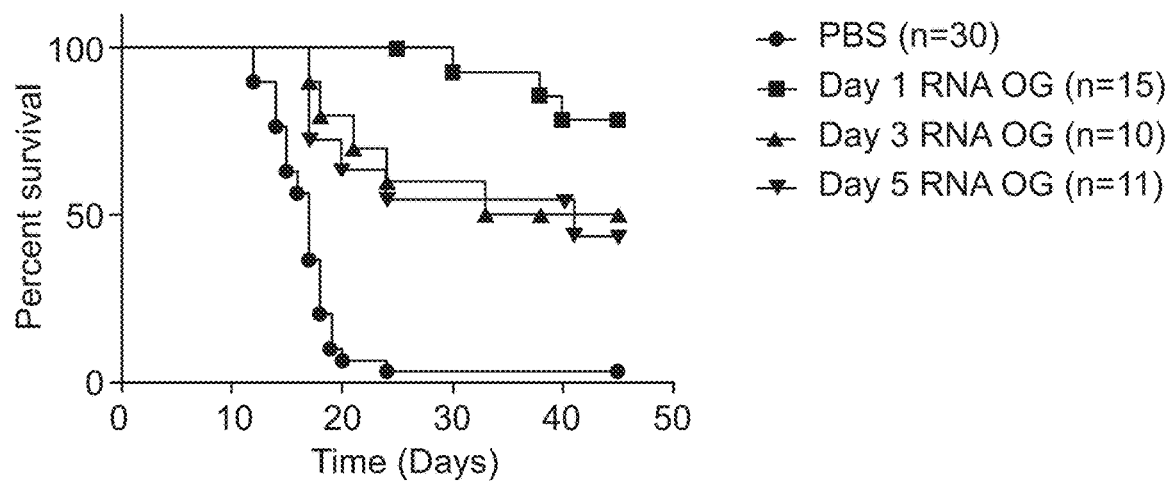

To further test the anti-tumor effect of RNA-OG, we delayed the treatment in tumor-bearing mice, i.e., RNA-OG was initiated 3 days post tumor inoculation and continued biweekly (FIG. 25A). All untreated control mice developed tumor by day 14 (FIG. 25B), and reached the endpoint before day 21. In the mice treated with RNA-OG, visible tumor did grow out initially on day 10 when the mice receiving two doses of RNA-OG. Then, the tumor cluster gradually disappeared overtime in four of the five treated mice, and the mice remained tumor-free for an extended time (FIGS. 25B and 25C). The mouse survival data compiled from multiple experiments showed that although the immediate treatment of RNA-OG induced noticeably better effect than the one with 3-day delay in RNA-OG treatment both treatments offered superior anti-tumor effect and survivability over the PBS control (FIG. 25C, and FIG. 34C). This finding indicates that RNA-OG could induce an effective tumor-inhibitory effect when the tumor burden is relatively low in the peritoneal compartment, which resembles a scenario with residual disease condition after cytoreductive surgery or hyperthermal intraperitoneal hyperthermic chemotherapy (HIPEC), which are the current therapeutic modality for managing patients with PM/MC[44]. To determine whether the mice showed tumor regression developed anti-tumor immunity, the surviving mice were re-challenged with IP injections of CT26-iRFP on day 47 (FIG. 25A). A control group also received the same number of CT26-iRFP cells via IP. iRFP fluorescence appeared in all naïve control mice but not in any of the re-challenged mice (FIG. 25D). Similarly, when tumor cells were administered subcutaneously, none of the re-challenged mice showing tumor growth whereas four out of five naïve mice succumbed to tumor formation (FIG. 35A). Thus, the tumor-bearing mice treated with RNA-OG developed a systemic and long-term anti-tumor immunity.

NK and T-Cell Dependent Anti-Tumor Immunity

Figure 26:
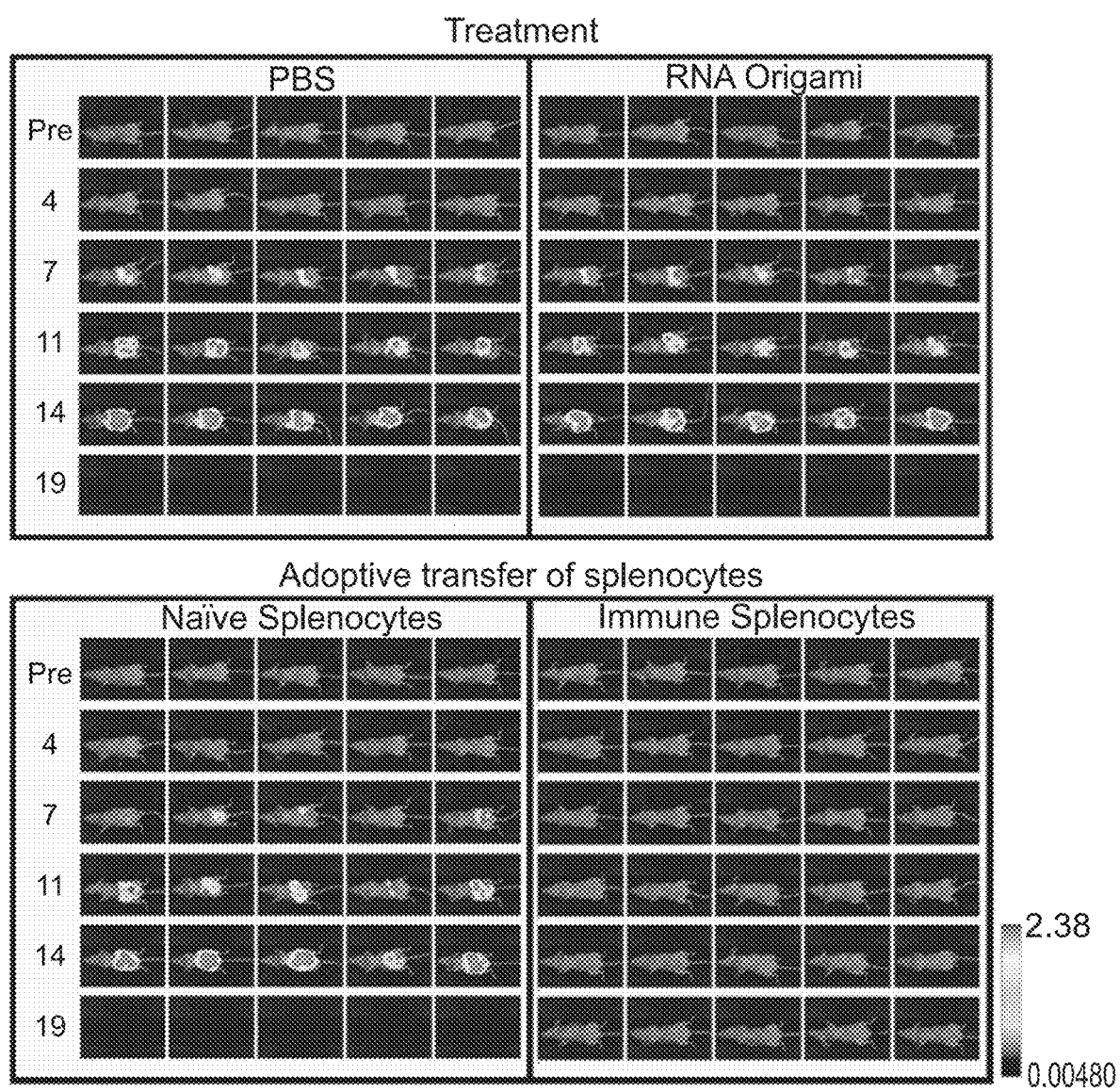
FIG. 26. T-cell dependent anti-tumor immunity. Top panel: Inability of RNA-OG to halt tumor growth in T-cell deficient (athymic nude) mice. Bottom panel. Effect of adoptive transfer of immune cells on tumor growth. Lack of protection in athymic mice even after receiving splenocytes from immune competent, but naïve mice (Bottom left). However, upon receiving the splenocytes taken from the mice that had developed anti-tumor immunity, these athymic nude mice were resistant to the tumor challenge and showed tumor regression (Bottom right).

We next tested the role of CD8 T cells and NK cells in the RNA-OG mediated anti-tumor immunity by depleting CD8 and NK cells in RNA-OG treated mice (FIGS. 35B-D). Interestingly, NK cell depletion completely abrogate the RNA-OG activity in containing tumor growth whereas reduction of CD8 cells significantly compromised the tumor-inhibitor activity (FIGS. 35B-D). To further investigate whether T cells are essential to the anti-tumor activity, we conducted similar experiments described in FIGS. 24A-24B in T-cell deficient athymic Balb/C mic. As shown in the top panel of FIG. 26, despite the RNA-OG treatment started as early as one day post tumor injection, which resulted in good anti-tumor immunity in immune competent Balb/C mice (FIG. 24B), tumor grew rapidly in the athymic mice, regardless of the treatment with PBS or RNA-OG treatment. This result indicates that in the absence of functional T cells, RNA-OG failed to initiate protective immunity against tumor cells. On the other hand, these same mice, after receiving an adoptive transfer of the immune cells taken from the tumor-immuned mice that demonstrated resistance to tumor re-challenge, the one shown in FIG. 25D, became immune to the tumor challenge (FIG. 26, bottom right). However, an adoptive transfer of naïve splenocytes was unable to confer the immunity to the athymic mice (FIG. 26, bottom left). Thus, RNA-OG requires the presence of T cells to induce anti-tumor immunity.

Figure 27A:
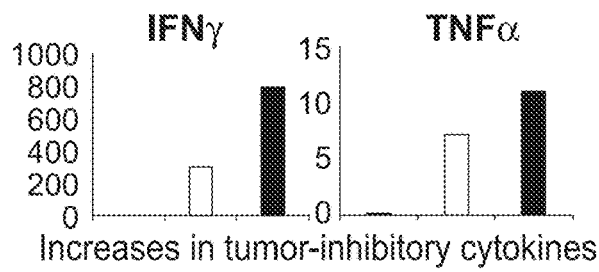
FIGS. 27A-27D. RNA-OG mediated reprograming of peritoneal tumor microenvironment. Cytokine profiles of tumor-bearing mice. Levels of pro-inflammatory cytokines (A) and anti-inflammatory cytokines (B) present in ascites fluid collected from tumor bearing mice treated with or without RNA-OG, as well as mouse serum, were analyzed. Flow cytometry analysis of myeloid derived suppressive cells (MDSCs). ■: Normal serum; □: Ascites fluid from tumor bearing mice; and ▨ represents ascites fluid from RNA-OG treated tumor bearing mice. C. Myeloid derived suppressor cells (MDSC) analysis of peritoneal cavity (PC) cells. The PC cells retrieved from PBS-treated tumor-bearing mice (top panel) or RNA-treated mice that showed tumor regression or low tumor load (bottom panel) were stained with fluorophore-conjugated anti-CD11b, anti-Ly6C, and anti-Ly6G. The gated CD11b+ cells are displayed for Ly6C and Ly6G staining profiles. The number next to each plot shows the total percentage of MDSCs in CD11b+ cells (i.e., the sum of Q1, Q2 and Q4). D. The averages of MDSCs among several individual mice per each group are displayed.
Figure 27C:
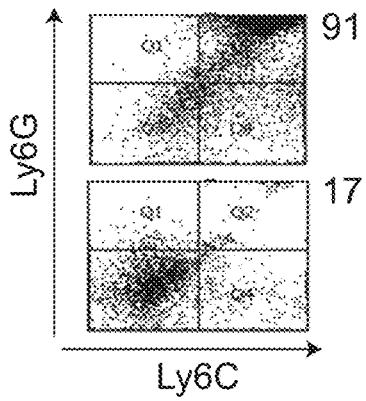
Figure 27B:
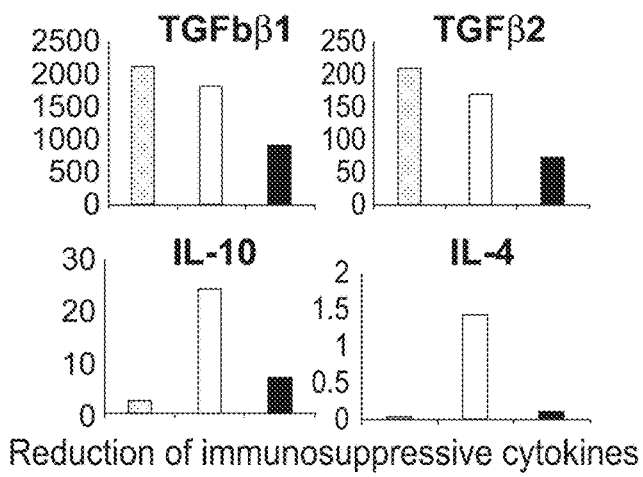
Figure 27D:
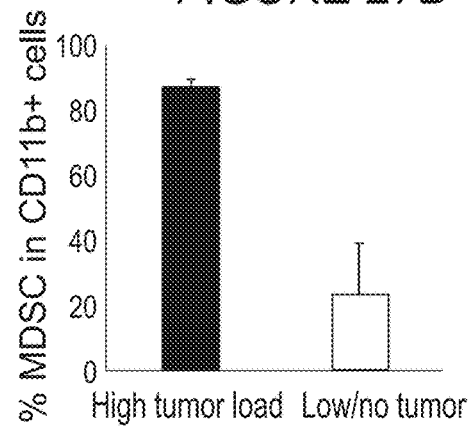

RNA-OG Mediated Reprograming Tumor Microenvironment from Immunosuppression to Pro-Inflammatory Reaction The peritoneal cavity of intraperitoneal malignancies constitutes an excellent environment for tumor progression since it consists of various types of tumor-supporting cells, stromal cells and immunosuppressor cells, like myeloid derived suppressor cells (MDSCs), and is highly rich in tumor promoting and immune-inhibitory factors, such as VEGF, TGFβ and IL10[45]. Given the potent effect of RNA-OG on tumor progression of IP-injected CT26-iRFP cells, we asked whether RNA-OG could function to mitigate the peritoneal tumor microenvironment. The ascite fluids were collected from mice treated with PBS or RNA-OG. The ascites supernatants were prepared for cytokine analysis. As presented in FIGS. 27A and 27B, the level of IFNγ and TNFα that are cytotoxic to tumor cells, was found elevated in mice treated with RNA-OG as compared to the PBS-treated control mice. In contrast, levels of immunosuppressive cytokines, including TGFβ1, TGFβ2, IL10 and IL4 were found lower in RNA-OG treated mice than the control. Thus, RNA-OG treatment resulted in shift of tumor environment from pro-tumor immunosuppressive to anti-tumor immune reactive status. This finding is in line with the cellular analysis of peritoneal cells recovered from the ascites and peritoneal lavages. Based on the gating of Ly6C and Ly6G in CD11b+ peritoneal cells, the percentage of MDSCs, that express Ly6C and/or Ly6G, reaches to 91% in the tumor-bearing mouse that received PBS injection, whereas that number was found significantly reduced in the mice treated with RNA-OG (FIGS. 27C and 27D). Taken together, by stimulating the TLR3 signaling pathway, RNA-OG could activate NK and T-cell dependent anti-tumor immunity, and also reprogram the peritoneal cavity from immunosuppressive environment into immune-reactive milieu to sustain the immunity.

Discussion

In this study, we discovered that the self-assembled RNA-OGs functions as a potent TLR3 agonist to activate immune cells in vitro and exert anti-tumor activity in vivo. Using a TLR3-reporter line and RIG/MDA5-responsive or knockout cell lines, we demonstrated that RNA-OG preferentially activates TLR3-signaling pathway. Although the folds of the activation with RNA-OG in the HEK-TLR3 reporter line is slightly lower than the one with polyIC-H, RNA-OG exhibits much stronger activation than polyIC in its stimulation of immune cells, as revealed in both a RAW264 macrophage line and primary splenocyte culture (FIGS. 22A&B). The potent stimulation displayed by RNA-OG could be attributed to its higher structural stability than polyIC in serum-containing medium, as shown in FIGS. 21D&E). Alternatively, immune cells may take up more RNA-OG than polyIC for their activation in the immune cells, as compared to those non-immune cells, e.g., the two reporter lines used on this study (HEK, human embryonic kidney cells and A549, lung epithelial carcinoma cells). These two scenarios are not mutually exclusive. The fact, that the stimulation of the RAW macrophage line could be blocked in a dose-dependent manner by phosphorothioate GpCs and dextran sulfate, suggests that the uptake of RNA-OG by these immune cells is likely mediated through scavenger receptors that are known to transport nucleic acids, including CpG or GpC oligonucleotides (ODNs) and polyIC[46] although other receptors have also been reported involved in dsRNA binding and transport[47].

As compared to polyIC, RNA-OG possesses several advantages. First, RNA-OGs are monodispersed and highly uniformed nanostructures with well-defined geometry. The structural uniformity of RNA-OG makes it possible to make consistent and reproducible characterization of structure/function relationship, unlike polyIC that are heterogeneous in sizes, which causes variabilities in its functions and mode of actions[38]. For in vivo application, polyIC with high molecular weight (i.e., polyIC-H) was reported to be more potent than the polyIC with low molecular weight (polyIC-L) and therefore polyIC-H was used here as a positive control (FIGS. 22A-D and 23A-B). Moreover, the well-defined nanostructure of RNA-OG makes it possible to rationally design and optimize RNA-OG based adjuvants for better efficacy and safety. Secondly, RNA-OG is highly stable, demonstrated by its long shelf-life (>10 months) kept in PBS, a physiological solution without cations, and resistance to the nuclease present in serum/plasma, more so than polyAU and polyIC-H (FIG. 22D). We speculate that the high stability of RNA-OG is likely attributed to its highly-compact structure, which makes it less accessible for the serum RNases for degradation. Thus, upon addition, the bare RNA-OG structures without being complexed with any other components, such as lipid or polymers, can function as a strong TLR3 agonist to stimulate immune cells in vitro, which is more potent than polyIC-H (FIGS. 22A and 22D). Similarly, RNA-OG administered in vivo also induces strong production of CXCL10, at a level comparable to the one stimulated by polyIC-H (FIG. 23), indicating that RNA-OG, having a single chemical entity, possess potent adjuvant activity. Thirdly, despite its strong stimulatory activity on the immune cells in vitro and CXCL10 chemokine production in vivo, RNA-OG did not trigger a systemic production of type-I Interferons. Although these interferons play important roles in eliciting innate and adaptive immunity to contain tumor growth, systemic product of these cytokines, e.g., triggered by polyIC, has also been blamed for a cytokine storm and in vivo toxicity[48]. As a result, effort has been directed to modify polyIC structures to reduce its systemic toxicity or to restrict its application to local delivery, such as subcutaneous, intradermal or intranasal administration[49]. Two polyIC derived products are currently in clinical trials as cancer vaccine adjuvants[49]. One is Hiltonol (made by Oncovir Inc), known as Poly-ICLC that is polyIC complexed with poly-lysine carboxymethylcellulose to increase its stability, and another is Ampligen (Hemispherx Biopharma), poly(I:C12 U), that is polyIC with a U mismatch at every 12th base of the C strand for reduced stability. Ampligen was reported to be well-tolerated in human and its intraperitoneal (IP) administration in combination with DC-vaccination or other chemotherapeutics is currently in phase I/II clinical trial for treating recurrent ovarian cancer toxicity[49]. On the other hand, clinical trials (phase I/II) with Hiltonol use exclusively local delivery routes, presumably due to its systemic toxicity[49]. Alternatively, dsRNAs other than polyIC have also been tested to search for effective and safe adjuvants. Interestingly, polyAU and a synthetic dsRNA structure, known as ARNAX[50], have been shown to function primarily as a TLR3 agonists and they exhibit no systemic production of type-I interferons[51,52] Thus, dsRNA analogues with an exclusive usage of the TLR3-signaling pathway without activating cytoplasmic RNA sensors, such as RIG-I and MDA5, seem to correlate with their inability to induce systemic cytokine storm in vivo[40]. Thus, it has been suggested that dsRNA analogues that trigger exclusively the TLR3 signaling pathway may constitute a line of adjuvants that are effective and safe[30]. Based on their stimulatory profiles in vitro (FIGS. 22A-D) and cytokine production in vivo (FIGS. 23A-D) characterized here, the self-assembled RNA-OGs likely fall into this category of dsRNA adjuvants.

Indeed, in testing the anti-cancer activities of RNA-OGs in vivo, we demonstrated that similar to polyIC-H, RNA-OG could induce strong tumor retardation or tumor regression (FIGS. 24A-B). The tumor-bearing mice treated with RNA-OG developed a systemic and long-term immunity as they were resistant to the second challenge of tumor cells (FIGS. 25A-D). Interestingly, the generation of this anti-tumor immunity is dependent on the presence of both NK cells and CD8+ T cells as missing either one of the two cell types compromised the ability of RNA-OG to elicit anti-tumor immunity (FIGS. 35B-D). Thus, the characteristics of RNA-OG mediated immune cell activation and anti-tumor immunity resembles many features previously reported for polyIC and ARNAX, i.e., activating innate immune cells, including DCs, macrophages and NK cells, which in turn help recruit and prime cytotoxic T lymphocytes to attack tumor cells[30], as well as mitigating immunosuppressive environment[53].

Taken together, RNA-OG represents a new line of dsRNA adjuvants that are structurally monodispersed and stable, and functionally effective and safe, which are ideal for in vivo application. For example, the disease condition associated with peritoneal metastasis (PM) or peritoneal carcinomatosis (PC) is considered as an end stage with very poor prognosis[45,54]. The current therapeutic modalities for treating PM/PC relies on cytoreductive surgery and intraperitoneal hyperthermal chemotherapy, which are ineffective and sometime not applicable to certain patients[44]. Although intraperitoneal injection of polyIC was tested in animal models for treating PM/PC, the systemic application of the stabilized polyICLC in clinical trials was found intolerable and associated with high toxicity[49]. It is conceivable that RNA-OG, that was demonstrated in this study to induce strong local anti-tumor activity without inflicting systemic reactions, could serve as an ideal immunotherapeutics for treating PM/PC.

Methods

RNA-OG Production

Rectangle RNA-OG design, sequence generation, and DNA template cloning were carried out as previously described. Before the RNA transcription, the DNA plasmid was linearized by EcoRI restriction enzyme and followed by phenol/chloroform extraction and ethanol precipitation. The large scale RNA production was performed with 0.05 mg/ml linear plasmid template in the 1× transcription reaction buffer (80 mM HEPES, pH 7.5, 24 mM MgCl$_2$, 40 mM DTT, and 2 mM spermidine) supplemented with 20 mM NTP mix, 400 U/ml SUPERase IN (ThermoFisher Scientific), 1 U/ml pyrophosphatase, inorganic (New England Biolabs), and 0.01 mg/ml homemade T7 RNA polymerase. The in vitro transcription reaction was incubated at 30° C. for 5 hours, followed by a 15 minute incubation at 37° C. with the addition of 20 U/ml DNase I (New England Biolabs) to completely digest the DNA template. The transcribed RNA was then purified using RNA clean & concentrator 100 kit (Zymo research) following the manufacturer's instruction. The typical yield of RNA molecule is >5 mg per each ml transcription mixture. The RNA-OG was self-assembled in 1×PBS buffer from 65° C. to 25° C. at a ramp of −1° C. per 15 minutes.

RNA-OG Stability Analysis

RNase I digestion was performed with 1 μg RNA-OG mixed with 1 U of RNase I (ThermoFisher Scientific) in 10 μl 1×PBS buffer. The reaction was incubated at room temperature for 20 minutes followed by 1% agarose gel electrophoresis. The serum/plasma stability test was carried out by supplementing 1 μg of RNA-OG or polyIC-H (Invivogen) or polyAU (Invivogen) with 10% mouse serum/human plasma in 10 μl 1×PBS buffer. The mixtures were incubated at 37° C. with various time points and terminated by addition of 1× purple gel loading dye (New England Biolabs).

The UV thermal curves were measured in quartz cuvettes (Starna Cells) using a CARY 300B10 UV-vis spectrometer with temperature control accessories. The RNA-OG was pre-annealed in 1×PBS buffer and diluted to A260 ~0.9. The RNA-OG (135 μL) was pipetted in the cuvette and 300 μL of mineral oil was layered on top of the strands mixture to prevent sample evaporation during the temperature ramps. The UV absorbance of RNA at 260 nm (A260) was recorded at 1-min intervals throughout the thermal program. 1×PBS buffer was used as the background reference. The sample was held at 15° C. for 10 min and heated to 90° C. at +0.1° C./min.

RAW 264.7 Cell In Vitro Stimulation

RAW 264.7 cells were cultured in DMEM medium supplemented with 10% heat-inactivated FBS. Cells were seeded in a 24-well plate with 2×10$^5$ cells per well and incubated at 37° C. overnight. The medium was replaced and PBS, dextran sulfate (200 μg/mL), or phosphorothioate-bond human GpC (50 μg/mL) were added as inhibitors. After incubation at 37° C. for 30 minutes, RNA-OG, PIC-H, or PIC-L (5 μg/mL) were added as a stimulator and the cells were incubated at 37° C. for additional 60 minutes. The cells were recovered from the plate and collected by centrifugation for 5 minutes at 380×g. They were washed once in PBS, once in staining buffer (1×PBS, 2% BSA, 0.01% sodium azide) and then stained with PE anti-mouse CD40 for 30 minutes at 4° C. Following twice wash with staining buffer and resuspension in 200 μL PBS, the cell samples were analyzed on a FACSAria II instrument. The mean fluorescent intensity (MFI) of each sample was employed to evaluate the activation.

Animals

Female BALB/c mice were obtained from Charles River Laboratories and maintained in a pathogen-free animal facility at the Arizona State University Animal Resource Center. All mice were handled in accordance with the Animal Welfare Act and Arizona State University Institutional Animal Care and Use Committee (IACUC). Before experimental treatment, the mice were randomly distributed in cages and allowed to acclimate for at least 1 week prior to treatments. At 8 weeks of age, the mice received 5×10$^5$ CT26-iRFP cells on day 0 via IP injection in 100 μL sterile PBS. Treatments of PBS, RNA-OG, and polyIC-H began at day 1, 3, or 5. IP treatments were given 4-6 times biweekly and contained 16 μg of nucleic acids suspended in 100 uL of sterile PBS. Tumor progress was monitored via the fluorescence of iRFP (ex: 690 nm, em: 713 nm) on a LI-COR Biosciences Pearl Impulse small animal imager using inhaled isoflurane (Henry Schein) to anesthetize the mice.

Nude female athymic BALB/c mice were handled according to the IACUC protocols. The PBS and RNA-OG groups were treated in the same manner as the immunocompetent mice described above. The adoptive transfer groups received 1.1×10$^7$ splenocytes from either a naïve, immunocompetent female BALB/c or a CT26-iRFP-immune female BALB/c that had been treated with RNA-OG after its initial CT26-iRFP challenge and confirmed to be immune with a second CT26-iRFP challenge. The splenocytes were suspended in 100 μL of sterile PBS and injected IP. They were obtained and isolated according to the splenocyte isolation procedure below, but were suspended in PBS for injection instead of in RPMI for culturing.

For immune cell depletion, mice were injected IP with 250 ug/dose monoclonal rat anti-mouse CD8b, control IgG (clone Lyt 3.2 and TNP6A7, Bio X cell) or 50 ul of polyclonal rabbit anti-mouse NK cells antibody (Ultra-LEAF™ Purified anti-Asialo-GM1 Antibody, Poly21460, Biolegend) on day 0, 4, 7 and 11, i.e., one day before each injection of RNA-OG.

Splenocyte Isolation and Stimulation

Mice were euthanized with carbon dioxide asphyxia, and the spleens were removed and sterilized by quickly dipping in 70% ethanol for 1 second before being transferred to sterile RPMI-1640 medium supplemented with 10% fetal bovine serum (FBS) in the biosafety cabinet. The spleen was cut on one end, and a thin, sealed L-shaped glass tube was used to push spleen marrows out. The extracted spleen cells were pelleted and washed by spinning at 380×g for 3 min in the sterile RPMI-1640 medium described above, and red blood cells were depleted by ACT lysis buffer (combination of 0.16 M NH$_4$Cl and 0.17 M Tris [pH 7.65] at a volume ratio of 9:1, pH adjusted to 7.2 with 1 M HCl, and filter sterilized). After washing twice in RPMI-1640 medium supplemented with 10% FBS and antibiotics, the splenocytes were seeded in 12-well plates at a density of 4×10$^6$ cells/mL. RNA origami, PolyIC or PBS controls were added into each well at desired concentrations, 50 ng/mL lipopolysaccharide (LPS) was added to the positive control well and Polymyxin B (PMB) was added into each well except for the LPS alone well at a final concentration of 100 μg/mL to prevent endotoxin contamination. 24 hours after stimulation, cells were harvested, stained with antibody cocktails, and analyzed by flow cytometry.

Flow Cytometry

Stimulated splenocytes were harvested by spinning down at 380×g for 3 min, and supernatants were saved for cytokine analysis. Pelleted cells were washed once with 1×PBS, and labeled with Zombie Violet viability dye (Biolegend, Cat #423114) at room temperature for 15 minutes. After washing twice in staining buffer (1×PBS, 2% BSA, 0.01% sodium azide), cells were incubated in the following antibody cocktail containing FcR block: (a) FITC anti-mouse CD3, PE anti-mouse CD69, pacific blue anti-B220, APC anti-CD49b, and PE/Cy7 anti-mouse CD4; b) FITC anti-mouse CD11b, PE anti-mouse CD86, PE/Cy5 anti-mouse B220, and PE/Cy7 anti-mouse CD11c. After 30 minutes of incubation at 4° C., cells were washed twice in staining buffer and resuspended in 200 μL staining buffer. Each sample was analyzed on a FACSAria II instrument at Biodesign Institute, Arizona State University. Live cells were defined as Zombie Violet-low cell population and gated for live CD3 T cells. Percentage of CD69+ cells in CD3 T cell population were plotted for T cell stimulation measurement. NK cells and CD69+NK cells were based on the gating for CD49+B220−CD3− and CD69+CD49b+B220−CD3− populations, respectively, which are displayed as percentages of total live splenocytes. Plasmacytoid dendritic cells (pDC) were defined as CD11b−CD11c+B220+ live cells, and conventional dendritic cells (cDC) were defined as CD11b+CD11c+ cells. Mean fluorescent intensity of CD86 in each DC cell population was plotted as an indicator of DC stimulation status.

Cytokine Analysis

The cell culture supernatants from ex vivo splenocyte culture were examined for a panel of 13 cytokines, using the BioLegend's LEGENDplex™ bead-based Mouse Anti-Virus Response Panel (13-plex, Cat. 740621) array that allows simultaneous quantification of 13 mouse proteins, including IFN-γ, CXCL1 (KC), TNF-α, CCL2 (MCP-1), IL-12p70, CCL5 (RANTES), IL-1β, CXCL10 (IP-10), GM-CSF, IL-10, IFN-β, IFN-α, IL-6. The analysis was performed, according to the manufacture's instruction, including cytokine staining, flow cytometry analysis, and data acquisition for quantification. For serum cytokine analysis, 100 µL of RNA-OG (16 µg), PolyIC (16 µg) or 1×PBS were I.P. injected to naive 8-10 weeks old mice, and mouse blood was collected at 3 hrs and 24 hrs post injection from mouse facial vein and serum was recovered from the blood samples by spinning at 7000 rpm for 10 minutes at 4° C. The serum was analyzed using the same Biolegend's LEGENDplex™ cytokine array with slight modification designed for the serum analysis. Jason Lehmann from Biolegend provided assistance in the data analysis.

For the assessment of both pro-inflammatory and immunosuppressive cytokines present in the peritoneal cavity, the ascites fluid recovered from the tumor-bearing mice that were treated with either PBS or RNA-OG (which had a very low amount of ascites fluid), the ascites supernatant was sent to Eve Technologies for testing both TGF-beta 3-Plex (TGFB1-3) and Mouse Cytokine Array Proinflammatory Focused 10-plex (MDF10). The latter detects GM-CSF, IFNy, IL-1B, IL-2, IL-4, IL-6, IL-10, IL-12p70, MCP-1 and TNF-α.

Cell Viability Assay

Viability of cells after incubation with RNA origami was analyzed by MTT assay, (Vybrant® MTT cell proliferation assay kit from Thermo Fisher) following manufacture's protocol. Camptothecin (Sigma-Aldrich, catalog no. C9911) at a final concentration of 5 µM served as the positive control, as it is known to induce apoptosis.

TLR3 Agonist Test

A reporter cell line expressing mouse TLR3, HEK-Blue™ mTLR3 cells, was purchased from Invivogen. Agonist activity of RNA origami and other adjuvants were quantified by the absorbance of HEK-Blue medium after co-incubation of these adjuvants with cells, following manufacture's protocol. ssRNA40/LyoVec™ purchased from Invivogen served as negative control.

Example 4 References

1 Pinheiro, A. V., Han, D. R., Shih, W. M. & Yan, H. Challenges and opportunities for structural DNA nanotechnology. *Nature Nanotechnology* 6, 763-772, doi: 10.1038/Nnano.2011.187 (2011).

2 Zhang, F., Nangreave, J., Liu, Y. & Yan, H. Structural DNA Nanotechnology: State of the Art and Future Perspective. *Journal of the American Chemical Society* 136, 11198-11211, doi:10.1021/ja505101a (2014).

3 Rothemund, P. W. K. Folding DNA to create nanoscale shapes and patterns. *Nature* 440, 297-302, doi:10.1038/nature04586 (2006).

4 Wei, B., Dai, M. J. & Yin, P. Complex shapes self-assembled from single-stranded DNA tiles. *Nature* 485, 623−+, doi:10.1038/nature11075 (2012).

5 Han, D. R. et al. Single-stranded DNA and RNA origami. *Science* 358, doi:ARTN eaao2648 10.1126/science.aao2648 (2017).

6 Douglas, S. M. et al. Self-assembly of DNA into nanoscale three-dimensional shapes. *Nature* 459, 414-418, doi: 10.1038/nature08016 (2009).

7 Dietz, H., Douglas, S. M. & Shih, W. M. Folding DNA into Twisted and Curved Nanoscale Shapes. *Science* 325, 725-730, doi:10.1126/science.1174251 (2009).

8 Han, D. R. et al. DNA Origami with Complex Curvatures in Three-Dimensional Space. *Science* 332, 342-346, doi: 10.1126/science.1202998 (2011).

9 Han, D. R. et al. DNA Gridiron Nanostructures Based on Four-Arm Junctions. *Science* 339, 1412-1415, doi: 10.1126/science.1232252 (2013).

10 Geary, C., Rothemund, P. W. K. & Andersen, E. S. A single-stranded architecture for cotranscriptional folding of RNA nanostructures. *Science* 345, 799-804, doi: 10.1126/science.1253920 (2014).

11 Zhang, F. et al. Complex wireframe DNA origami nanostructures with multi-arm junction vertices. *Nature Nanotechnology* 10, 779−+, doi:10.1038/Nnano.2015.162 (2015).

12 Ball, P. Nanosystems—Molecular Machinery, Manufacturing, and Computation—Drexler, Ke. *Nature* 362, 123-123 (1993).

13 Lee, H. et al. Molecularly self-assembled nucleic acid nanoparticles for targeted in vivo siRNA delivery. *Nature Nanotechnology* 7, 389-393, doi:10.1038/Nnano.2012.73 (2012).

14 Li, S. P. et al. A DNA nanorobot functions as a cancer therapeutic in response to a molecular trigger in vivo. *Nature Biotechnology* 36, 258−+, doi:10.1038/nbt.4071 (2018).

15 Jiang, Q. et al. DNA Origami as a Carrier for Circumvention of Drug Resistance. *Journal of the American Chemical Society* 134, 13396-13403, doi:10.1021/ja304263n (2012).

16 Liu, X. W. et al. A DNA Nanostructure Platform for Directed Assembly of Synthetic Vaccines. *Nano Letters* 12, 4254-4259, doi:10.1021/nl301877 k (2012).

17 Schlee, M. & Hartmann, G. Discriminating self from non-self in nucleic acid sensing. *Nat Rev Immunol* 16, 566-580, doi:10.1038/nri.2016.78 (2016).

18 Alexopoulou, L., Holt, A. C., Medzhitov, R. & Flavell, R. A. Recognition of double-stranded RNA and activation of NF-kappa B by Toll-like receptor 3. *Nature* 413, 732-738, doi:Doi 10.1038/35099560 (2001).

19 Diebold, S. S., Kaisho, T., Hemmi, H., Akira, S. & Sousa, C. R. E. Innate antiviral responses by means of TLR7-mediated recognition of single-stranded RNA. *Science* 303, 1529-1531, doi:10.1126/science.1093616 (2004).

19 Heil, F. et al. Species-specific recognition of single-stranded RNA via toll-like receptor 7 and 8. *Science* 303, 1526-1529, doi:10.1126/science.1093620 (2004).

21 Hemmi, H. et al. A Toll-like receptor recognizes bacterial DNA. *Nature* 408, 740-745 (2000).

22 Kawai, T. & Akira, S. Innate immune recognition of viral infection. *Nature Immunology* 7, 131-137, doi:10.1038/ni1303 (2006).

23 Klinman, D. M. Immunotherapeutic uses of CpG oligodeoxynucleotides. *Nature Reviews Immunology* 4, 248-257, doi:10.1038/nri1329 (2004).

24 Gungor, B. et al. CpG ODN Nanorings Induce IFN alpha from Plasmacytoid Dendritic Cells and Demonstrate Potent Vaccine Adjuvant Activity. *Science Translational Medicine* 6, doi:ARTN 235ra61 10.1126/scitranslmed.3007909 (2014).

25 Lacour, J. et al. Adjuvant Treatment with Polyadenylic-Polyuridylic Acid in Operable Breast-Cancer—Updated Results of a Randomized Trial. *British Medical Journal* 288, 589-592, doi:DOI 10.1136/bmj.288.6417.589 (1984).

26 Kato, H. et al. Differential roles of MDA5 and RIG-I helicases in the recognition of RNA viruses. *Nature* 441, 101-105, doi:10.1038/nature04734 (2006).

27 Gitlin, L. et al. Essential role of mda-5 in type I IFN responses to polyriboinosinic:polyribocytidylic acid and encephalomyocarditis picornavirus. *Proc Natl Acad Sci USA* 103, 8459-8464, doi:10.1073/pnas.0603082103 (2006).

28 Robinson, R. A. et al. A Phase I-II trial of multiple-dose polyriboinosic-polyribocytidylic acid in patients with leukemia or solid tumors. *J. Natl. Cancer. Inst.* 57, 599-602 (1976).

29 Christopher, M. E. & Wong, J. P. Use of Toll-Like Receptor 3 Agonists Against Respiratory Viral Infections. *Anti-Inflamm. & Anti-Allergy Agents in Med. Chem.* 10, 327-338 (2011).

30 Matsumoto, M. et al. Defined TLR3-specific adjuvant that induces NK and CTL activation without significant cytokine production in vivo. *Nature Communications* 6, doi:ARTN 6280 10.1038/ncomms7280 (2015).

31 Matsumoto, M., Takeda, Y., Tatematsu, M. & Seya, T. Toll-Like Receptor 3 Signal in Dendritic Cells Benefits Cancer Immunotherapy. *Frontiers in Immunology* 8, doi:ARTN 1897 10.3389/fimmu.2017.01897 (2017).

32 Wei, X. X., Nangreave, J., Jiang, S. X., Yan, H. & Liu, Y. Mapping the Thermal Behavior of DNA Origami Nanostructures. *Journal of the American Chemical Society* 135, 6165-6176, doi:10.1021/ja4000728 (2013).

33 Hahn, J., Wickham, S. F. J., Shih, W. M. & Perrault, S. D. Addressing the Instability of DNA Nanostructures in Tissue Culture. *Acs Nano* 8, 8765-8775, doi:10.1021/nn503513p (2014).

34 Ranjith-Kumar, C. T. et al. Single-Stranded oligonucleodides can inhibit cytokine production induced by human Toll-like receptor 3. *Mol. Cell. Biol.* 28, 4507-4519 (2008).

35 Itoh, K., Watanabe, A., Funami, K., Seya, T. & Matsumoto, M. Matsumoto M. The clathrin-mediated endocytic pathway participates in dsRNA-induced IFN-g production. *J. Immunol.* 181, 5222-5229 (2008).

36 Zhu, X. et al. Poly-ICLC promotes the infiltration of effector T cells into intracranial gliomas via induction of CXCL10 in IFN-alpha and IFN-gamma dependent manners. *Cancer Immunol Immunother* 59, 1401-1409, doi:10.1007/s00262-010-0876-3 (2010).

37 Kistner, L., Doll, D., Holtorf, A., Nitsche, U. & Janssen, K.-P. Interferon-inducible CXC-chemokines are crucial immune modulators and survival predictors in colorectal cancer. *Oncotarget* 8, 89998-90012 (2017).

38 Kato, H. et al. Length-dependent recognition of doublestranded ribonucleic acids by retinoic acid-inducible gene-I and melanoma differentiation—associated gene 5. *J. Exp. Med.* 205, 1601-1610 (2008).

39 Zhou, Y. et al. TLR3 activation efficiency by high or low molecular mass poly I:C. *Innate Immun* 19, 184-192, doi:10.1177/1753425912459975 (2013).

40 Takeda, Y. et al. A TLR3-Specific Adjuvant Relieves Innate Resistance to PD-L1 Blockade without Cytokine Toxicity in Tumor Vaccine Immunotherapy. *Cell Rep* 19, 1874-1887, doi:10.1016/j.celrep.2017.05.015 (2017).

41 Gatti, G. et al. Direct effect of dsRNA mimetics on cancer cells induces endogenous IFN-b production capable of improving dendritic cell function. *Eur. J. Immunol* 43, 1849-1861 (2013).

42 Mikula-Pietrasik, J., Uruski, P., Tykarski, A. & Ksiazek, K. The peritoneal "soil" for a cancerous "seed": a comprehensive review of the pathogenesis of intraperitoneal cancer metastases. *Cell Mol Life Sci* 75, 509-525, doi:10.1007/s00018-017-2663-1 (2018).

43 Hock, A. K. et al. iRFP is a sensitive marker for cell number and tumor growth in high-throughput systems. *Cell Cycle* 13, 220-226, doi:10.4161/cc.26985 (2014).

44 Castro-Mesta, J. F., Gonzalez-Guerrero, J. F., Barrops-Sanchez, P. & G., V.-C. Bases and foundations of the treatment of peritoneal carcinomatosis: Review article. *Medicina Universitaria* 18, 98-104 (2016).

45 Coccolini, F. et al. Peritoneal carcinomatosis. *World J Gastroenterol* 19, 6979-6994, doi:10.3748/wjg.v19.i41.6979 (2013).

46 Limmon, G. V. et al. Scavenger receptor class-A is a novel cell surface receptor for double-stranded RNA. *FASEB J* 22, 159-167, doi:10.1096/fj.07-8348com (2008).

47 Matsumoto, M. & Tatematsu, M. Cell type-specific role of Raftlin in the regulation of endosomal TLR signaling. *Inflammation and Cell Signaling* 3, 1-8 (2016).

48 Tatematsu, M., Seya, T. & Matsumoto, M. Beyond dsRNA: Toll-like receptor 3 signalling in RNA-induced immune responses. *Biochem J* 458, 195-201, doi:10.1042/BJ20131492 (2014).

49 Iribarren, K. et al. Trial Watch: Immunostimulation with Toll-like receptor agonists in cancer therapy. *Oncoimmunology* 5, e1088631, doi:10.1080/2162402X.2015.1088631 (2016).

50 Tatematsu, M., Nishikawa, F., Seya, T. & Matsumoto, M. Toll-like receptor 3 recognizes incomplete stem structures in single-stranded viral RNA. *Nat Commun* 4, 1833, doi:10.1038/ncomms2857 (2013).

51 Seya, T., Takeda, Y. & Matsumoto, M. Tumor vaccines with dsRNA adjuvant ARNAX induces antigen-specific tumor shrinkage without cytokinemia. *Oncoimmunology* 5, e1043506, doi:10.1080/2162402X.2015.1043506 (2016).

52 Takeda, Y. et al. Vaccine immunotherapy with ARNAX induces tumor-specific memory T cells and durable antitumor immunity in mouse models. *Cancer Sci* 109, 2119-2129, doi:10.1111/cas.13649 (2018).

53 Shime, H. et al. Toll-like receptor 3 signaling converts tumor-supporting myeloid cells to tumoricidal effectors. *Proc Natl Acad Sci USA* 109, 2066-2071, doi:10.1073/pnas.1113099109 (2012).

54 van Baal, J. et al. Development of Peritoneal Carcinomatosis in Epithelial Ovarian Cancer: A Review. *J Histochem Cytochem* 66, 67-83, doi:10.1369/0022155417742897 (2018).

Example 5

Figure 43:
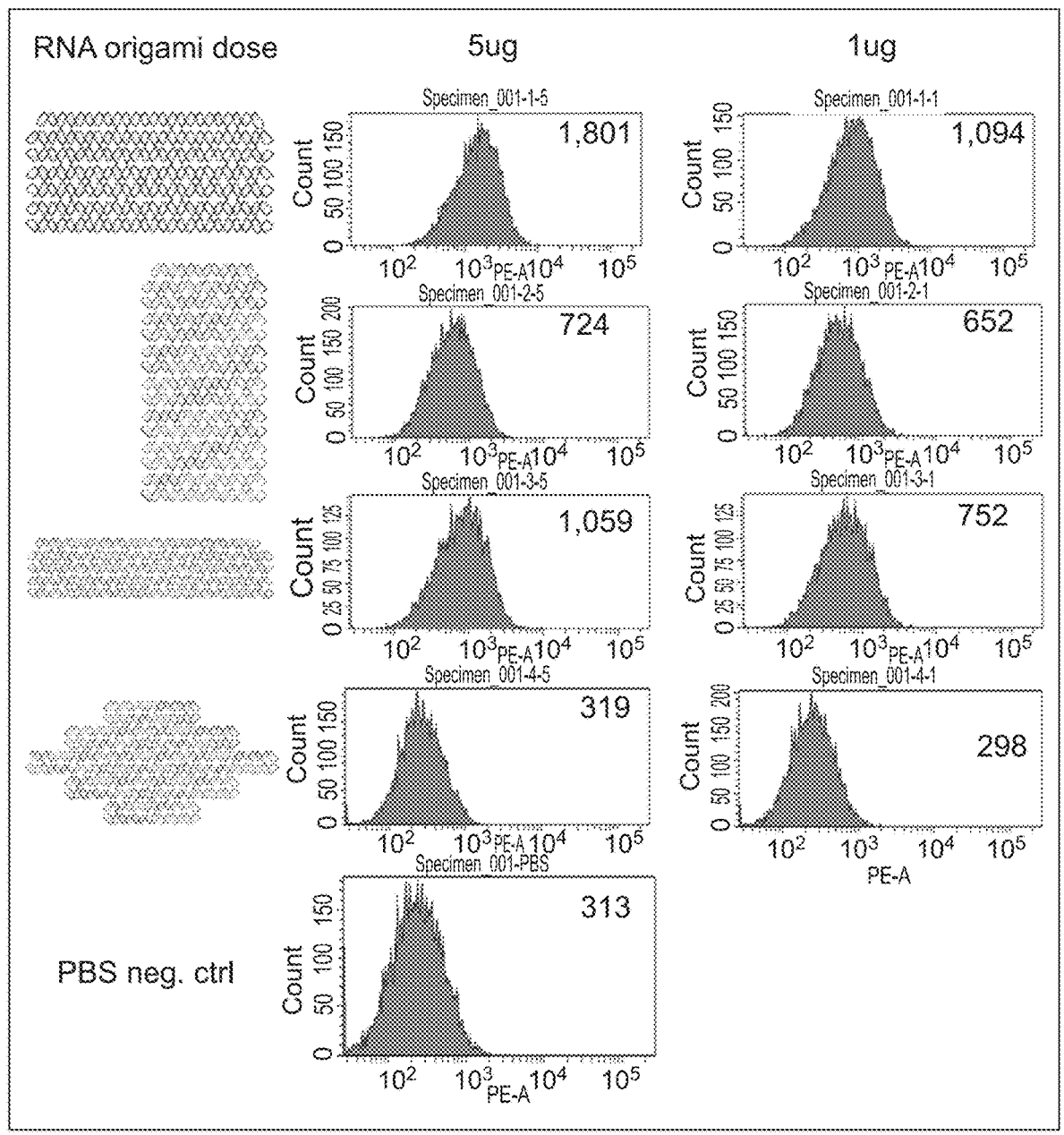
FIG. 43. RAW 264.7 cell in vitro stimulation using various shapes of RNA origami. The flow cytometry fluorescence image was shown with each design and each dose. The MFI number was listed.

Three different rectangle shapes and one diamond shape RNA origami were designed, all of which had U rich loops (see, FIGS. 39-42; SEQ ID NOs:1, 7-8 and 10). The immuno-stimulating effect of RNA nanostructures was examined in a mouse macrophage cell line, RAW 264.7, measuring the upregulation of CD40, a co-stimulatory molecule expressed on the surface of immune cells upon activation. Different doses of RNA nanostructures were incubated with RAW 264.7 cells for 20 hours. The cells were then stained with PE anti-mouse CD40 antibody and analyzed with a flow cytometer. The original rectangle nanostructure (the structure formed by SEQ ID NO:1) exhibited higher mean fluorescence intensity (MFI), implying stronger immune-stimulating effect (FIG. 43).

Figure 44:
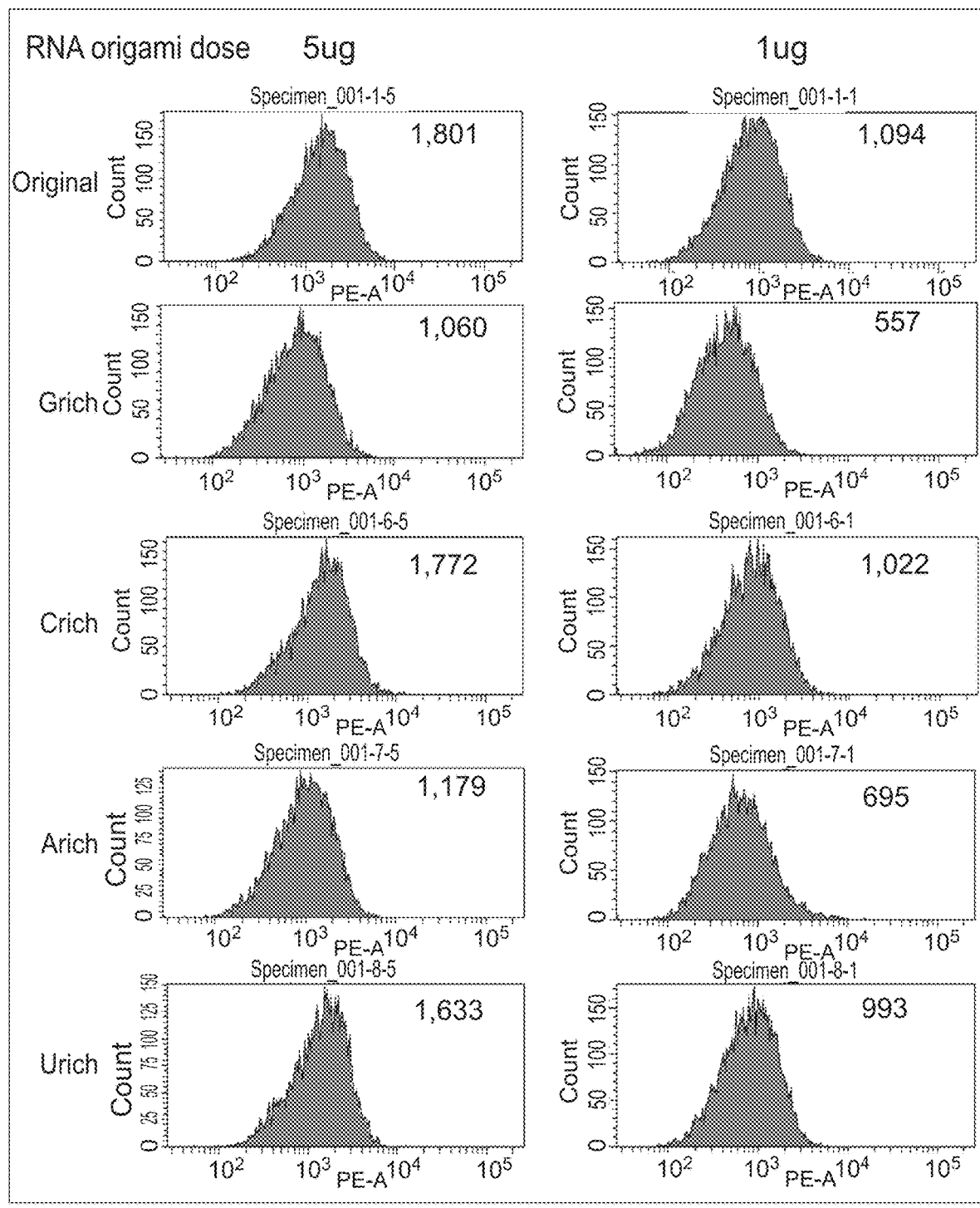
FIG. 44. RAW 264.7 cell in vitro stimulation using rectangle RNA origami with various loop sequences. The MFI number was compared for their immuno-stimulating effect.
Figure 48:
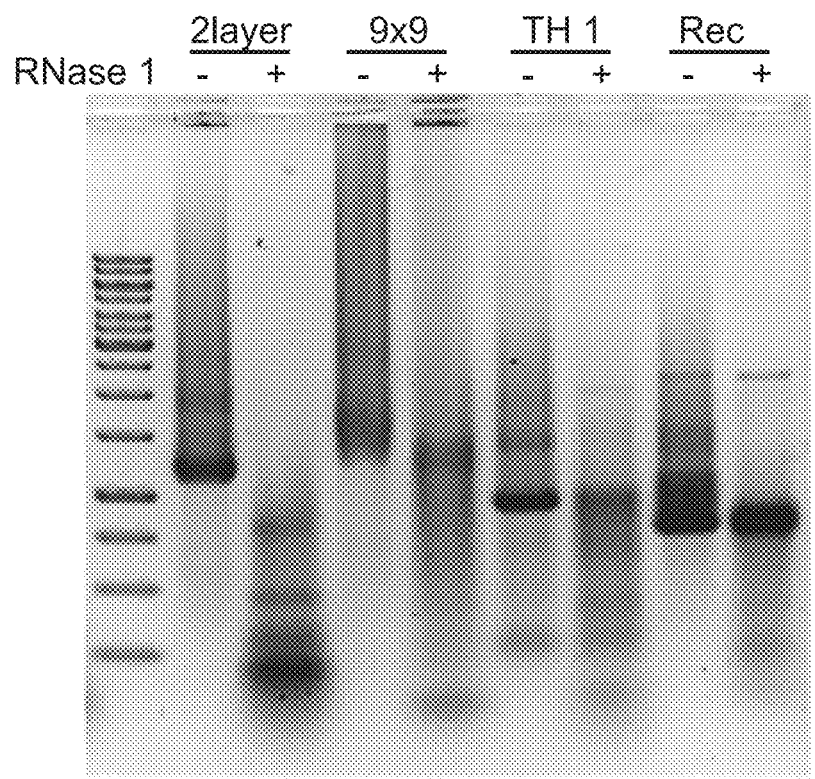
FIG. 48. Nuclease resistance of RNA origamis. As compared to RNA-Rec (SEQ ID NO:1), other RNA-origamis were less stable.
Figure 49:
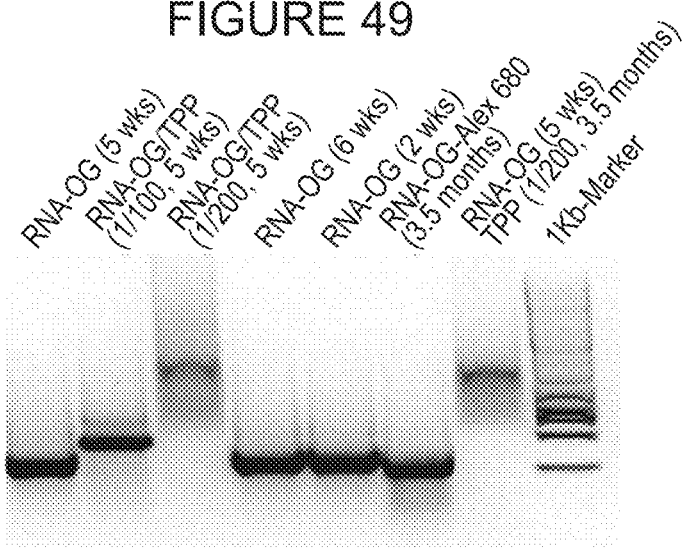
FIG. 49. Stability of RNA origamis. RNA-origami have been maintained in PBS at 4° C. for more than four months and still retain a structure similar to freshly prepared origami. The structures were stable even when stored without cations.
Figure 50:
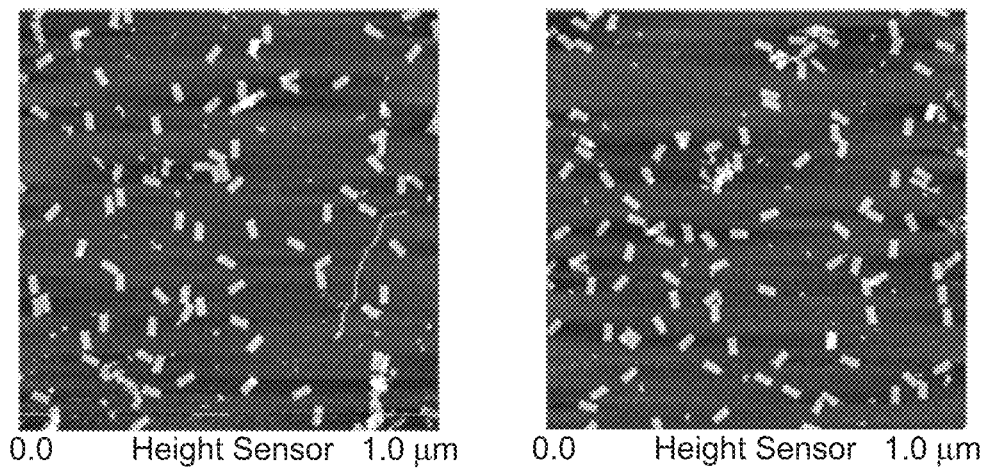
FIG. 50. RNA origami AF689 stability at 4° C.
Figure 51:
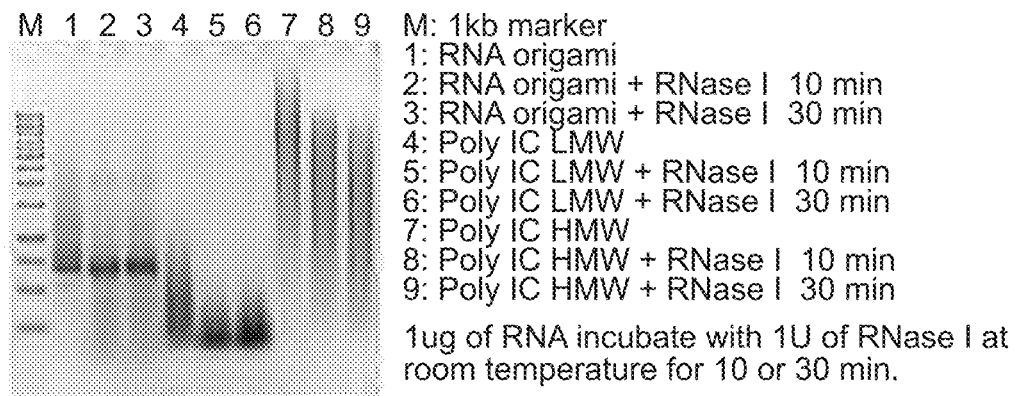
FIG. 51. RNase sensitivity of RNA origami vs Poly IC. PolyIC with high molecular weight (HMW) appears to be more resistant to Rnase than polyIC with LMW. Yet, under the same condition, no degradation was observed with RNA-OG.

A comparison of the loop sequences was also examined. The RNA nanostructures described herein may comprise double-stranded RNA as a major part of the structure along with short loops on two edges. Original rectangle RNA nanostructure contains 13 tetraloops with sequence 'UUUC' (SEQ ID NO:1). In the new designs, the loop was modified to other sequences listed as follows: 'G rich': 'GGGAGGG'; 'C rich': 'CCCUCCC'; 'A rich': 'AAAGAAA' and 'U rich': 'UUUCUUU' (see, SEQ ID NOs:2-5). The immuno-stimulating effect of RNA nanostructures was examined using a method described previously in Example 4. The RNA origami with 'C rich' and 'U rich' loops showed similar immuno-stimulating effect to the original one which contains 'UUUC' loops, while the 'G rich' and 'A rich' loops were slightly less effective (FIG. 44).

Example 6

Further experiments were performed to test the effectiveness of the RNA origami (SEQ ID NO:1) on A20-iRFP lymphoma tumors in vivo in mice. Tumor cells were injected on day −10 to form tumor nodules. The treatment was started on day 0, followed by two additional injections intratumorally. Injections were subcutaneous in the A20 tumor. For the anti-PD1 experiment, a similar treatment schedule was followed, except that anti-PD1 was delivered 2-days post RNA-OG treatment, and only two rounds of anti-PD1 were given. The black arrows indicate the injection of RNA-OG. FIG. 45. A further experiment was performed in which anti-PD1 was combined with RNA-origami, where both tumor growth and mouse survival were monitored. FIG. 15.

Example 7

A series of experiments were performed to evaluate the stimulation of primary splenocytes by certain RNA nanostructures. The methods used in these experiments were similar to those used in Example 4. These experiments indicated that 1) RNA-Rec (SEQ ID NO:1) is a potent stimulator to activate B cells (revealed by increased CD69 expression); 2) RNA-Rec induces upregulation of CD69 in T cells; 3) RNA-Rec does not appear to directly inhibit tumor cell growth. Additionally, the experiments indicated that the other RNA-origamis that were tested induced less potent activation of B and T cells.

Cytokine analysis revealed that RNA-Rec induces local production of IFN-alpha and IFN-beta. Cell culture supernatant were collected at 24-hr or 48-hr post co-culture of RNA-Rec and mouse splenocytes, and IFN-alpha and IFN-beta level of RNA-Rec group was elevated compared to other groups (FIG. 10). When administered through retro-orbital route in mouse, RNA-Rec induced elevated production of IFN-alpha and IFN-beta in mouse serum (FIG. 11).

In a mouse colon cancer model, RNA-Rec induced tumor regression. (FIG. 18) Ascites fluid was collected from tumor bearing mice that were treated with RNA-Rec or PBS, and cytokine profile of these ascites fluid reveal that anti-tumor (pro-inflammatory) cytokine level was increased in RNA Rec-treated mice, while immunosuppressive (anti-inflammatory) cytokine level was reduced in RNA Rec-treated mice (FIG. 19).

In a mouse lymphoma model, checkpoint inhibitor (anti-PD1 antibody) was administered with or without RNA-rec to tumor bearing mice through intratumor injection. Significant tumor regression was observed in mice treated with RNA-Rec+anti-PD1 antibody. (FIG. 15)

Example 8

The role of CD8 and NK cells in RNA-OG-mediated anti-tumor immunity was investigated. As used this example, the term RNA-OG refers to the RNA nanostructure comprising SEQ ID NO:1. A schematic showing the experimental design that was used to evaluate the effect of the depletion of CD8 or NK cells using anti-CD8 or anti-NK monoclonal antibodies, respectively, is shown in FIG. 46A. The antibody was injected on the same day of, but 4 hrs post tumor injection. RNA-OG was administered one day post antibody treatment (100 ug/dose for total four doses). An irrelevant IgG was included as a negative control for CD8/NK depletion. As shown in FIG. 46B, tumor growth monitored by measuring iRFP fluorescence intensity in mice receiving various treatments. These experiments indicate that depletion of NK cells completely abrogates the anti-tumor immunity induced by RNA-OG and depletion of CD8 compromises the anti-tumor immunity induced by RNA-OG.

Example 9

Adjuvant Activity of RNA Origami

Single-stranded RNA (ssRNA) and double-stranded RNA (dsRNA) can be detected by pattern recognition receptors in mammalian cells. Synthetic ssRNA and synthetic dsRNA have been explored as immunostimulating adjuvants (Alexopoulou, et al., 2001. Nature 413:732-738.). For example, polyinosinic: polycytidylic acid (polyIC), a synthetic analog of dsRNA, has been widely studied as an adjuvant in treating diseases such as upper respiratory tract infections and tumors, therefore, allowing it to be explored as an adjuvant in flu and cancer vaccines. However, susceptibility of dsRNA to nuclease digestion tends to be a concern, especially when such dsRNA are used in vivo. As described in the experiments below, the RNA nanostructures described herein may have immuno-stimulatory and/or nuclease resistant properties. The methods used to perform the experiment described below were similar to those described in Example 4.

Figure 52:
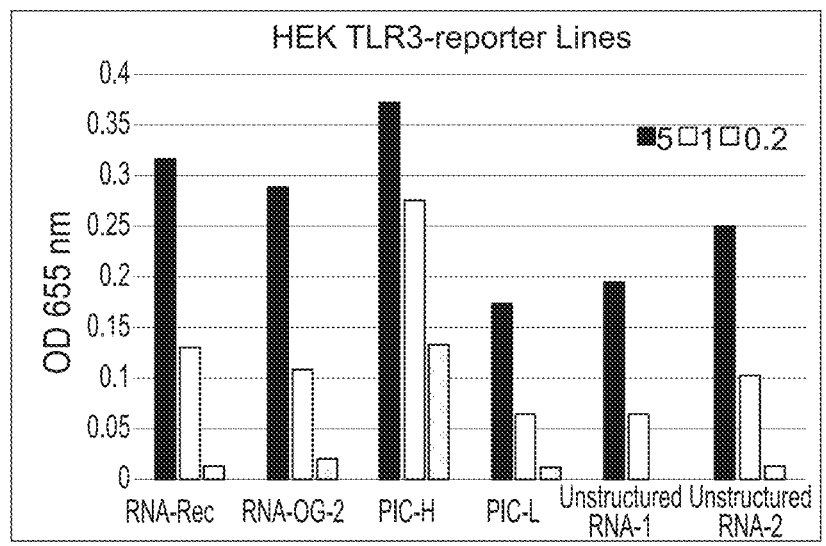
FIG. 52. HEK TLR3-reporter lines.
Figure 53:
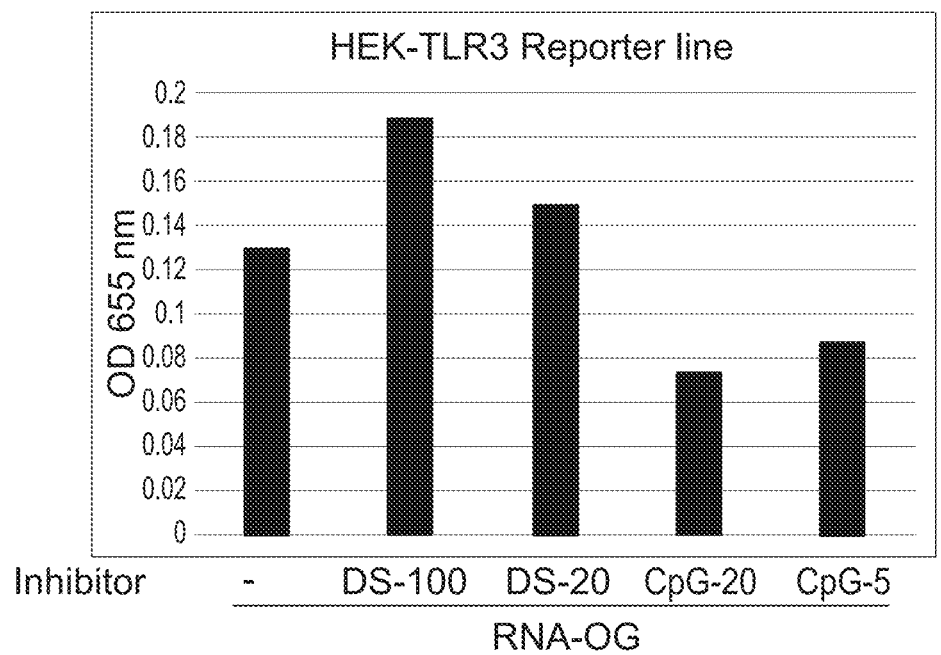
FIG. 53. HEK-TLR3 Reporter line.
Figure 54:
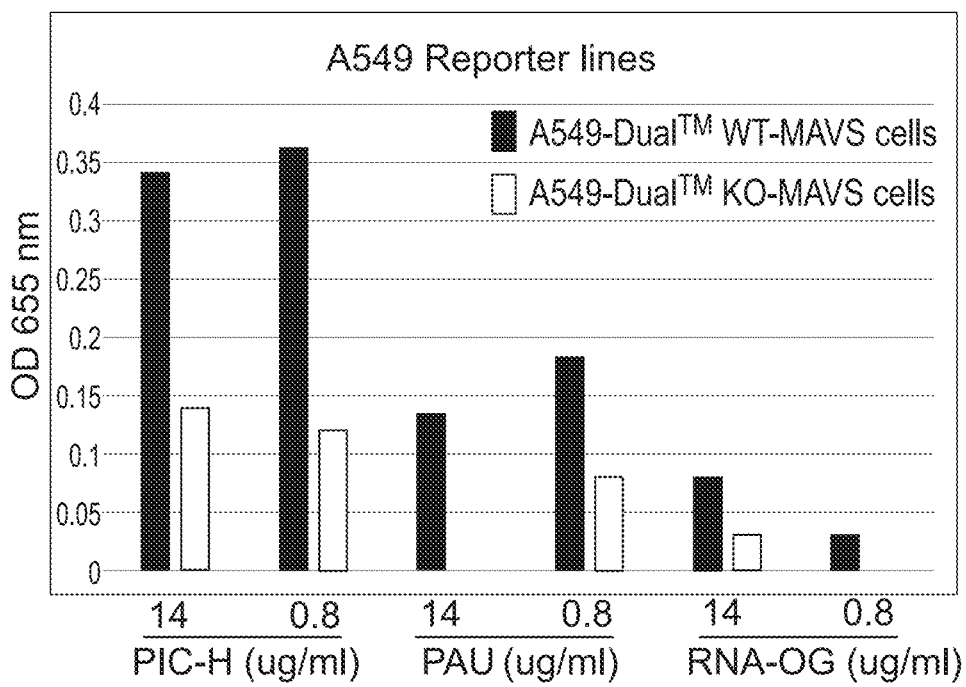
FIG. 54. A549 Reporter Lines.
Figure 55:
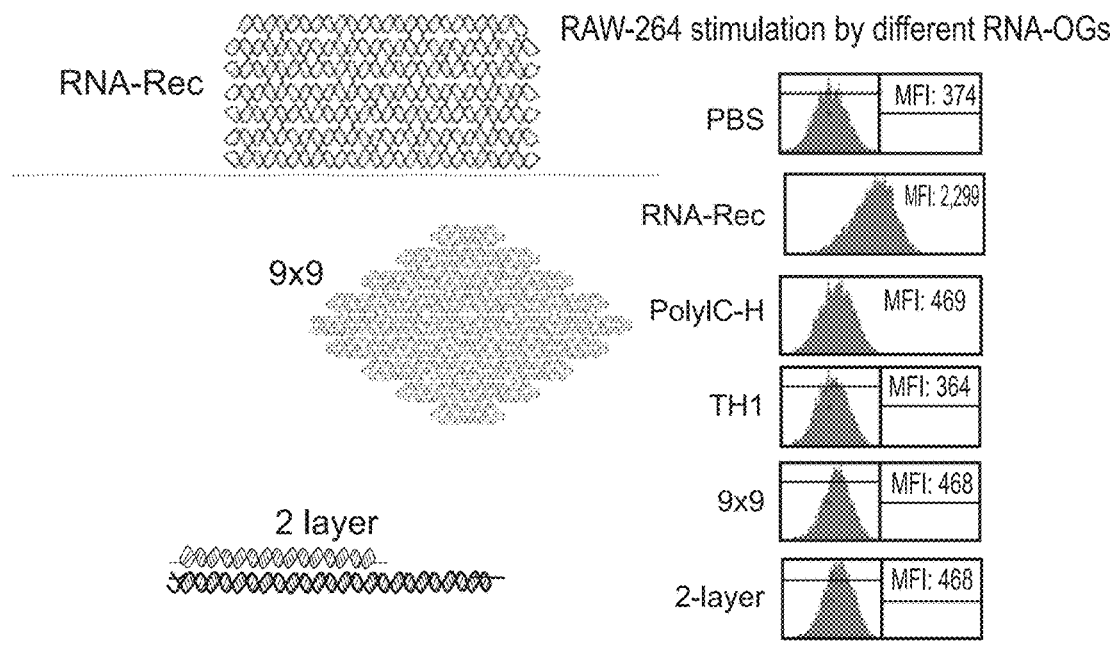
FIG. 55. RAW-264 stimulation by different RNA-OGs.
Figure 56:
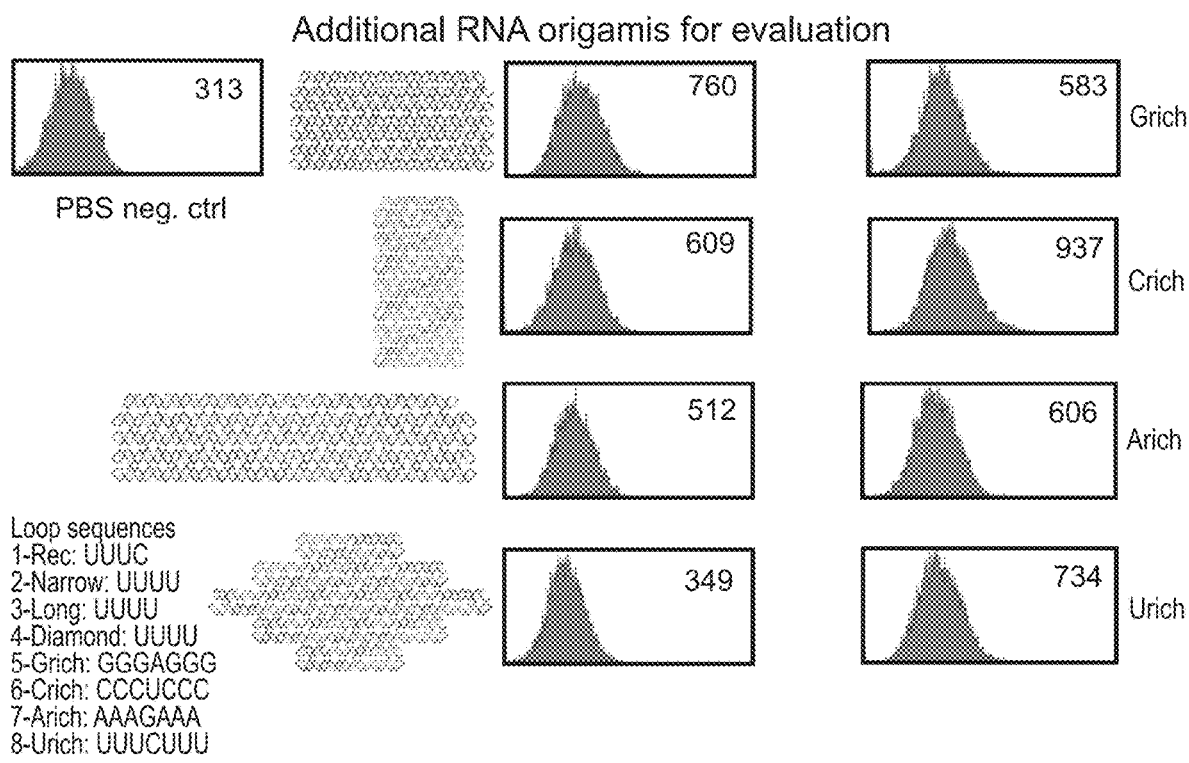
FIG. 56. Additional RNA origamis for evaluation.
Figure 57:
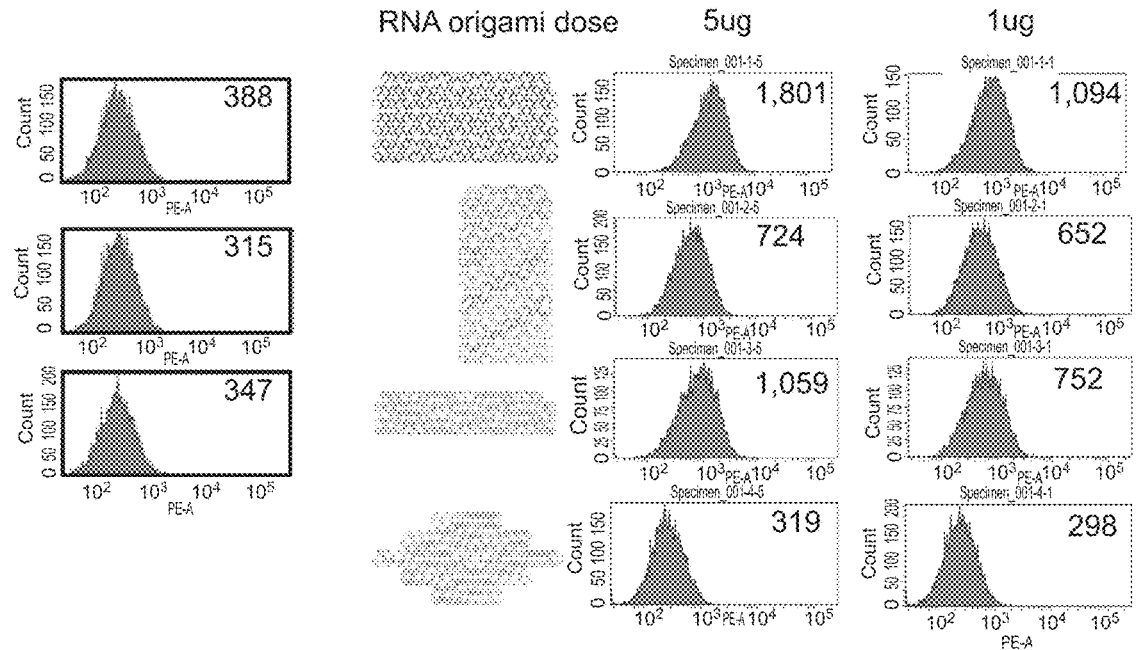
FIG. 57. Dose dependent activation of various RNA origami shapes.
Figure 58:
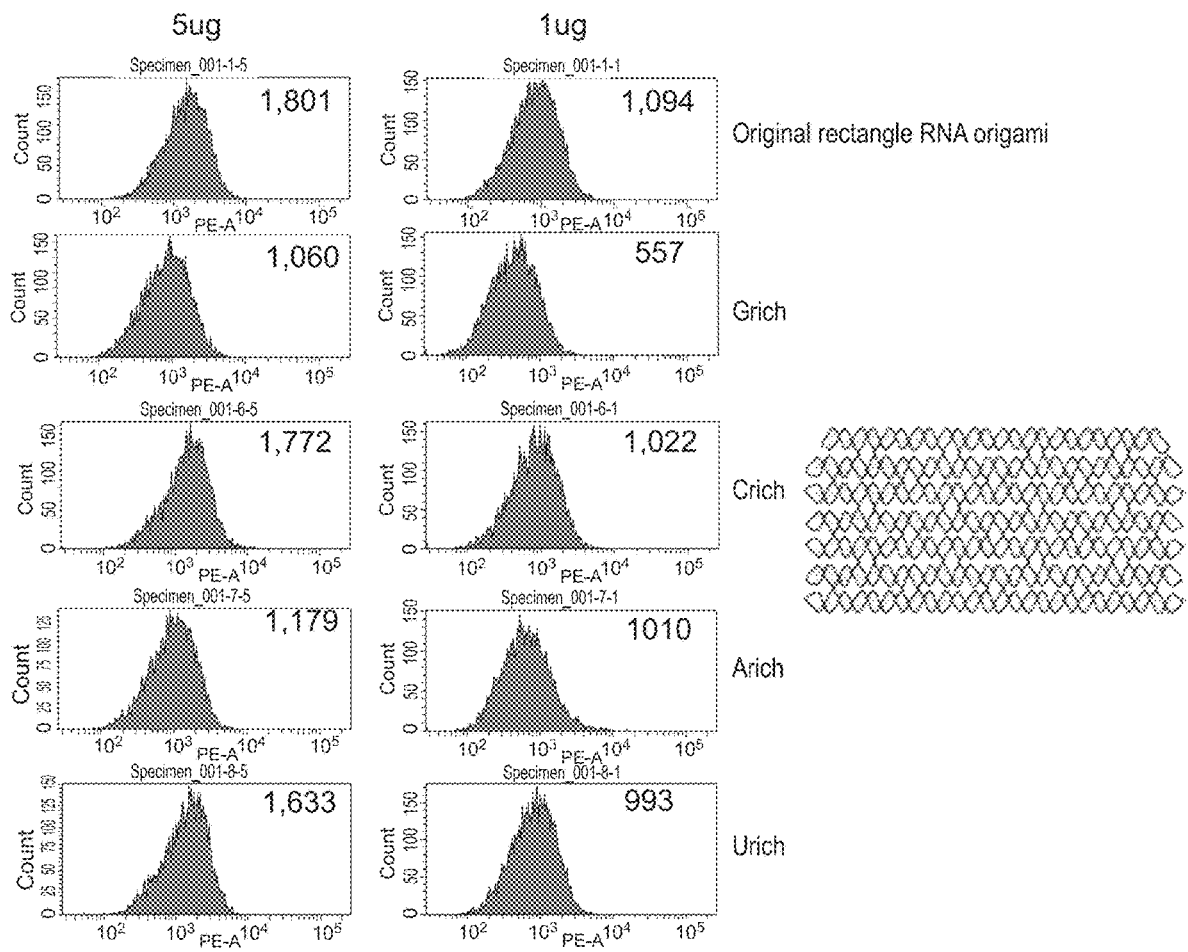
FIG. 58. Dose dependent activation of rectangular RNA origami.

As described below, RNA-OG (SEQ ID NO:1) was shown to have adjuvant activity. Specifically, the RNA origami stimulated TLR3 reporter lines (FIGS. 52-53), functioning as a potent TLR3 ligand. It also stimulated A549 reporter lines (FIG. 54). RAW-264 was stimulated by different RNA-OGs (FIGS. 55-56). The cell lines were activated in a dose-dependent fashion (FIGS. 57-58). RNA-OGs have much more potent stimulatory activity than PolyIC, which may be dependent on the shape of RNA-origami and/or the nucleotide composition at the loop of the RNA-rectangle.

Figure 59:
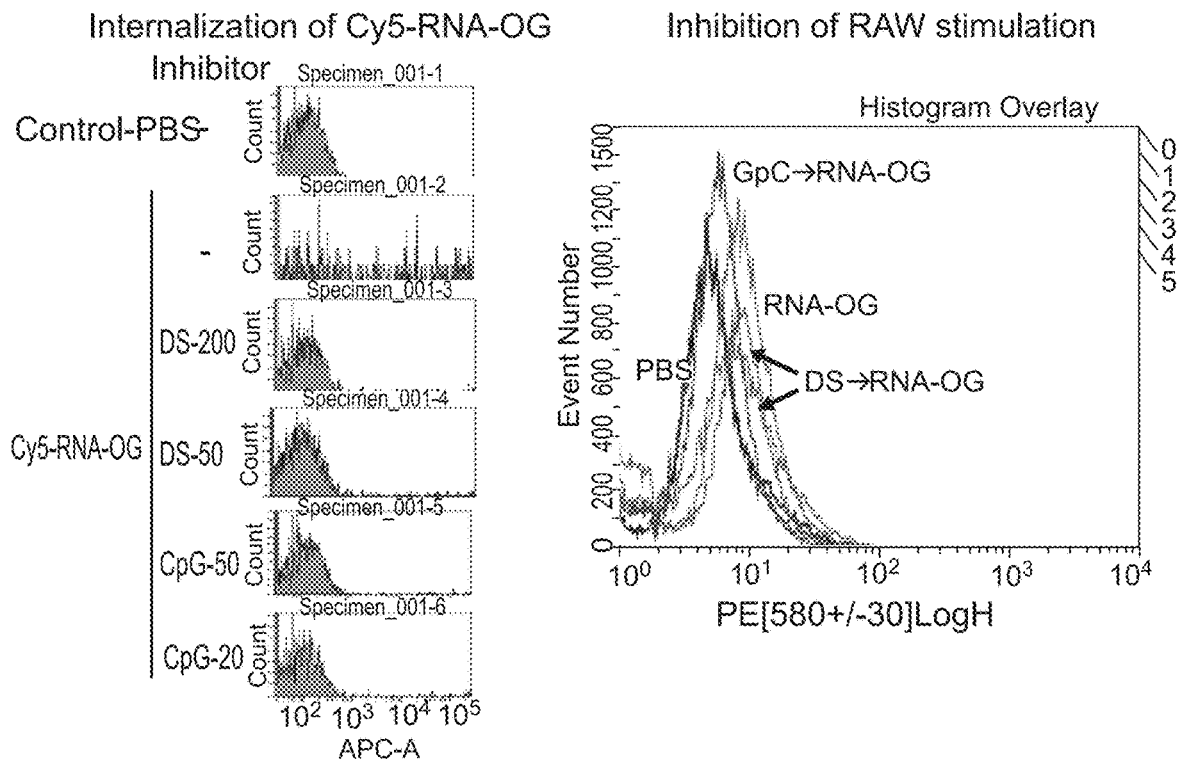
FIG. 59. Internalization of Cy5-RNA-OG and Inhibition of RAW stimulation.
Figure 60:
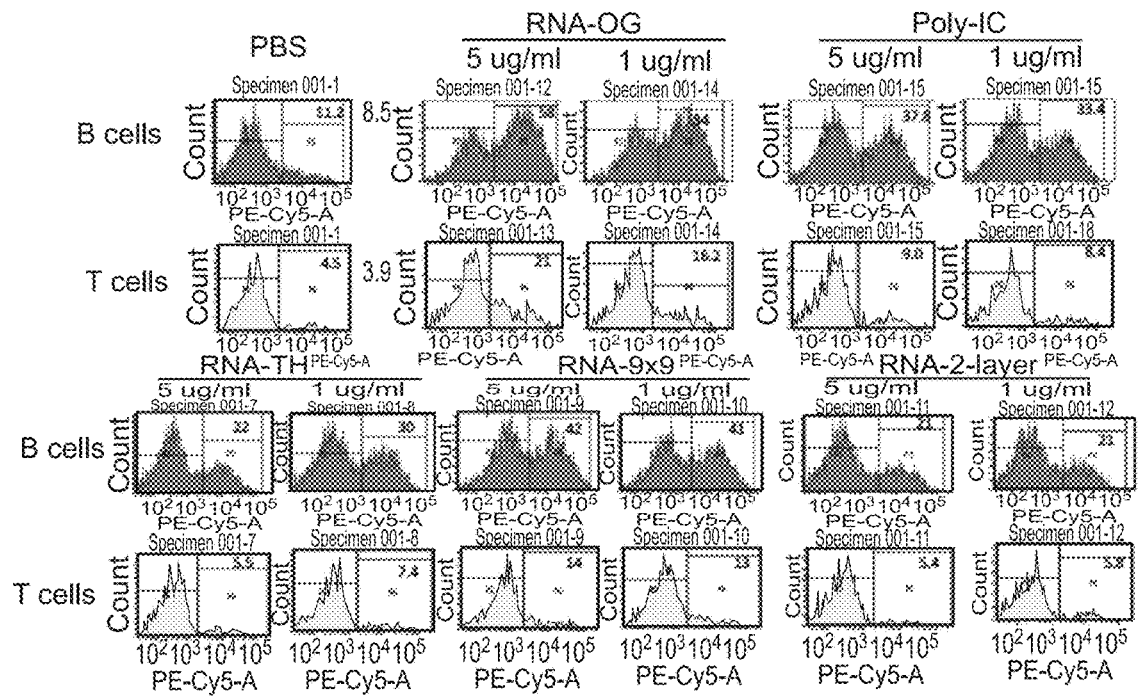
FIG. 60. Activation of splenic B and T cells, revealed by percentage of CD69+ cells over total B and T cells, respectively, 24 hrs after incubation with various RNA-origamis, polyIC with high-molecular weight, as well as PBS control.

The TLR3-dependent activation was inhibited by CpG oligonucleotides (ODNs) (FIGS. 59-60), indicating RNA-OG and CpG-ODN share the same internalization pathway.

RNA-OG does not activate the cytoplasmic RIG/MDA5 signaling pathway (unlike polyIC). Similar to the finding in TLR3-reporter line, the stimulation of RAW cells could be inhibited by GpC-ODNs, presumably via blocking cellular uptake of RNA-OGs.

Figure 61:
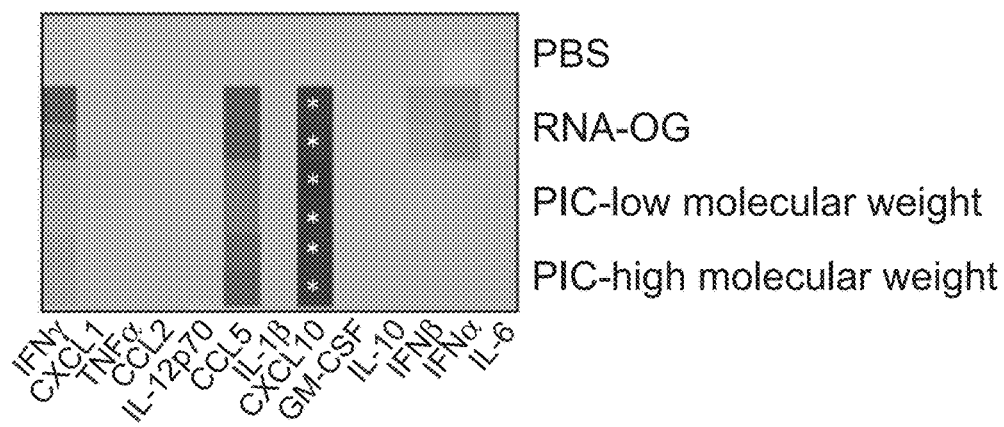
FIG. 61. Production of pro-inflammatory cytokines by splenocytes stimulated in vitro.
Figure 62:
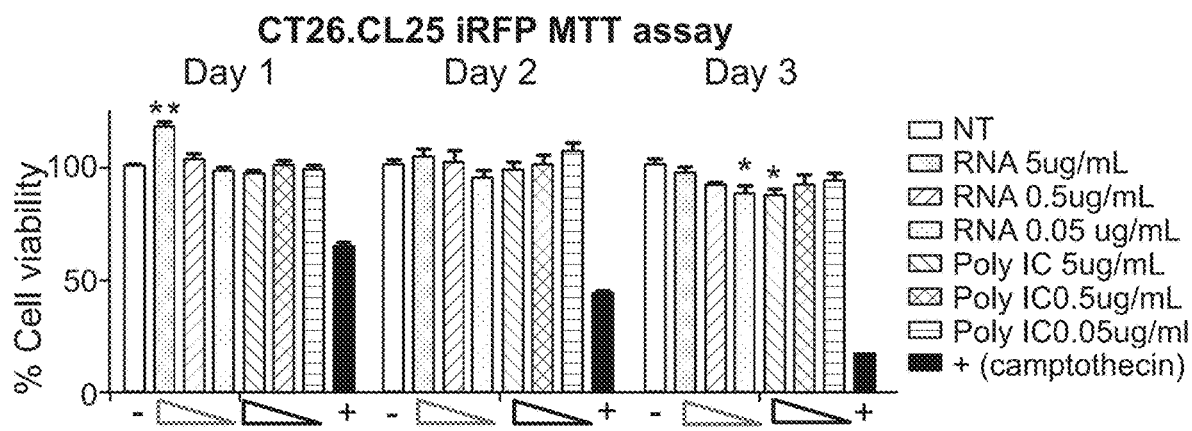
FIG. 62. RNA-origami exerts no direct inhibition on tumor cells.

RNA-OGs induce a higher production of pro-inflammatory cytokines in stimulated splenocytes than PolyIC (FIG. 61). As shown in FIG. 62, the RNA-OGs did not show a direct inhibition on tumor growth in several murine tumor lines.

Anti-Tumor Activities of RNA Origami In Vivo

Figure 64A:
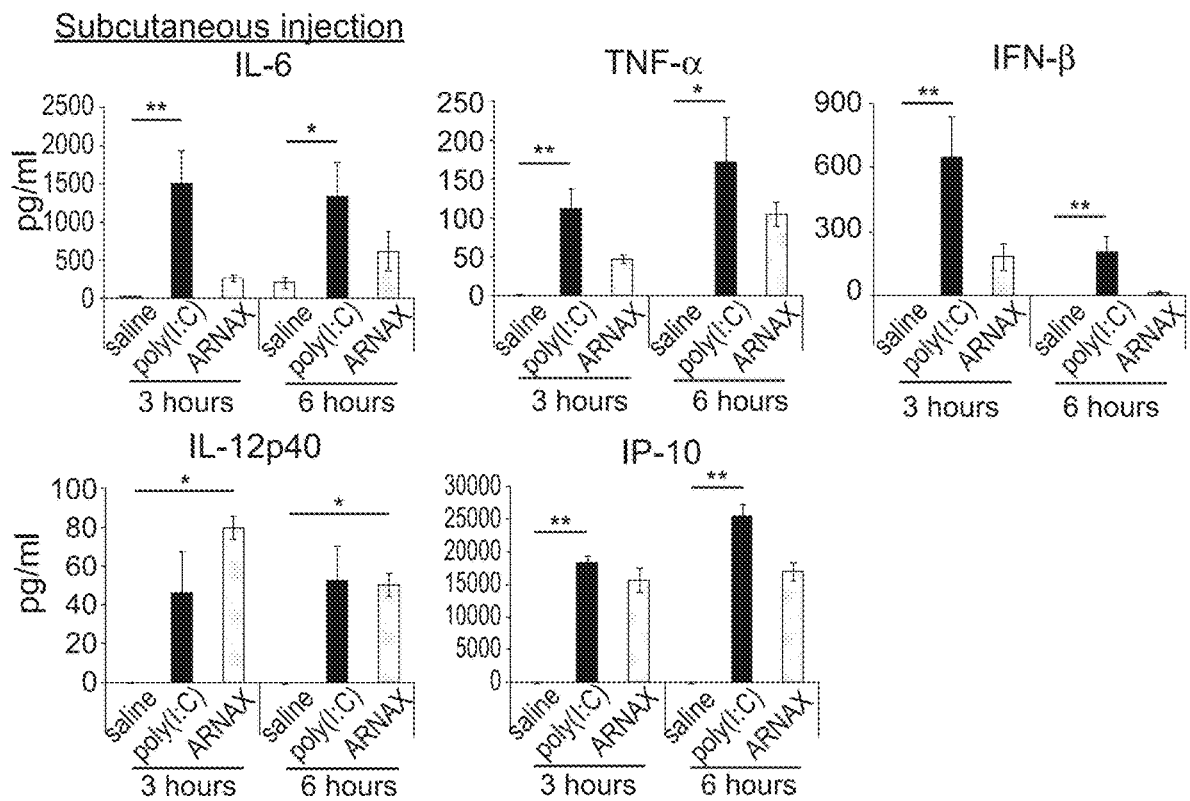
FIGS. 64A-64B. (A) Subcutaneous and (B) intravenous injections. Experimental data provided by the same group, showing that lower levels of IL6, TNFa and IFNb produced by ARNAX than PolyIC, but comparable levels of IP-10 (also known as CXCL-10). Takeda, Y. et al. 2017 Cell Reports.
Figure 64B:
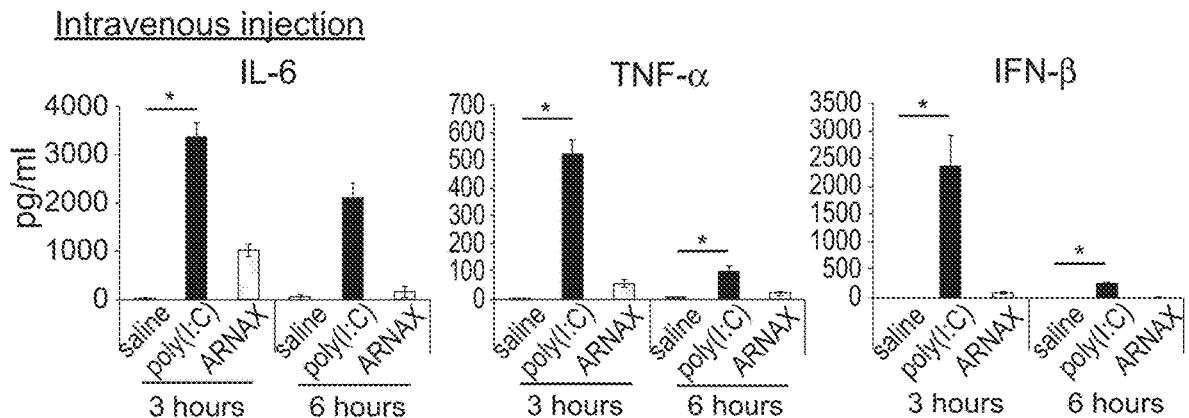
Figure 65:
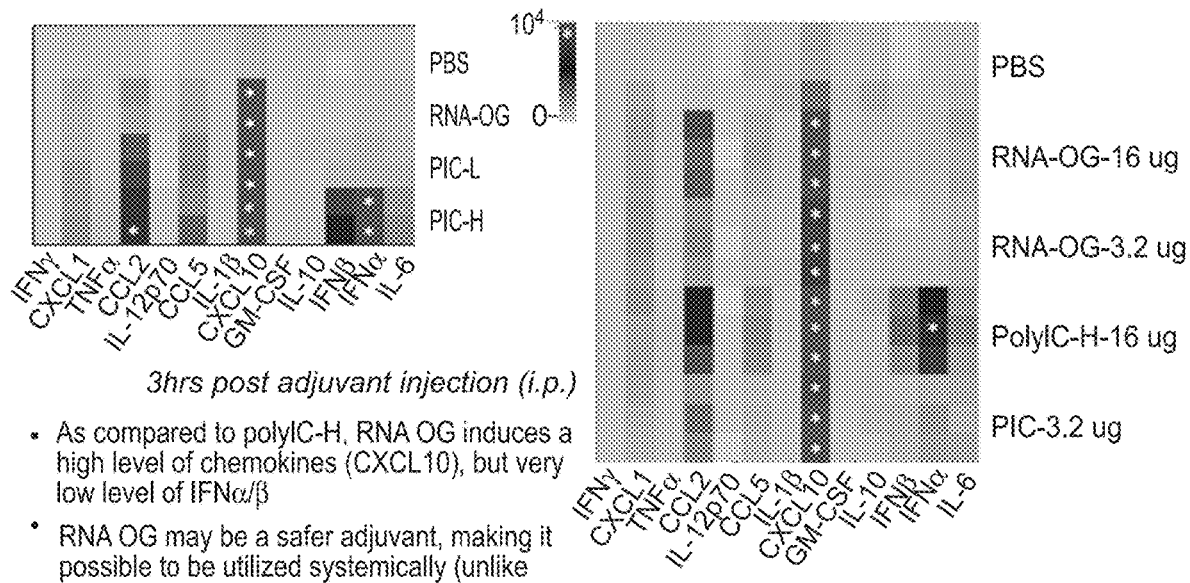
FIG. 65. Serum Cytokines. As compared to polyIC-H, RNA OG induces a high level of chemokines (CXCL10), but very low level of IFNa/b. RNA OG may be a safer adjuvant, making it possible to be utilized systemically (unlike polyIC that is currently tested only locally in clinical trials, due to its high toxicity in human).
Figure 66:
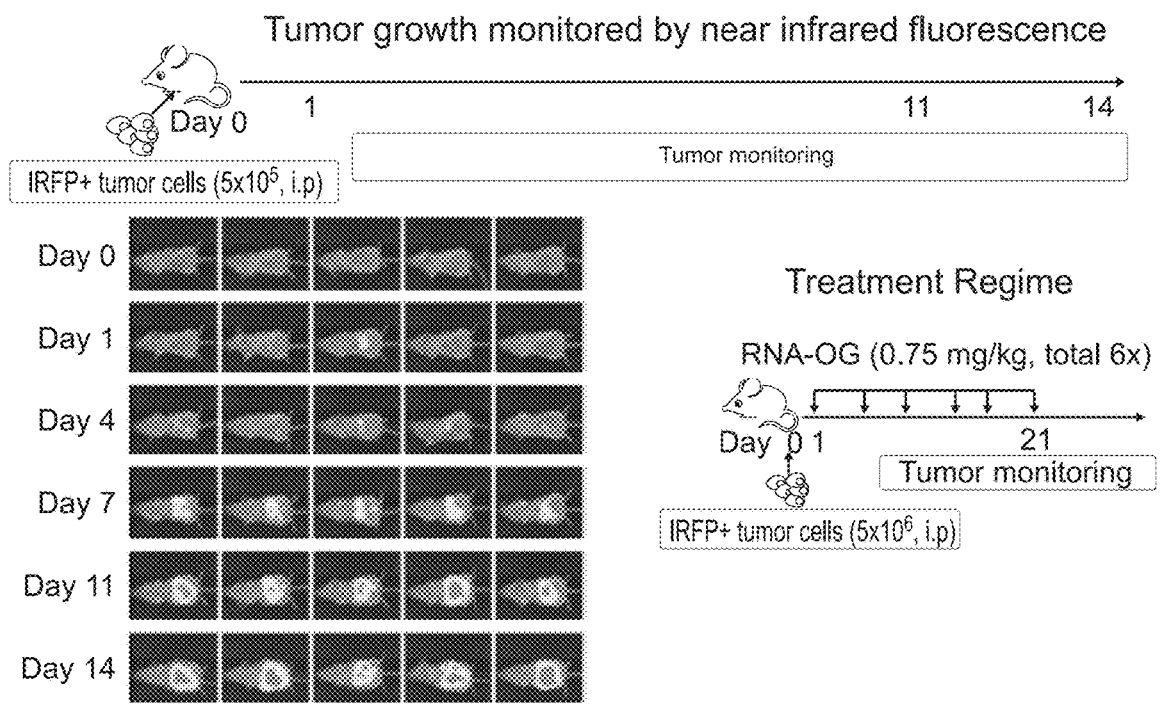
FIG. 66. Tumor growth monitored by near infrared fluorescence.
Figure 67:
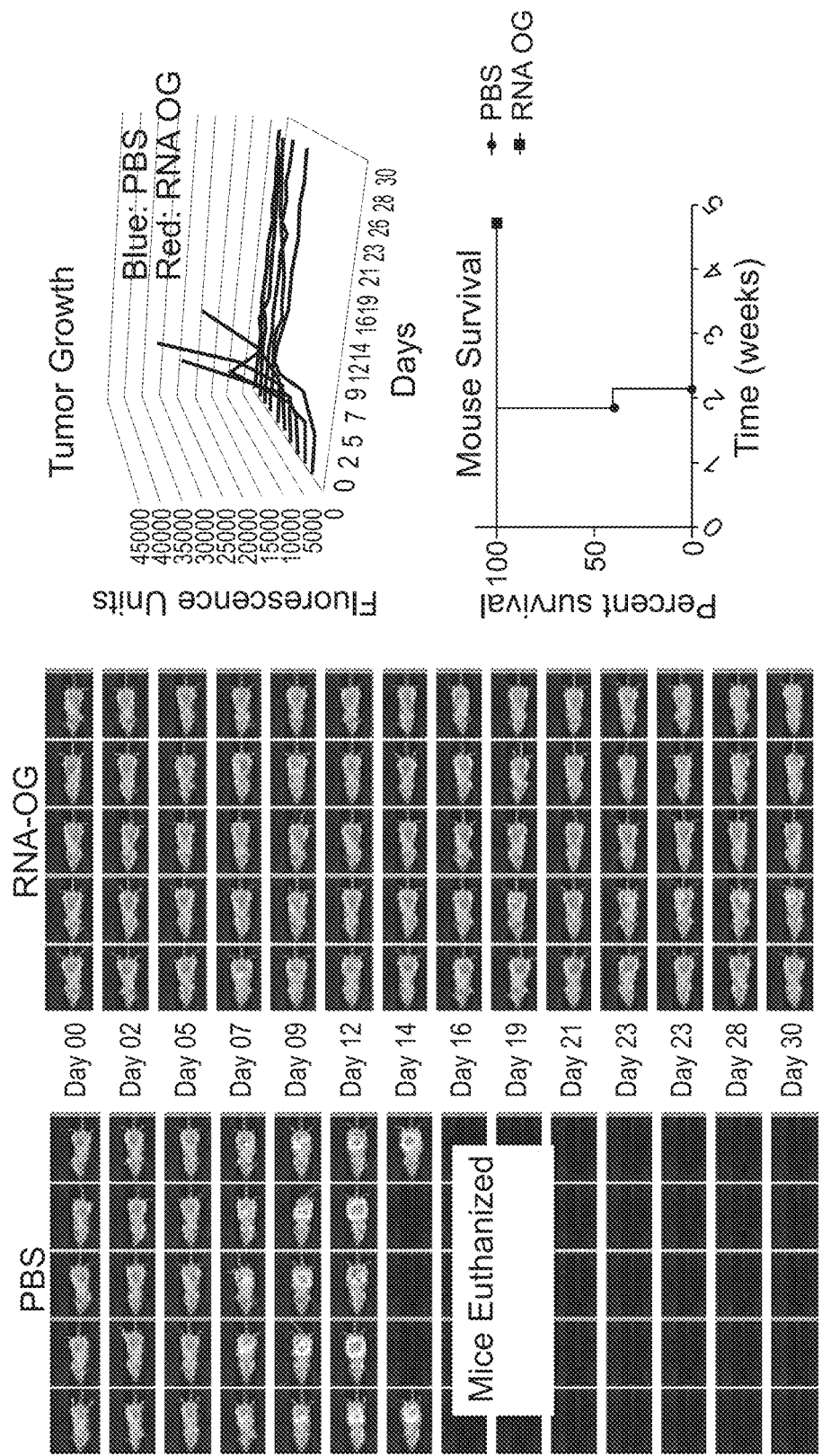
FIG. 67. Treatment with RNA-OG in tumor-bearing mice, starting 1 day post tumor inoculation, resulted in significant delay or regression of tumor growth.
Figure 68:
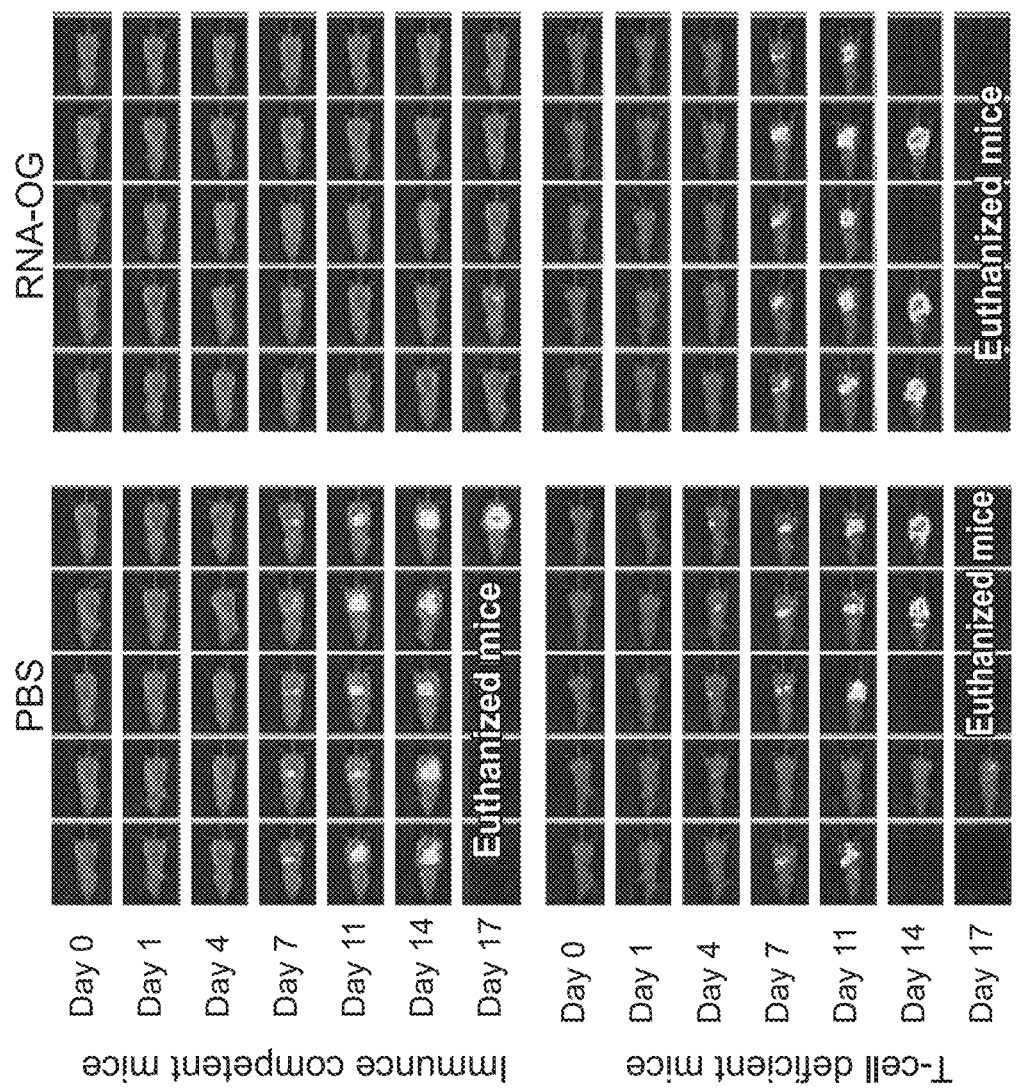
FIG. 68. Comparison of RNA-OG-mediated anti-tumor effect between immunocompetent Balb/c mice (top panels) and T-cell deficient nude mice (bottom panels). Tumor growth of five control and five RNA-OG treated mice was monitored over time via near infrared imaging of iRFP. The fluorescence intensities of these individual mice are displayed on the right panels to show time-dependent tumor progression or regression. The mice with large tumor loads were euthanized between day 14-day 17 post tumor injection.
Figure 69:
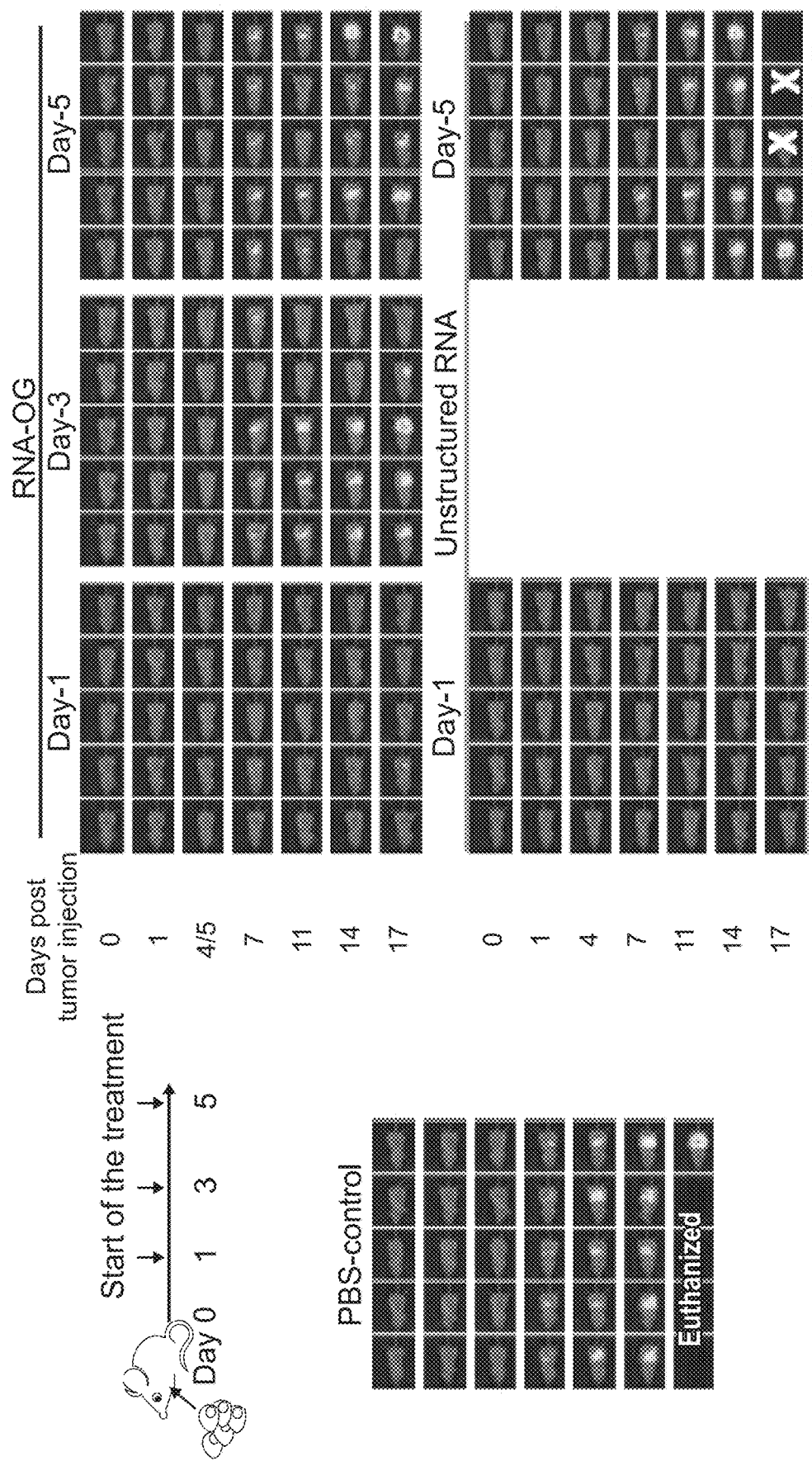
FIG. 69. Time-dependent anti-tumor effect.

Low levels of pro-inflammatory cytokines are produced in vivo in response to RNA-OG, making it safer adjuvant than polyIC. PolyIC-H induced both TLR3 and MDA5/RIG pathways. The latter has been implicated to toxicity (FIG. 63). Experimental data show that lower levels of IL6, TNFα and IFNb produced by ARNAX than PolyIC, but comparable levels of IP-10 (also known as CXCL-10) (FIG. 64A-B). Different cell types activated by these adjuvants in vitro vs in vivo. RNA-OG does not activate RIG/MDA5 pathway that has been linked to systemic cytokine toxicity, therefore representing its better safety profile than polyIC (FIG. 65). RNA-OGs inhibited tumor growth (FIG. 66-69). Repetitive injections of low dose (16 µg/dose) result in delay and regression of tumor growth. The observed anti-tumor activity is dependent on the intact adaptive immune system.

The analysis of the ascites cytokines collected from tumor-bearing mice showed that treatment with RNA-OG resulted in a significant reduction and increase of immunosuppressive and anti-tumor pro-inflammatory cytokines, as compared to the PBS control mice (FIG. 19).

The combination of anti-PD1 antibody and RNA-origami enhances anti-tumor activity (FIG. 15).

Thus, RNA-OGs are effective as anti-tumor immunotherapeutics. They have potent adjuvant activity without systemic cytokine profile. The induction of tumor regression is dependent on T-cell mediated immunity.

Example 10

Figure 70:
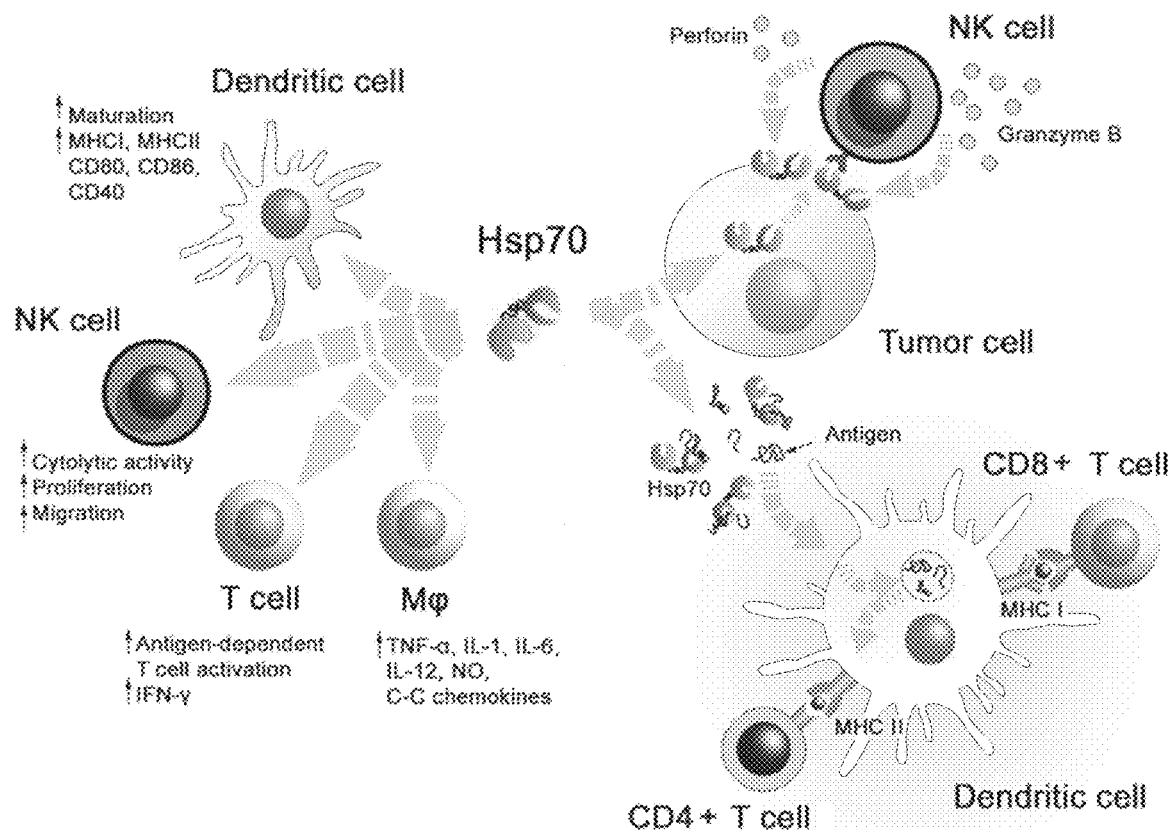
FIG. 70. Schematic of functions of HSP70 protein and derived peptides (known as TPP or TKD).

Heat shock proteins (HSPs) with the molecular weights of approximately 70 and 90 kDa have the capacity to stimulate antitumor immune responses as carriers for antigenic peptides. (Shevtsov M. and Multhoff G. Heat Shock Protein-Peptide and HSP-Based Immunotherapies for the Treatment of Cancer, 2016 Apr. 29; 7:171, Frontiers in Immunology, see FIG. 70.) Heat Shock Protein-70 (HSP70) and derived peptides function as chaperones. Functionally, they can act as tumor-specific antigens and as immunogens. Linking HSP70 to nanoparticles allows for the capture of tumor cell lysates to present antigens to dendritic cells (DCs). HSP70 protein and derived peptides can pre-activate NK cells for direct killing of HSP-70$^+$ tumor cells. Dose-dependent and saturable enhancement was found at 0.2-2.0 µg/ml for activation, and at >4 µg/ml no responses. HSP70 induced the proliferation of tumor cells, induced NK cell migration toward HSP70$^+$ tumor cells, the lysis of HSP70$^+$ tumor cells by binding to granzymes and inducing apoptosis of target cells, and increased CD94 expression that can associate with NKG2A and bind to HSP70 to engage with tumor cells. HSP70 also increase DC maturation and cross-presentation, increased Th1 and CTL activity, and increased M1 activity. HSP70/TKD moved to clinical trials (I & II), where one out of 12 patients with brain tumor showed CR, who showed increased Th1 and reduced Treg, and where 7 out of 12 patients with HCV-HCC showed CR or SD after receiving HSP70-mRNA transfected to DC.

Nucleic acid-based Toll-like receptor ligands, such as poly IC, ssRNA and CpG oligonucleotides are potent adjuvants via activation of TLR3, TLR7/8 and TLR9 signaling pathways, respectively. Tumor-specific antigens in combination with these TLR ligands have been explored as cancer vaccines to reduce tumor growth. Building on the finding of RNA origami as a TLR3 ligand discussed above, peptide-tagged RNA-origami complexes were constructed, and the complexes were shown to be stable and able to induce strong anti-tumor immunity.

Heat shock protein 70 (HSP70) is a cellular stress response protein, presumably protecting cells from toxic agents and harsh environment. On the other hand, because of its chaperon function in associated with tumor specific or tumor-associated antigens (TSAs or TAAs), HSP70 has also been explored as a TAA. It was reported to induce multi-faceted responses against cancer cells, including both innate and adaptive immunity. Interestingly, one peptide derived from the C-terminus of HSP70, known as TKD peptide, has been demonstrated (1) to activate NK cells, (2) to direct tumor-targeted binding and internalization, and (3) to promote DC cross-presentation and ultimately induction of cytotoxic T cell responses toward tumor cells. It was investigated whether the combination of this peptide with RNA-origami would constitute a potent cancer vaccine.

Given the potent and unique adjuvant activity of RNA-origami, it was hypothesized that complexing RNA-origami with TKD peptide would increase tumor-specific immunity. RNA-origami was complexed with tumor targeting peptide (TPP) TKD-peptide. TKD (TPP)-peptide has the sequence TKDNNLLGRFELSG (SEQ ID NO:19) (C-terminal region of human HSP70), which is highly homologous to murine HSP70 sequence TRDNNLLGRFELSG (SEQ ID NO:20).

To simplify the complex formation with RNA-origami, the TKD was modified by adding a cystine (C) at the N-terminus and adding 10 lysine residues (SEQ ID NO: 21) to the C-terminus of the TKD peptide, thus creating CTKD-K10: CTKDNNLLGRFELSGGGSK$_{10}$ (SEQ ID NO:18). The C residue allows peptide-dimerization to promote peptide binding to and clustering of HSP70 on the surface of tumor cells. Pre-incubation of CTKD-K10 with splenocytes can activate NK cells, which in turn kill tumor cells. CTKD-K10 can also bind to many tumor cells, known as tumor penetrating peptide (TPP) and upon binding, it can induce internalization of the peptides, possibly via HSP70 oligomerization, reaching to endosome, lysosome and even mitochondria.

Figure 71:
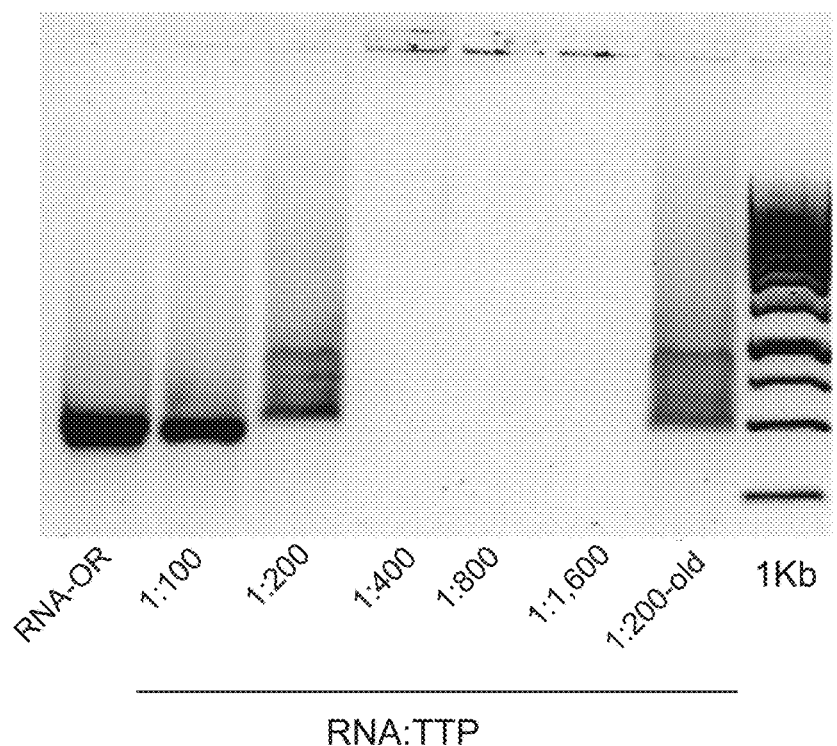
FIG. 71. Different RNA-OG/TTP ratios lead to different sizes of complexes. The complex appears stable after its formation as the old and new complexes formed at 1:200 ratios displayed similar pattern of mobility (lane 3 and lane7).

RNA-origami are negatively charged structure, so the positive charge of polylysine on the TKD-K peptides enables direct, non-covalent complex formation with the RNA-origami. The complex formation was demonstrated by gel electrophoresis (FIG. 71). Depending on the RNA: peptide ratios, the size of the complexes is increased and some become aggregated. Different RNA-OG/TTP ratios lead to different sizes of complexes. The complex appears stable after its formation as the old and new complexes formed at 1:200 ratios displayed similar pattern of mobility (FIG. 71, lane 3 and lane 7).

Figure 72:
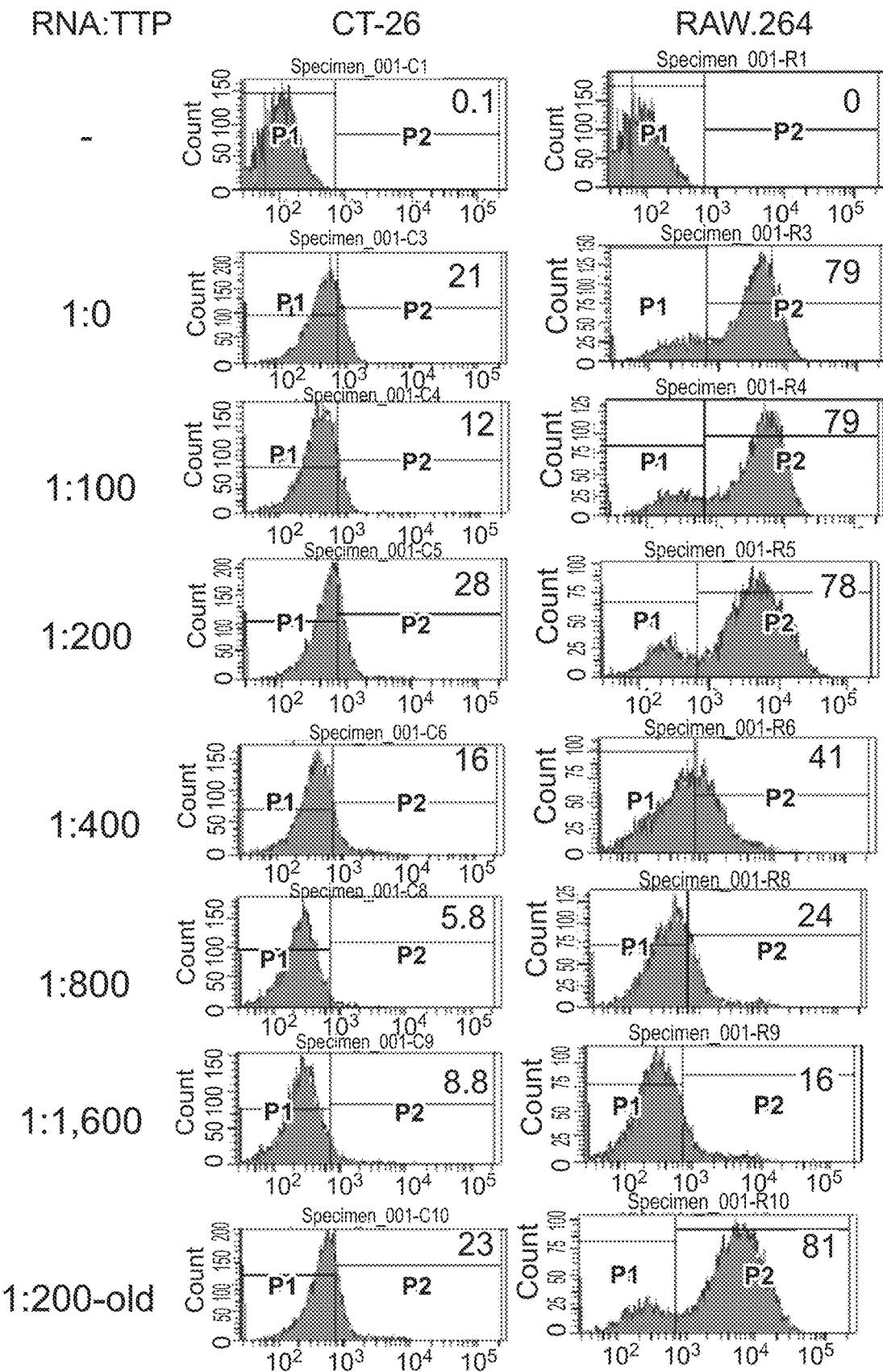
FIG. 72. Different complexes exhibit different binding/internalization profiles, as shown by flow cytometry. Higher internalization of RNA-OG by RAW cells than CT-26. Upon increase amount of the peptide, the lower level of binding to both CT-26 and RAW cells. The complex formation of RNA-OG with TPP-lysine peptide. The complexes formed under different peptide to RNA-OG ratios were analyzed by electrophoresis (Left panel). The higher the peptide/RNA ratios, the larger the complex displayed (i.e., slower migration). The impact of TPP on the binding TPP-RNA-OG complexes, revealed by the fluorescence intensity of fluorescence-labeled RNA-OG (right panel). When the RNA/TPP ratio reaches to 1:400, the internalization of the TPP/RNA-OG complexes is significantly reduced.

Different complexes exhibit different binding/internalization profiles, as shown by flow cytometry (FIG. 72). It was observed that the internalization of RNA-OG-peptide complex could be hindered if more peptides associated with the RNA. It was found that at RNA-OG:peptide ratio of 1:100 or 1:200, the complex size was slightly shifted up, but could still be taken up by both CT-26 colon cancer cell line and RAW-264 macrophage line (FIG. 72). Higher internalization of RNA-OG by RAW cells than CT-26. Upon increase amount of the peptide, there was lower level of binding to both CT-26 and RAW cells. It was predicted that the combination of the RNA-origami and TKD peptide would further enhance and integrate TLR3 activation, NK-activation, antigen-cross presentation for effective induction of cytotoxic T cell responses.

Figure 73:
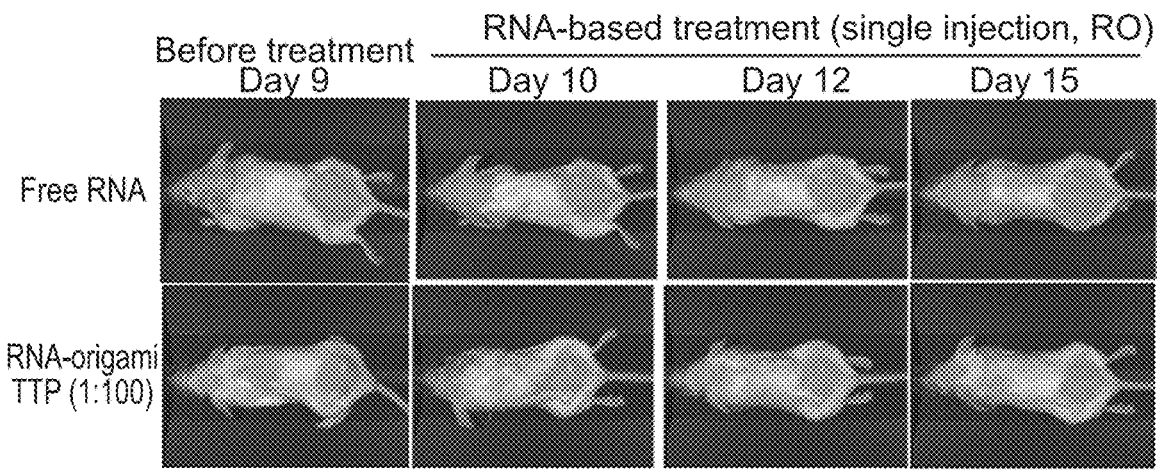
FIG. 73. Fluorescence positive tumor cells were inoculated at day 0 and tumor nodule formed on day 9 (i.e., pretreatment). These mice were then treated with a single injection of different types of RNA structures, free RNA or RNA-origami coated with tumor-targeting peptide (TTP). The mice were monitored for more than 20 days, and tumor regression was found in the mouse receiving the RNA-Origami polymer, but not the mouse administered free RNA.

In an in vivo tumor model, the RNA-OG—peptide complex was tested at the 1:100 ratio. Interestingly, a single injection of this complex into a mouse-bearing tumor led to complete tumor regression (FIG. 73). Fluorescence positive tumor cells were inoculated at day 0 and tumor nodule formed on day 9 (i.e., pre-treatment). These mice were then treated with a single injection of different types of RNA structures, free RNA or RNA-origami coated with tumor-targeting peptide (TTP). The mice were monitored for more than 20 days, and tumor regression was found in the mouse receiving the RNA-Origami polymer, but not other groups (including RNA-origami only group).

Figure 74A:
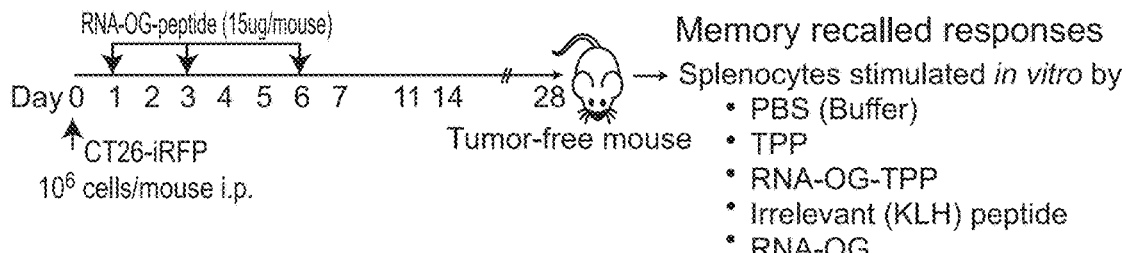
FIGS. 74A-74C. A. Memory recalled responses. Splenocytes stimulated by PBS (Buffer), TPP, RNA-OG-TPP, Irrelevant (KLH) peptide, or RNA-OG; B. Representative ELISPOT redout, where each spot represents an IFNg-producing immune cell that was activated by different stimuli; and C. Quantification of ELISPOTS. Tumor-free mouse developed TPP-specific immunity as revealed by ELISPOT assay, in which TTP-stimulated splenocytes produced IFNg after the splenocyte cultured with TPP, but not irrelevant peptides.
Figure 74B:
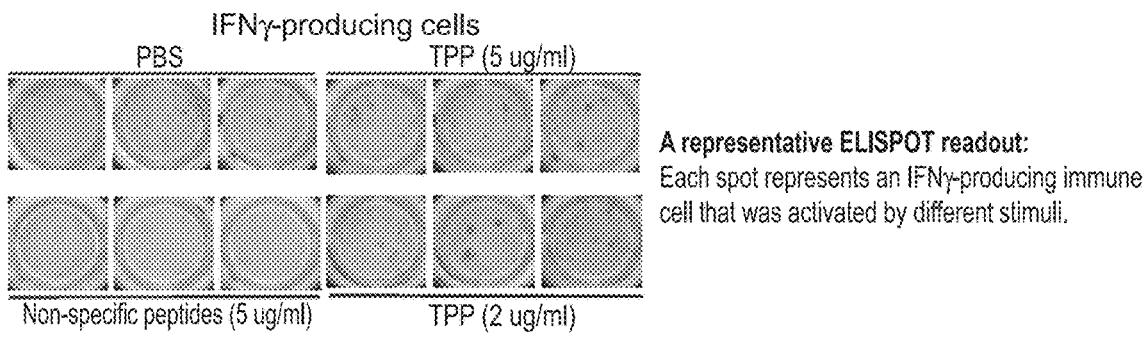
Figure 74C:
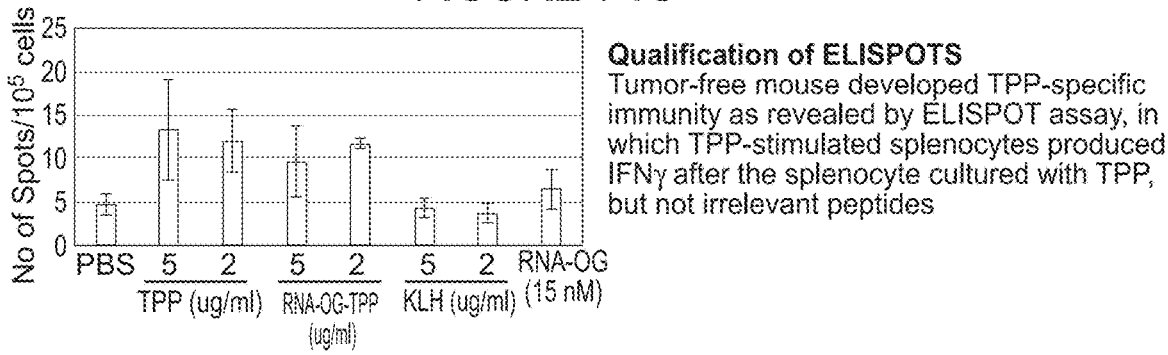

In a separate experiment, RNA-OG-peptide complex (1:200 ratio) were also injected intraperitoneally, where the intraperitoneal colon tumor cells were inoculated (FIG. 74A). One RNA-OG/TPP and RNA-OG out of five treated mice showed tumor regression, whereas all the control groups, including the mice receiving free RNA, succumbed to tumor growth. The adaptive immunity of splenocytes recovered from the tumor-free mouse treated with RNA-OG/TPP were further tested and it was found that these cells could be reactivated in vitro by the co-culture with TPP, but not when administered irrelevant KLH peptides (FIGS. 74B-74C). Thus, tumor-targeted adaptive immunity was elicited by the RNA-OG-TPP complexes.

Example 11

Figure 75:
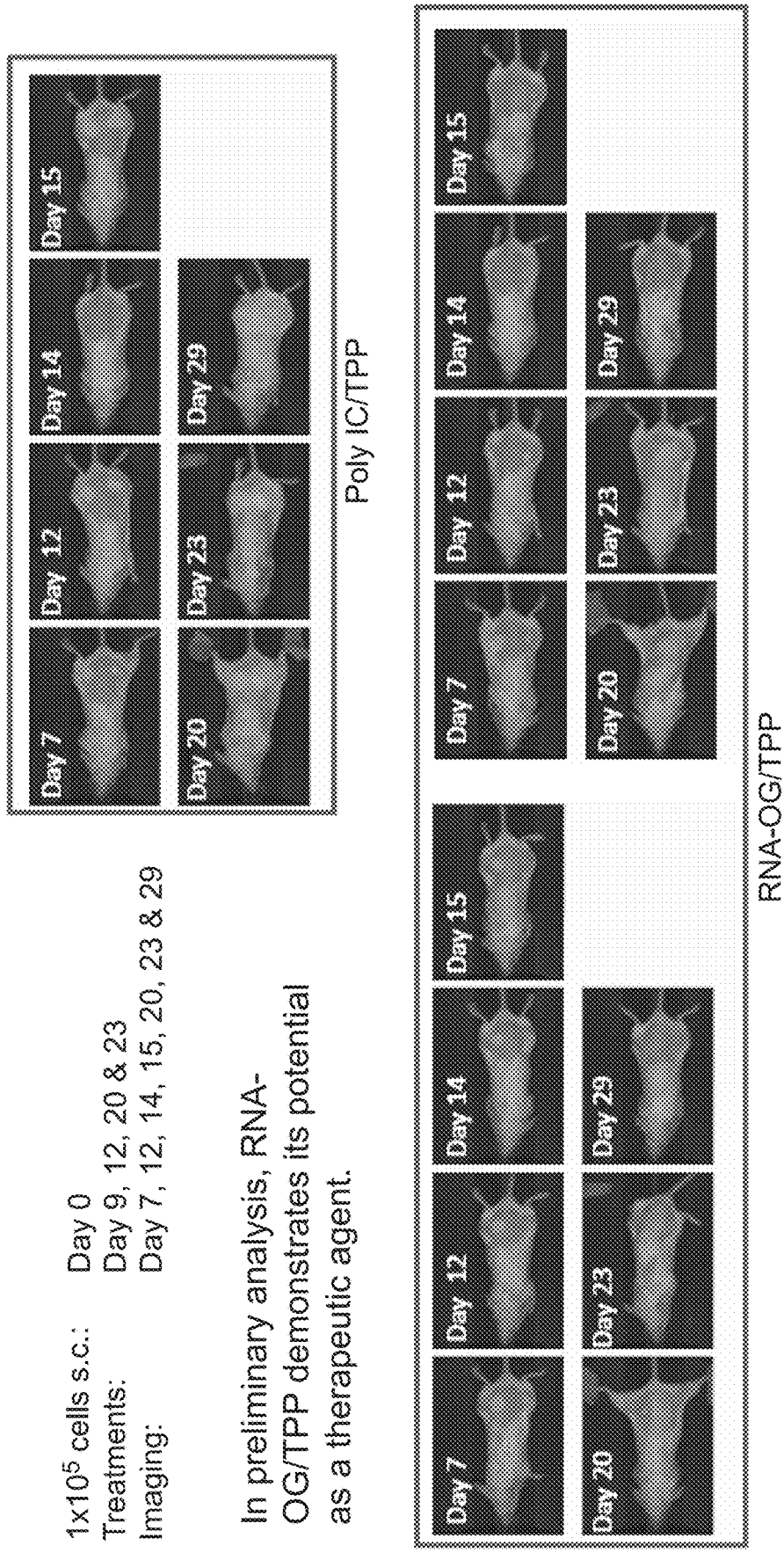
FIG. 75. Anti-tumor activity of RNA-OG/TPP complexes.

Stimulation of antigen-specific immunity (AG-specific immunity), wherein the antigen is TPP. Anti-tumor activity of RNA-OG/TPP complexes were studied. The mice treated with RNA/TPP did show an elevated number of ELISPOTs specific to TPP, which reflects TPP-specific T cell responses. Thus, the RNA-OG/TPP demonstrated its potential as at therapeutic agent (FIG. 75).

Example 12

Figure 76:
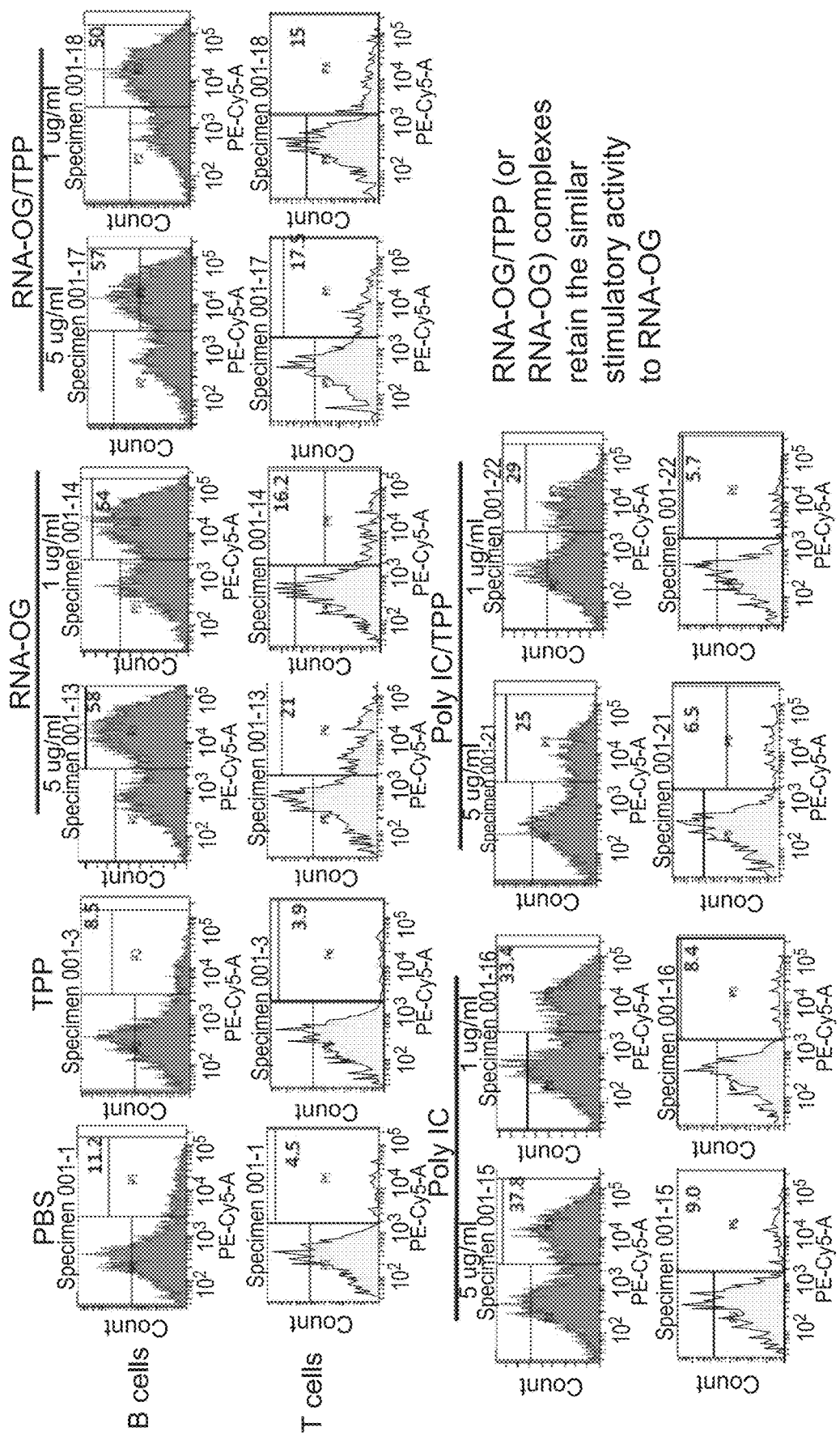
FIG. 76. RNA-OG/TPP (or RNA-OG) complexes retain the similar stimulatory activity to RNA-OG. At the TPP/RNA ratio of 100:1, the TPP/RNA-OG complexes displayed comparable stimulatory activity as RNA-OG.
Figure 77:
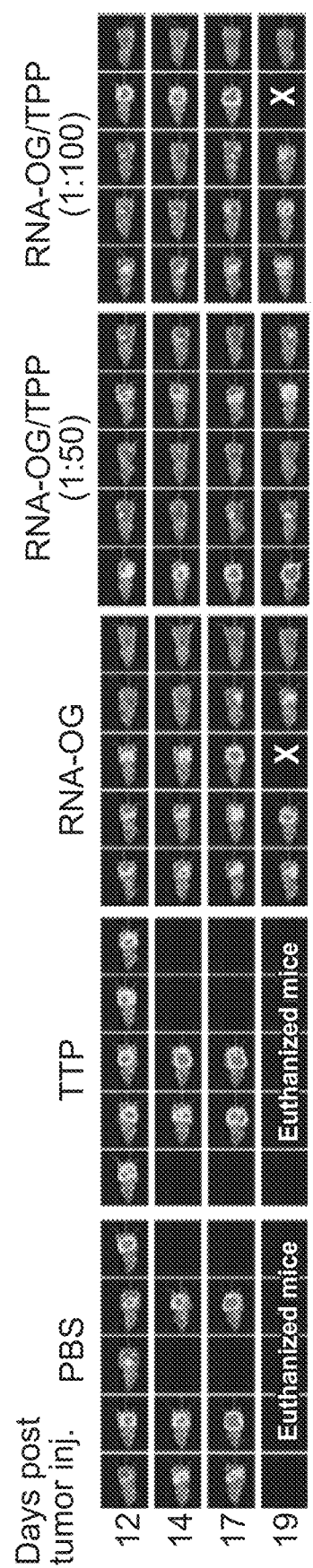
FIG. 77. Anti-tumor effect of RNA-OG complexed with TPP. The combination of RNA-OG and TPP further delays tumor growth. The tumor-bearing mice treated with RNA-OG with or without complexed with TPP were monitored for tumor growth. The mice treated with RNA-OG/TPP at 1:50 ratio appeared to show slower tumor progression than those treated with RNA-OG alone or RNA-OG/TPP at 1:100.

In certain embodiments, RNA-OG is complexed with peptides, such as the HSP70 peptide. In certain embodiments, a stable association of RNA-OG with lysine-linked peptides is formed. The cellular uptake of RNA-Pep complexes is dependent on RNA:peptide ratios (FIG. 72). In certain embodiments, an RNA-OG/peptide polymer is formed. The complex can be internalized, inducing stimulation. RNA-OG/TPP (or RNA-OG) complexes retain the similar stimulatory activity to RNA-OG (FIG. 76). In vivo anti-tumor effects of RNA-OG complexed with TPP were observed (FIG. 77). The combination of RNA-OG and TPP further delays tumor growth. Anti-tumor activity correlates with tumor-specific IFNg production.

Example 13

An important landmark in the development of nanotechnology is using nucleic acids (DNA and RNA) as programmable materials to build desire nano-architectures and nano-devices for precise control of specific objects at the nanometer scale. During the past thirty years, diverse design techniques and approaches for DNA self-assembly have been exploited, resulting a wide variety of nanostructures that exhibit comparable or even beyond the geometric complicity found in nature (1-6). Several computational design tools (7-13) have been developed along parallel lines, which broaden the participation of scientists from various academic disciplines and accelerates potential applications in many research fields.

RNA has emerged as a unique polymeric material, having its own distinct advantages for nano-construction. Unlike DNA, RNA has its inherent architectural potential to form a variety of distinct interaction far beyond the Watson-Crick family (14, 15). Numerous naturally existing 3D molecules and RNA building blocks/tiles at atomic resolution can be modified and have provided a versatile toolkit to build a variety of structures. In addition, functionalities associated with RNA molecules, such as catalysis (16), gene regulation (17) and organizing proteins into large machineries (18), enable potential applications in biomedical and material sciences. However, it remains one of the primary challenges in RNA nanotechnology that rational designing objects with comparable size or complexity to natural RNA machines, or current highly sophisticated DNA nanostructures with heavy molecule weights. The recent discovery of single-stranded RNA (ssRNA) origami method pushed forward the ability to scale up RNA assembly and enabled creating large RNA tiles up to 660 nucleotides, marked as a record of programmed synthetic RNA assemblies (19).

Here a general method is presented for automatic design of large 2D and 3D ssRNA nanostructures with the size up to 6300 nucleotides in length, comparing to the size of 28S ribosomal RNA, the largest catalytic RNA molecule in nature. An RNA rectangle was constructed with 1.7 k bases to test the approach and designed structures were successfully obtained, confirmed by high-resolution atomic force microscope (AFM) images. Next, diamond-shape RNA objects were generated with unprecedented size of 6.3 k bases, and demonstrating the generality of the approach for scaling up ssRNA origami structures. The design strategy allows the building, in principle, of any arbitrary shapes in 2D and can be adapted to form more complex 3D architectures. Contrast to previous bottom-up manual programming tools in DNA and RNA nanotechnology, the design strategies presented here together with the customized top-down design tools could enable efficient screening of large RNA molecular objects and functional nano-devices. Broadly speaking, the work not only enriched the toolbox of RNA de novo design and but also advanced nanoscale fabrication abilities that allow the building of structures and functions with increasing size and complexity.

Overview Design Method

Figure 78:
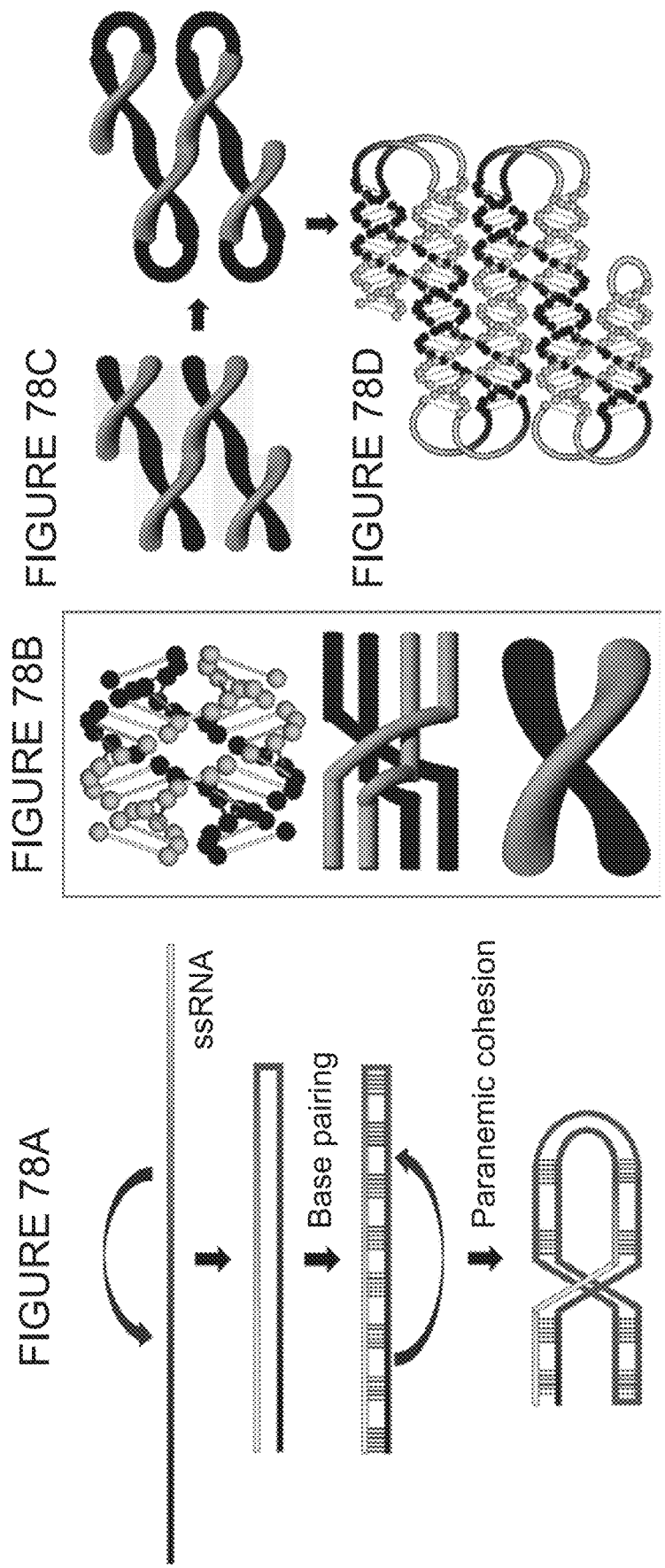
FIGS. 78A-D. The routing of ssRNA nanostructures. A. The formation of base pairing and paranemic cohesion. B. Paranemic crossover tiles. C and D shows the single-stranded RNA scaffold routing pathway.

To create a scalable ssRNA structure, a two-step folding strategy was followed using a simple RNA motif as modular building block. FIG. 78A shows how to route a long ssRNA into geometric shapes in two steps. First, half-length of one ssRNA will fold back to partially pair with the other half, leaving several unpaired single stranded regions. Second, those designed free regions will match each other by paranemic cohesive interactions and finally fold the target architecture (FIG. 78A illustrates the formation of one paranemic cohesion).

Modular Motifs

Figure 79:
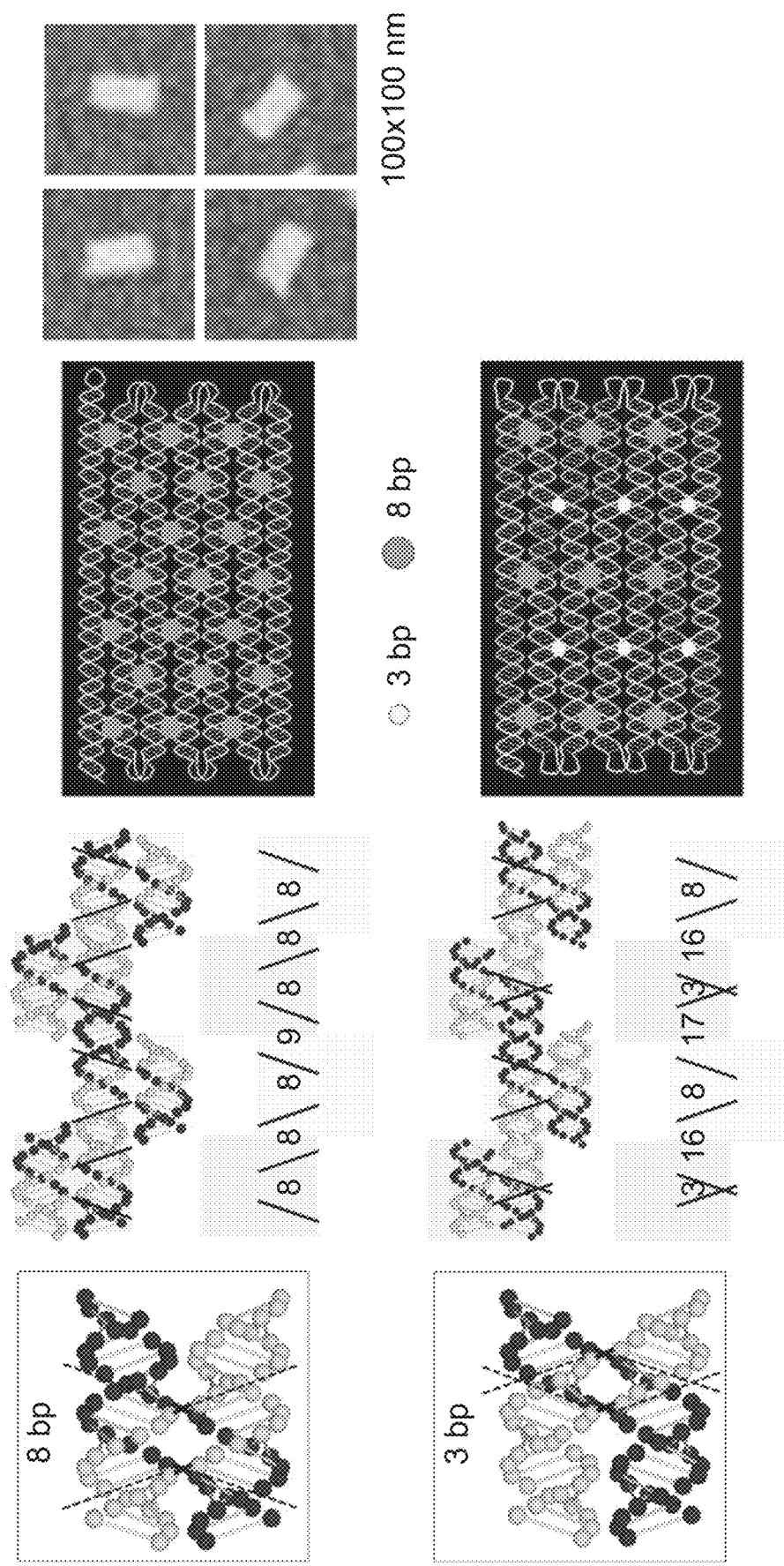
FIG. 79. The design parameters for ssRNA nanostructures and its corresponding AFM images.

To warrant the scalability of the ssRNA structures, a robust RNA motif was first constructed as the modular building block. Two key parameters needed to be determined: how many bases for paranemic cohesion, and how long for the stem of a region of a double helix. The first parameter determines the rigidity of the cohesive interaction. Based on 3D modeling of A-form helix, 8 or 3 bases were chosen as the internal length between two crossovers as the best geometrically fitting (FIG. 79A). For the 8 bases cohesion, the total of 4$^8$=65536 possibilities provides an adequate sequence space for the selection of unique complementarity. The 3 bases cohesion has 4$^3$=64 possible combinations. The second parameter determines the flatness of final assembled structures of motifs. Given the 11 base pairs per turn of standard dsRNA, the inter-motif stems length was assigned as shown in FIG. 79. Two layouts of RNA motifs assembly were chosen: one contains 8 bases paranamic cohesion and the other one contains 8 bases and 3 bases cohesion alternatively. The reason for skipping the design with 3 bases cohesion only is its weak interaction as well as the limitation of unique sequence combinations. After looping neighboring ends to form an ssRNA, appropriate sequences were assigned to the scaffold strand (scaffold routing and sequence assignment were discussed below). The experimental results revealed the only successful formation for 8-bases design (FIG. 79), indicating the 3-bases cohesion did not provide sufficient binding or specific recognitions.

The arrangement of building blocks was planned as a periodic isogonal tiling, laying rows of rectangles with vertical offsets. Each building block contains a pair of double stranded helices. Every two vertical rows of building blocks shift half unit as well as one helix to each other, One block consists of 17 base pairs long helix, representing one editable pixel in the design canvas. Selecting identical blocks in same row automatically generates continuous one long dsRNA. A pair of adjacent blocks represents one paranamic RNA motif, displaying as an X-shape line.

Routing ssRNA

After selecting desired modules to represent target structure, the next step is routing all the helices into one single strand. Given the fact that each click highlights one module and creates zero or two more ends, the total number of terminals of lines in any shape will be even. Looping any construction with 2N ends to single line needs N−1 linkages. Additionally, the spatial accessibility also needs to be considered when linking neighboring ends. It was enforced that the linkage only can be created between two adjacent ends in the same vertical column. Thus, appropriated adjustments for the length of terminals may be needed to facilitate effective linking. For example, the tilting edge of a triangular shape may yield odd number of helices ending in one vertical row, where the length of one helix must be adjusted to promote possible linkage.

The final step is to create an ssRNA cap (loop) at one end of this line to produce an ssRNA strand. Feasible scaffold paths for one structure can be various.

The next step in the design procedure is to assign appropriated sequence for long ssRNA with structural complexity, which can be truly challenging. The built-in sequence generating algorithm is similar with software Tiamat, in which three constraints applied to any randomly generated sequence: unique sequence limit, repetition limit (G repetitions were listed separately), and GC percentage. This format of output can be used to assign an ssDNA structure.

Several criteria were established for generating a valid sequence: First, the ideal percentage range of GC content in all regions of the RNA sequences is between 30% and 70% since any peaks outside of this range will adversely affect RNA synthesis. Second, bases used to form the crossovers were checked to make sure the position of crossover is stable. Third, the GC percentage in each paranemic cohesion regions were examined separately after generating a sequence that satisfied the requirement of overall GC content, such that all paranamic cohesions for the second step folding have relatively consistent melting temperature.

Synthesis Long ssRNA

The ssRNA were obtained by dividing the full-length RNA sequence into two segments and individually synthesizing and cloning them. With optimized RNA sequences, neither segment will contain strong secondary structures. They are thus very easy to synthesize and clone into plasmid vectors. After the two RNA segments are completely synthesized and cloned into the plasmid vector, RNA sequencing will be carried out to ensure accuracy. If mutations are identified, site-directed mutagenesis can be performed to correct the mutations. After the correct clones were obtained, sub-cloning will be performed to combine the two segments into a single vector using the designed restriction enzyme sites.

Adapted into 3D

The set of design tools presented here, in principle, could enable the construction of any arbitrary shapes in 2D. The method also can be adapted to crested 3D subjects. The versatility of the method is demonstrated by constructing a wire-frame polyhedral mesh.

A similar method for creating DNA octahedron, consisting of a 1.7 k bases scaffold and small number of auxiliary strands, was reported by Shih et al. in 2004. There are two major differences between previous strategy and the present method. First, the present method employed only paranemic cohesive interactions to complete a 2.8 k ssRNA scaffold routing, while in previous work, double crossover (DX) motifs were also utilized to fold the octahedron and the auxiliary strands were required to form DX regions. Second, due to physical and chemical difference between RNA and DNA, the ssRNA tetrahedron created in the present method is based on A-form instead of B-form. Thus, the geometric parameters for designing RNA structures is different. Additionally, the sequence design for ssRNA needs more dedicated tuning.

Compared to previous techniques for constructing RNA nanostructures, the present approach enabled robustly scaling up RNA into unprecedented size and complexity. The scalability of the present method to the four criteria that were established for designing routing path of ssRNA and sequence optimization. First, the first step folding of the present structure is transforming an ssRNA scaffold into a large hairpin that contains double-stranded RNA (dsRNA) region in more than half of its length, which enabled splitting the original long ssRNA into two shorter ssRNA to obtain the scaffold. Each of those two ssRNA can be synthesized relatively easily since there is no predesigned long dsRNA domain or significant secondary structure. Second, the present folding process is stepwise and hierarchical, which facilitates the formation of large and complex structures with high efficiency. The first step folding is easily accomplished since it highly preferred undergoing a zipping mechanism. The second step decreases the complexity of assembly by converting folding thousands of individual bases into matching tens of paranemic cohesive interactions. Third, arbitrary geometric shapes were converted into modular blocks. The present top-down design procedure allows formation of various geometries by repeating one designed robust modular building block, which minimizes potential topological or kinetic traps during assembling. Lastly, the present sequence-generating program optimizes the specificity of recognition in two-step folding with fewer spurious interactions.

Here a general blueprint is demonstrated for the construction of complex ssRNA objects that rival those already achieved for DNA objects. An important ongoing aim is to develop large ssRNA origamis with a variety of functionalities. Similar with DNA nanostructures, the ssRNA could be used as templates to organize other functional materials by introducing loops protruding out of structures. Kissing-loop interaction can be used for binding other materials. Unlike DNA structures, biologically active RNA motifs exist, notably ribozymes of various kinds, siRNA, and natural RNA aptamers embedded in riboswitches. The unique functionality manifest in natural RNA complexes could be implemented into large ssRNA origami structures to produce biologically active nano-devices.

Example 13 References and Notes

1. F. Zhang, J. Nangreave, Y. Liu, H. Yan, Structural DNA Nanotechnology: State of the Art and Future Perspective. *J Am Chem Soc* 136, 11198-11211 (2014).
2. R. M. Zadegan, M. L. Norton, Structural DNA Nanotechnology: From Design to Applications. *Int J Mol Sci* 13, 7149-7162 (2012).
3. R. F. Service, DNA Nanotechnology Grows Up. *Science* 332, 1140-1142 (2011).
4. A. V. Pinheiro, D. R. Han, W. M. Shih, H. Yan, Challenges and opportunities for structural DNA nanotechnology. *Nat Nanotechnol* 6, 763-772 (2011).
5. N. C. Seeman, Nanomaterials Based on DNA. *Annu Rev Biochem* 79, 65-87 (2010).
6. F. A. Aldaye, A. L. Palmer, H. F. Sleiman, Assembling materials with DNA as the guide. *Science* 321, 1795-1799 (2008).
7. E. Benson et al., DNA rendering of polyhedral meshes at the nanoscale. Nature 523, 441-U139 (2015).
8. D. N. Kim, F. Kilchherr, H. Dietz, M. Bathe, Quantitative prediction of 3D solution shape and flexibility of nucleic acid nanostructures. *Nucleic Acids Res* 40, 2862-2868 (2012).
9. J. N. Zadeh et al., NUPACK: Analysis and Design of Nucleic Acid Systems. *J Comput Chem* 32, 170-173 (2011).
10. S. Williams et al., Tiamat: A Three-Dimensional Editing Tool for Complex DNA Structures. 5347, 90-101 (2009).
11. S. M. Douglas et al., Rapid prototyping of 3D DNA-origami shapes with caDNAno. *Nucleic Acids Res* 37, 5001-5006 (2009).
12. E. S. Andersen et al., DNA origami design of dolphin-shaped structures with flexible tails. *Acs Nano* 2, 1213-1218 (2008).
13. N. C. Seeman, De NovoDesign of Sequences for Nucleic Acid Structural Engineering. *Journal of Biomolecular Structure and Dynamics* 8, 573-581 (1990).
14. N. B. Leontis, E. Westhof, Geometric nomenclature and classification of RNA base pairs. *Rna* 7, 499-512 (2001).
15. S. E. Butcher, A. M. Pyle, The Molecular Interactions That Stabilize RNA Tertiary Structure: RNA Motifs, Patterns, and Networks. *Accounts Chem Res* 44, 1302-1311 (2011).
16. E. A. Doherty, J. A. Doudna, Ribozyme structures and mechanisms. *Annu Rev Bioph Biom* 30, 457-475 (2001).
17. S. M. Elbashir et al., Duplexes of 21-nucleotide RNAs mediate RNA interference in cultured mammalian cells. *Nature* 411, 494-498 (2001).
18. Z. Shajani, M. T. Sykes, J. R. Williamson, Assembly of Bacterial Ribosomes. *Annual Review of Biochemistry*, Vol 80 80, 501-526 (2011).
19. C. Geary, P. W. K. Rothemund, E. S. Andersen, A single-stranded architecture for cotranscriptional folding of RNA nanostructures. *Science* 345, 799-804 (2014).

Although the foregoing specification and examples fully disclose and enable certain embodiments, they are not intended to limit the scope, which is defined by the claims appended hereto.

All publications, patents and patent applications are incorporated herein by reference, with the exception of U.S. Application Ser. No. 62/596,697. While in the foregoing specification certain embodiments have been described, and many details have been set forth for purposes of illustration, it will be apparent to those skilled in the art that additional embodiments and certain details described herein may be varied considerably without departing from basic principles.

The use of the terms "a" and "an" and "the" and similar referents are to be construed to cover both the singular and the plural, unless otherwise indicated herein or clearly contradicted by context.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the technology and does not pose a limitation on the scope of the technology unless otherwise claimed. No language in the specification should be construed as indicating any non-claimed element as essential to the practice of the technology.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the embodiment.

Embodiments are described herein, including the best mode known to the inventors. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this technology includes all modifications and equivalents of the subject matter recited in the claims appended hereto as permitted by applicable law. Moreover, any combination of the above-described elements in all possible variations thereof is encompassed by embodiments unless otherwise indicated herein or otherwise clearly contradicted by context.

We claim:

1. An RNA nanostructure comprising at least one single-stranded RNA (ssRNA) molecule,
   wherein the RNA nanostructure comprises at least two structural repeating units of 33 nucleotides in length, and wherein each structural repeating unit comprises, in order: a first region of a double helix 8 nucleotides in length, a first paranemic cohesion crossover 8 nucleotides in length, a second region of a double helix 9 nucleotides in length, and a second paranemic cohesion crossover 8 nucleotides in length.

2. An RNA nanostructure comprising a nucleic acid sequence having at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

3. The RNA nanostructure of claim 2, wherein the nucleic acid sequence has at least about 85% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

4. The RNA nanostructure of claim 2, wherein the nucleic acid sequence has at least about 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

5. The RNA nanostructure of claim 2 wherein the nucleic acid sequence has at least about 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, SEQ ID NO:12 or SEQ ID NO:13.

6. The RNA nanostructure of claim 2, comprising SEQ ID NO:1.

7. The RNA nanostructure of claim 2, consisting of SEQ ID NO:1.

8. The RNA nanostructure of any one of claims 1-7, wherein the RNA nanostructure has rectangular, diamond, triangle, or tetrahedron shape.

9. A nucleic acid having at least about 75% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

10. The nucleic acid of claim 9, wherein the nucleic acid has at least about 90% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

* * * * *